(12) United States Patent
Rothberg et al.

(10) Patent No.: US 8,470,164 B2
(45) Date of Patent: Jun. 25, 2013

(54) METHODS AND APPARATUS FOR MEASURING ANALYTES USING LARGE SCALE FET ARRAYS

(75) Inventors: Jonathan Rothberg, Guilford, CT (US); Wolfgang Hinz, Killingworth, CT (US); Kim Johnson, Carlsbad, CA (US); James Bustillo, Castro Valley, CA (US); John Leamon, Guilford, CT (US); Jonathan Schultz, Oxford, MA (US)

(73) Assignee: Life Technologies Corporation, Carlsbad, CA (US)

(*) Notice: Subject to any disclaimer, the term of this patent is extended or adjusted under 35 U.S.C. 154(b) by 193 days.

(21) Appl. No.: 13/001,182

(22) PCT Filed: Jun. 25, 2009

(86) PCT No.: PCT/US2009/003766
§ 371 (c)(1),
(2), (4) Date: May 23, 2011

(87) PCT Pub. No.: WO2010/008480
PCT Pub. Date: Jan. 21, 2010

(65) Prior Publication Data
US 2011/0217697 A1    Sep. 8, 2011

(30) Foreign Application Priority Data

Jun. 25, 2008  (GB) .................................. 0811656.8
Jun. 25, 2008  (GB) .................................. 0811657.6

(51) Int. Cl.
*G01N 27/414* (2006.01)
*C12Q 1/68* (2006.01)

(52) U.S. Cl.
CPC .......... *G01N 27/4145* (2013.01); *C12Q 1/6869* (2013.01)
USPC ..................... 205/793.5; 205/789; 422/82.03; 506/1

(58) Field of Classification Search
CPC ............ B01J 19/0046; B01J 2219/0059; B01J 19/0093; B01J 19/00317; B01J 2219/00295; B01J 2219/00828; B01J 2219/00529; B01J 2219/00608; B82Y 15/00; C12Q 1/6837; C12Q 1/6825; C12Q 1/6816; C12Q 2565/607; C12Q 1/6809; C12Q 1/6869; C12Q 1/6841; C12Q 2565/629; C12Q 2535/101; C12Q 1/6834; C07H 21/00; B01L 2300/0636; B01L 2200/10; B01L 9/527; G01N 27/403; G01N 27/27414; G01N 27/274491; G01N 30/6095
USPC ..................... 257/253; 205/789, 792, 793.5; 422/82.01–82.03; 435/6, 285.1, 287.1, 287.3; 436/103–105, 150, 182; 506/1, 9
See application file for complete search history.

(56) References Cited

U.S. PATENT DOCUMENTS 4,411,741 A    10/1983    Janata
(Continued)

FOREIGN PATENT DOCUMENTS

CN    102203282    9/2011
(Continued)

OTHER PUBLICATIONS

EP7867780.4 Examination Report Mailed Jul. 3, 2012.
(Continued)

*Primary Examiner* — J. Christopher Ball

(57) ABSTRACT

Methods and apparatus relating to very large scale FET arrays for analyte measurements. ChemFET (e.g., ISFET) arrays may be fabricated using conventional CMOS processing techniques based on improved FET pixel and array designs that increase measurement sensitivity and accuracy, and at the same time facilitate significantly small pixel sizes and dense arrays. Improved array control techniques provide for rapid data acquisition from large and dense arrays. Such arrays may be employed to detect a presence and/or concentration changes of various analyte types in a wide variety of chemical and/or biological processes. In one example, chemFET arrays facilitate DNA sequencing techniques based on monitoring changes in the concentration of inorganic pyrophosphate (PPi), hydrogen ions, and nucleotide triphosphates.

20 Claims, 101 Drawing Sheets

U.S. PATENT DOCUMENTS

| | | |
|---|---|---|
| 4,490,678 A | 12/1984 | Kuisl et al. |
| 4,641,084 A | 2/1987 | Komatsu |
| 4,701,253 A | 10/1987 | Litenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,971,903 A | 11/1990 | Hyman |
| 5,009,766 A | 4/1991 | Lauks |
| 5,038,192 A | 8/1991 | Bonneau et al. |
| 5,110,441 A | 5/1992 | Kinlen et al. |
| 5,113,870 A | 5/1992 | Rossenfeld |
| 5,151,759 A | 9/1992 | Vinal |
| 5,164,319 A | 11/1992 | Hafeman et al. |
| 5,284,566 A | 2/1994 | Cuomo et al. |
| 5,317,407 A | 5/1994 | Michon |
| 5,436,149 A | 7/1995 | Barnes |
| 5,439,839 A | 8/1995 | Jang |
| 5,466,348 A | 11/1995 | Holm-Kennedy |
| 5,554,339 A | 9/1996 | Cozzette et al. |
| 5,583,462 A | 12/1996 | Grasshoff |
| 5,593,838 A | 1/1997 | Zanzucchi et al. |
| 5,600,451 A | 2/1997 | Maki |
| 5,631,704 A | 5/1997 | Dickinson et al. |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,911,873 A | 6/1999 | McCarron et al. |
| 5,922,591 A | 7/1999 | Anderson et al. |
| 5,923,421 A | 7/1999 | Rajic et al. |
| 5,958,703 A | 9/1999 | Dower et al. |
| 5,965,452 A | 10/1999 | Kovacs |
| 6,002,299 A | 12/1999 | Thomsen |
| 6,107,032 A | 8/2000 | Kilger et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,327,410 B1 | 12/2001 | Walt et al. |
| 6,355,431 B1 | 3/2002 | Chee et al. |
| 6,361,671 B1 | 3/2002 | Mathies et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,537,881 B1 | 3/2003 | Parce et al. |
| 6,538,593 B2 | 3/2003 | Yang et al. |
| 6,545,620 B2 | 4/2003 | Groeneweg |
| 6,602,702 B1 | 8/2003 | McDevitt et al. |
| 6,605,428 B2 | 8/2003 | Kilger et al. |
| 6,613,513 B1 | 9/2003 | Rangarajan et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,682,899 B2 | 1/2004 | Bryan et al. |
| 6,682,936 B2 | 1/2004 | Kovacs |
| 6,700,814 B1 | 3/2004 | Nahas et al. |
| 6,780,591 B2 | 8/2004 | Williams et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,859,570 B2 | 2/2005 | Walt et al. |
| 6,919,211 B1 | 7/2005 | Fodor et al. |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,033,754 B2 | 4/2006 | Chee et al. |
| 7,037,687 B2 | 5/2006 | Williams et al. |
| 7,049,645 B2 | 5/2006 | Sawada et al. |
| 7,060,431 B2 | 6/2006 | Chee et al. |
| 7,085,502 B2 | 8/2006 | Shushakob et al. |
| 7,087,387 B2 | 8/2006 | Gerdes et al. |
| 7,090,975 B2 | 8/2006 | Shultz et al. |
| 7,097,973 B1 | 8/2006 | Zenhausern |
| 7,105,300 B2 | 9/2006 | Parce et al. |
| 7,169,560 B2 | 1/2007 | Lapidus et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg |
| 7,223,540 B2 | 5/2007 | Pourmand et al. |
| 7,226,734 B2 | 6/2007 | Chee et al. |
| 7,238,323 B2 | 7/2007 | Knapp et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,276,749 B2 | 10/2007 | Martin et al. |
| 7,282,370 B2 | 10/2007 | Bridgham et al. |
| 7,291,496 B2 | 11/2007 | Holm-Kennedy |
| 7,297,518 B2 | 11/2007 | Quake et al. |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,762 B2 | 2/2008 | Rothberg et al. |
| 7,381,936 B2 | 6/2008 | Tan et al. |
| 7,394,263 B2 | 7/2008 | Pechstein et al. |
| 7,455,971 B2 | 11/2008 | Chee et al. |
| 7,462,512 B2 | 12/2008 | Levon et al. |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,515,124 B2 | 4/2009 | Yaguma et al. |
| 7,575,865 B2 | 8/2009 | Leamon et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,303 B1 | 10/2009 | Lee |
| 7,612,817 B2 | 11/2009 | Tay |
| 7,667,501 B2 | 2/2010 | Surendranath et al. |
| 7,686,929 B2 | 3/2010 | Toumazou et al. |
| 7,785,790 B1 | 8/2010 | Church et al. |
| 7,859,029 B2 | 12/2010 | Lee et al. |
| 7,888,013 B2 | 2/2011 | Miyahara et al. |
| 7,923,240 B2 | 4/2011 | Su |
| 7,932,034 B2 | 4/2011 | Esfandyarpour et al. |
| 7,948,015 B2 | 5/2011 | Rothberg et al. |
| 8,199,859 B2 | 6/2012 | Zerbe et al. |
| 8,231,831 B2 | 7/2012 | Hartzell et al. |
| 8,232,813 B2 | 7/2012 | Burdett et al. |
| 8,263,336 B2 | 9/2012 | Rothberg et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0061529 A1 | 5/2002 | Bridgham et al. |
| 2002/0086318 A1 | 7/2002 | Manalis et al. |
| 2002/0094533 A1 | 7/2002 | Hess et al. |
| 2002/0117659 A1 | 8/2002 | Lieber et al. |
| 2002/0117694 A1 | 8/2002 | Migliorato et al. |
| 2002/0131899 A1 | 9/2002 | Kovacs |
| 2002/0132221 A1 | 9/2002 | Chee et al. |
| 2002/0137062 A1 | 9/2002 | William et al. |
| 2002/0168678 A1 | 11/2002 | Williams et al. |
| 2002/0172963 A1 | 11/2002 | Kelley et al. |
| 2002/0187515 A1 | 12/2002 | Chee et al. |

| | | |
|---|---|---|
| 2003/0032052 A1 | 2/2003 | Hadd et al. |
| 2003/0049624 A1 | 3/2003 | Shultz et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0077615 A1 | 4/2003 | Bridgham et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0124599 A1 | 7/2003 | Chen et al. |
| 2003/0138809 A1 | 7/2003 | Williams et al. |
| 2003/0148301 A1 | 8/2003 | Aono et al. |
| 2003/0148344 A1 | 8/2003 | Rothberg et al. |
| 2003/0157504 A1 | 8/2003 | Chee et al. |
| 2003/0186262 A1 | 10/2003 | Cailloux |
| 2003/0194740 A1 | 10/2003 | Williams |
| 2003/0215857 A1 | 11/2003 | Kilger et al. |
| 2003/0224419 A1 | 12/2003 | Corcoran et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0049237 A1 | 3/2004 | Larson et al. |
| 2004/0134798 A1 | 7/2004 | Toumazou et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0197803 A1 | 10/2004 | Yaku et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0106587 A1 | 5/2005 | Klapproth et al. |
| 2005/0119497 A1 | 6/2005 | Hong et al. |
| 2005/0130173 A1 | 6/2005 | Leamon et al. |
| 2005/0130188 A1 | 6/2005 | Walt et al. |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0212016 A1 | 9/2005 | Brunner et al. |
| 2005/0221473 A1 | 10/2005 | Dubin et al. |
| 2005/0224346 A1 | 10/2005 | Holm-Kennedy |
| 2005/0227264 A1 | 10/2005 | Nobile et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2006/0016699 A1 | 1/2006 | Kamahori et al. |
| 2006/0024711 A1 | 2/2006 | Lapidus et al. |
| 2006/0040297 A1 | 2/2006 | Leamon et al. |
| 2006/0051807 A1 | 3/2006 | Fuller |
| 2006/0057604 A1 | 3/2006 | Chen et al. |
| 2006/0073513 A1 | 4/2006 | Chee et al. |
| 2006/0093488 A1 | 5/2006 | Wong et al. |
| 2006/0105373 A1 | 5/2006 | Pourmand et al. |
| 2006/0115857 A1 | 6/2006 | Keen |
| 2006/0121670 A1 | 6/2006 | Stasiak |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0183145 A1 | 8/2006 | Turner |
| 2006/0197118 A1 | 9/2006 | Migliorato et al. |
| 2006/0199193 A1 | 9/2006 | Koo et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0244147 A1 | 11/2006 | Lee et al. |
| 2006/0246497 A1 | 11/2006 | Huang et al. |
| 2006/0269927 A1 | 11/2006 | Lieber |
| 2007/0059741 A1 | 3/2007 | Kamahori et al. |
| 2007/0069291 A1 | 3/2007 | Stuber et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0099208 A1 | 5/2007 | Drmanac et al. |
| 2007/0099351 A1 | 5/2007 | Peters et al. |
| 2007/0109454 A1 | 5/2007 | Chou |
| 2007/0117099 A1 | 5/2007 | Engelhardt et al. |
| 2007/0117137 A1 | 5/2007 | Jaeger |
| 2007/0138028 A1 | 6/2007 | Chodavarapu et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0032295 A1 | 2/2008 | Toumazou et al. |
| 2008/0035494 A1 | 2/2008 | Gomez et al. |
| 2008/0096216 A1 | 4/2008 | Quake |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0145910 A1 | 6/2008 | Ward et al. |
| 2008/0166727 A1 | 7/2008 | Esfandyarpour et al. |
| 2008/0176271 A1 | 7/2008 | Silver et al. |
| 2008/0186093 A1 | 8/2008 | Forbes |
| 2008/0213770 A1 | 9/2008 | Williams et al. |
| 2008/0230386 A1 | 9/2008 | Srinivasan et al. |
| 2008/0265985 A1 | 10/2008 | Toumazou et al. |
| 2008/0286762 A1 | 11/2008 | Miyahara et al. |
| 2008/0286767 A1 | 11/2008 | Miyahara et al. |
| 2009/0026082 A1 | 1/2009 | Rothberg et al. |
| 2009/0030117 A1 | 1/2009 | Lanphere et al. |
| 2009/0032401 A1 | 2/2009 | Ronaghi et al. |
| 2009/0033370 A1 | 2/2009 | Sarig et al. |
| 2009/0048124 A1 | 2/2009 | Leamon et al. |
| 2009/0062132 A1 | 3/2009 | Borner |
| 2009/0079414 A1 | 3/2009 | Levon et al. |
| 2009/0108831 A1 | 4/2009 | Levon et al. |
| 2009/0127589 A1 | 5/2009 | Rothberg et al. |
| 2009/0140763 A1 | 6/2009 | Kim |
| 2009/0143244 A1 | 6/2009 | Bridgham et al. |
| 2009/0156425 A1 | 6/2009 | Walt et al. |
| 2009/0170728 A1 | 7/2009 | Walt et al. |
| 2009/0316477 A1 | 12/2009 | Horiuchi |
| 2010/0007326 A1 | 1/2010 | Nakazato |
| 2010/0137143 A1 | 6/2010 | Rothberg et al. |
| 2010/0156454 A1 | 6/2010 | Weir |
| 2010/0188073 A1 | 7/2010 | Rothberg et al. |
| 2010/0197507 A1 | 8/2010 | Rothberg et al. |
| 2010/0255595 A1 | 10/2010 | Toumazou et al. |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0165557 A1 | 7/2011 | Ah et al. |
| 2011/0181253 A1 | 7/2011 | Isham et al. |
| 2011/0217697 A1 | 9/2011 | Rothberg et al. |
| 2011/0247933 A1 | 10/2011 | Rothberg et al. |
| 2011/0263463 A1 | 10/2011 | Rothberg et al. |
| 2011/0275522 A1 | 11/2011 | Rothberg et al. |
| 2011/0287945 A1 | 11/2011 | Rothberg et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife |
| 2012/0001237 A1 | 1/2012 | Fife et al. |
| 2012/0001615 A1 | 1/2012 | Levine |
| 2012/0001646 A1 | 1/2012 | Bolander et al. |
| 2012/0001685 A1 | 1/2012 | Levine et al. |
| 2012/0022795 A1 | 1/2012 | Johnson et al. |
| 2012/0040844 A1 | 2/2012 | Rothberg et al. |
| 2012/0056248 A1 | 3/2012 | Fife |
| 2012/0129728 A1 | 5/2012 | Rothberg et al. |
| 2012/0129732 A1 | 5/2012 | Rothberg et al. |

FOREIGN PATENT DOCUMENTS

| | | |
|---|---|---|
| EP | 0223618 | 5/1987 |
| EP | 1371974 A1 | 12/2003 |
| EP | 1432818 | 6/2004 |
| EP | 1542009 | 6/2005 |
| EP | 2307577 | 4/2011 |
| GB | 2457851 A | 9/2009 |
| GB | 2461127 B | 7/2010 |
| JP | 2002272463 | 9/2002 |
| JP | 2005-518541 | 6/2005 |
| JP | 2011-525810 | 9/2011 |
| KR | 10-0442838 | 7/2004 |
| KR | 10-0455283 | 10/2004 |
| WO | WO-89/09283 | 10/1989 |
| WO | WO-98/13523 | 4/1998 |
| WO | WO-98/46797 | 10/1998 |
| WO | WO-01/20039 | 3/2001 |
| WO | WO-01/42498 | 6/2001 |
| WO | WO-01/81896 | 11/2001 |
| WO | WO-02/077287 | 10/2002 |
| WO | WO-02/086162 | 10/2002 |
| WO | 03073088 A2 | 9/2003 |
| WO | WO-03/073088 | 9/2003 |
| WO | 2004040291 A1 | 5/2004 |
| WO | WO-2004/040291 | 5/2004 |
| WO | WO-2005/047878 | 5/2005 |
| WO | WO-2005/054431 | 6/2005 |
| WO | WO-2005/084367 | 9/2005 |
| WO | WO-2006/005967 | 1/2006 |
| WO | 2006022370 A1 | 3/2006 |
| WO | WO-2007/086935 | 8/2007 |
| WO | WO-2008/007716 | 1/2008 |
| WO | WO-2008/058282 | 5/2008 |
| WO | 2008076406 A2 | 6/2008 |
| WO | WO-2008/107014 | 9/2008 |
| WO | WO-2009/012112 | 1/2009 |
| WO | WO-2009/158006 | 12/2009 |
| WO | WO-2010/008480 | 1/2010 |
| WO | WO-2010/047804 | 4/2010 |
| WO | WO-2010/047804 A8 | 4/2010 |
| WO | WO-2010/138182 | 12/2010 |
| WO | WO-2010/138188 | 12/2010 |
| WO | WO-2012/003359 | 1/2012 |
| WO | WO-2012/003363 | 1/2012 |
| WO | WO-2012/003368 | 1/2012 |
| WO | WO-2012/003380 | 1/2012 |
| WO | WO-2012/006222 | 1/2012 |

OTHER PUBLICATIONS

PCT/JP2005/015522 International Preliminary Report on Patentability Mailed Mar. 19, 2007.
PCT/US2011/042665 International Search Report Mailed Nov. 2, 2011.
PCT/US2011/042668 International Search Report Mailed Oct. 28, 2011.
Ronaghi, M. et al., "A Sequencing Method Based on Real-Time Pyrophosphate", *Science*, vol. 281, 1998, pp. 363-365.
PCT/US2009/003766 International Preliminary Report on Patentability Mailed Jan. 5, 2011.
PCT/US2009/003766 Written Opinion Mailed Apr. 8, 2010.
[No Author Listed], "ISFET Wikipedia article", *Wikipedia*, Last modified Nov. 7, 2006.
Ahmadian, A. et al., "Single-nucleotide polymorphism analysis by pyrosequencing", *Anal. Biochem*, vol. 280, 2000, pp. 103-110.
Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.
AU2011226767 Search Information Statement Mailed Oct. 26, 2011, pp. 1-3.
Bandiera, L et al., "A fully electronic sensor for the measurement of cDNA hybridization kinetics", *Biosens Bioelectron*, vol. 22, 2007, pp. 2108-2114.
Barbaro, M et al., "A Charge-Modulated FET for Detection of Biomolecular Processes: Conception, Modeling, and Simulation", *IEEE Transactions on Electron Devices*, vol. 53(1), 2006, pp. 158-166.
Barbaro, M et al., "A CMOS, Fully Integrated Sensor for Electronic Detection of DNA Hybridization", *IEEE Electron Device Letters*, vol. 27(7), 2006, pp. 595-597.
Barbaro, M et al., "Fully electronic DNA hybridization detection by a standard CMOS biochip", *Sensors and Actuators B Chemical*, vol. 118, 2006, pp. 41-46.
Bashford, G et al., "Automated bead-trapping apparatus and control system for single-molecule DNA sequencing", *Optics Express*, vol. 16(5), Mar. 3, 2008, pp. 3445-3455.
Baumann, W et al., "Microelectronic sensor system for microphysiological application on living cells", *Sensors Actuators B*, vol. 55, 1999, pp. 77-89.
Bausells, J et al., "Ion-sensitive field-effect transistors fabricated in a commercial CMOS technology", *Sensors and Actuators B Chemical*, vol. 57, 1999, pp. 56-62.
Bergveld, P., "ISFET, Theory and Practice", *IEEE Sensor Conference*, Toronto, Oct. 2003, 2003, pp. 1-26.
Bergveld, P., "Thirty years of Isfetology What happened in the past 30 years and what may happen in the next 30 years", *Sensors and Actuators B*, vol. 88, vol. 88, 2003, pp. 1-20.
Besselink, G et al., "ISFET Affinity Sensor", *Methods in Biotechnology*, vol. 7: *Affinity Biosensors: Techniques and Protocols*, 1998, pp. 173-185.
Bobrov, P et al., "Chemical sensitivity of an ISFET with Ta2O5 membrane in strong acid and alkaline solutions", *Sensors and Actuators B*, vol. 3, 1991, pp. 75-81.
Bousse, L et al., "A process for the combined fabrication of ion sensors and CMOS circuits", *IEEE Electron Device Letters*, vol. 9(1), 1988, pp. 44-46.
Bousse, L et al., "Zeta potential measurements of Ta2O5 and SiO2 thin films", *J. Colloid. Interface Sci.*, vol. 147(1), 1991, pp. 22-32.
Chen, et al., "Nanoscale field effect transistor for biomolecular signal amplification", *App Phys Letter*, vol. 91, 2007, pp. 243511-1-243511-3.
Chen, et al., "Silicon-based nanoelectronic field-effect pH sensor with local gate control", *App Phys Letter*, vol. 89, 2006, pp. 223512-1-223512-3.
Chou, J. et al., "Letter to the Editor on Simulation of Ta2O5 gate ISFET temperature characteristics", *Sensors and Actuators B*, vol. 80, 2001, pp. 290-291.
Chou, J. et al., "Simulation of Ta2O5 gate ISFET temperature characteristics", *Sensor and Actuators B*, vol. 71, Letter to the Editor, 2000, pp. 73-61.
Chung, W-Y et al., "ISFET interface circuit embedded with noise rejection capability", *Electronics Letters*, vol. 40(18), e-pub ; 2 pages, 2004.
Chung, W-Y et al., "ISFET performance enhancement by using the improved circuit techniques", *Sensors and Actuators B*, vol. 113, 2006, pp. 555-562.
Eijkel, J. et al., "Measuring Donnan-related phenomena using a solid-state ion sensor and a concentration-step method", *J. Membrane Sci.*, vol. 127, 1997, pp. 203-221.
Eijkel, J., "Potentiometric detection and characterization of adsorbed protein using stimulus-response measurement techniques", *Thesis*, Sep. 3, 1955, pp. 1-147; 160-192.
Eltoukhy, H et al., "A 0.18um CMOS 10-6 lux Bioluminescence Detection System-on-Chip", *ISSCC 2004/Session12/Biomicrosystems/12.3*, 2004, pp. 1-3.
Eltoukhy, H. et al., "A. 0.18-um CMOS Bioluminescence Detection Lab-on-Chip", *IEEE J Solid-State Circuits*, vol. 41(3), 2006, pp. 651-662.
Eriksson, J et al., "Pyrosequencing technology at elevated temperature", *Electrophoresis*, vol. 25, 2004, pp. 20-27.
Esfandyarpour, H. et al., "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.
Eversmann, B. et al., "A 128 × 128 CMOS Biosensor Array for Extracellular Recording of Neural Activity", *IEEE J. Solid-State Circ.*, vol. 38(12), Dec. 12, 2003, pp. 2306-2317.
Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.

Finn, A et al., "Towards an Optimization of FET-Based Bio-Sensors", *European Cells and Materials*, vol. 4, Sup 2, 2002, pp. 21-23.
Fraden, J., "Handbook of Modern Sensors—Physics, Designs, and Applications . . . ", *17.3.2 CHEMFET Sensors*, 1996, pp. 499-501.
Fritz, et al., "Electronic detection of DNA by its intrinsic molecular charge", *PNAS*, vol. 99(22), 2002, pp. 14142-14146.
GB0811656.8 Search and Examination Report Mailed Mar. 12, 2010.
GB0811656.8 Search Report Mailed Sep. 21, 2009.
GB0811657.6 Examination Report Mailed Jun. 30, 2010.
GB0811657.6 Search Report under Section 17 Mailed Oct. 26, 2009.
Gracia, I. et al., "Test Structures for ISFET Chemical Sensors", *Proc IEEE 1992 Intl Conf Microelec Test Struct*, vol. 5, 1992, pp. 156-159.
Hammond, P et al., "A System-on-Chip Digital pH Meter for Use in a Wireless Diagnostic Capsule", *IEEE Transactons on Biomedical Engineering*, vol. 52(4), 2005, pp. 687-694.
Hammond, P et al., "Design of a Single-Chip pH Sensor Using a Conventional 0.6—μm CMOS Process", *IEEE Sensors Journal*, vol. 4(6), 2004, pp. 706-712.
Hammond, P et al., "Encapsulation of a liquid-sensing microchip using SU-8 photoresist", *MicoElectronic Engineering*, vol. 73-74, 2004, pp. 893-897.
Hammond, S. et al., "Genomic sequencing and analysis of a Chinese Hampster ovary cell line using Illumina sequencing technology", *BMC Genomics*, 12:67, 2011, pp. 1-8.
Han, Y., "Label-free detection of biomolecules by a field-effect transistor microarray biosensor with bio-functionalized gate surfaces", Masters Dissertation, 2006, pp. 1-63.
Hara, H. et al., "Dynamic response of a Ta2O5-gate pH-sensitive field-effect transistor", *Sensors Actuators B*, vol. 32, 1996, pp. 115-119.
Hermon, Z. et al., "Miniaturized bio-electronic hybrid for chemical sensing applications", *Tech Connect News*, Apr. 22, 2008, pp. 1.
Hideshima, S. et al., "Detection of tumor marker in blood serum using antibody-modified field effect ransistor with optimized BSA blocking", *Sensors and Actuations B: Chemical*, vol. 161, 2012, pp. 146-150.
Hijikata, M. et al., "Identification of a Single Nucleotide Polymorphism in the MXA Gene Promoter (T/T at nt -88) Correlated with the Response of Hepatitis C Patients to Interferon", *Intervirology*, vol. 43, 2000, pp. 124-127.
Hizawa, T et al., "Fabrication of a two-dimensional pH image sensor using a charge transfer technique", *Sensors and Actuators B Chemical*, 117, 2006, pp. 509-515.
Hizawa, T. et al., "32 × 32 pH Image Sensors for Real Time Observation of Biochemical Phenomena", *Transducers & Eurosensors '07*, 14th International Conference on Solid-State, Actuators and Microsystems, Lyon, France, Jun. 10-14, 2007, pp. 1311-1312.
Jakobson, C. et al., "Low frequency noise and drift in Ion Senstive Field Effect Transistors", Sensors Actuators B, vol. 68, 2000, pp. 134-139.
Ji, H. et al., "A CMOS contact imager for locating individual cells", *ISCAS*, 2006, pp. 3357-3360.
Ji, H. et al., "Contact Imaging: Simulation and Experiment", *IEEE Trans Circuits Systems-I: Regular Papers*, vol. 54(8), 2007, pp. 1698-1710.
Kim, D. et al., "An FET-type charger sensor for highly sensitive detection of DNA sequence", *Biosens Bioelectron*, vol. 20(1), Jul. 30, 2004, pp. 69-74.
Klein, M., "Time effects of ion-sensitive field-effect transistors", *Sens Act B*, vol. 17, 1989, pp. 203-208.
Koch, S et al., "Protein detection with a novel ISFET-based zeta potential analyzer", *Biosensors & Bioelectronics*, vol. 14, 1999, pp. 413-421.
Kruise, J. et al., "Detection of protein concentrations using a pH-step titration method", *Sensors Actuators B*, vol. 44, 1997, pp. 297-303.
Leamon, J et al., "A Massively Parallel PicoTiterPlate Based Platform for Discrete Picoliter-Scale Polymerase Chain Reactions", *Electrophoresis*, vol. 24, Nov. 24, 2003, pp. 3769-3777.
Leamon, J. et al., "Cramming More Sequencing Reactions onto Microreactor Chips", *Chemical Reviews*, 107:, 2007, 3367-3376.
Lee, C-S et al., "Ion-sensitive Field-Effect Transistor for Biological Sensing", *Sensors*, vol. 9, 2009, pp. 7111-7131.

Li, et al., "Sequence-Specific Label-Free DNA Sensors Based on Silico Nanowires", *Nano Letters*, vol. 4(2), 2004, pp. 245-247.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Prooceedings of the 1996 IEEE International Conference on Microelectronic Test Structures*, vol. 9, 1996, pp. 123-128.
Margulies, M. et al., "Genome sequencing in microfabricated high-density picolitre reactors", *Nature*, vol. 437, 2005, pp. 376-380.
Marshall, A. et al., "DNA chips: an array of possibilities", *Nature Biotechnology*, vol. 16, Jan. 1998, pp. 27-31.
Martinoia, S. et al., "A behavioral macromodel of the ISFET in SPICE", *Sensors Actuators B*, vol. 62, 2000, pp. 182-189.
Martinoia, S., "Development of ISFET Array-Based Microsystems for Bioelectrochemical measurements of cell populations", *Biosensors & Bioelectronics*, vol. 16, 2001, pp. 1043-1050.
Medoro, G. et al., "A Lab-on-a-Chip for Cell Detection and Manipulation", *IEEE Sensors J*, vol. 3(3), 2003, pp. 317-325.
Meyburg, S. et al., "N-Channel field-effect transistors with floating gates for extracellular recordings", *Biosens Bioelectron*, vol. 21(7), Jan. 15, 2006, pp. 1037-1044.
Milgrew, M et al., "A large transistor based sensor array chip for direct extracellular imaging", *Sensors and Actuators B Chemical*, vol. 111-112, 2005, pp. 347-353.
Milgrew, M et al., "Microsensor Array Technology for Direct Extracellular Imaging", Apr. 5, 2006, pp. 1-23.
Milgrew, M et al., "The development of scalable sensor arrays using standard CMOS technology", *Sensors and Actuators B*, 103, 2004, pp. 37-42.
Milgrew, M et al., "The fabrication of scalable multi-sensor arrays using standard CMOS technology", *2003 IEEE Custom Integrated Circuits Conference*, 2003, pp. 513-516.
Milgrew, M. et al., "A 16 × 16 CMOS proton camera array for direct extracellular imaging of hydrogen-ion activity", *IEEE Intl Solid-State Circuits Conf*, Session 32:24, 2008, pp. 590-591; 638.
Milgrew, M. et al., "Matching the transconductance characteristics of CMOS ESFET arrays by removing trapped charge", *IEEE Trans Electron Devices*, vol. 55(4), 2008, pp. 1074-1079.
Miyahara, Y et al., "Direct Transduction of Primer Extension into Electrical Signal Using Genetic Field Effect Transistor", *Micro Total Analysis Systems 2004*, vol. 1, Proceedings of uTAS 2004, 8th International Conference on Miniaturized Systems for Chemistry and Life Sciences, Malmo, Sweden, Sep. 26-30, 2004, pp. 303-305.
Miyahara, Y. et al., "Biochip Using Micromatchining Technology", *J. Institute of Electrostatics*, Japan, vol. 27(6), 2003, pp. 268-272.
Miyahara, Y. et al., "Potentiometric Detection of DNA Molecules Using Field Effect Transistor", *The Japan Society of Applied Physics*, No. 3 (Translation included), 2003, pp. 1180, 30A-S2.
Nyren, P. et al., "Enzymatic Method for Continuous Monitoring of Inorganic Pyrophosphate Synthesis", *Analytical Biochemistry*, vol. 151, 1985, 504-509.
Oelbner, W. et al., "Encapsulation of ESFET sensor chips", *Sensors Actuators B*, vol. 105, 2005, pp. 104-117.
Oelbner, W. et al., "Investigation of the dynamic response behaviour of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12(8), 1997, pp. 819-826.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Patolsky, F. et al., "Nanowire-Based Biosensors", *Analyt Chem 1*, vol. 78(13), Jul. 1, 2006, pp. 4261-4269.
PCT/JP2005/001987 International Search Report Mailed Apr. 5, 2005.
PCT/JP2005/015522 International Search Report (includes English translation) Mailed Sep. 27, 2005.
PCT/US/2009/05745 International Preliminary Report on Patentability.
PCT/US/2009/05745 International Search Report.
PCT/US/2009/05745 Written Opinion.

PCT/US2007/025721 Declaration of Non-Establishment of International Search Report Mailed Jul. 15, 2008.
PCT/US2007/025721 International Prelimary Report on Patentability Mailed Jun. 16, 2009.
PCT/US2007/025721 Written Opinion Mailed Jun. 16, 2009.
PCT/US2009/003797 International Search Report Mailed Mar. 12, 2010.
PCT/US2009/003797 Written Opinion.
PCT/US2010/001543 International Preliminary Report on Patentability Mailed Nov. 29, 2011, pp. 1-8.
PCT/US2010/001543 International Search Report and Written Opinion Mailed Oct. 13, 2010, pp. 1-12.
PCT/US2010/001553 International Preliminary Report on Patentability Mailed Dec. 8, 2011, pp. 1-10.
PCT/US2010/001553 International Search Report Mailed Jul. 28, 2010, pp. 1-2.
PCT/US2010/001553 Written Opinion Mailed Jul. 14, 2010, pp. 1-6.
PCT/US2010/48835 International Search Report and Written Opinion Mailed Dec. 16, 2010, pp. 1-12.
PCT/US2011/042655 International Search Report Mailed Oct. 21, 2011, pp. 1-2.
PCT/US2011/042660 International Search Report Mailed Nov. 2, 2011.
PCT/US2011/42669 International Search Report Mailed Jan. 9, 2012, pp. 1-5.
PCT/US2011/42669 Written Opinion Mailed Jan. 9, 2012, pp. 1-5.
PCT/US2011/42683 International Search Report Mailed Feb. 16, 2012.
PCT/US2011/42683 Written Opinon Mailed Feb. 16, 2012.
Poghossian, A. et al., "Functional testing and characterization of ISFETs on wafer level by means of a micro-droplet cell", *Sensors*, vol. 6, 2006, pp. 397-404.
Pourmand, N. et al., "Direct electrical detection of DNA synthesis", *PNAS*, vol. 103(17), 2006, pp. 6466-6470.
Pouthas, F. et al., "Spatially resolved electronic detection of biopolymers", *Phys Rev*, vol. 70, 2004, pp. 031906-1-031906-8.
Premanode, B. et al., "A composite ISFED readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Ultra-low power precision ISFET readout using global current feedback", *Electronic Lett*, vol. 42(22), Oct. 26, 2006, 2 pages.
Purushothaman, S. et al., "Towards Fast Solid State DNA Sequencing", *IEEE ISCAS 2002 Proceedings*, 2002, pp. IV-169-IV-172.
Rodriguez-Villegas, E. , "Solution to trapped charge in FGMOS transistors, vol. 39(19)", *Electronics Letters*, 2003.
Sakata, T. et al., "Cell-based field effect devices fo cell adhesion analysis", *International Conference on Microtechnologies in Medicine and Biology*, May 9-12, 2006, Okinawa, Japan, 2006, pp. 177-179.
Sakata, T. et al., "Detection of DNA recognition events using multi-well field effect transistor", *Biosensors and Bioelectronics* vol. 21, 2005, pp. 827-832.
Sakata, T. et al., "Detection sensitivity of genetic field effect transistor combined with charged nanoparticle-DNA conjugate", *Proceedings of 2006 International Conference on Microtechnologies in Medicine and Biology*, May 9-12, 2005, Okinawa, Japan, 2006, pp. 97-100.
Sakata, T. et al., "Direct detection of single nucleotide polymorphism using genetic field effect transistor", *Digest of Papers Microprocesses and Nanotechnology 2004*, Osaka, Japan, 2004 International Microprocesses and Nanotechnology Conference, 2004, pp. 226-227.
Sakata, T. et al., "Direct Detection of Single-Base Extension Reaction Using Genetic Field Effect Transistor", *Proceedings of 3rd Annual International IEEE EMBS Special Topic Conference on Microtechnologies in Medicine and Biology*, Kahuku, Oahu, HI, May 12-15, 2005, 2005, pp. 219-222.
Sakata, T. et al., "DNA Analysis Chip Based on Field-Effect Transistors", *Japanese Journal of Applied Physics*, vol. 44, No. 4B, 2005, pp. 2854-2859.
Sakata, T. et al., "DNA Sequencing Based on Intrinsic Molecular Charges", *Angewandte Chemie International Edition*, 2006, vol. 118, 2006, pp. 2283-2286.
Sakata, T. et al., "DNA Sequencing Using Genetic Field Effect Transistor", *13th International Conference on Solid-State Sensors, Actuators and Microsystems*, Jun. 5-9, 2005, Seoul, Korea, 2005, pp. 1676-1679.
Sakata, T. et al., "Immobilization of oligonucleotide probes on Si3N4 surface and its application to genetic field effect transistor", *Materials Science and Engineering: C*, vol. 24, 2004, pp. 827-832.
Sakata, T. et al., "Potential Behavior of Biochemically Modified Gold Electrode for Extended-Gate Field-Effect Transistor", *Japanese Journal of Applied Physics*, vol. 44, No. 4B, 2005, 2005, pp. 2860-2863.
Sakata, T. et al., "Potential Response of Genetic Field Effect Transistor to Charged Nanoparticle-DNA Conjugate", *Digest of Papers Microprocesses and Nanotechnology 2005*, Tokyo, Japan, 2005 Intl Microprocesses and Nanotech Conference, Hotel Bellclassic, 2005, pp. 42-43.
Sakata, T. et al., "Potentiometric Detection of Allele Specific Oligonucleotide Hybridization Using Genetic Field Effect Transistor", *Micro Total Anslysis Systems 2004*, vol. 1, 8th International Conference on Miniaturized Systems for Chemistry and Life Sciences, Sep. 26-30, 2004, Malmo, Sweden, 2004, pp. 300-302.
Sakata, T. et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston, Massachusetts, 2004, pp. 393-398.
Sakata, T. et al., "Potentiometric Detection of DNA Using Genetic Transistor", *Denki Gakkai Kenkyukai Shiryo Chemical Sensor Kenkuykai*, CHS-03-51-55, 2003, pp. 1-5.
Sakata, T. et al., "Potentiometric Detection of Single Nucleotide Polymorphism by Using a Genetic Field-effect transistor", *ChemBioChem 2005*, vol. 6, 2005, pp. 703-710.
Sakurai, T. et al., "Real-Time Monitoring of DNA Polymerase Reactions by a Micro ISFET pH Sensor", *Anal Chem*, vol. 64(17), 1992, pp. 1996-1997.
Salama, K., "CMOS luminescence detection lab-on-chip: modeling, design, and characterization", *Thesis*, Presented at Stanford University, 2005, pp. ii-78.
Salama, K., "Modeling and simulation of luminescence detection platforms", *Biosensors & Bioelectronics*, 2004, 1377-1386.
Sawada, K. et al., "A novel fused sensor for photo- and ion-sensing", *Sensors Actuators B*, vol. 106, 2005, pp. 614-618.
Sawada, K. et al., "Highly sensitive ion sensors using charge transfer technique", *Sensors Actuators B*, vol. 98, 2004, pp. 69-72.
Schasfoort, RB et al., "Field-effect flow control for microfabricated fluidic networks", *Science*, vol. 286(5441), Oct. 29, 1999, pp. 942-945.
Schasfoort, B. et al., "A new approach to immunoFET operation", *Biosensors & Bioelectronics*, vol. 5, 1990, pp. 103-124.
Schoning, M. et al., "Bio FEDs (Field-Effect Devices): State-of-the-Art and New Directions", *Electroanalysis*, vol. 18(19-20), 2006, pp. 1893-1900.
SG200903992-6 Search and Examination Report Mailed Jan. 20, 2011.
Shah, N., "Microfabrication of a parellel-array DNA pyrosequencing chip", NNIN REU Research Accomplishments, 2005, pp. 130-131.
Shepherd, L. et al., "A biochemical translinear principle with weak inversion ISFETs", *IEEE Trans Circuits Syst—I*, vol. 52(12), Dec. 2005, pp. 2614-2619.
Shepherd, L. et al., "A novel voltage-clamped CMOS ISFET sensor interface", *IEEE*, 2007, pp. 3331-3334.
Shepherd, L. et al., "Towards direct biochemical analysis with weak inversion ISFETS", *Intl Workshop on Biomedical . . .* , 2004, S1.5-5-S1.5-8.
Shepherd, L. et al., "Weak inversion ISFETs for ultra-low power biochemical sensing and real-time analysis", *Sensors Actuators B*, vol. 107, 2005, pp. 468-473.
Shi, Y. et al., "Radical Capillary Array Electrophoresis Microplace and Scanner for High-Performance Nucleic Acid Analysis", *Anal. Chem.*, vol. 71(23), 1999, pp. 5354-5361.

Simonian, A. L. et al., "FET bases biosensors for the direct detection of organophosphate neurotoxins", *Electroanalysis*, vol. 16(22), 2004, pp. 1896-1906.

Souteyrand, E. et al., "Direct detection of the hybridization of synthetic homo-oligomer DNA sequences by field effect", *J Phys Chem B*, vol. 101(15), 1997, pp. 2980-2985.

Starodub, N. et al., "Immunosensor for the determination of the herbicide simazine based on an ion-selective field-effect transistor", *Analytica Chimica Acta*, vol. 424, 2000, pp. 37-43.

Takenaka, S. et al., "DNA Sensing on a DNA Probe-Modified Electrode Using Ferrocenylnaphthalene Dimide as the Electrochemically Active Ligand", *Anal. Chem.*, vol. 72(6), 2000, pp. 1334-1341.

Tomaszewski, D. et al., "Electrical characterization of ISFETs", *J Telecomm Info Technol*, Mar. 2007, pp. 55-60.

Toumazou, C. et al., "Using transistors to linearase biochemistry", *Electronics Letters*, vol. 43(2), Jan. 18, 2007, 3 pages.

Truman, P., "Monitoring liquid transport and chemical composition in lab on . . . ", *Lab on a Chip*, vol. 6, 2006, pp. 1220-1228.

Uslu, F. et al., "Labelfree fully electronic nucleic acid detection system based on a field-effect transistor device", *Biosens & Bioelectron*, vol. 19(12), 2004, pp. 1723-1731.

Van Der Wouden, E. et al., "Directional flow induced by synchronized longitudinal and zeta-potential controlling AC-electrical fields", *Lab Chip*, vol. 6(10), 2006, pp. 1300-1305.

Van Hal, R.E.G. et al., "A general model to describe the electrostatic potential at electrolyte oxide interfaces", *Advances in Colloid and Interface Science*, vol. 69, 1996, pp. 31-62.

Van Kerkhof, J et al., "The ISFET based heparin sensor with a monolayer of protamine as affinity ligand", *Biosensors & Bioelectronics*, vol. 10(3), 1995, pp. 269-282.

Van Kerkhof, J. et al., "ISFET Responses on a stepwise change in electrolyte concentration at constant pH", *Sensors Actuators B: Chemical*, vol. 18-19, Mar. 1994, pp. 56-59.

Van Kerkhof, J., "The Development of an ISFET-based Heparin Sensor", *Thesis*, 1994.

Wagner, T et al., ""All-in-one" solid-state device based on a light-addressable potentiometric sensor platform", *Sensors and Actuators B*, vol. 117, 2006, pp. 472-479.

Wang, W. et al., "Label-free detection of small-molecule-protein interactions by using nanowire nanosensors", *Proceedings of the National Academy of Sciences (PNAS)*, vol. 102,(9), 2005, pp. 3208-3212.

Woias, P., "Modelling the short time response of ISFET sensors", *Sensors and Actuators B*, vol. 24-25, 1995, pp. 211-217.

Woias, P. et al., "Slow pH response effects of silicon nitride ISFET sensors", *Sensors and Actuators B*, vol. 48, 1998, pp. 501-504.

Wu, P. et al., "DNA and protein microarray printing on silicon nitride waveguide surfaces", *Biosensens Bioelectron*, vol. 21(7), 2006, pp. 1252-1263.

Xu, J-J et al., "Analytical Aspects of FET-Based Biosensors", *Frontiers in Bioscience*, 10, 2005, pp. 420-430.

Yeow, T.C.W., "A very large integrated pH-ISFET sensor array chip compatible with standard CMOS processes", *Sensor and Actuators B*, vol. 44, 1997, pp. 434-440.

Yuqing, M. et al., "Ion sensitive field effect trnasducer-based biosensors", *Biotechnology Advances*, vol. 21, 2003, 527-534.

Zhang, X et al., "32-Channel Full Customized CMOS Biosensor Chip for Extracellular neural Signal Recording", *Proceedings of the 2nd International IEEE EMBs Conference on Neural Engineering*, Arlington, VA—, 2005, pp. v-viii.

Zhou, G. et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, pp. 1-11.

Purushothaman, et al., "Protons and single nucleotide polymorphism detection: a simple use for the Ion sensitive field effect transistor," Sensor & Actuators B, vol. 114, 2006, pp. 964-968.

Sakata, et al., "DNA sequencing based on intrinsic molecular charges," Angew. Chem, Int. Ed., vol. 45, 2007, pp. 2225-2228.

Sakata, et al., "Direct transduction of allele-specific primer extension into electrical signal using genetic field effect transistor," Biosensors & Bioelectronics, vol. 22, 2007, pp. 1311-1316.

Korean Patent Office, International Search Report in PCT/US2009/003766, dated Apr. 8, 2010.

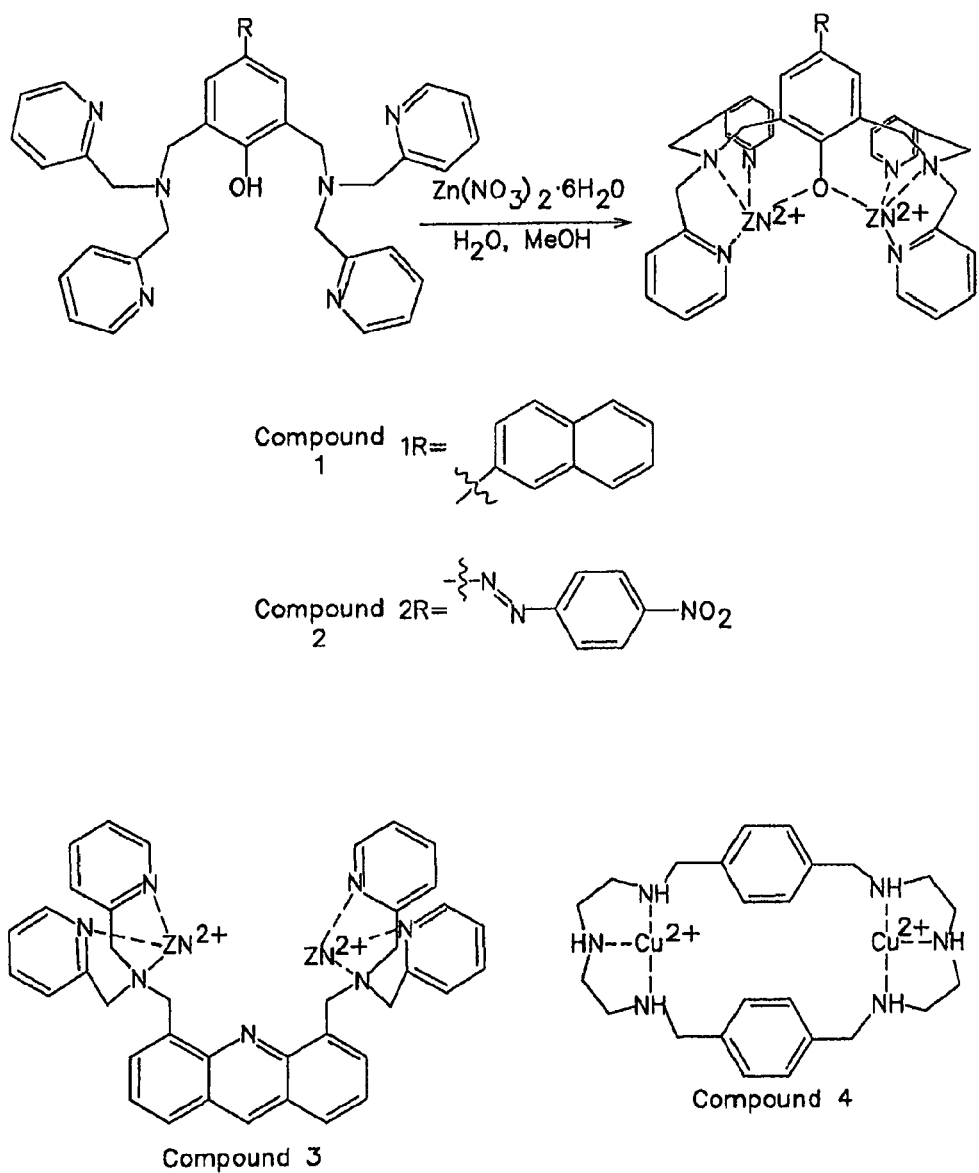
FIG. 11B(1)

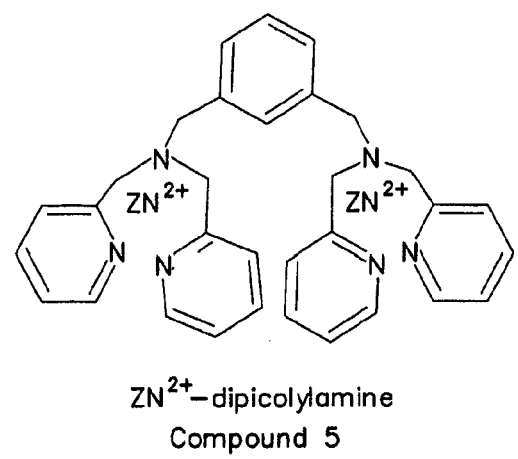
ZN²⁺-dipicolylamine
Compound 5
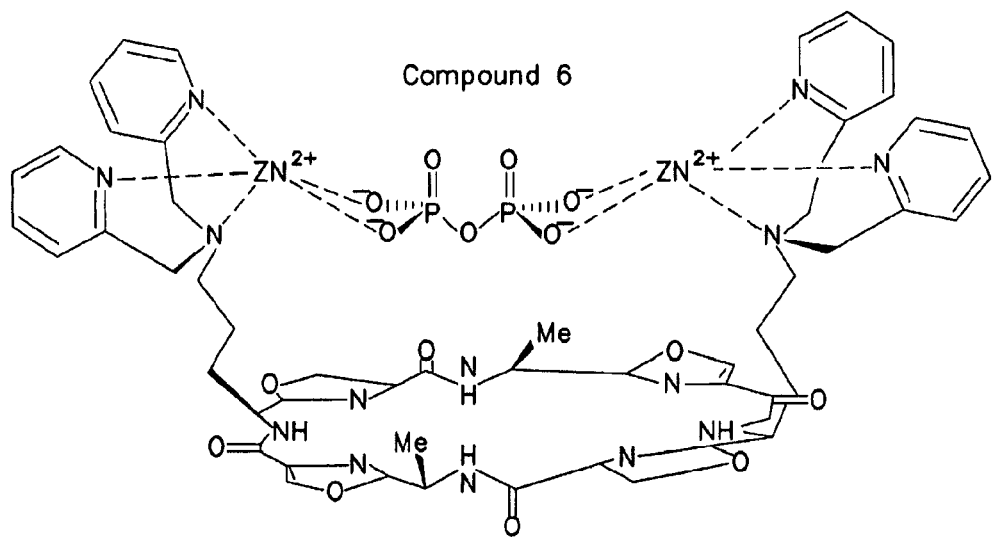
Compound 6
FIG. 11B(2)

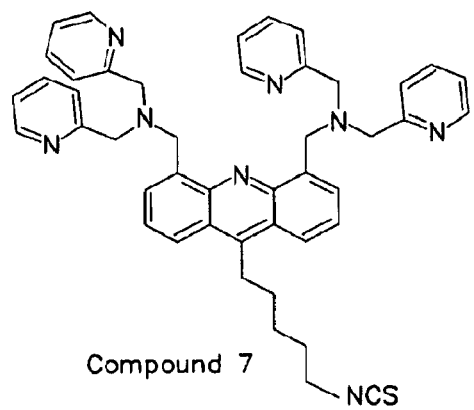
Compound 7
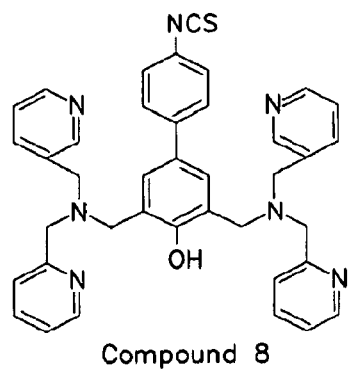
Compound 8
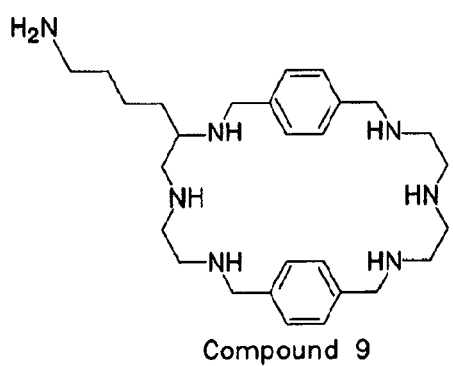
Compound 9
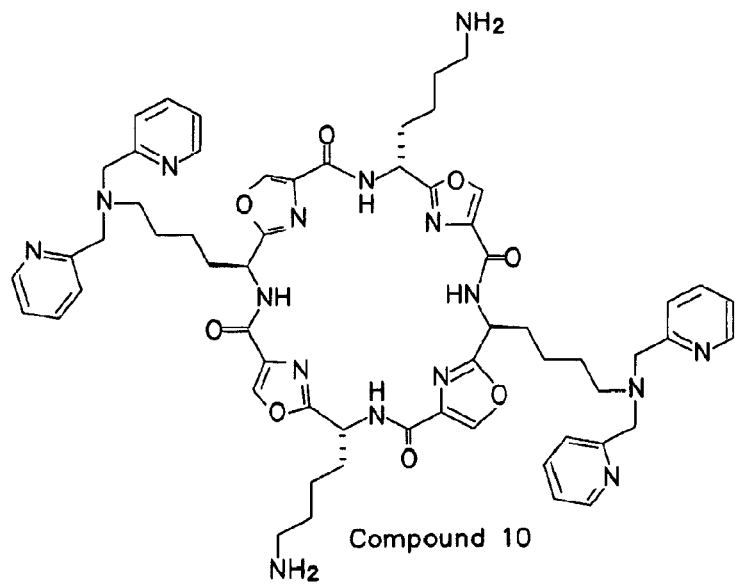
Compound 10
*FIG. 11B(3)*

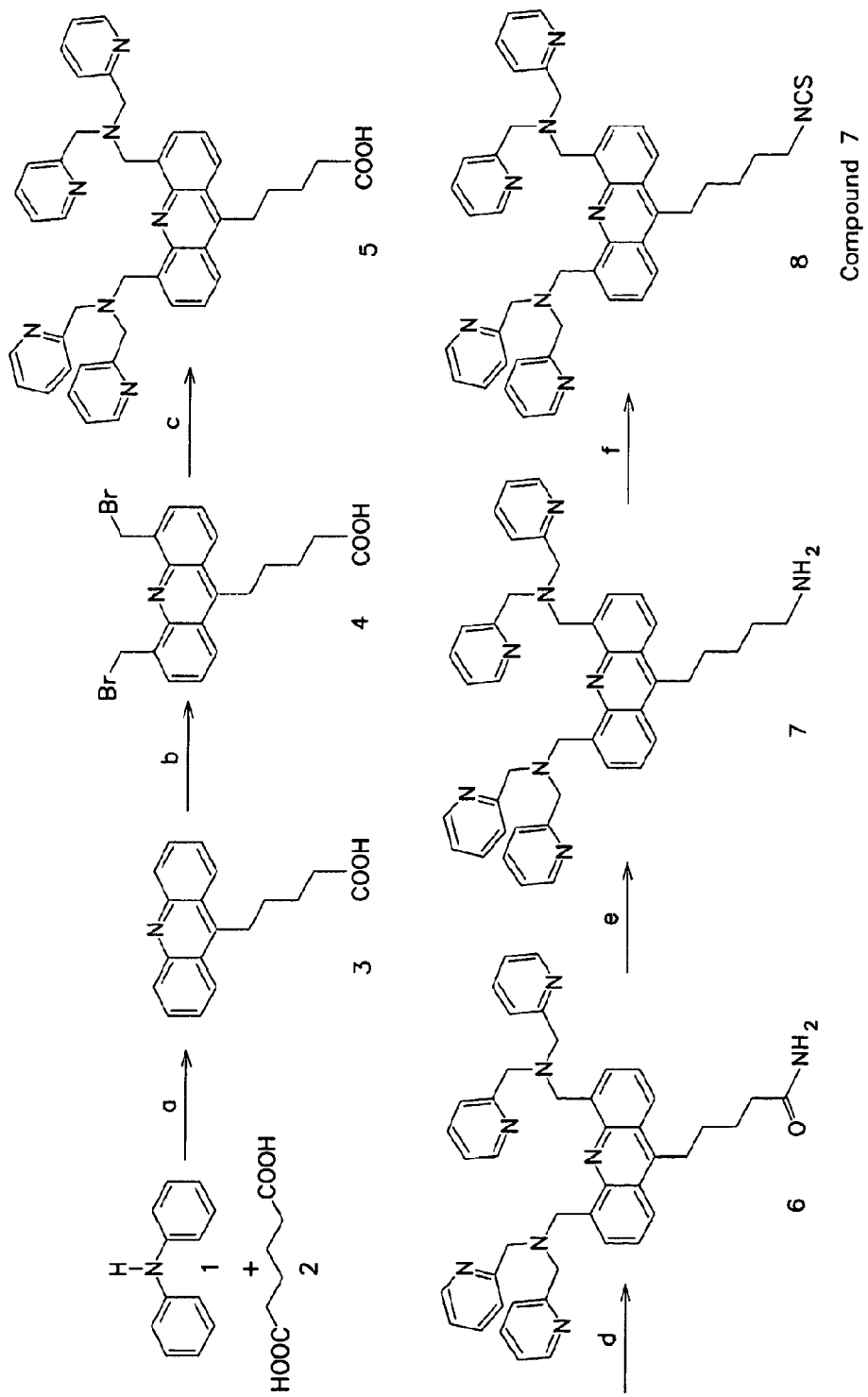
FIG. 11C(1)-1

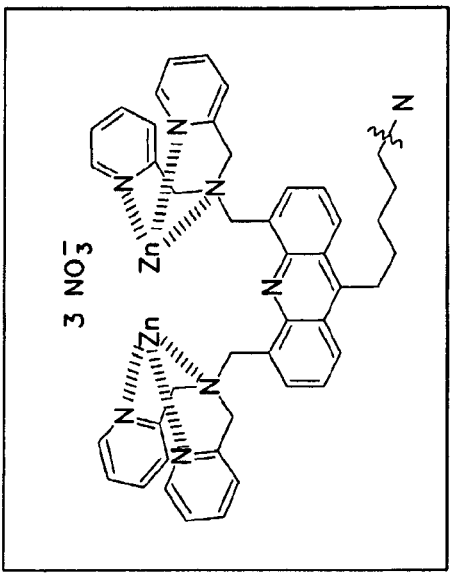
a. $ZnCl_2$; 20% $H_2SO_4$,
b. $BrCH_2OCH_3$, $H_2SO_4$, 50° C, 18%
c. dipicorylamine, $K_2CO_3$, $CH_2Cl_2$, 66%
d. $NH_2CONH_2$, heat
e. $LiAlH_4$, $Et_2O$ or $BH_3$
di-2-pyridyl thiocarbonate, $CH_2Cl_2$, 46%
Note: Zn ion are added post covalent linking to surface.
FIG. 11C(1)-2

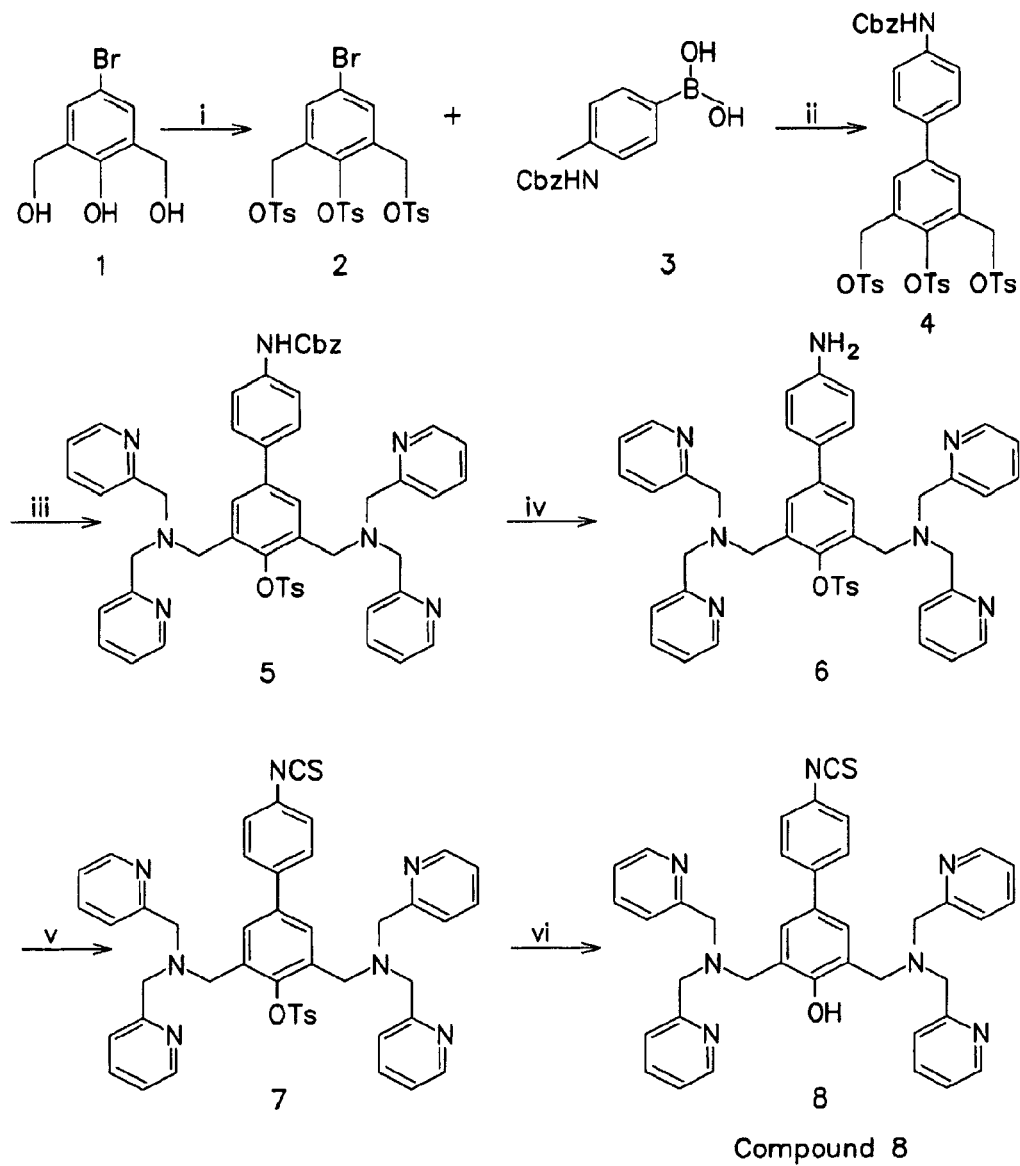
i. TsCl, TEA, 4-DMAP, THF
ii. Pd(PPh$_3$)$_4$, aq Na$_2$CO$_3$, EtOH/benzene
iii. dipicoylamine, K$_2$CO$_3$, KI, MeCN
iv. H$_2$, Pd/C, MeOH
v. DPT, MeCN, r.t.
vi. NaOH, MeOH, THF
FIG. 11C(2)

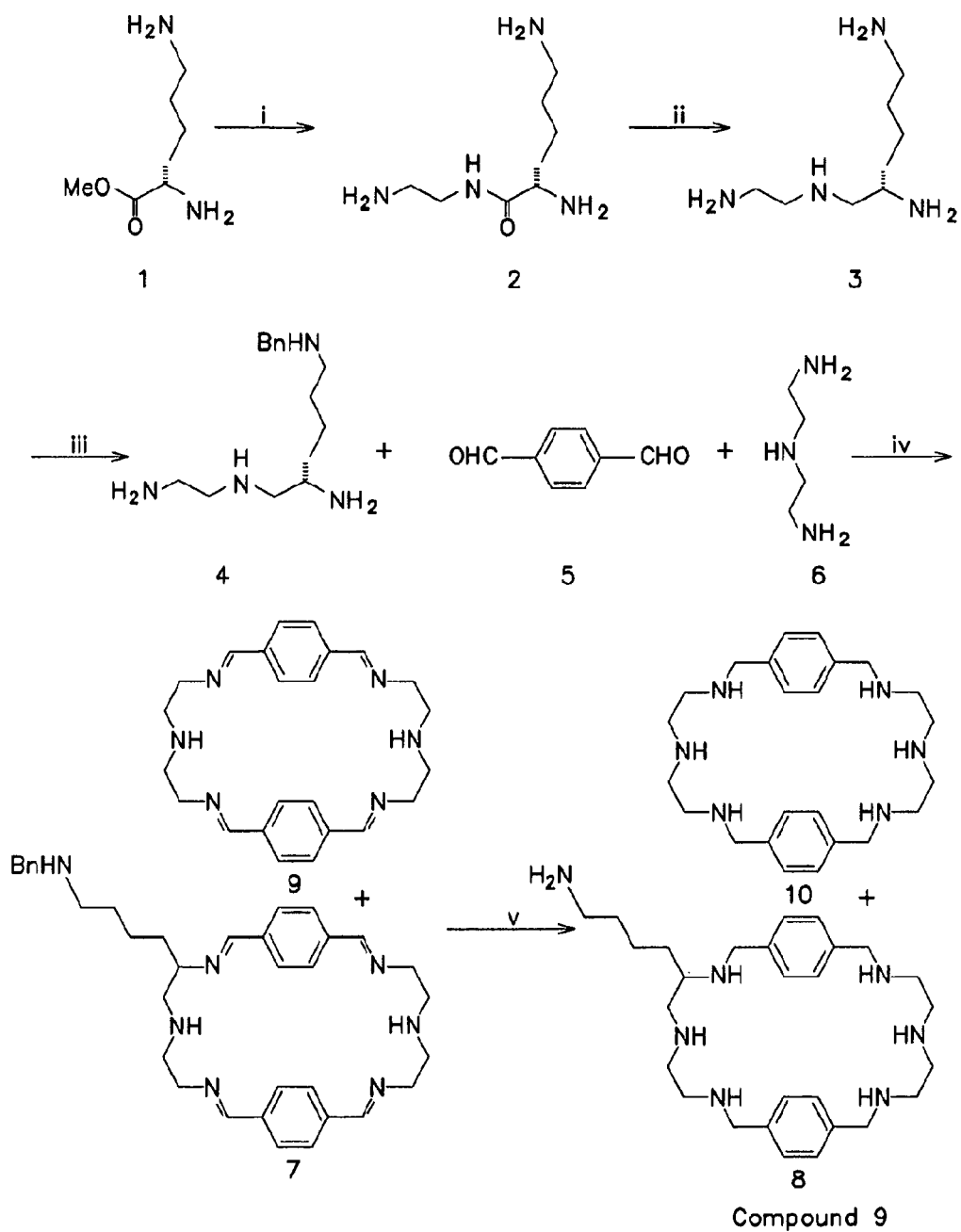
Compound 9
i. ethylenediamine, 90°C
ii. BH$_3$–THF
iii. KOH, CuCO$_3$, benzoyl chloride
iv. 1:4 ratio of 4:6, MeCN, r.t.
v. NaBH$_4$, MeOH; H$_2$NNH$_2$ if necessary
*FIG. 11C(3)*

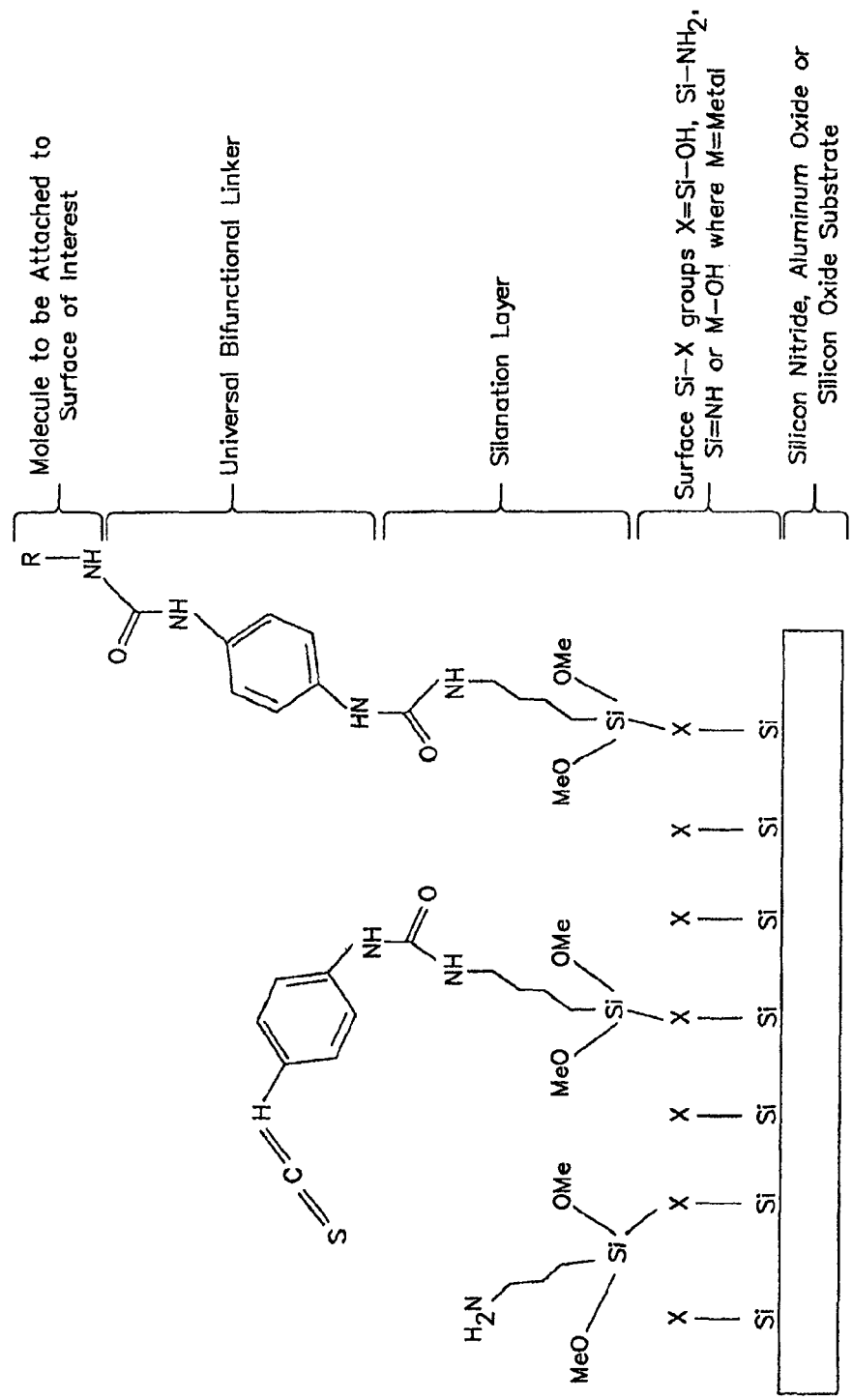
FIG. 11D(1)

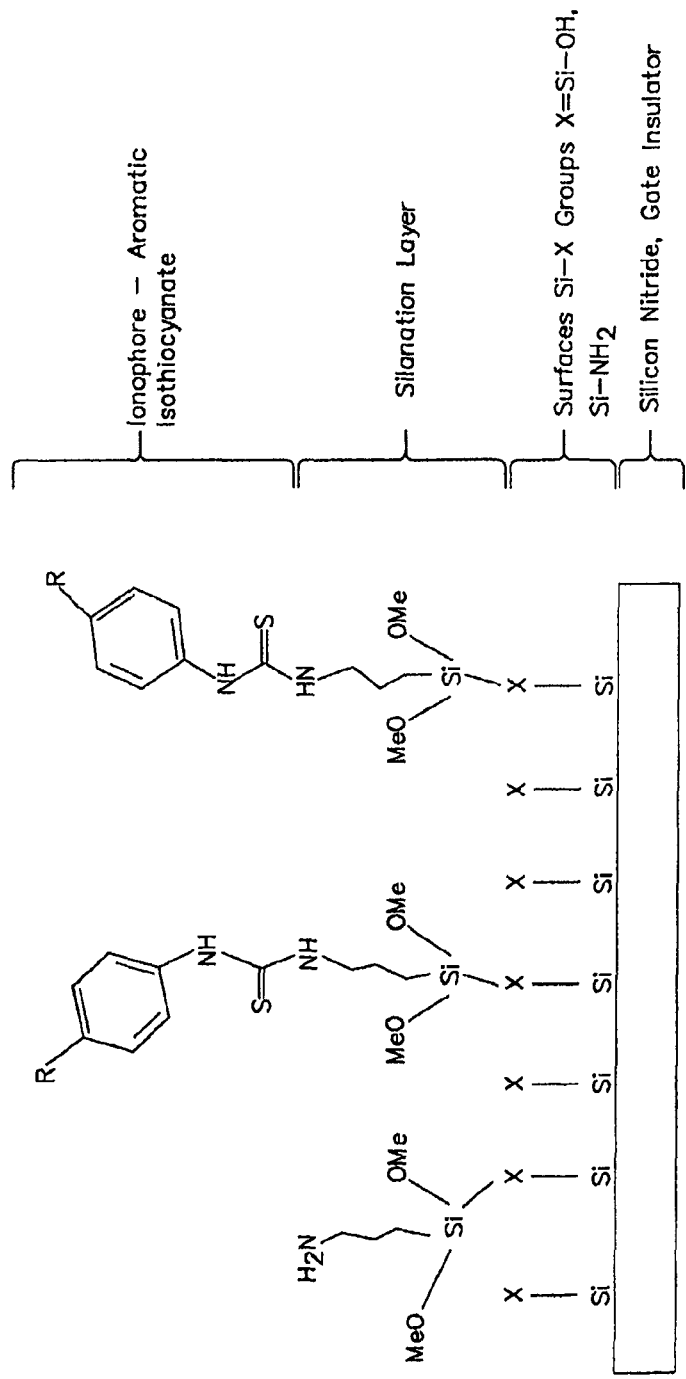
FIG. 11D(2)

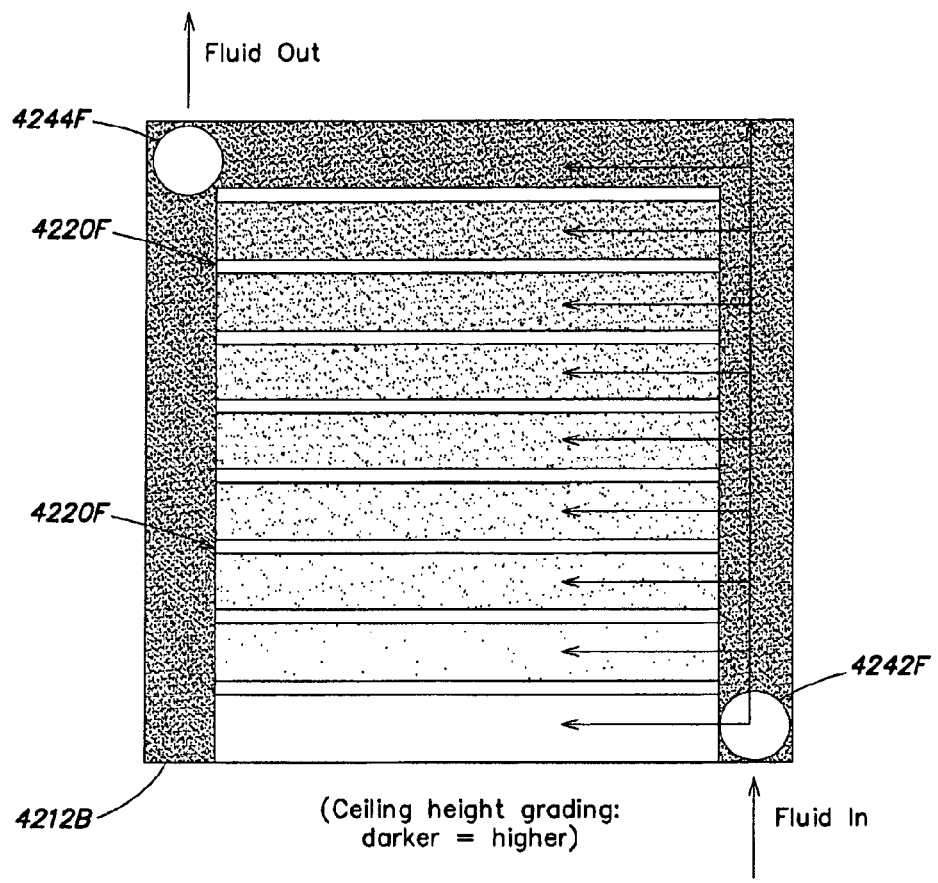
FIG. 42F1

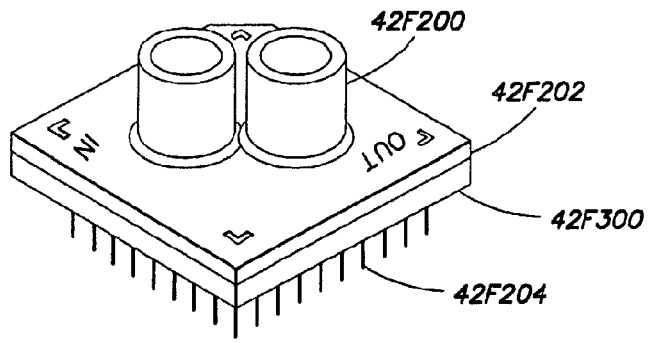
FIG. 42F2
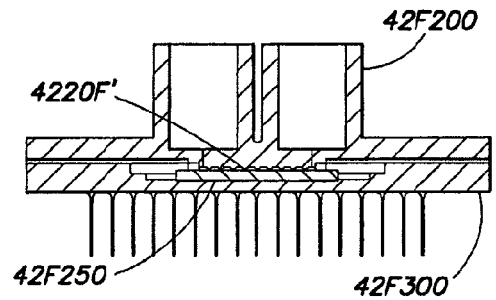
FIG. 42F3
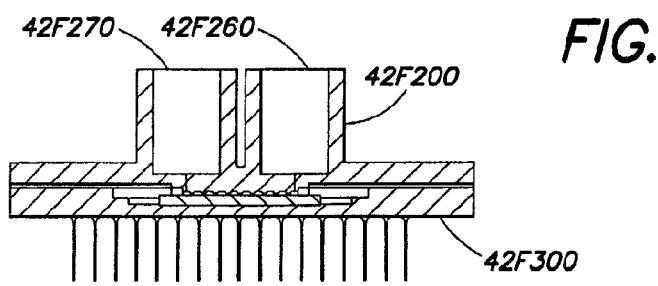
FIG. 42F4
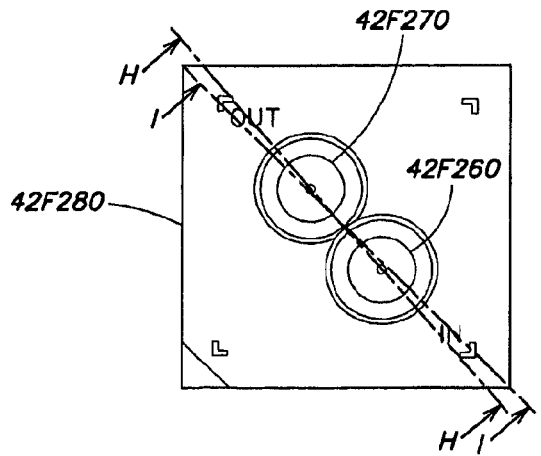
FIG. 42F5

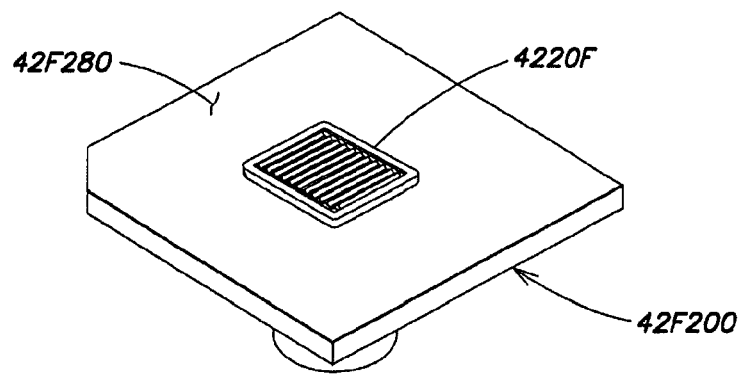
FIG. 42F6
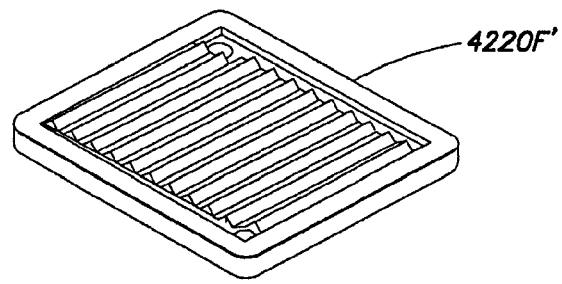
FIG. 42F7
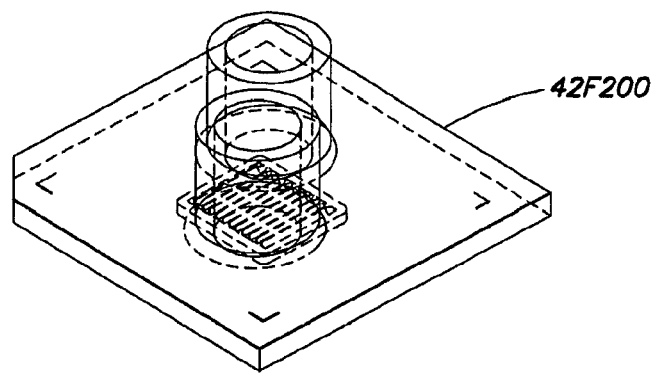
FIG. 42F8

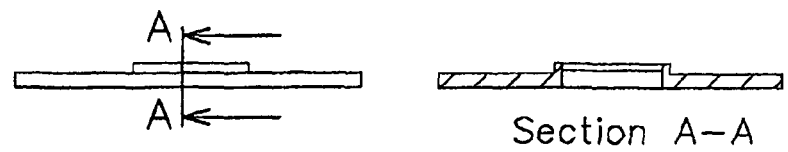
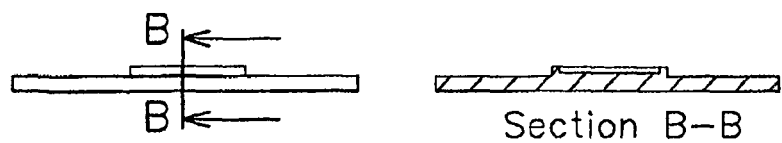
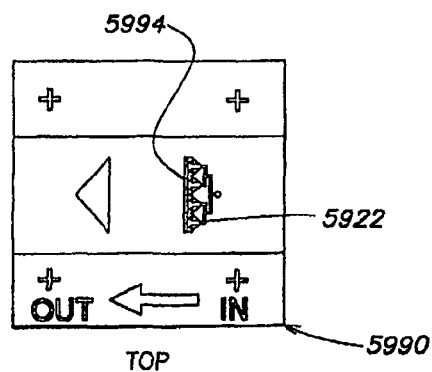
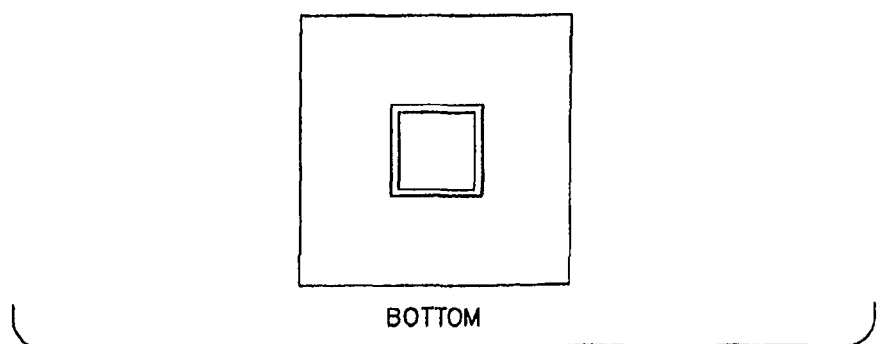
FIG. 59C

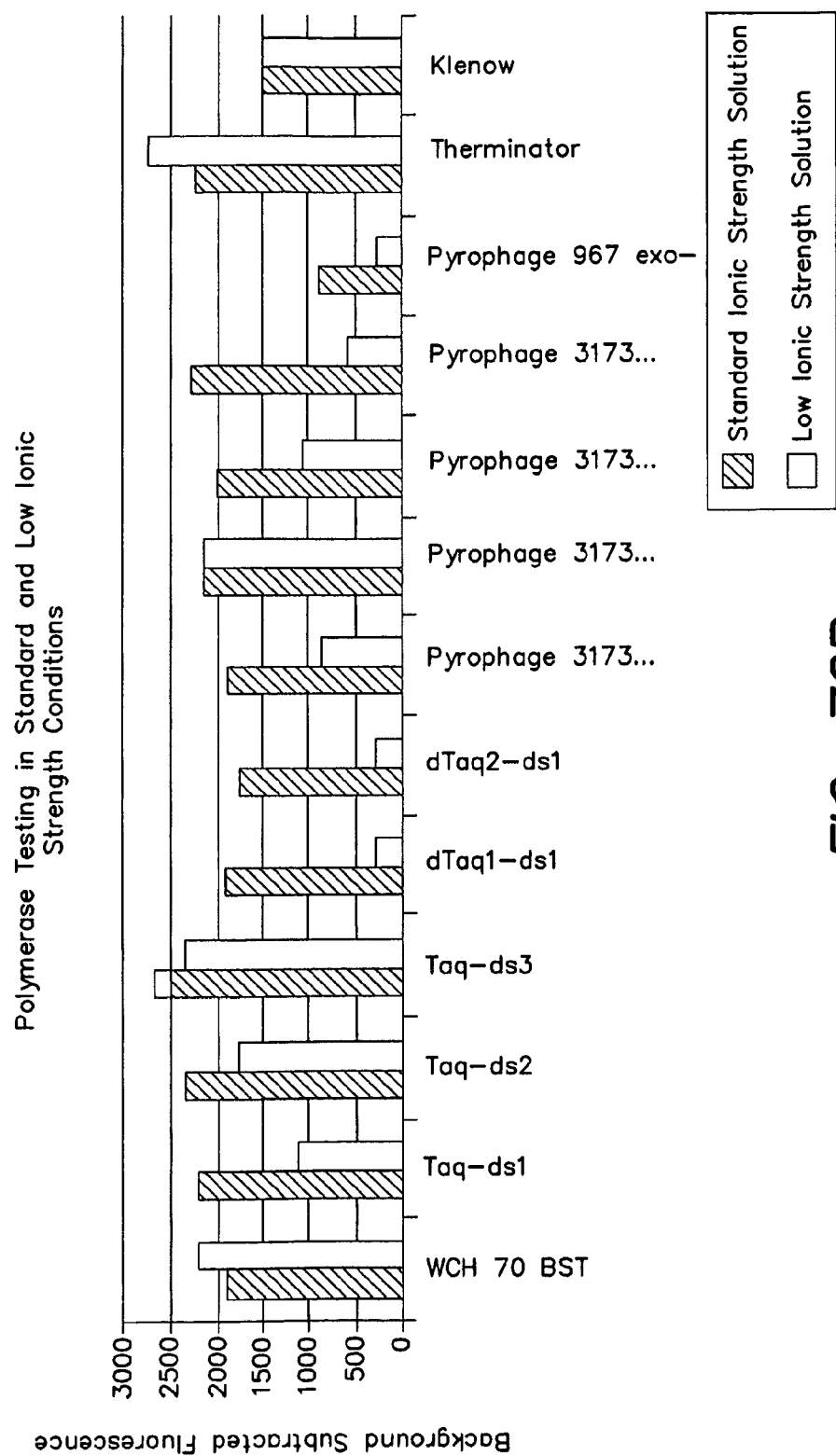

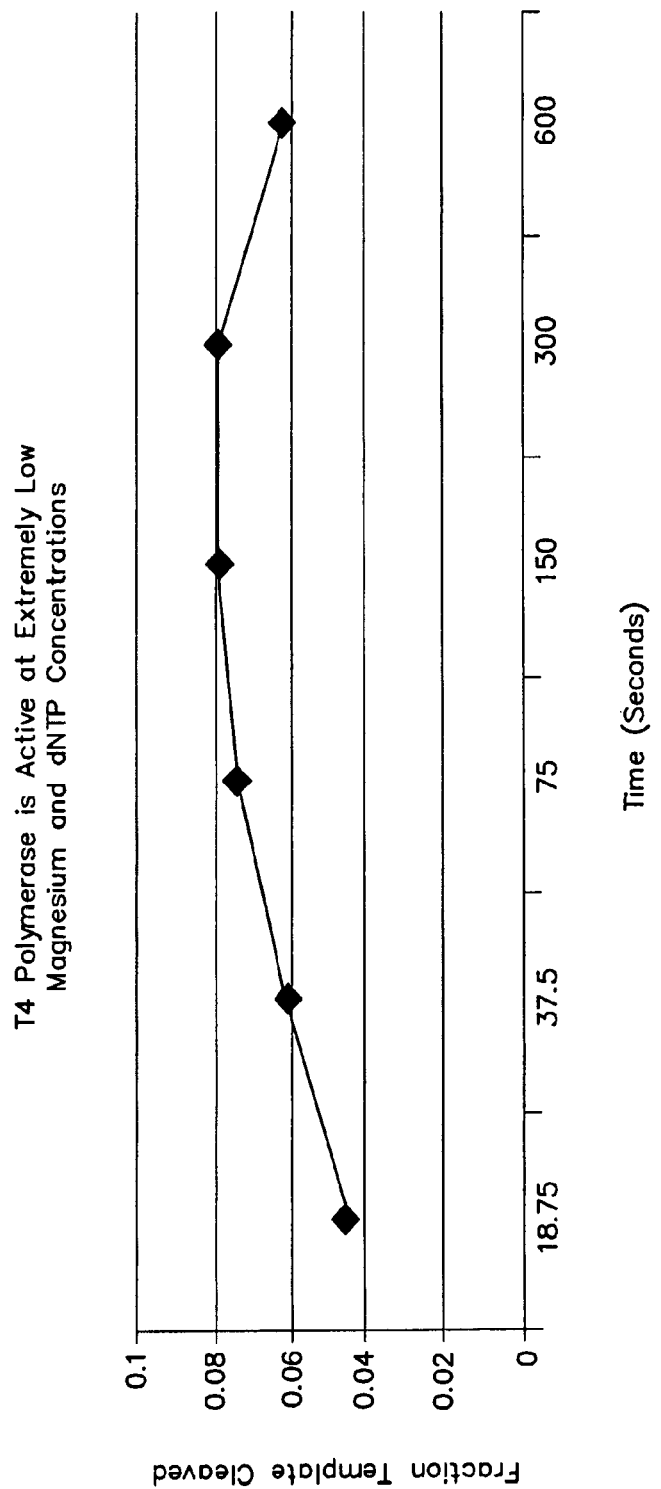

```
                          SEQUENCE LISTING

<160> NUMBER OF SEQ ID NOS: 7

<210> SEQ ID NO 1
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 1
gcaagtgccc ttaggcttca gttcaaaagt cctaactggg caaggcacac aggggatagg      60

<210> SEQ ID NO 2
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 2
ccatgtcccc ttaagccccc cccattcccc cctgaacccc caaggcacac aggggatagg      60

<210> SEQ ID NO 3
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 3
aagctcaaaa acggtaaaaa aaagccaaaa aactggaaaa caaggcacac aggggatagg      60

<210> SEQ ID NO 4
<211> LENGTH: 60
<212> TYPE: DNA
<213> ORGANISM: Artificial Sequence
```

```
<220> FEATURE:
<223> OTHER INFORMATION: Synthetic Oligonucleotide

<400> SEQUENCE: 4
ttcgagtttt tgccattttt tttcggtttt ttgacctttt caaggcacac aggggatagg      60

<210> SEQ ID NO 5
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 5
actggtccag cattagccgt acgac                                           25

<210> SEQ ID NO 6
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 6
gtcgtacggc taa                                                        13

<210> SEQ ID NO 7
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 7
gtcgtacggc taat                                                       14
```

METHODS AND APPARATUS FOR MEASURING ANALYTES USING LARGE SCALE FET ARRAYS

RELATED APPLICATIONS

This application is a national stage filing under 35 U.S.C. §371 of PCT International application PCT/US2009/003766, filed Jun. 25, 2009, PCT Article 21(2) in English, which claims priority to patent applications GB 0811657.6 and GB 0811656.8, both filed on Jun. 25, 2008, the entire contents of all of which are incorporated by reference.

FIELD OF THE DISCLOSURE

The present disclosure is directed generally to inventive methods and apparatus relating to detection and measurement of one or more analytes via electronic sensors.

BACKGROUND

Electronic devices and components have found numerous applications in chemistry and biology (more generally, "life sciences"), especially for detection and measurement of various chemical and biological reactions and identification, detection and measurement of various compounds. One such electronic device is referred to as an ion-sensitive field effect transistor, often denoted in the relevant literature as ISFET (or pHFET). ISFETs conventionally have been explored, primarily in the academic and research community, to facilitate measurement of the hydrogen ion concentration of a solution (commonly denoted as "pH").

More specifically, an ISFET is an impedance transformation device that operates in a manner similar to that of a MOSFET (Metal Oxide Semiconductor Field Effect Transistor), and is particularly configured to selectively measure ion activity in a solution (e.g., hydrogen ions in the solution are the "analytes"). A detailed theory of operation of an ISFET is given in "Thirty years of ISFETOLOGY: what happened in the past 30 years and what may happen in the next 30 years," P. Bergveld, *Sens. Actuators,* 88 (2003), pp. 1-20, which publication is hereby incorporated herein by reference (hereinafter referred to as "Bergveld").

FIG. 1 illustrates a cross-section of a p-type (p-channel) ISFET 50 fabricated using a conventional CMOS (Complimentary Metal Oxide Semiconductor) process. However, biCMOS (i.e., bipolar and CMOS) processing may also be used, such as a process that would include a PMOS FET array with bipolar structures on the periphery. Taking the CMOS example, P-type ISFET fabrication is based on a p-type silicon substrate 52, in which an n-type well 54 forming a transistor "body" is formed. Highly doped p-type (p+) regions S and D, constituting a source 56 and a drain 58 of the ISFET, are formed within the n-type well 54. A highly doped n-type (n+) region B is also formed within the n-type well to provide a conductive body (or "bulk") connection 62 to the n-type well. An oxide layer 65 is disposed above the source, drain and body connection regions, through which openings are made to provide electrical connections (via electrical conductors) to these regions; for example, metal contact 66 serves as a conductor to provide an electrical connection to the drain 58, and metal contact 68 serves as a conductor to provide a common connection to the source 56 and n-type well 54, via the highly conductive body connection 62. A polysilicon gate 64 is formed above the oxide layer at a location above a region 60 of the n-type well 54, between the source 56 and the drain 58. Because it is disposed between the polysilicon gate 64 and the transistor body (i.e., the n-type well), the oxide layer 65 often is referred to as the "gate oxide."

Like a MOSFET, the operation of an ISFET is based on the modulation of charge concentration caused by a MOS (Metal-Oxide-Semiconductor) capacitance constituted by the polysilicon gate 64, the gate oxide 65 and the region 60 of the n-type well 54 between the source and the drain. When a negative voltage is applied across the gate and source regions ($V_{GS}$<0 Volts), a "p-channel" 63 is created at the interface of the region 60 and the gate oxide 65 by depleting this area of electrons. This p-channel 63 extends between the source and the drain, and electric current is conducted through the p-channel when the gate-source potential $V_{GS}$ is negative enough to attract holes from the source into the channel. The gate-source potential at which the channel 63 begins to conduct current is referred to as the transistor's threshold voltage $V_{TH}$ (the transistor conducts when $V_{GS}$ has an absolute value greater than the threshold voltage $V_{TH}$). The source is so named because it is the source of the charge carriers (holes for a p-channel) that flow through the channel 63; similarly, the drain is where the charge carriers leave the channel 63.

In the ISFET 50 of FIG. 1, the n-type well 54 (transistor body), via the body connection 62, is forced to be biased at a same potential as the source 56 (i.e., $V_{SB}$=0 Volts), as seen by the metal contact 68 connected to both the source 56 and the body connection 62. This connection prevents forward biasing of the p+ source region and the n-type well, and thereby facilitates confinement of charge carriers to the area of the region 60 in which the channel 63 may be formed. Any potential difference between the source 56 and the body/n-type well 54 (a non-zero source-to-body voltage $V_{SB}$) affects the threshold voltage $V_{TH}$ of the ISFET according to a non-linear relationship, and is commonly referred to as the "body effect," which in many applications is undesirable.

As also shown in FIG. 1, the polysilicon gate 64 of the ISFET 50 is coupled to multiple metal layers disposed within one or more additional oxide layers 75 disposed above the gate oxide 65 to form a "floating gate" structure 70. The floating gate structure is so named because it is electrically isolated from other conductors associated with the ISFET; namely, it is sandwiched between the gate oxide 65 and a passivation layer 72. In the ISFET 50, the passivation layer 72 constitutes an ion-sensitive membrane that gives rise to the ion-sensitivity of the device; i.e., the presence of—analytes such as ions in an "analyte solution" 74 (i.e., a solution containing analytes (including ions) of interest or being tested for the presence of analytes of interest) in contact with the passivation layer 72, particularly in a sensitive area 78 above the floating gate structure 70, alters the electrical characteristics of the ISFET so as to modulate a current flowing through the p-channel 63 between the source 56 and the drain 58. The passivation layer 72 may comprise any one of a variety of different materials to facilitate sensitivity to particular ions; for example, passivation layers comprising silicon nitride or silicon oxynitride, as well as metal oxides such as silicon, aluminum or tantalum oxides, generally provide sensitivity to hydrogen ion concentration (pH) in the analyte solution 74, whereas passivation layers comprising polyvinyl chloride containing valinomycin provide sensitivity to potassium ion concentration in the analyte solution 74. Materials suitable for passivation layers and sensitive to other ions such as sodium, silver, iron, bromine, iodine, calcium, and nitrate, for example, are known.

With respect to ion sensitivity, an electric potential difference, commonly referred to as a "surface potential," arises at the solid/liquid interface of the passivation layer 72 and the analyte solution 74 as a function of the ion concentration in the sensitive area 78 due to a chemical reaction (e.g., usually involving the dissociation of oxide surface groups by the ions in the analyte solution 74 in proximity to the sensitive area 78). This surface potential in turn affects the threshold voltage $V_{TH}$ of the ISFET; thus, it is the threshold voltage $V_{TH}$ of the ISFET that varies with changes in ion concentration in the analyte solution 74 in proximity to the sensitive area 78.

FIG. 2 illustrates an electric circuit representation of the p-channel ISFET 50 shown in FIG. 1. With reference again to FIG. 1, a reference electrode 76 (a conventional Ag/AgCl electrode) in the analyte solution 74 determines the electric potential of the bulk of the analyte solution 74 itself and is analogous to the gate terminal of a conventional MOSFET, as shown in FIG. 2. In a linear or non-saturated operating region of the ISFET, the drain current $I_D$ is given as:

$$I_D = \beta\left(V_{GS} - V_{TH} - \frac{1}{2}V_{DS}\right)V_{DS}, \tag{1}$$

where $V_{DS}$ is the voltage between the drain and the source, and $\beta$ is a transconductance parameter (in units of Amps/Volts$^2$) given by:

$$\beta = \mu C_{ox}\left(\frac{W}{L}\right), \tag{2}$$

where $\mu$ represents the carrier mobility, $C_{ox}$ is the gate oxide capacitance per unit area, and the ratio W/L is the width to length ratio of the channel 63. If the reference electrode 76 provides an electrical reference or ground ($V_G=0$ Volts), and the drain current $I_D$ and the drain-to-source voltage $V_{DS}$ are kept constant, variations of the source voltage $V_S$ of the ISFET directly track variations of the threshold voltage $V_{TH}$, according to Eq. (1); this may be observed by rearranging Eq. (1) as:

$$V_S = -V_{TH} - \left(\frac{I_D}{\beta V_{DS}} + \frac{V_{DS}}{2}\right). \tag{3}$$

Since the threshold voltage $V_{TH}$ of the ISFET is sensitive to ion concentration as discussed above, according to Eq. (3) the source voltage $V_S$ provides a signal that is directly related to the ion concentration in the analyte solution 74 in proximity to the sensitive area 78 of the ISFET. More specifically, the threshold voltage $V_{TH}$ is given by:

$$V_{TH} = V_{FB} - \frac{Q_B}{C_{ox}} + 2\phi_F, \tag{4}$$

where $V_{FB}$ is the flatband voltage, $Q_B$ is the depletion charge in the silicon and $\phi_F$ is the Fermi-potential. The flatband voltage in turn is related to material properties such as work-functions and charge accumulation. In the case of an ISFET, with reference to FIGS. 1 and 2, the flatband voltage contains terms that reflect interfaces between 1) the reference electrode 76 (acting as the transistor gate G) and the analyte solution 74; and 2) the analyte solution 74 and the passivation layer 72 in the sensitive area 78 (which in turn mimics the interface between the polysilicon gate 64 of the floating gate structure 70 and the gate oxide 65). The flatband voltage $V_{FB}$ is thus given by:

$$V_{FB} = E_{ref} - \Psi_0 + \chi_{sol} - \frac{\Phi_{Si}}{q} - \frac{Q_{ss} + Q_{ox}}{C_{ox}}, \tag{5}$$

where $E_{ref}$ is the reference electrode potential relative to vacuum, $\Psi_0$ is the surface potential that results from chemical reactions at the analyte solution/passivation layer interface (e.g., dissociation of surface groups in the passivation layer), and $\chi_{sol}$ is the surface dipole potential of the analyte solution 74. The fourth term in Eq. (5) relates to the silicon workfunction (q is the electron charge), and the last term relates to charge densities at the silicon surface and in the gate oxide. The only term in Eq. (5) sensitive to ion concentration in the analyte solution 74 is $\Psi_0$, as the ion concentration in the analyte solution 74 controls the chemical reactions (dissociation of surface groups) at the analyte solution/passivation layer interface. Thus, substituting Eq. (5) into Eq. (4), it may be readily observed that it is the surface potential $\Psi_0$ that renders the threshold voltage $V_{TH}$ sensitive to ion concentration in the analyte solution 74.

Regarding the chemical reactions at the analyte solution/passivation layer interface, the surface of a given material employed for the passivation layer 72 may include chemical groups that may donate protons to or accept protons from the analyte solution 74, leaving at any given time negatively charged, positively charged, and neutral sites on the surface of the passivation layer 72 at the interface with the analyte solution 74. A model for this proton donation/acceptance process at the analyte solution/passivation layer interface is referred to in the relevant literature as the "Site-Dissociation Model" or the "Site-Binding Model," and the concepts underlying such a process may be applied generally to characterize surface activity of passivation layers comprising various materials (e.g., metal oxides, metal nitrides, metal oxynitrides).

Using the example of a metal oxide for purposes of illustration, the surface of any metal oxide contains hydroxyl groups that may donate a proton to or accept a proton from the analyte to leave negatively or positively charged sites, respectively, on the surface. The equilibrium reactions at these sites may be described by:

$$AOH \rightleftarrows AO^- + H_s^+ \tag{6}$$

$$AOH_2^+ \rightleftarrows AOH + H_s^+ \tag{7}$$

where A denotes an exemplary metal, $H_s^+$ represents a proton in the analyte solution 74, Eq. (6) describes proton donation by a surface group, and Eq. (7) describes proton acceptance by a surface group. It should be appreciated that the reactions given in Eqs. (6) and (7) also are present and need to be considered in the analysis of a passivation layer comprising metal nitrides, together with the equilibrium reaction:

$$ANH_3^+ \rightleftarrows ANH_2 + H^+, \tag{7b}$$

wherein Eq. (7b) describes another proton acceptance equilibrium reaction. For purposes of the present discussion however, again only the proton donation and acceptance reactions given in Eqs. (6) and (7) are initially considered to illustrate the relevant concepts.

Based on the respective forward and backward reaction rate constants for each equilibrium reaction, intrinsic dissociation constants $K_a$ (for the reaction of Eq. (6)) and $K_b$ (for the reaction of Eq. (7)) may be calculated that describe the equilibrium reactions. These intrinsic dissociation constants in turn may be used to determine a surface charge density $\sigma_0$ (in units of Coulombs/unit area) of the passivation layer 72 according to:

$$\sigma_0 = -qB, \tag{8}$$

where the term B denotes the number of negatively charged surface groups minus the number of positively charged surface groups per unit area, which in turn depends on the total number of proton donor/acceptor sites per unit area $N_S$ on the passivation layer surface, multiplied by a factor relating to the intrinsic dissociation constants $K_a$ and $K_b$ of the respective proton donation and acceptance equilibrium reactions and the surface proton activity (or $pH_S$). The effect of a small change in surface proton activity ($pH_S$) on the surface charge density is given by:

$$\frac{\partial \sigma_0}{\partial pH_S} = -q\frac{\partial B}{\partial pH_S} = -q\beta_{int}, \quad (9)$$

where $\beta_{int}$ is referred to as the "intrinsic buffering capacity" of the surface. It should be appreciated that since the values of $N_S$, $K_a$ and $K_b$ are material dependent, the intrinsic buffering capacity $\beta_{int}$ of the surface similarly is material dependent.

The fact that ionic species in the analyte solution 74 have a finite size and cannot approach the passivation layer surface any closer than the ionic radius results in a phenomenon referred to as a "double layer capacitance" proximate to the analyte solution/passivation layer interface. In the Gouy-Chapman-Stern model for the double layer capacitance as described in Bergveld, the surface charge density $\sigma_0$ is balanced by an equal but opposite charge density in the analyte solution 74 at some position from the surface of the passivation layer 72. These two parallel opposite charges form a so-called "double layer capacitance" $C_{dl}$ (per unit area), and the potential difference across the capacitance $C_{dl}$ is defined as the surface potential $\Psi_0$, according to:

$$\sigma_0 = C_{dl}\Psi_0 = -\sigma_{dl} \quad (10)$$

where $\sigma_{dl}$ is the charge density on the analyte solution side of the double layer capacitance. This charge density $\sigma_{dl}$ in turn is a function of the concentration of all ion species or other analyte species (i.e., not just protons) in the bulk analyte solution 74; in particular, the surface charge density can be balanced not only by hydrogen ions but other ion species (e.g., $Na^+$, $K^+$) in the bulk analyte solution.

In the regime of relatively lower ionic strengths (e.g., <1 mole/liter), the Debye theory may be used to describe the double layer capacitance $C_{dl}$ according to:

$$C_{dl} = \frac{k\varepsilon_0}{\lambda} \quad (11)$$

where k is the dielectric constant $\in/\in_0$ (for relatively lower ionic strengths, the dielectric constant of water may be used), and $\lambda$ is the Debye screening length (i.e., the distance over which significant charge separation can occur). The Debye length $\lambda$ is in turn inversely proportional to the square root of the strength of the ionic species in the analyte solution, and in water at room temperature is given by:

$$\lambda = \frac{0.3 \text{ nm}}{\sqrt{I}}. \quad (12)$$

The ionic strength I of the bulk analyte is a function of the concentration of all ionic species present, and is given by:

$$I = \frac{1}{2}\sum_s z_s^2 c_s, \quad (13)$$

where $z_s$ is the charge number of ionic species s and $c_s$ is the molar concentration of ionic species s. Accordingly, from Eqs. (10) through (13), it may be observed that the surface potential is larger for larger Debye screening lengths (i.e., smaller ionic strengths).

The relation between pH values present at the analyte solution/passivation layer interface and in the bulk solution is expressed in the relevant literature by Boltzman statistics with the surface potential $\Psi_0$ as a parameter:

$$(pH_s - pH_B) = \frac{q\Psi_0}{kT}. \quad (14)$$

From Eqs. (9), (10) and (14), the sensitivity of the surface potential $\Psi_0$ particularly to changes in the bulk pH of the analyte solution (i.e., "pH sensitivity") is given by:

$$\frac{\Delta\Psi_0}{\Delta pH} = -2.3\frac{kT}{q}\alpha, \quad (15)$$

where the parameter $\alpha$ is a dimensionless sensitivity factor that varies between zero and one and depends on the double layer capacitance $C_{dl}$ and the intrinsic buffering capacity of the surface $\beta_{int}$ as discussed above in connection with Eq. (9). In general, passivation layer materials with a high intrinsic buffering capacity $\beta_{int}$ render the surface potential $\Psi_0$ less sensitive to concentration in the analyte solution 74 of ionic species other than protons (e.g., $\alpha$ is maximized by a large $\beta_{int}$). From Eq. (15), at a temperature T of 298 degrees Kelvin, it may be appreciated that a theoretical maximum pH sensitivity of 59.2 mV/pH may be achieved at $\alpha=1$. From Eqs. (4) and (5), as noted above, changes in the ISFET threshold voltage $V_{TH}$ directly track changes in the surface potential $\Psi_0$; accordingly, the pH sensitivity of an ISFET given by Eq. (15) also may be denoted and referred to herein as $\Delta V_{TH}$ for convenience. In exemplary conventional ISFETs employing a silicon nitride or silicon oxynitride passivation layer 72 for pH-sensitivity, pH sensitivities $\Delta V_{TH}$ (i.e., a change in threshold voltage with change in pH of the analyte solution 74) over a range of approximately 30 mV/pH to 60 mV/pH have been observed experimentally.

Another noteworthy metric in connection with ISFET pH sensitivity relates to the bulk pH of the analyte solution 74 at which there is no net surface charge density $\Psi_0$ and, accordingly, a surface potential $\Psi_0$ of zero volts. This pH is referred to as the "point of zero charge" and denoted as $pH_{pzc}$. With reference again to Eqs. (8) and (9), like the intrinsic buffering capacity $\beta_{int}$, $pH_{pzc}$ is a material dependent parameter. From the foregoing, it may be appreciated that the surface potential at any given bulk $pH_B$ of the analyte solution 74 may be calculated according to:

$$\Psi_0(pH_B) = (pH_B - pH_{pzc})\frac{\Delta\Psi_0}{\Delta pH}. \quad (16)$$

Table 1 below lists various metal oxides and metal nitrides and their corresponding points of zero charge ($pH_{pzc}$), pH sensitivities ($\Delta V_{TH}$), and theoretical maximum surface potential at a pH of 9:

TABLE 1

| Metal | Oxide/Nitride | $pH_{pzc}$ | $\Delta V_{TH}$ (mV/pH) | Theoretical $\Psi_0$ (mV) @ pH = 9 |
|---|---|---|---|---|
| Al | $Al_2O_3$ | 9.2 | 54.5 (35° C.) | −11 |
| Zr | $ZrO_2$ | 5.1 | 50 | 150 |
| Ti | $TiO_2$ | 5.5 | 57.4-62.3 (32° C., pH 3-11) | 201 |
| Ta | $Ta_2O_5$ | 2.9, 2.8 | 62.87 (35° C.) | 384 |
| Si | $Si_3N_4$ | 4.6, 6-7 | 56.94 (25° C.) | 251 |
| Si | $SiO_2$ | 2.1 | 43 | 297 |
| Mo | $MoO_3$ | 1.8-2.1 | 48-59 | 396 |
| W | $WO_2$ | 0.3, 0.43, 0.5 | 50 | 435 |

Prior research efforts to fabricate ISFETs for pH measurements based on conventional CMOS processing techniques typically have aimed to achieve high signal linearity over a pH range from 1-14. Using an exemplary threshold sensitivity of approximately 50 mV/pH, and considering Eq. (3) above, this requires a linear operating range of approximately 700 mV for the source voltage $V_S$. As discussed above in connection with FIG. 1, the threshold voltage $V_{TH}$ of ISFETs (as well as MOSFETs) is affected by any voltage $V_{SB}$ between the source and the body (n-type well 54). More specifically, the threshold voltage $V_{TH}$ is a nonlinear function of a nonzero source-to-body voltage $V_{SB}$. Accordingly, so as to avoid compromising linearity due to a difference between the source and body voltage potentials (i.e., to mitigate the "body effect"), as shown in FIG. 1 the source 56 and body connection 62 of the ISFET 50 often are coupled to a common potential via the metal contact 68. This body-source coupling also is shown in the electric circuit representation of the ISFET 50 shown in FIG. 2.

While the foregoing discussion relates primarily to a steady state analysis of ISFET response based on the equilibrium reactions given in Eqs. (6) and (7), the transient or dynamic response of a conventional ISFET to an essentially instantaneous change in ionic strength of the analyte solution 74 (e.g., a stepwise change in proton or other ionic species concentration) has been explored in some research efforts. One exemplary treatment of ISFET transient or dynamic response is found in "ISFET responses on a stepwise change in electrolyte concentration at constant pH," J. C. van Kerkof, J. C. T. Eijkel and P. Bergveld, Sensors and Actuators B, 18-19 (1994), pp. 56-59, which is incorporated herein by reference.

For ISFET transient response, a stepwise change in the concentration of one or more ionic species in the analyte solution in turn essentially instantaneously changes the charge density $\sigma_{dl}$ on the analyte solution side of the double layer capacitance $C_{dl}$. Because the instantaneous change in charge density $\sigma_{dl}$ is faster than the reaction kinetics at the surface of the passivation layer 72, the surface charge density $\sigma_0$ initially remains constant, and the change in ion concentration effectively results in a sudden change in the double layer capacitance $C_{dl}$. From Eq. (10), it may be appreciated that such a sudden change in the capacitance $C_{dl}$ at a constant surface charge density $\sigma_0$ results in a corresponding sudden change in the surface potential $\Psi_0$. FIG. 2A illustrates this phenomenon, in which an essentially instantaneous or stepwise increase in ion concentration in the analyte solution, as shown in the top graph, results in a corresponding change in the surface potential $\Psi_0$, as shown in the bottom graph of FIG. 2A. After some time, as the passivation layer surface groups react to the stimulus (i.e., as the surface charge density adjusts), the system returns to some equilibrium point, as illustrated by the decay of the ISFET response "pulse" 79 shown in the bottom graph of FIG. 2A. The foregoing phenomenon is referred to in the relevant literature (and hereafter in this disclosure) as an "ion-step" response.

As indicated in the bottom graph of FIG. 2A, an amplitude $\Delta \Psi_0$ of the ion-step response 79 may be characterized by:

$$\Delta \Psi_0 = \Psi_1 - \Psi_2 = \frac{\sigma_0}{C_{dl,1}} - \frac{\sigma_0}{C_{dl,2}} = \Psi_1 \left(1 - \frac{C_{dl,1}}{C_{dl,2}}\right), \quad (17)$$

where $\Psi_1$ is an equilibrium surface potential at an initial ion concentration in the analyte solution, $C_{dl,1}$ is the double layer capacitance per unit area at the initial ion concentration, $\Psi_2$ is the surface potential corresponding to the ion-step stimulus, and $C_{dl,2}$ is the double layer capacitance per unit area based on the ion-step stimulus. The time decay profile 81 associated with the response 79 is determined at least in part by the kinetics of the equilibrium reactions at the analyte solution/passivation layer interface (e.g., as given by Eqs. (6) and (7) for metal oxides, and also Eq. (7b) for metal nitrides). One instructive treatment in this regard is provided by "Modeling the short-time response of ISFET sensors," P. Woias et al., Sensors and Actuators B, 24-25 (1995) 211-217 (hereinafter referred to as "Woias"), which publication is incorporated herein by reference.

In the Woias publication, an exemplary ISFET having a silicon nitride passivation layer is considered. A system of coupled non-linear differential equations based on the equilibrium reactions given by Eqs. (6), (7), and (7a) is formulated to describe the dynamic response of the ISFET to a step (essentially instantaneous) change in pH; more specifically, these equations describe the change in concentration over time of the various surface species involved in the equilibrium reactions, based on the forward and backward rate constants for the involved proton acceptance and proton donation reactions and how changes in analyte pH affect one or more of the reaction rate constants. Exemplary solutions, some of which include multiple exponential functions and associated time constants, are provided for the concentration of each of the surface ion species as a function of time. In one example provided by Woias, it is assumed that the proton donation reaction given by Eq. (6) dominates the transient response of the silicon nitride passivation layer surface for relatively small step changes in pH, thereby facilitating a mono-exponential approximation for the time decay profile 81 of the response 79 according to:

$$\Psi_0(t) = \Delta \Psi_0 e^{-t/\tau}, \quad (18)$$

where the exponential function essentially represents the change in surface charge density as a function of time. In Eq. (16), the time constant $\tau$ is both a function of the bulk pH and material parameters of the passivation layer, according to:

$$\tau = \tau_0 \times 10^{pH/2} \quad (19)$$

where $\tau_0$ denotes a theoretical minimum response time that only depends on material parameters. For silicon nitride, Woias provides exemplary values for $\tau_0$ on the order of 60 microseconds to 200 microseconds. For purposes of providing an illustrative example, using $\tau_0 = 60$ microseconds and a bulk pH of 9, the time constant $\tau$ given by Eq. (19) is 1.9 seconds. Exemplary values for other types of passivation materials may be found in the relevant literature and/or determined empirically.

Previous efforts to fabricate two-dimensional arrays of ISFETs based on the ISFET design of FIG. 1 have resulted in a maximum of 256 ISFET sensor elements (or "pixels") in an array (i.e., a 16 pixel by 16 pixel array). Exemplary research in ISFET array fabrication is reported in the publications "A large transistor-based sensor array chip for direct extracellular imaging," M. J. Milgrew, M. O. Riehle, and D. R. S. Cumming, *Sensors and Actuators, B: Chemical,* 111-112, (2005), pp. 347-353, and "The development of scalable sensor arrays using standard CMOS technology," M. J. Milgrew, P. A. Hammond, and D. R. S. Cumming, *Sensors and Actuators, B: Chemical,* 103, (2004), pp. 37-42, which publications are incorporated herein by reference and collectively referred to hereafter as "Milgrew et al." Other research efforts relating to the realization of ISFET arrays are reported in the publications "A very large integrated pH-ISFET sensor array chip compatible with standard CMOS processes," T. C. W. Yeow, M. R. Haskard, D. E. Mulcahy, H. I. Seo and D. H. Kwon, *Sensors and Actuators B: Chemical,* 44, (1997), pp. 434-440 and "Fabrication of a two-dimensional pH image sensor using a charge transfer technique," Hizawa, T., Sawada, K., Takao, H., Ishida, M., *Sensors and Actuators, B: Chemical* 117 (2), 2006, pp. 509-515, which publications also are incorporated herein by reference.

FIG. 3 illustrates one column $85_j$ of a two-dimensional ISFET array according to the design of Milgrew et al. The column $85_j$ includes sixteen (16) pixels $80_1$ through $80_{16}$ and, as discussed further below in connection with FIG. 7, a complete two-dimensional array includes sixteen (16) such columns $85_j$ (j=1, 2, 3, ... 16) arranged side by side. As shown in FIG. 3, a given column $85_j$ includes a current source $I_{SOURCEj}$ that is shared by all pixels of the column, and ISFET bias/readout circuitry $82_j$ (including current sink $I_{SINKj}$) that is also shared by all pixels of the column. Each ISFET pixel $80_1$ through $80_{16}$ includes a p-channel ISFET 50 having an electrically coupled source and body (as shown in FIGS. 1 and 2), plus two switches S1 and S2 that are responsive to one of sixteen row select signals ($RSEL_1$ through $RSEL_{16}$, and their complements). As discussed below in connection with FIG. 7, a row select signal and its complement are generated simultaneously to "enable" or select a given pixel of the column $85_j$, and such signal pairs are generated in some sequence to successively enable different pixels of the column one at a time.

As shown in FIG. 3, the switch S2 of each pixel 80 in the design of Milgrew et al. is implemented as a conventional n-channel MOSFET that couples the current source $I_{SOURCEj}$ to the source of the ISFET 50 upon receipt of the corresponding row select signal. The switch S1 of each pixel 80 is implemented as a transmission gate, i.e., a CMOS pair including an n-channel MOSFET and a p-channel MOSFET, that couples the source of the ISFET 50 to the bias/readout circuitry $82_j$ upon receipt of the corresponding row select signal and its complement. An example of the switch $S1_1$ of the pixel $80_1$ is shown in FIG. 4, in which the p-channel MOSFET of the transmission gate is indicated as $S1_{1P}$ and the n-channel MOSFET is indicated as $S1_{1N}$. In the design of Milgrew et al., a transmission gate is employed for the switch S1 of each pixel so that, for an enabled pixel, any ISFET source voltage within the power supply range $V_{DD}$ to $V_{SS}$ may be applied to the bias/readout circuitry $82_j$ and output by the column as the signal $V_{Sj}$. From the foregoing, it should be appreciated that each pixel 80 in the ISFET sensor array design of Milgrew et al. includes four transistors, i.e., a p-channel ISFET, a CMOS-pair transmission gate including an n-channel MOSFET and a p-channel MOSFET for switch S1, and an n-channel MOSFET for switch S2.

As also shown in FIG. 3, the bias/readout circuitry $82_j$ employs a source-drain follower configuration in the form of a Kelvin bridge to maintain a constant drain-source voltage $V_{DSj}$ and isolate the measurement of the source voltage $V_{Sj}$ from the constant drain current $I_{SOURCEj}$ for the ISFET of an enabled pixel in the column $85_j$. To this end, the bias/readout circuitry $82_j$ includes two operational amplifiers A1 and A2, a current sink $I_{SINKj}$, and a resistor $R_{SDj}$. The voltage developed across the resistor $R_{SDj}$ due to the current $I_{SINKj}$ flowing through the resistor is forced by the operational amplifiers to appear across the drain and source of the ISFET of an enabled pixel as a constant drain-source voltage $V_{DSj}$. Thus, with reference again to Eq. (3), due to the constant $V_{DSj}$ and the constant $I_{SOURCEj}$, the source voltage $V_{Sj}$ of the ISFET of the enabled pixel provides a signal corresponding to the ISFETs threshold voltage $V_{TH}$, and hence a measurement of pH in proximity to the ISFETs sensitive area (see FIG. 1). The wide dynamic range for the source voltage $V_{Sj}$ provided by the transmission gate S1 ensures that a full range of pH values from 1-14 may be measured, and the source-body connection of each ISFET ensures sufficient linearity of the ISFETs threshold voltage over the full pH measurement range.

In the column design of Milgrew et al. shown in FIG. 3, it should be appreciated that for the Kelvin bridge configuration of the column bias/readout circuitry $82_j$ to function properly, a p-channel ISFET 50 as shown in FIG. 1 must be employed in each pixel; more specifically, an alternative implementation based on the Kelvin bridge configuration is not possible using an n-channel ISFET. With reference again to FIG. 1, for an n-channel ISFET based on a conventional CMOS process, the n-type well 54 would not be required, and highly doped n-type regions for the drain and source would be formed directly in the p-type silicon substrate 52 (which would constitute the transistor body). For n-channel FET devices, the transistor body typically is coupled to electrical ground. Given the requirement that the source and body of an ISFET in the design of Milgrew et al. are electrically coupled together to mitigate nonlinear performance due to the body effect, this would result in the source of an n-channel ISFET also being connected to electrical ground (i.e., $V_S=V_B=0$ Volts), thereby precluding any useful output signal from an enabled pixel. Accordingly, the column design of Milgrew et al. shown in FIG. 3 requires p-channel ISFETs for proper operation.

It should also be appreciated that in the column design of Milgrew et al. shown in FIG. 3, the two n-channel MOSFETs required to implement the switches S1 and S2 in each pixel cannot be formed in the n-type well 54 shown in FIG. 1, in which the p-channel ISFET for the pixel is formed; rather, the n-channel MOSFETs are formed directly in the p-type silicon substrate 52, beyond the confines of the n-type well 54 for the ISFET. FIG. 5 is a diagram similar to FIG. 1, illustrating a wider cross-section of a portion of the p-type silicon substrate 52 corresponding to one pixel 80 of the column 85j shown in FIG. 3, in which the n-type well 54 containing the drain 58, source 56 and body connection 62 of the ISFET 50 is shown alongside a first n-channel MOSFET corresponding to the switch S2 and a second n-channel MOSFET $S1_{1N}$ constituting one of the two transistors of the transmission gate $S1_1$ shown in FIG. 4.

Furthermore, in the design of Milgrew et al., the p-channel MOSFET required to implement the transmission gate S1 in each pixel (e.g., see $S1_{1P}$ in FIG. 4) cannot be formed in the same n-type well in which the p-channel ISFET 50 for the pixel is formed. In particular, because the body and source of the p-channel ISFET are electrically coupled together, implementing the p-channel MOSFET $S1_{1P}$ in the same n-well as the p-channel ISFET 50 would lead to unpredictable operation of the transmission gate, or preclude operation entirely. Accordingly, two separate n-type wells are required to implement each pixel in the design of Milgrew et al. FIG. 6 is a diagram similar to FIG. 5, showing a cross-section of another portion of the p-type silicon substrate 52 corresponding to one pixel 80, in which the n-type well 54 corresponding to the ISFET 50 is shown alongside a second n-type well 55 in which is formed the p-channel MOSFET $S1_{1P}$ constituting one of the two transistors of the transmission gate $S1_1$ shown in FIG. 4. It should be appreciated that the drawings in FIGS. 5 and 6 are not to scale and may not exactly represent the actual layout of a particular pixel in the design of Milgrew et al.; rather these figures are conceptual in nature and are provided primarily to illustrate the requirements of multiple n-wells, and separate n-channel MOSFETs fabricated outside of the n-wells, in the design of Milgrew et al.

The array design of Milgrew et al. was implemented using a 0.35 micrometer (μm) conventional CMOS fabrication process. In this process, various design rules dictate minimum separation distances between features. For example, according to the 0.35 μm CMOS design rules, with reference to FIG. 6, a distance "a" between neighboring n-wells must be at least three (3) micrometers. A distance "a/2" also is indicated in FIG. 6 to the left of the n-well 54 and to the right of the n-well 55 to indicate the minimum distance required to separate the pixel 80 shown in FIG. 6 from neighboring pixels in other columns to the left and right, respectively. Additionally, according to typical 0.35 μm CMOS design rules, a distance "b" shown in FIG. 6 representing the width in cross-section of the n-type well 54 and a distance "c" representing the width in cross-section of the n-type well 55 are each on the order of approximately 3 μm to 4 μm (within the n-type well, an allowance of 1.2 μm is made between the edge of the n-well and each of the source and drain, and the source and drain themselves have a width on the order of 0.7 μm). Accordingly, a total distance "d" shown in FIG. 6 representing the width of the pixel 80 in cross-section is on the order of approximately 12 μm to 14 μm. In one implementation, Milgrew et al. report an array based on the column/pixel design shown in FIG. 3 comprising geometrically square pixels each having a dimension of 12.8 μm by 12.8 μm.

In sum, the ISFET pixel design of Milgrew et al. is aimed at ensuring accurate hydrogen ion concentration measurements over a pH range of 1-14. To ensure measurement linearity, the source and body of each pixel's ISFET are electrically coupled together. To ensure a full range of pH measurements, a transmission gate S1 is employed in each pixel to transmit the source voltage of an enabled pixel. Thus, each pixel of Milgrew's array requires four transistors (p-channel ISFET, p-channel MOSFET, and two n-channel MOSFETs) and two separate. n-wells (FIG. 6). Based on a 0.35 micrometer conventional CMOS fabrication process and corresponding design rules, the pixels of such an array have a minimum size appreciably greater than 10 μm, i.e., on the order of approximately 12 μm to 14 μm.

FIG. 7 illustrates a complete two-dimensional pixel array 95 according to the design of Milgrew et al., together with accompanying row and column decoder circuitry and measurement readout circuitry. The array 95 includes sixteen columns $85_1$ through $85_{16}$ of pixels, each column having sixteen pixels as discussed above in connection with FIG. 3 (i.e., a 16 pixel by 16 pixel array). A row decoder 92 provides sixteen pairs of complementary row select signals, wherein each pair of row select signals simultaneously enables one pixel in each column $85_1$ through $85_{16}$ to provide a set of column output signals from the array 95 based on the respective source voltages $V_{S1}$ through $V_{S16}$ of the enabled row of ISFETs. The row decoder 92 is implemented as a conventional four-to-sixteen decoder (i.e., a four-bit binary input $ROW_1$-$ROW_4$ to select one of $2^4$ outputs). The set of column output signals $V_{S1}$ through $V_{S16}$ for an enabled row of the array is applied to switching logic 96, which includes sixteen transmission gates S1 through S16 (one transmission gate for each output signal). As above, each transmission gate of the switching logic 96 is implemented using a p-channel MOSFET and an n-channel MOSFET to ensure a sufficient dynamic range for each of the output signals $V_{S1}$ through $V_{S16}$. The column decoder 94, like the row decoder 92, is implemented as a conventional four-to-sixteen decoder and is controlled via the four-bit binary input $COL_1$-$COL_4$ to enable one of the transmission gates S1 through S16 of the switching logic 96 at any given time, so as to provide a single output signal $V_S$ from the switching logic 96. This output signal $V_S$ is applied to a 10-bit analog to digital converter (ADC) 98 to provide a digital representation $D_1$-$D_{10}$ of the output signal $V_S$ corresponding to a given pixel of the array.

As noted earlier, individual ISFETs and arrays of ISFETs similar to those discussed above have been employed as sensing devices in a variety of chemical and biological applications. In particular, ISFETs have been employed as pH sensors in the monitoring of various processes involving nucleic acids such as DNA. Some examples of employing ISFETs in various life-science related applications are given in the following publications, each of which is incorporated herein by reference: Massimo Barbaro, Annalisa Bonfiglio, Luigi Raffo, Andrea Alessandrini, Paolo Facci and Imrich Barák, "Fully electronic DNA hybridization detection by a standard CMOS biochip," *Sensors and Actuators B: Chemical*, Volume 118, Issues 1-2, 2006, pp. 41-46; Toshinari Sakurai and Yuzuru Husimi, "Real-time monitoring of DNA polymerase reactions by a micro ISFET pH sensor," *Anal. Chem.*, 64(17), 1992, pp 1996-1997; S. Purushothaman, C. Toumazou, J. Georgiou, "Towards fast solid state DNA sequencing," *Circuits and Systems*, vol. 4, 2002, pp. IV-169 to IV-172; S. Purushothaman, C. Toumazou, C. P. Ou, "Protons and single nucleotide polymorphism detection: A simple use for the Ion Sensitive Field Effect Transistor," *Sensors and Actuators B: Chemical*, Vol. 114, no. 2, 2006, pp. 964-968; A. L. Simonian, A. W. Flounders, J. R. Wild, "FET-Based Biosensors for The Direct Detection of Organophosphate Neurotoxins," *Electroanalysis*, Vol. 16, No. 22, 2004, pp. 1896-1906; C. Toumazou, S. Purushothaman, "Sensing Apparatus and Method," United States Patent Application 2004-0134798, published Jul. 15, 2004; and T. W. Koo, S. Chan, X. Su, Z. Jingwu, M. Yamakawa, V. M. Dubin, "Sensor Arrays and Nucleic Acid Sequencing Applications," United States Patent Application 2006-0199193, published Sep. 7, 2006.

In general, the development of rapid and sensitive nucleic acid sequencing methods utilizing automated DNA sequencers has significantly advanced the understanding of biology. The term "sequencing" refers to the determination of a primary structure (or primary sequence) of an unbranched biopolymer, which results in a symbolic linear depiction known as a "sequence" that succinctly summarizes much of the atomic-level structure of the sequenced molecule. "DNA sequencing" particularly refers to the process of determining the nucleotide order of a given DNA fragment. Analysis of entire genomes of viruses, bacteria, fungi, animals and plants is now possible, but such analysis generally is limited due to the cost and time required to sequence such large genomes. Moreover, present conventional sequencing methods are limited in terms of their accuracy, the length of individual templates that can be sequenced, and the rate of sequence determination.

Despite improvements in sample preparation and sequencing technologies, none of the present conventional sequencing strategies, including those to date that may involve ISFETs, has provided the cost reductions required to increase throughput to levels required for analysis of large numbers of individual human genomes. The ability to sequence many human genomes facilitates an analysis of the genetic basis underlying disease (e.g., such as cancer) and aging, for example. Some recent efforts have made significant gains in both the ability to prepare genomes for sequencing and to sequence large numbers of templates simultaneously. However, these and other efforts are still limited by the relatively large size of the reaction volumes needed to prepare templates that are detectable by these systems, as well as the need for special nucleotide analogues, and complex enzymatic or fluorescent methods to "read out" nucleotide sequence.

SUMMARY OF INVENTION

We have recognized and appreciated that large arrays of ISFETs may be particularly configured and employed to facilitate DNA sequencing techniques based on monitoring changes in chemical processes, including DNA synthesis. More generally, Applicants have recognized and appreciated that large arrays of chemically-sensitive FETs (i.e., chemFETs) may be employed to detect and measure static and/or dynamic concentrations/levels of a variety of analytes (e.g., hydrogen ions, other ions, non-ionic molecules or compounds, etc.) in a host of chemical and/or biological processes (e.g., biological or chemical reactions, cell or tissue cultures or monitoring, neural activity, nucleic acid sequencing, etc.) in which valuable information may be obtained based on such analyte measurements.

Accordingly, various embodiments of the present disclosure are directed generally to inventive methods and apparatus relating to large scale FET arrays for measuring one or more analytes. In the various embodiments disclosed herein, FET arrays include multiple chemFETs, that act as chemical sensors. An ISFET, as discussed above, is a particular type of chemFET that is configured for ion detection, and ISFETs may be employed in various embodiments disclosed herein. Other types of chemFETs contemplated by the present disclosure include enzyme FETs (EnFETs) which employ enzymes to detect analytes. It should be appreciated, however, that the present disclosure is not limited to ISFETs and EnFETs, but more generally relates to any FET that is configured for some type of chemical sensitivity. As used herein, chemical sensitivity broadly encompasses sensitivity to any molecule of interest, including without limitation organic, inorganic, naturally occurring, non-naturally occurring, and synthetic chemical and biological compounds, such as ions, small molecules, polymers such as nucleic acids, proteins, peptides, polysaccharides, and the like.

According to yet other embodiments, the present disclosure is directed generally to inventive methods and apparati relating to the use of the above-described large scale chemFET arrays in the analysis of chemical or biological samples. These samples are typically liquid (or are dissolved in a liquid) and of small volume, to facilitate high-speed, high-density determination of analyte (e.g., ion or other constituent) presence, concentration or other measurements on the analyte.

For example, some embodiments are directed to a "very large scale" two-dimensional chemFET sensor array (e.g., greater than 256 sensors), in which one or more chemFET-containing elements or "pixels" constituting the sensors of such an array are configured to monitor one or more independent biological or chemical reactions or events occurring in proximity to the pixels of the array. In some exemplary implementations, the array may be coupled to one or more microfluidics structures that form one or more reaction chambers, or "wells" or "microwells," over individual sensors or groups of sensors of the array, and apparatus which delivers analyte samples (i.e., analyte solutions) to the wells and removes them from the wells between measurements. Even when microwells are not employed, the sensor array may be coupled to one or more microfluidics structures for the delivery of one or more analytes to the pixels and for removal of analyte(s) between measurements. Accordingly, inventive aspects of this disclosure, which are desired to be protected, include the various microfluidic structures which may be employed to flow analytes and where appropriate other agents useful in for example the detection and measurement of analytes to and from the wells or pixels, the methods of manufacture of the array of wells, methods and structures for coupling the arrayed wells with arrayed pixels, and methods and apparatus for loading the wells with sample to be analyzed, including for example loading the wells with DNA-bearing beads when the apparatus is used for DNA sequencing or related analysis, as will be discussed in greater detail below.

In association with the microfluidics, unique reference electrodes and their coupling to the flow cell are also shown.

In various aspects of the invention, an analyte of particular interest is a byproduct of nucleic acid synthesis. Such a byproduct can be monitored as the readout of a sequencing-by-synthesis method. One particularly important byproduct is inorganic pyrophosphate (PPi) which is released upon the addition (or incorporation) of a deoxynucleotide triphosphate (also referred to herein as dNTP) to the 3' end of a nucleic acid (such as a sequencing primer). PPi may be hydrolyzed to orthophosphate (Pi) and free hydrogen ion ($H^+$) in the presence of water (and optionally and far more rapidly in the presence of pyrophosphatase). As a result, nucleotide incorporation, and thus a sequencing-by-synthesis reaction, can be monitored by detecting PPi, Pi and/or $H^+$. Conventionally, PPi has not been detected or measured by chemFETs. Optically based sequencing-by-synthesis methods have detected PPi via its sulfurylase-mediated conversion to adenosine triphosphate (ATP), and then luciferase-mediated conversion of luciferin to oxyluciferin in the presence of the previously generated ATP, with concomitant release of light. Such detection is referred to herein as "enzymatic" detection of PPi. The invention provides methods for detecting PPi using non-enzymatic methods. As used herein, non-enzymatic detection of PPi is detection of PPi that does not require an enzyme other than any enzyme required to produce or release the PPi in the first instance (e.g., a polymerase). An example of non-enzymatic detection of PPi is a detection method that does not require conversion of PPi to ATP.

H+ has been detected by measuring pH changes using standard pH meters or in some instances ISFETs. Importantly, many if not all prior attempts to detect nucleotide incorporation using ISFETs have focused solely on pH changes and not on detection or measurement of released PPi.

The instant invention contemplates and thus provides methods for monitoring nucleic acid sequencing reactions and thus determining the nucleotide sequence of nucleic acids by detecting $H^+$ (or changes in pH), PPi (or Pi) in the absence of presence of PPi (or Pi) specific receptors, unincorporated dNTP, or some combination thereof. Some aspects therefore are aimed at monitoring pH while others are aimed at monitoring (and detecting) ion pulses at the FET surface resulting from changes in ionic species in the solution in contact with such surface.

Thus, various aspects of the invention provide methods and apparati for directly detecting released PPi as an indicator of nucleotide incorporation into a nucleic acid. The invention does so through the use of the chemFET arrays described herein. In some embodiments, a nucleic acid synthesis reaction is performed in a solution that is in contact with the chemFET and the released PPi is detected (or sensed) by the chemFET surface. Importantly, given the ability of the chemFETs of the invention to detect PPi directly, such synthesis and/or sequencing reactions may be performed, and in some instances are preferably performed, in an environment that is substantially pH insensitive (i.e., an environment in which changes in pH are not detected due to for example the strong buffering capacity of the environment).

In other embodiments, the analyte of interest is hydrogen ion, and large scale ISFET arrays according to the present disclosure are specifically configured to measure changes in $H^+$ concentration (i.e., changes in pH).

In other embodiments, other biological or chemical reactions may be monitored, and the chemFET arrays may be specifically configured to measure hydrogen ions and/or one or more other analytes that provide relevant information relating to the occurrence and/or progress of a particular biological or chemical process of interest.

In various aspects, the chemFET arrays may be fabricated using conventional CMOS (or biCMOS or other suitable) processing technologies, and are particularly configured to facilitate the rapid acquisition of data from the entire array (scanning all of the pixels to obtain corresponding pixel output signals).

With respect to analyte detection and measurement, it should be appreciated that in various embodiments discussed in greater detail below, one or more analytes measured by a chemFET array according to the present disclosure may include any of a variety of biological or chemical substances that provide relevant information regarding a biological or chemical process (e.g., binding events such as hybridization of nucleic acids to each other, antigen-antibody binding, receptor-ligand binding, enzyme-inhibitor binding, enzyme-substrate binding, and the like). In some aspects, the ability to measure absolute or relative as well as static and/or dynamic levels and/or concentrations of one or more analytes, in addition to merely determining the presence or absence of an analyte, provides valuable information in connection with biological and chemical processes. In other aspects, mere determination of the presence or absence of an analyte or analytes of interest may provide valuable information may be sufficient.

A chemFET array according to various inventive embodiments of the present disclosure may be configured for sensitivity to any one or more of a variety of analytes. In one embodiment, one or more chemFETs of an array may be particularly configured for sensitivity to one or more analytes, and in other embodiments different chemFETs of a given array may be configured for sensitivity to different analytes. For example, in one embodiment, one or more sensors (pixels) of the array may include a first type of chemFET configured to be sensitive to a first analyte, and one or more other sensors of the array may include a second type of chemFET configured to be sensitive to a second analyte different from the first analyte. In one embodiment, the first and second analytes may be related to each other. As an example, the first and second analytes may be byproducts of the same biological or chemical reaction/process and therefore they may be detected concurrently to confirm the occurrence of a reaction (or lack thereof). Such redundancy is preferably in some analyte detection methods. Of course, it should be appreciated that more than two different types of chemFETs may be employed in any given array to detect and/or measure different types of analytes, and optionally to monitor biological or chemical processes such as binding events. In general, it should be appreciated in any of the embodiments of sensor arrays discussed herein that a given sensor array may be "homogeneous" and thereby consist of chemFETs of substantially similar or identical type that detect and/or measure the same analyte (e.g., pH or other ion concentration), or a sensor array may be "heterogeneous" and include chemFETs of different types to detect and/or measure different analytes. In another embodiment, the sensors in an array may be configured to detect and/or measure a single type (or class) of analyte even though the species of that type (or class) detected and/or measured may be different between sensors. As an example, all the sensors in an array may be configured to detect and/or measure nucleic acids, but each sensor detects and/or measures a different nucleic acid.

In yet other aspects, Applicants have specifically improved upon the ISFET array design of Milgrew et al. discussed above in connection with FIGS. 1-7, as well as other conventional ISFET array designs, so as to significantly reduce pixel size, and thereby increase the number of pixels of a chemFET array for a given semiconductor die size (i.e., increase pixel density). In various embodiments, this increase in pixel density is accomplished while at the same time increasing the signal-to-noise ratio (SNR) of output signals corresponding to monitored biological and chemical processes, and the speed with which such output signals may be read from the array. In particular, Applicants have recognized and appreciated that by relaxing requirements for chemFET linearity and focusing on a more limited measurement output signal range (e.g., output signals corresponding to a pH range of from approximately 7 to 9 or smaller, rather than 1 to 14, as well as output signals that do not necessarily relate significantly to pH), individual pixel complexity and size may be significantly reduced, thereby facilitating the realization of very large scale dense chemFET arrays. Applicants have also recognized and appreciated that alternative less complex approaches to pixel selection in an chemFET array (e.g., alternatives to the row and column decoder approach employed in the design of Milgrew et al. as shown in FIG. 7, whose complexity scales with array size), as well as various data processing techniques involving ISFET response modeling and data extrapolation based on such modeling, facilitate rapid acquisition of data from significantly large and dense arrays.

With respect to chemFET array fabrication, Applicants have further recognized and appreciated that various techniques employed in a conventional CMOS fabrication process, as well as various post-fabrication processing steps (wafer handling, cleaning, dicing, packaging, etc.), may in some instances adversely affect performance of the resulting chemFET array. For example, with reference again to FIG. 1, one potential issue relates to trapped charge that may be induced in the gate oxide 65 during etching of metals associated with the floating gate structure 70, and how such trapped charge may affect chemFET threshold voltage $V_{TH}$. Another potential issue relates to the density/porosity of the chemFET passivation layer (e.g., see ISFET passivation layer 72 in FIG. 1) resulting from low-temperature material deposition processes commonly employed in aluminum metal-based CMOS fabrication. While such low-temperature processes generally provide an adequate passivation layer for conventional CMOS devices, they may result in a somewhat low-density and porous passivation layer which may be potentially problematic for chemFETs in contact with an analyte solution; in particular, a low-density porous passivation layer over time may absorb and become saturated with analytes or other substances in the solution, which may in turn cause an undesirable time-varying drift in the chemFETs threshold voltage $V_{TH}$. This phenomenon may in turn impede accurate measurements of one or more particular analytes of interest. In view of the foregoing, other inventive embodiments disclosed herein relate to methods and apparatuses which mitigate potentially adverse effects on chemFET performance that may arise from various aspects of fabrication and post-fabrication processing/handling of chemFET arrays.

Accordingly, one embodiment of the present invention is directed to an apparatus, comprising an array of CMOS-fabricated sensors, each sensor comprising one chemically-sensitive field effect transistor (chemFET) and occupying an area on a surface of the array of 10 $\mu m^2$ or less.

Another embodiment is directed to a sensor array, comprising a two-dimensional array of electronic sensors including at least 512 rows and at least 512 columns of the electronic sensors, each sensor comprising one chemically-sensitive field effect transistor (chemFET) configured to provide at least one output signal representing a presence and/or concentration of an analyte proximate to a surface of the two-dimensional array.

Another embodiment is directed to an apparatus, comprising an array of CMOS-fabricated sensors, each sensor comprising one chemically-sensitive field effect transistor (chemFET). The array of CMOS-fabricated sensors includes more than 256 sensors, and a collection of chemFET output signals from all chemFETs of the array constitutes a frame of data. The apparatus further comprises control circuitry coupled to the array and configured to generate at least one array output signal to provide multiple frames of data from the array at a frame rate of at least 1 frame per second. In one aspect, the frame rate may be at least 10 frames per second. In another aspect, the frame rate may be at least 20 frames per second. In yet other aspects, the frame rate may be at least 30, 40, 50, 70 or up to 100 frames per second.

Another embodiment is directed to an apparatus, comprising an array of CMOS-fabricated sensors, each sensor comprising a chemically-sensitive field effect transistor (chemFET). The chemFET comprises a floating gate structure, and a source and a drain having a first semiconductor type and fabricated in a region having a second semiconductor type, wherein there is no electrical conductor that electrically connects the region having the second semiconductor type to either the source or the drain.

Another embodiment is directed to an apparatus, comprising an array of electronic sensors, each sensor consisting of three field effect transistors (FETs) including one chemically-sensitive field effect transistor (chemFET).

Another embodiment is directed to an apparatus, comprising an array of electronic sensors, each sensor comprising three or fewer field effect transistors (FETs), wherein the three or fewer FETs includes one chemically-sensitive field effect transistor (chemFET).

Another embodiment is directed to an apparatus, comprising an array of electronic sensors, each sensor comprising a plurality of field effect transistors (FETs) including one chemically-sensitive field effect transistor (chemFET), and a plurality of electrical conductors electrically connected to the plurality of FETs, wherein the plurality of FETs are arranged such that the plurality of electrical conductors includes no more than four conductors traversing an area occupied by each sensor and interconnecting multiple sensors of the array.

Another embodiment is directed to an apparatus, comprising an array of CMOS-fabricated sensors, each sensor comprising a plurality of field effect transistors (FETs) including one chemically-sensitive field effect transistor (chemFET), wherein all of the FETs in each sensor are of a same channel type and are implemented in a single semiconductor region of an array substrate.

Another embodiment is directed to a sensor array, comprising a plurality of electronic sensors arranged in a plurality of rows and a plurality of columns. Each sensor comprises one chemically-sensitive field effect transistor (chemFET) configured to provide at least one and in some instances at least two output signals representing a presence and/or a concentration of an analyte proximate to a surface of the array. For each column of the plurality of columns, the array further comprises column circuitry configured to provide a constant drain current and a constant drain-to-source voltage to respective chemFETs in the column, the column circuitry including two operational amplifiers and a diode-connected FET arranged in a Kelvin bridge configuration with the respective chemFETs to provide the constant drain-to-source voltage.

Another embodiment is directed to a sensor array, comprising a plurality of electronic sensors arranged in a plurality of rows and a plurality of columns. Each sensor comprises one chemically-sensitive field effect transistor (chemFET) configured to provide at least one output signal and in some instances at least two output signals representing a concentration of ions in a solution proximate to a surface of the array. The array further comprises at least one row select shift register to enable respective rows of the plurality of rows, and at least one column select shift register to acquire chemFET output signals from respective columns of the plurality of columns.

Another embodiment is directed to an apparatus, comprising an array of CMOS-fabricated sensors, each sensor comprising a chemically-sensitive field effect transistor (chemFET). The chemFET comprises a floating gate structure, and a source and a drain having a first semiconductor type and fabricated in a region having a second semiconductor type, wherein there is no electrical conductor that electrically connects the region having the second semiconductor type to either the source or the drain. The array includes a two-dimensional array of at least 512 rows and at least 512 columns of the CMOS-fabricated sensors. Each sensor consists of three field effect transistors (FETs) including the chemFET, and each sensor includes a plurality of electrical conductors electrically connected to the three FETs. The three FETs are arranged such that the plurality of electrical conductors includes no more than four conductors traversing an area occupied by each sensor and interconnecting multiple sensors of the array. All of the FETs in each sensor are of a same channel type and implemented in a single semiconductor region of an array substrate. A collection of chemFET output signals from all chemFETs of the array constitutes a frame of data. The apparatus further comprises control circuitry coupled to the array and configured to generate at least one array output signal to provide multiple frames of data from the array at a frame rate of at least 20 frames per second.

Another embodiment is directed to a method for processing an array of CMOS-fabricated sensors, each sensor comprising a chemically-sensitive field effect transistor (chemFET). The method comprises: A) dicing a semiconductor wafer including the array to form at least one diced portion including the array; and B) performing a forming gas anneal on the at least one diced portion.

Another embodiment is directed to a method for manufacturing an array of chemFETs. The method comprises: fabricating an array of chemFETs; depositing on the array a dielectric material; applying a forming gas anneal to the array before a dicing step; dicing the array; and applying a forming gas anneal after the dicing step. The method may further comprise testing the semiconductor wafer between one or more deposition steps.

Another embodiment is directed to a method for processing an array of CMOS-fabricated sensors. Each sensor comprises a chemically-sensitive field effect transistor (chemFET) having a chemically-sensitive passivation layer of silicon nitride and/or silicon oxynitride deposited via plasma enhanced chemical vapor deposition (PECVD). The method comprises depositing at least one additional passivation material on the chemically-sensitive passivation layer so as to reduce a porosity and/or increase a density of the passivation layer.

Other aspects of the invention relate to methods for monitoring nucleic acid synthesis reactions, including but not limited to those integral to sequencing-by-synthesis methods. Thus, various aspects of the invention provide methods for monitoring nucleic acid synthesis reactions, methods for determining or monitoring nucleotide incorporation into a nucleic acid, methods for determining the presence or absence of nucleotide incorporation, methods for determining the number of incorporated nucleotides, and the like.

In one such aspect, the invention provides a method for sequencing a nucleic acid comprising disposing (e.g., placing or positioning) a plurality of template nucleic acids into a plurality of reaction chambers, wherein the plurality of reaction chambers is in contact with a chemFET array comprising at least one chemFET for each reaction chamber, and wherein each of the template nucleic acids is hybridized to a sequencing primer (thereby forming a template/primer hybrid) and is bound to a polymerase, synthesizing a new nucleic acid strand (or extending the sequencing primer) by incorporating one or more known nucleotide triphosphates (also referred to generically herein as dNTP) sequentially at the 3' end of the sequencing primer, and detecting the incorporation of the one or more known nucleotide triphosphates by a change in voltage and/or current at the at least one chemFET. The array (and thus the plurality) of chemFETs may be comprised of at least two, at least three, at least four, at least five, at least six, at least seven, at least eight, at least nine, at least ten, at least 100, at least 200, at least 300, at least 400, at least 500, at least 1000, at least $10^4$, at least $10^5$, at least $10^6$, at least $10^7$, or more chemFET (or chemFET sensors, or sensors, as the terms are used interchangeably herein). Similarly, the plurality of reaction chambers may be at least two, at least three, at least four, at least five, at least six, at least seven, at least eight, at least nine, at least ten, at least 100, at least 200, at least 300, at least 400, at least 500, at least 1000, at least $10^4$, at least $10^5$, at least $10^6$, at least $10^7$, or more reaction chambers.

In another aspect, the invention provides a method for sequencing a nucleic acid comprising disposing a plurality of template nucleic acids into a plurality of reaction chambers, wherein the plurality of reaction chambers is in contact with a chemFET array, wherein at least one chemFET is in contact with each reaction chamber, and wherein each of the template nucleic acids is hybridized to a sequencing primer (thereby forming a template/primer hybrid) and is bound to a polymerase, synthesizing a new nucleic acid strand (or extending the sequencing primer) by incorporating one or more known nucleotide triphosphates sequentially at the 3' end of the sequencing primer, and detecting the incorporation of the one or more known nucleotide triphosphates by a change in voltage and/or current at the at least one chemFET, wherein the chemFET array is any of the foregoing arrays.

In another aspect, the invention provides a method for sequencing a nucleic acid comprising disposing a plurality of template nucleic acids into a plurality of reaction chambers, wherein the plurality of reaction chambers is in contact with a chemFET array comprising at least one chemFET for each reaction chamber, and wherein each of the template nucleic acids is hybridized to a sequencing primer (thereby forming a template/primer hybrid) and is bound to a polymerase, synthesizing a new nucleic acid strand (by extending the sequencing primer) by incorporating one or more known nucleotide triphosphates sequentially at the 3' end of the sequencing primer, and detecting the incorporation of the one or more known nucleotide triphosphates by a change in voltage and/or current at the at least one chemFET within the array, wherein a center-to-center distance between adjacent reaction chambers (or "pitch") is 1-10 µm.

In another aspect, the invention provides a method for sequencing a nucleic acid comprising disposing a plurality of template nucleic acids into a plurality of reaction chambers, wherein the plurality of reaction chambers is in contact with a chemFET array comprising at least one chemFET for each reaction chamber, and wherein each of the template nucleic acids is hybridized to a sequencing primer (thereby forming a template/primer hybrid) and is bound to a polymerase, synthesizing a new nucleic acid strand (by extending the sequencing primer) by incorporating one or more known nucleotide triphosphates sequentially at the 3' end of the sequencing primer, and detecting the incorporation of the one or more known nucleotide triphosphates by the generation of sequencing reaction byproduct, wherein (a) the chemFET array comprises more than 256 sensors, or (b) a center-to-center distance between adjacent reaction chambers is 1-10 µm. In an important embodiment, the sequencing reaction byproduct is PPi.

In yet another aspect, the invention provides a method for sequencing a nucleic acid comprising fragmenting (or isolating, for example in the context of enriched exon isolation) a target nucleic acid to generate a plurality of fragmented (or isolated) nucleic acids, attaching each of the plurality of fragmented (or isolated) nucleic acids to individual beads to generate a plurality of beads each attached to a single fragmented (or isolated) nucleic acid, amplifying the number of fragmented (or isolated) nucleic acids on each bead, delivering the plurality of beads attached to amplified fragmented (or isolated) nucleic acids to a chemFET array having a separate reaction chamber for each sensor in the array, wherein only one bead is situated in each reaction chamber, and performing simultaneous sequencing reactions in the plurality of reaction chambers.

It is to be understood, as described in greater detail herein, that the nucleic acids to be sequenced may be derived from longer nucleic acids that are then subsequently fragmented (i.e., converted into shorter nucleic acids) or they may be isolated at a length that is suitable to the reactions contemplated herein and thus would not have to be shortened (or fragmented). It should therefore be understood that for every aspect and limitation discussed herein that refers to the process of fragmenting a target nucleic acid, the method can also be carried out by isolating a target nucleic acid in the absence of fragmenting.

In still another aspect, the invention provides a method for sequencing nucleic acids comprising fragmenting a target nucleic acid to generate a plurality of fragmented nucleic acids, amplifying each fragmented nucleic acid separately in the presence of a bead and binding amplified copies of the fragmented nucleic acid to the bead, thereby producing a plurality of beads each attached to a plurality of identical fragmented nucleic acids, delivering the plurality of beads each attached to a plurality of identical fragmented nucleic acids to a chemFET array having a separate reaction chamber for each chemFET sensor in the array, wherein only one bead is situated in each reaction chamber, and performing simultaneous sequencing reactions in the plurality of reaction chambers.

In another aspect, the invention provides a method for sequencing a nucleic acid comprising disposing a plurality of template nucleic acids into a plurality of reaction chambers, wherein the plurality of reaction chambers is in contact with a chemFET array comprising at least one chemFET for each reaction chamber, and wherein each of the template nucleic acids is hybridized to a sequencing primer (thereby forming a template/primer hybrid) and is bound to a polymerase, synthesizing a new nucleic acid strand (by extending the sequencing primer) by incorporating one or more known nucleotide triphosphates sequentially at the 3' end of the sequencing primer, and detecting a change in the level of a sequencing byproduct as an indicator of incorporation of the one or more known nucleotide triphosphates.

The change in the level may an increase or a decrease in a level relative to a level prior to incorporation of the one or more known nucleotide triphosphates. The change in the level may be read as a change in voltage and/or current at a chemFET sensor or a change in pH, but it is not so limited.

In another aspect, the invention provides a method for sequencing a nucleic acid comprising disposing a plurality of template nucleic acids into a plurality of reaction chambers, wherein the plurality of reaction chambers is in contact with a chemFET array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, directly detecting release of PPi as an indicator of incorporation of the one or more known nucleotide triphosphates.

In another aspect, the invention provides a method for sequencing nucleic acids comprising fragmenting a template nucleic acid to generate a plurality of fragmented nucleic acids, attaching one strand from each of the plurality of fragmented nucleic acids individually to beads to generate a plurality of beads each having a single stranded fragmented nucleic acid attached thereto, delivering the plurality of beads having a single stranded fragmented nucleic acid attached thereto to a chemFET array having a separate reaction chamber for each sensor in the area, and wherein only one bead is situated in each reaction chamber, and performing simultaneous sequencing reactions in the plurality of chambers.

In one aspect, the invention provides a method for sequencing a nucleic acid comprising sequencing a plurality of identical template nucleic acids in a reaction chamber in contact with a chemFET, in an array which comprises at least 3 (and up to millions) of such assemblies of reaction chambers and chemFETs.

In another aspect, the invention provides a method for sequencing a nucleic acid comprising detecting incorporation of one or more known nucleotide triphosphates to a 3' end of a sequencing primer hybridized to a template nucleic acid in a reaction chamber in contact with a chemFET of a chemFET array that comprises at least three chemFET.

In one aspect, the invention provides a method for sequencing a nucleic acid comprising fragmenting a target nucleic acid to generate a plurality of fragmented nucleic acids, individually amplifying one or more of the plurality of fragmented nucleic acids, and sequencing the individually amplified fragmented nucleic acids using a chemFET array. In one embodiment, the chemFET array comprises at least three chemFETs. In some embodiments, the chemFET array comprises at least 500 chemFETs, or at least 100,000 chemFETs. In some embodiments, the plurality of fragmented nucleic acids is individually amplified using a water in oil emulsion amplification method.

In another aspect, the invention provides a method for sequencing a nucleic acid comprising fragmenting a target nucleic acid to generate a plurality of fragmented nucleic acids, attaching each of the plurality of fragmented nucleic acids to individual beads to generate a plurality of beads each attached to a single fragmented nucleic acid, amplifying the fragmented nucleic acids on each bead resulting in a plurality of identical fragmented nucleic acids on each bead, delivering a plurality of beads attached to fragmented nucleic acids to a chemFET array having a separate reaction chamber for each sensor in the array, wherein only one bead is situated in each reaction chamber, and performing sequencing reactions simultaneously in the plurality of reaction chambers.

In another aspect, the invention provides a method for sequencing a nucleic acid comprising fragmenting a target nucleic acid to generate a plurality of fragmented nucleic acids, individually amplifying one or more of the plurality of fragmented nucleic acids, and sequencing the individually amplified fragmented nucleic acids in a plurality of reaction chambers having a center-to-center distance of about 1-10 μm using a chemFET array. In various embodiments, the center-to-center distance is about 9 μm, about 5 μm, or about 2 μm.

In another aspect, the invention provides a method for sequencing a nucleic acid comprising disposing a plurality of template nucleic acids into a plurality of reaction chambers, wherein the plurality of reaction chambers is in contact with a chemFET array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, and detecting incorporation of the one or more known nucleotide triphosphates by a change in voltage at the at least one chemFET within the array in the absence of a detectable pH change.

In another aspect, the invention provides a method for sequencing a nucleic acid comprising disposing a plurality of template nucleic acids into a reaction chamber, wherein the plurality of template nucleic acids is attached to a single bead, each of the template nucleic acids is hybridized to a sequencing primer and is bound to a polymerase, and the reaction chamber is in contact with a chemFET, synthesizing a new nucleic acid strand by incorporating one or more known nucleotide triphosphates sequentially at the 3' end of the sequencing primer, and detecting incorporation of the one or more known nucleotide triphosphates by detection of a first and a second voltage pulse at the chemFET.

In still another aspect, the invention provides a method for sequencing a nucleic acid comprising disposing a plurality of template nucleic acids into a plurality of reaction chambers, wherein the plurality of reaction chambers is in contact with a chemFET array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, and detecting incorporation of the one or more known nucleotide triphosphates by non-enzymatically detecting released inorganic pyrophosphate. In one embodiment, the detecting step occurs in the absence of a detectable pH change.

In still another aspect, the invention provides a method for sequencing a nucleic acid comprising disposing a plurality of template nucleic acids into a plurality of reaction chambers, wherein the plurality of reaction chambers is in contact with a chemFET array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, and detecting incorporation of the one or more known nucleotide triphosphates by detecting released inorganic pyrophosphate and unincorporated nucleotide triphosphates.

In one embodiment, the released inorganic pyrophosphate is detected at $t_0$ and unincorporated nucleotide triphosphates are detected at time $t_1$. In a related embodiment, a time difference of $t_1-t_0$ indicates a number of known nucleotide triphosphates incorporated.

In another aspect, the invention provides a method for sequencing a nucleic acid comprising contacting a template nucleic acid with a sequencing primer and a polymerase for times and conditions sufficient to allow the template nucleic acid to bind to the sequencing primer for form a template/primer hybrid and to allow the polymerase to bind to the template/primer hybrid, and synthesizing a new nucleic acid strand by incorporating nucleotide triphosphates sequentially at the 3' end of the sequencing primer, and detecting incorporation of the one or more known nucleotide triphosphates by detecting released inorganic pyrophosphate and unincorporated nucleotide triphosphates.

In one embodiment, the released inorganic pyrophosphate is detected at $t_0$ and unincorporated nucleotide triphosphates are detected at time $t_1$. In a related embodiment, the time difference between $t_1$ and $t_0$ (i.e., $t_1-t_0$) indicates the number of known nucleotide triphosphates incorporated.

In still another aspect, the invention provides a method for sequencing a nucleic acid comprising contacting a template nucleic acid with a sequencing primer and a polymerase for times and conditions sufficient to allow the template nucleic acid to bind to the sequencing primer for form a template/primer hybrid and to allow the polymerase to bind to the template/primer hybrid, and synthesizing a new nucleic acid strand (or extending sequencing primer) by incorporating one or more known nucleotide triphosphates sequentially at the 3' end of the sequencing primer in a low ionic strength environment, and detecting incorporation of the one or more known nucleotide triphosphates by detection of one or more voltage pulses at the chemFET.

Depending on the embodiment, the low ionic strength environment may comprise less than 1 mM $MgCl_2$, less than 0.5 mM $MgCl_2$, less than 100 μM $MgCl_2$, or less than 50 μM $MgCl_2$. In other embodiments, the low ionic strength environment may comprise less than 1 mM $MnCl_2$, less than 0.5 mM $MnCl_2$, less than 100 μM $MnCl_2$, or less than 50 μM $MnCl_2$. In still other embodiments, the salt may be another $Mg^{2+}$ or $Mn^{2+}$ containing salt, or it may be a $Ca^{2+}$ or $Co^{2+}$ containing salt, or it may be a combination of one or more such salts.

In another aspect, the invention provides a method for determining incorporation of a nucleotide triphosphate into a newly synthesized nucleic acid (or onto a primer such as a sequencing primer) comprising combining a nucleotide triphosphate, a template/primer hybrid, and a polymerase, in a solution in contact with a chemFET, and detecting voltage pulses at the chemFET, wherein detection of a first and a second voltage pulse indicates incorporation of a nucleotide triphosphate and wherein detection of a first but not a second voltage pulse indicates lack of incorporation of a nucleotide triphosphate.

In one embodiment, the voltage pulses are detected at the chemFET independent of a binding event at the passivation layer of the chemFET.

In another aspect, the invention provides a method for determining incorporation of a nucleotide triphosphate into a newly synthesized nucleic acid (or onto a primer such as a sequencing primer) comprising combining a nucleotide triphosphate, a template/primer hybrid, and a polymerase, in a solution in contact with a chemFET, and detecting voltage pulses at the chemFET independent of a binding event at the passivation layer of the chemFET, wherein detection of a first and a second voltage pulse indicates incorporation of at least one nucleotide triphosphate.

In various embodiments of the some of the foregoing aspect, the first voltage pulse occurs at time $t_0$ and the second voltage pulse occurs at time $t_1$, and $t_1-t_0$ indicates the number of nucleotide triphosphates incorporated. In various embodiments, the incorporated nucleotide triphosphate is known. In various embodiments, the nucleotide triphosphate is a plurality of identical nucleotide triphosphates, the template/primer hybrid is a plurality of identical template/primer hybrids, and the polymerase is a plurality of identical polymerases. Alternatively, the polymerase may be a plurality of polymerases that are not identical and that rather may be comprised of 2, 3, or more types of polymerase. In some instances, a mixture of two polymerases may be used with one having suitable processivity and the other having suitable rate of incorporation. The ratio of the different polymerases can vary and the invention is not to be limited in this regard. Similarly the template/primer hybrid may be a plurality of template/primer hybrids which may not be identical to each other, provided that any template/primer hybrids in a single reaction chamber or attached to a single bead are identical to each other.

In still another aspect, the invention provides a method for sequencing a nucleic acid comprising disposing (e.g., placing or positioning) a plurality of template nucleic acids into a plurality of reaction chambers, wherein the plurality of reaction chambers is in contact with a chemFET array comprising at least one chemFET for each reaction chamber, and wherein each of the template nucleic acids is hybridized to a sequencing primer and is bound to a polymerase, synthesizing a new nucleic acid strand (or extending the sequencing primer) by incorporating one or more known nucleotide triphosphates sequentially at the 3' end of the sequencing primer, and detecting incorporation of the one or more known nucleotide triphosphates by detecting at the at least one chemFET a first voltage pulse at time $t_0$ having height $h_0$ and a second pulse at time $t_1$ having height $h_1$, wherein $h_0$ and $h_1$ are each at least about 5 mV over baseline, and $t_1-t_0$ is at least 1 millisecond. In some embodiments, $t_1-t_0$ is at least 5 millisecond, at least 10 milliseconds, at least 20 milliseconds, at least 30 milliseconds, at least 40 milliseconds, or at least 50 milliseconds.

In another aspect, the invention provides a method for sequencing a nucleic acid comprising disposing a plurality of beads into a plurality of reaction chambers, wherein each reaction chamber comprises a single bead, each bead is attached to a plurality of identical template nucleic acids, each of the template nucleic acids is hybridized to a sequencing primer and is bound to a polymerase, and wherein the plurality of reaction chambers is in contact with a chemFET array comprising at least one chemFET for each reaction chamber, synthesizing a new nucleic acid strand (or extending the sequencing primer) by incorporating one or more known nucleotide triphosphates sequentially at the 3' end of the sequencing primer, and detecting the incorporation of the one or more known nucleotide triphosphates by detecting a first and a second voltage pulse at least one chemFET within the array, wherein the chemFET array comprises at least three chemFET.

In another aspect, the invention provides a method for sequencing a nucleic acid comprising disposing a plurality of beads into a plurality of reaction chambers, wherein each reaction chamber comprises a single bead, each bead is attached to a plurality of identical template nucleic acids, each of the template nucleic acids is hybridized to a sequencing primer and is bound to a polymerase, and wherein the plurality of reaction chambers is in contact with a chemical-sensitive field effect transistor (chemFET) array comprising at least one chemFET for each reaction chamber, initiating synthesis of a new nucleic acid strand (or extension of the sequencing primer) by introducing a plurality of known identical nucleotide triphosphates into each reaction chamber, synthesizing a new nucleic acid strand by incorporating one or more known nucleotide triphosphates sequentially at the 3' end of the sequencing primer, and detecting the incorporation of the one or more known nucleotide triphosphates by detecting a first and a second voltage pulse at least one chemFET within the array.

In one embodiment, each reaction chamber comprises adenosine triphosphate prior to introducing a plurality of known triphosphates into each reaction chamber.

In another aspect, the invention provides a method for sequencing a nucleic acid comprising (a) disposing a plurality of beads into a plurality of reaction chambers, each reaction chamber comprising a single bead, each bead attached to a plurality of identical template nucleic acids, each of the template nucleic acids hybridized to a sequencing primer and bound to a polymerase, and each reaction chamber in contact with at least one chemFET, (b) introducing a plurality of known identical nucleotide triphosphates into each reaction chamber, (c) detecting sequential incorporation at the 3' end of the sequencing primer of one or more nucleotide triphosphates if complementary to corresponding nucleotides in the template nucleic acid, (d) washing unincorporated nucleotide triphosphates from the reaction chambers, and (e) repeating steps (b) through (d) in the same reaction chamber using a different plurality of known nucleotide triphosphates.

In one embodiment, sequential incorporation of one or more nucleotide triphosphates is detected by a first and a second voltage pulse at the chemFET. In some embodiments, step (e) comprises repeating steps (b) through (d) by separately introducing each different plurality of known nucleotide triphosphates into each reaction chamber In another aspect, the invention provides a method for sequencing a nucleic acid comprising disposing a plurality of beads into a plurality of reaction chambers, wherein each reaction chamber comprises a single bead, each bead is attached to a plurality of identical template nucleic acids, each of the template nucleic acids is hybridized to a sequencing primer and is bound to a polymerase, and wherein the each of the plurality of reaction chambers is in contact with at least one chemFET in a chemFET array, initiating synthesis of a new nucleic acid strand by introducing a divalent cation into each reaction chamber, synthesizing a new nucleic acid strand by incorporating one or more known nucleotide triphosphates sequentially at the 3' end of the sequencing primer, and detecting the incorporation of the one or more known nucleotide triphosphates by detecting a first and a second voltage pulse at least one chemFET within the array.

In one embodiment, the divalent cation is $Mg^{2+}$. In another embodiment, the divalent cation is $Mn^{2+}$. In still a further embodiment, the divalent cation is a mixture of $Mg^{2+}$ and $Mn^{2+}$. Depending on the embodiment, the divalent cation is at a concentration of less than 1 mM, or less than 100 μM, or about 50 μM.

In yet another aspect, the invention provides a method for sequencing a nucleic acid comprising disposing a plurality of identical template nucleic acids into a reaction chamber, wherein the reaction chamber is in contact with a chemFET, and wherein each of the template nucleic acids is hybridized to a sequencing primer and is bound to a polymerase, incorporating one or more known nucleotide triphosphates sequentially at the 3' end of the sequencing primer, and detecting the incorporation of the one or more known nucleotide triphosphates by a voltage pulse at the chemFET, wherein the incorporation of 10-1000 nucleotide triphosphates is detected.

Various embodiments may be embraced in the various foregoing aspects of the invention and these are recited below once for convenience and brevity.

It is to be understood that although various of the foregoing aspects and embodiments of the invention recite hybridization (or binding) of a sequencing primer to a template, the invention also contemplates the use of sequencing primers and/or template nucleic acids that hybridize to themselves (i.e., intramolecularly) thereby giving rise to free 3' ends onto which nucleotide triphosphates may be incorporated. Such templates, referred to herein as self-priming templates, may be used in any of the foregoing methods.

Similarly, the invention equally contemplates the use of double stranded templates that are engineered to have particular sequences at their free ends that can be acted upon by nicking enzymes such as DNA nickase. In this way, the polymerase incorporates nucleotide triphosphates at the nicked site. In these instances, there is no requirement for a separate sequencing primer.

In some embodiments, the incorporation of at least 10, at least 20, at least 30, at least 40, at least 50, at least 60, at least 70, at least 80, at least 90, or at least 100 nucleotide triphosphates is detected. In other embodiments, the incorporation of 100-1000 nucleotide triphosphates is detected. In still other some embodiments, the incorporation of 250-750 nucleotide triphosphates is detected.

In some embodiments, the reaction chamber comprises a plurality of packing beads. In some embodiments, the detecting step occurs in the presence of a plurality of packing beads.

In some embodiments, the reaction chamber comprises a soluble non-nucleic acid polymer. In some embodiments, the detecting step occurs in the presence of a soluble non-nucleic acid polymer. In some embodiments, the soluble non-nucleic acid polymer is polyethylene glycol, or PEA, or a dextran, or an acrylamide, or a cellulose (e.g., methyl cellulose). In some embodiments, the non-nucleic acid polymer such as polyethylene glycol is attached to the single bead. In some embodiments, the non-nucleic acid polymer is attached to one or more (or all) sides of a reaction chamber, except in some instances the bottom of the reaction chamber which is the FET surface In some embodiments, the non-nucleic acid polymer is biotinylated such as but not limited to biotinylated polyethylene glycol.

In some embodiments, the method is carried out at a pH of about 7-9, or at about 8.5 to 9.5, or at about 9.

In some embodiments, the synthesizing and/or detecting step is carried out in a weak buffer. In some embodiments, the weak buffer comprises Tris-HCl, boric acid or borate buffer, acetate, morpholine, citric acid, carbonic acid, or phosphoric acid as a buffering agent.

In some embodiments, the synthesizing and/or detecting step is carried out in about 1 mM Tris-HCl. In some embodiments, the synthesizing and/or detecting step is carried out in less than 1 mM Tris-HCl. In some embodiments, the synthesizing and/or detecting step is carried out in about 0.9 mM Tris-HCl, about 0.8 mM Tris-HCl, about 0.7 mM Tris-HCl, about 0.6 mM Tris-HCl, about 0.5 mM Tris-HCl, about 0.4 mM Tris-HCl, about 0.3 mM Tris-HCl, or about 0.2 mM Tris-HCl.

In some embodiments, the synthesizing and/or detecting step is carried out in about 1 mM borate buffer. In some embodiments, the synthesizing and/or detecting step is carried out in less than 1 mM borate buffer. In some embodiments, the synthesizing and/or detecting step is carried out in about 0.9 mM borate buffer, about 0.8 mM borate buffer, about 0.7 mM borate buffer, about 0.6 mM borate buffer, about 0.5 mM borate buffer, about 0.4 mM borate buffer, about 0.3 mM borate buffer, or about 0.2 mM borate buffer.

In some embodiments, the detection step occurs in the absence of a detectable pH change. In some embodiments, the detection step is carried out in an environment of constant pH. In some embodiment, the chemFET is relatively pH insensitive. In some embodiments, the synthesizing and/or detecting step is carried out in about 0.5 mM Tris-HCl.

In some embodiments, the synthesizing and/or detecting step is carried out in a low ionic strength environment. In some embodiments, synthesizing and/or detecting step is carried out in a low ionic strength environment that comprises less than 1 mM $MgCl_2$ or $MnCl_2$, less than 0.5 mM $MgCl_2$ or $MnCl_2$, or less than 100 µM $MgCl_2$ or $MnCl_2$. In some embodiments, the synthesizing and/or detecting step is carried out in a low ionic strength environment that comprises about 100 µM $MgCl_2$ or $MnCl_2$, about 75 µM $MgCl_2$ or $MnCl_2$, about 50 µM $MgCl_2$ or $MnCl_2$, about 40 µM $MgCl_2$ or $MnCl_2$, about 30 µM $MgCl_2$ or $MnCl_2$, about 20 µM $MgCl_2$ or $MnCl_2$, or about 10 µM $MgCl_2$ or $MnCl_2$. It is to be understood that the invention contemplates similarly amounts of other divalent cations and it is therefore not limited to $MgCl_2$ or $MnCl_2$ only. Similarly it should be understood that the invention contemplates the use of two or more divalent cations (and/or their corresponding salts) provided the total ion concentration is at the levels stated above.

In some embodiments, the synthesizing and/or detecting step is carried out in about 0.5 mM TRIS and about 50 µM $MgCl_2$ or $MnCl_2$.

In various embodiments, the nucleotide triphosphates are unblocked. As used herein, an unblocked nucleotide triphosphate is a nucleotide triphosphate with an unmodified end that can be incorporated into a nucleic acid (at its 3' end) and once it is incorporated can be attached to the following nucleotide triphosphate being incorporated. Blocked dNTP in contrast either cannot be added to a nucleic acid or their incorporation into a nucleic acid prevents any further nucleotide incorporation. In various embodiments, the nucleotide triphosphates are deoxynucleotide triphosphates (dNTPs).

In various embodiments, the chemFET comprises a silicon nitride passivation layer. In some embodiments, the chemFET comprises a passivation layer attached to inorganic pyrophosphate (PPi) receptors. In some embodiments, the chemFET comprises a passivation layer that is not bound to a nucleic acid.

In some embodiments, each reaction chamber is in contact with a single chemFET.

In some embodiments, the reaction chamber has a volume of equal to or less than about 1 picoliter (pL), including less than 0.5 pL, less than 0.1 pL, less than 0.05 pL, less than 0.01 pL, less than 0.005 pL. In some embodiment, the reaction chambers are separated by a center-to-center spacing of 1-10 µm. In some embodiments, the reaction chambers are separated by a center-to-center spacing of about 9 µm, about 5 microns, or about 2 microns. The reaction chambers may have a square cross section, for example at their base or bottom. Examples include an 8 µm by 8 µm cross section, a 4 µm by 4 µm cross section, or a 1.5 µm by 1.5 µm cross section. Alternatively, they may have a rectangular cross section, for example at their base or bottom. Examples include an 8 µm by 12 µm cross section, a 4 µm by 6 µm cross section, or a 1.5 µm by 2.25 µm cross section.

In some embodiments, the nucleotide triphosphates are pre-soaked in $Mg^{2+}$ (e.g., in the presence of $MgCl_2$) or $Mn^{2+}$ (for example in the presence of $MnCl_2$). In some embodiments, the polymerase is pre-soaked in $Mg^{2+}$ (e.g., in the presence of $MgCl_2$) or $Mn^{2+}$ (for example in the presence of $MnCl_2$).

In some embodiments, the method is carried out in a reaction chamber comprising a single capture bead, wherein a ratio of reaction chamber width to single capture bead diameter is at least 0.7, at least 0.8, or at least 0.9.

In some embodiments, the polymerase is free in solution. In some embodiments, the polymerase is immobilized to a bead. In some embodiments, the polymerase is immobilized to a capture bead. In some embodiments, the template nucleic acids are attached to capture beads.

In some embodiments, inorganic pyrophosphate (PPi) is not significantly hydrolyzed prior to detecting nucleotide incorporation. In some embodiments, inorganic pyrophosphate (PPi) is not significantly hydrolyzed prior to detecting a first voltage pulse.

In one aspect, the invention provides an apparatus comprising a chemFET array comprising a plurality of chemFET sensors each having a PPi receptor disposed on its surface, wherein the array comprises at least three chemFET sensors.

In one aspect, the invention provides an apparatus comprising a chemFET array comprising a plurality of chemFET sensors each having a PPi receptor disposed on its surface, wherein adjacent chemFET sensors in the array are separated by a center-to-center distance of about less than about 10 µm (e.g., using 0.18 µm CMOS fabrication, the pitch may be about 2.8 µm).

In another aspect, the invention provides an apparatus comprising a chemical-sensitive field effect transistor (chemFET) having disposed on its surface a PPi selective receptor. The PPi receptor may be immobilized to the chemFET surface.

In still another aspect, the invention provides an apparatus comprising a chemical-sensitive field effect transistor (chemFET) array comprising a plurality of chemFET sensors each having a PPi receptor disposed on its surface, wherein the plurality is a subset of the chemFET sensors in the array. In a related embodiment, the array comprises at least three chemFET sensors. The subset may represent 10%, 25%, 33%, 50%, 75% or more of the sensors in the array. The PPi selective receptor may be immobilized to the surface of each chemFET.

In some embodiments, the center-to-center distance between adjacent reaction chambers is about 1-9 µm, or about 2-9 µm, about 1 µm, about 2 µm, about 3 µm, about 4 µm, about 5 µm, about 6 µm, about 7 µm, about 8 µm, or about 9 µm. In some embodiments, the chemFET array comprises more than 256 sensors (and optionally more than 256 corresponding reaction chambers (or wells)), more than 300 sensors (and optionally more than 300 corresponding reaction chambers), more than 400 sensors (and optionally more than 400 corresponding reaction chambers), more than 500 sensors (and optionally more than 500 corresponding reaction chambers), more than 600 sensors (and optionally more than 600 corresponding reaction chambers), more than 700 sensors (and optionally more than 700 corresponding reaction chambers), more than 800 sensors (and optionally more than 800 corresponding reaction chambers), more than 900 sensors (and optionally more than 900 corresponding reaction chambers), more than $10^3$ sensors (and optionally more than $10^3$ corresponding reaction chambers), more than $10^4$ sensors (and optionally more than $10^4$ corresponding reaction chambers), more than $10^5$ sensors (and optionally more than $10^5$ corresponding reaction chambers), or more than $10^6$ sensors (and optionally more than $10^6$ corresponding reaction chambers). In some embodiments, the chemFET array comprises at least 512 rows and at least 512 columns of sensors.

In some embodiments, the sequencing byproduct is PPi. In some embodiments, PPi is measured directly. In related embodiments, PPi is detected by its binding to a PPi selective receptor immobilized on the surface of a chemFET sensor. In another embodiment, PPi is detected in the absence of a PPi selective receptor. In other embodiments, PPi is detected in a pH independent or insensitive environment.

In some embodiments, the sequencing reaction byproduct is hydrogen ion. In some embodiments, the sequencing reaction byproduct is Pi. In still other embodiments, the chemFET detects changes in any combination of the byproducts, optionally in combination with other parameters, as described herein.

In some embodiments, the PPi selective receptor is Compound 1, Compound 2, Compound 3, Compound 4, Compound 5, Compound 6, Compound 7, Compound 8, Compound 9 or Compound 10 as shown in FIG. 11B. In some embodiments, the chemFET is present in an array of chemFETs, each of which has disposed, including immobilized, on its surface a PPi selective receptor. In some embodiments, identical PPi selective receptors are disposed on each chemFET of the array. In some embodiments, the array comprises more than 256 sensors. In some embodiments, the array comprises at least 512 rows and at least 512 columns of sensors. In some embodiments, the chemFET is located at a bottom of a reaction chamber.

In another aspect, the invention provides an apparatus comprising a chemFET array having disposed on its surface a biological array or a chemical array.

The biological array may be a nucleic acid array, a protein array including but not limited to an enzyme array, an antibody array and an antibody fragment array, a cell array, and the like. The chemical array may be an organic small molecule array, or an inorganic molecule array, but it is not so limited. The chemFET array may comprise at least 5, at least 10, at least $10^2$, at least $10^3$, at least $10^4$, at least $10^5$, at least $10^6$, or more sensors. The biological or chemical array may be arranged into a plurality of "cells" or spatially defined regions, and each of these regions is situated over a different sensor in the chemFET array, in some embodiments.

In yet another aspect, the invention provides a method for detecting a nucleic acid comprising contacting a nucleic acid array disposed on a chemFET array with a sample, and detecting binding of a nucleic acid from the sample to one or more regions on the nucleic acid array.

In another aspect, the invention provides a method for detecting a protein comprising contacting a protein array disposed on a chemFET array with a sample, and detecting binding of a protein from the sample to one or more regions on the protein array.

In yet another aspect, the invention provides a method for detecting a nucleic acid comprising contacting a protein array disposed on a chemFET array with a sample, and detecting binding of a nucleic acid from the sample to one or more regions on the protein array.

In another aspect, the invention provides a method for detecting an antigen comprising contacting an antibody array disposed on a chemFET array with a sample, and detecting binding of an antigen from the sample to one or more regions on the antibody array.

In another aspect, the invention provides a method for detecting an enzyme substrate or inhibitor comprising contacting an enzyme array disposed on a chemFET array with a sample, and detecting binding of an entity from the sample to one or more regions on the enzyme array.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead being placed upon generally illustrating the various concepts discussed herein.

FIG. 10-1 illustrates a top view of a chip layout design for a cluster of four neighboring pixels of an chemFET array shown in FIG. 9, according to another inventive embodiment of the present disclosure.

FIG. 11A-1 shows a composite cross-sectional view of multiple neighboring pixels, along the line I-I of one of the pixels shown in FIG. 10-1, including additional elements of the pixel between the lines II-II, illustrating a layer-by-layer view of pixel fabrication according to another inventive embodiment of the present disclosure.

FIGS. 11B(1)-(3) provide the chemical structures of ten PPi receptors (compounds 1 through 10).

FIG. 11C(1) is a schematic of a synthesis protocol for compound 7 from FIG. 11B(3).

FIG. 11C(2) is a schematic of a synthesis protocol for compound 8 from FIG. 11B(3).

FIG. 11C(3) is a schematic of a synthesis protocol for compound 9 from FIG. 11B(3).

FIGS. 11D(1) and (2) are schematics illustrating a variety of chemistries that can be applied to the passivation layer in order to bind molecular recognition compounds (such as but not limited to PPi receptors).

FIGS. 12A through 12L provide top views of each of the fabrication layers shown in FIG. 11A, according to one inventive embodiment of the present disclosure.

FIGS. 12-1A through 12-1L provide top views of each of the fabrication layers shown in FIG. 11A-1, according to another inventive embodiment of the present disclosure.

FIG. 33B-1 is an image from a scanning electron microscope showing in cross-section a portion of an array architecture as taught herein, with microwells formed in a layer of silicon dioxide over ISFETs.

FIG. 33B-2 is a diagrammatic illustration of a microwell in cross-section, the microwell being produced as taught herein and having sloped sides, and showing how a bead of a correspondingly appropriate diameter larger than that of the well bottom can be spaced from the well bottom by interference with the well sidewalls.

FIG. 33B-3 is another diagrammatic illustration of such a microwell with beads of different diameters shown, and indicating optional use of packing beads below the nucleic acid-carrying bead such as a DNA-carrying bead.

FIG. 42F1 is a diagrammatic illustration of an example of a ceiling baffle arrangement for a flow cell in which fluid is introduced at one corner of the chip and exits at a diagonal corner, the baffle arrangement facilitating a desired fluid flow across the array.

FIGS. 42F2-42F8 comprise a set of illustrations of an exemplary flow cell member that may be manufactured by injection molding and may incorporate baffles to facilitate fluid flow, as well as a metalized surface for serving as a reference electrode, including an illustration of said member mounted to a sensor array package over a sensor array, to form a flow chamber thereover.

FIGS. 59A-59C are illustrations of the pieces for two examples of two-piece injection molded parts for forming a flow cell.

FIG. 61A is an optical microscope image and FIG. 61B is an image captured using the chemFET sensor underlying the microwell array.

FIGS. 72A-C provide a schematic of a polymerase assay (A), and extension data for various polymerases.

FIGS. 74A-C provide data relating to polymerase activity as a function of time.

DETAILED DESCRIPTION

Figure 1:
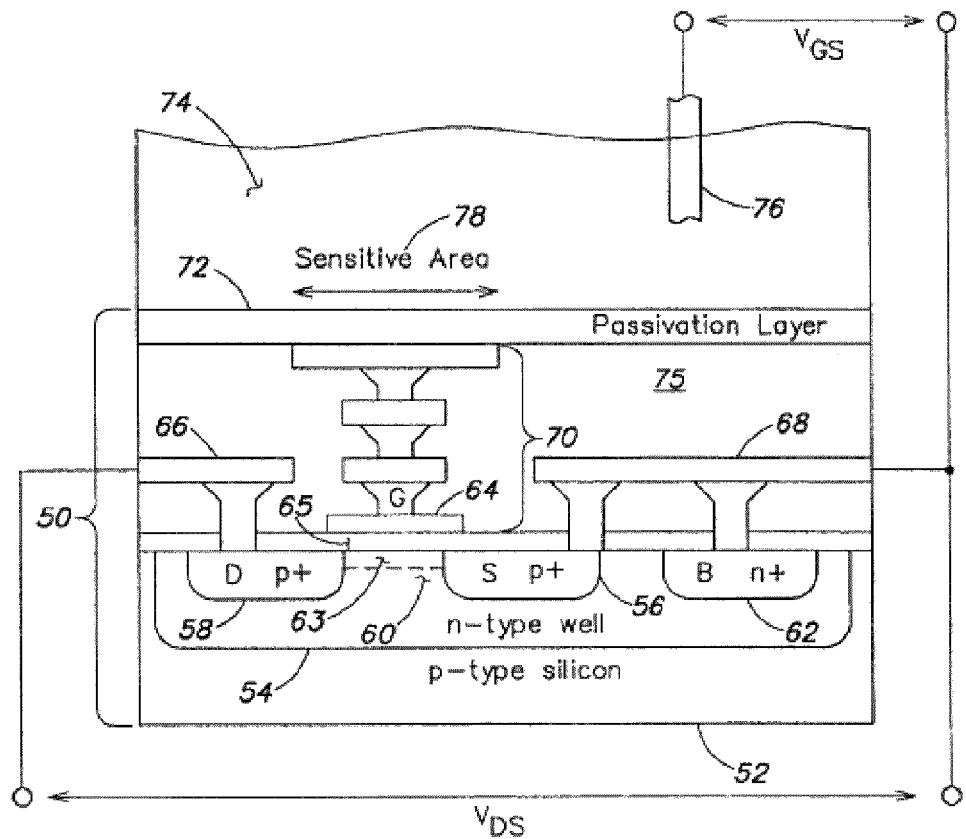
FIG. 1 illustrates a cross-section of a p-type (p-channel) ion-sensitive field effect transistor (ISFET) fabricated using a conventional CMOS process.

Following below are more detailed descriptions of various concepts related to, and embodiments of, inventive methods and apparatus relating to large scale chemFET arrays for analyte detection and/or measurement. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Various inventive embodiments according to the present disclosure are directed at least in part to a semiconductor-based/microfluidic hybrid system that combines the power of microelectronics with the biocompatibility of a microfluidic system. In some examples below, the microelectronics portion of the hybrid system is implemented in CMOS technology for purposes of illustration. It should be appreciated, however, that the disclosure is not intended to be limiting in this respect, as other semiconductor-based technologies may be utilized to implement various aspects of the microelectronics portion of the systems discussed herein.

One embodiment disclosed herein is directed to a large sensor array (e.g., a two-dimensional array) of chemically-sensitive field effect transistors (chemFETs), wherein the individual chemFET sensor elements or "pixels" of the array are configured to detect analyte presence (or absence), analyte levels (or amounts), and/or analyte concentration in an unmanipulated sample, or as a result of chemical and/or biological processes (chemical reactions, cell cultures, neural activity, nucleic acid sequencing processes, etc.) occurring in proximity to the array. Examples of chemFETs contemplated by various embodiments discussed in greater detail below include, but are not limited to, ion-sensitive field effect transistors (ISFETs) and enzyme-sensitive field effect transistors (ENFETs). In one exemplary implementation, one or more microfluidic structures is/are fabricated above the chemFET sensor array to provide for containment and/or confinement of a biological or chemical reaction in which an analyte of interest may be produced or consumed, as the case may be. For example, in one implementation, the microfluidic structure(s) may be configured as one or more "wells" (e.g., small reaction chambers or "reaction wells") disposed above one or more sensors of the array, such that the one or more sensors over which a given well is disposed detect and measure analyte presence, level, and/or concentration in the given well.

In another exemplary implementation, the invention encompasses a system for high-throughput sequencing comprising at least one two-dimensional array of reaction chambers, wherein each reaction chamber is coupled to a chemically-sensitive field effect transistor ("chemFET") and each reaction chamber is no greater than 10 µm³ (i.e., 1 pL) in volume. Preferably, each reaction chamber is no greater than 0.34 pL, and more preferably no greater than 0.096 pL or even 0.012 pL in volume. A reaction chamber can optionally be $2^2$, $3^2$, $4^2$, $5^2$, $6^2$, $7^2$, $8^2$, $9^2$, or $10^2$ square microns in cross-sectional area at the top. Preferably, the array has at least 100, 1,000, 10,000, 100,000, or 1,000,000 reaction chambers. The reaction chambers may be capacitively coupled to the chemFETs, and preferably are capacitively coupled to the chemFETs.

In some embodiments, such a chemFET array/microfluidics hybrid structure may be used to analyze solution(s)/material(s) of interest containing nucleic acids. For example, such structures may be employed to monitor sequencing of nucleic acids. Sequencing of nucleic acids may be performed to determine partial or complete nucleotide sequence of a nucleic acid, to detect the presence and in some instances nature of a single nucleotide polymorphism in a nucleic acid, to determine what therapeutic regimen will be most effective to treat a subject having a particular condition as can be determined by the subject's genetic make-up, to determine and compare nucleic acid expression profiles of two or more states (e.g., comparing expression profiles of diseased and normal tissue, or comparing expression profiles of untreated tissue and tissue treated with drug, enzymes, radiation or chemical treatment), to haplotype a sample (e.g., comparing genes or variations in genes on each of the two alleles present in a human subject), to karyotype a sample (e.g., analyzing chromosomal make-up of a cell or a tissue such as an embryo, to detect gross chromosomal or other genomic abnormalities), and to genotype (e.g., analyzing one or more genetic loci to determine for example carrier status and/or species-genus relationships).

The systems described herein can be utilized to sequence the nucleic acids of an entire genome, or any portion thereof. Genomes that can be sequenced include mammalian genomes, and preferably human genomes. Thus, in one exemplary embodiment, the invention encompasses a method for sequencing a genome or part thereof comprising: delivering fragmented nucleic acids from the genome or part thereof to a system for high-throughput sequencing comprising at least one two-dimensional array of reaction chambers, wherein each reaction chamber is coupled to a chemically-sensitive field effect transistor ("chemFET") and each reaction chamber is no greater than 1 pL in volume; and detecting a sequencing reaction in at least one of the reaction chambers via a signal from the chemFET of the reaction chamber.

In an alternative exemplary embodiment, the method comprises: delivering fragmented nucleic acids from the genome or part thereof to a sequencing apparatus comprising a two-dimensional array of reaction chambers, wherein each of the reaction chambers is disposed in a sensing relationship with an associated chemFET; and detecting a sequencing reaction in at least one of the reaction chambers via a signal from the associated chemFET.

Preferably, the sequencing reaction is performed by delivering a first deoxyribonucleotide triphosphate ("dNTP") to each of the reaction chambers. Preferably, the delivering step comprises delivering the first dNTP at substantially the same time to each of the reaction chambers. Once the first dNTP is delivered to the reaction chambers, an enzyme is typically delivered to the reaction chambers to degrade any unused dNTP, followed by washing to remove substantially all of the enzyme from the reaction chambers. Preferably, the enzyme also degrades PPi. The washing can also remove any degraded dNTP or degraded PPi.

The nucleic acids to be sequenced can be naturally or non-naturally occurring nucleic acids, and preferably are naturally occurring nucleic acids. The nucleic acids can be obtained from any of several sources including, but not limited to, deoxyribonucleic acid ("DNA") (e.g., messenger DNA, complementary DNA, or nuclear DNA), ribonucleic acid ("RNA") (e.g., micro RNA, transfer RNA, messenger RNA, or small interfering RNA), or peptides. When the source is DNA, the DNA can be obtained from any bodily fluid or tissue that contains DNA, including, but not limited to, blood, saliva, cerebrospinal fluid ("CSF"), skin, hair, urine, stool, and mucus. The starting amounts of nucleic acids to be sequenced determine the minimum sample requirements. Considering the following bead sizes, with an average of 450 bases in the single strand, with an average molecular weight of 325 g/mol per base we have the following:

| Bead Size (um) | femto gram of DNA |
|---|---|
| 0.2 | 0.124 |
| 0.3 | 0.279 |
| 0.7 | 1.52 |
| 1.05 | 3.42 |
| 2.8 | 24.3 |
| 5.9 | 108 |

Given the number of beads and microwells contemplated for use in an array, it will thus be apparent that a sample taken from a subject to be tested need only be on the order of 3 µg.

Preferably, at least $10^6$ base pairs are sequenced per hour, more preferably at least $10^7$ base pairs are sequenced per hour, even more preferably at least $10^8$ base pairs are sequenced per hour, even more preferably at least $10^9$ base pairs are sequenced per hour, and most preferably at least $10^{10}$ base pairs are sequenced per hour using the above-described method. Thus, the method may be used to sequence an entire human genome within about 24 hours, more preferably within about 20 hours, even more preferably within about 15 hours, even more preferably within about 10 hours, even more preferably within about 5 hours, and most preferably within about 1 hour.

The systems described herein can be utilized to sequence an entire genome of an organism from about 3 µg of DNA or less. In one embodiment, the invention encompasses a method for sequencing an entire genome of an organism comprising delivering about 3 µg of DNA or less from the organism to an array of chemically sensitive field effect transistors and determining a sequence of the genome. In another embodiment, the invention encompasses a device adapted for sequencing a complete human genome from about 1 ng of DNA or less without the use of optics or labels. Typically, the device comprises an array of chemFETs and/or an array of microfluidic reaction chambers and/or a semiconductor material coupled to a dielectric material.

The above-described sequencing can be performed in a reaction mixture having an ionic strength of up to 500 µM, 400 µM, or 300 µM. The ionic strength, I, of a solution is a function of the concentration of all ions present in a solution.

$$I_c = \frac{1}{2}\sum_{B=1}^{n} c_B z_B^2$$

where $c_B$ is the molar concentration of ion B (mol dm$^{-3}$), $z_B$ is the charge number of that ion, and the sum is taken over all ions in the solution. The Mg$^{+2}$ or Mn$^{2+}$ concentration may be 1000 µM, 500 µM, 200 µM, 100 µM, 50 µM, 10 µM, 5 µM, or even 1 µM.

Figure 71:
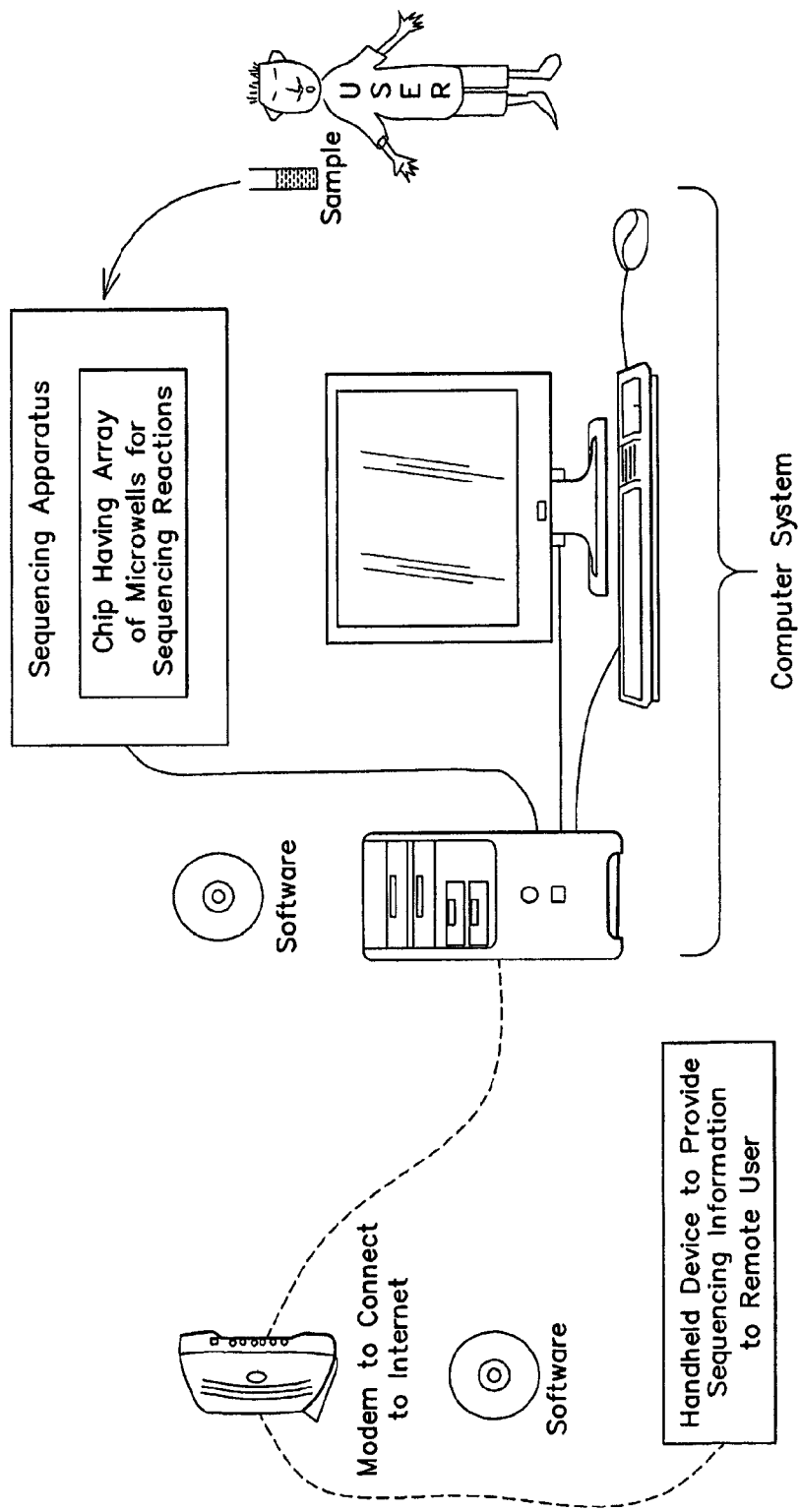
FIG. 71 illustrates an exemplary sequencing process.

The above-described method may be automated such that the sequencing reactions are performed via robotics. In addition, the sequencing information obtained via the signal from the chemFET of the reaction chamber may be provided to a personal computer, a personal digital assistant, a cellular phone, a video game system, or a television so that a user can monitor the progress of the sequencing reactions remotely. This process is illustrated, for example, in FIG. 71.

The systems described herein can also be used to aid in the identification and treatment of disease. For example, the system can be used for identifying a sequence associated with a particular disease or for identifying a sequence associated with a positive response to a particular active ingredient.

In one embodiment, the invention encompasses a method for identifying a sequence associated with a condition comprising: delivering nucleic acids from a plurality of subjects having the condition to a sequencing apparatus comprising a two-dimensional array of reaction chambers, wherein each of the reaction chambers is capacitively coupled to a chemFET; determining sequences of the nucleic acids from signal from said chemFETs; and identifying a common sequence between the DNA from the plurality of subjects. Preferably, the subject is a mammal, and more preferably a human. Preferably, the condition is cancer, an immunosuppressant condition, a neurological condition, or a viral infection.

In another embodiment, the invention encompasses a method for identifying a sequence associated with a positive response to a particular active agent, comprising: sequencing DNA from a plurality of subjects that have exhibited a positive response and from a plurality of subjects having a negative response to an active agent using one or more sequencing apparatuses, wherein each sequencing apparatus comprises an array of chemFETs; and identifying a common DNA sequence in the plurality of subjects that have exhibited a positive response or from the subjects that have exhibited a negative response that is not present in the other plurality of subjects. Preferably, the subject is a mammal, and more preferably a human.

It should be appreciated, however, that while some illustrative examples of the concepts disclosed herein focus on nucleic acid processing, the invention contemplates a broader application of these concepts and is not intended to be limited to these examples.

Figure 8:
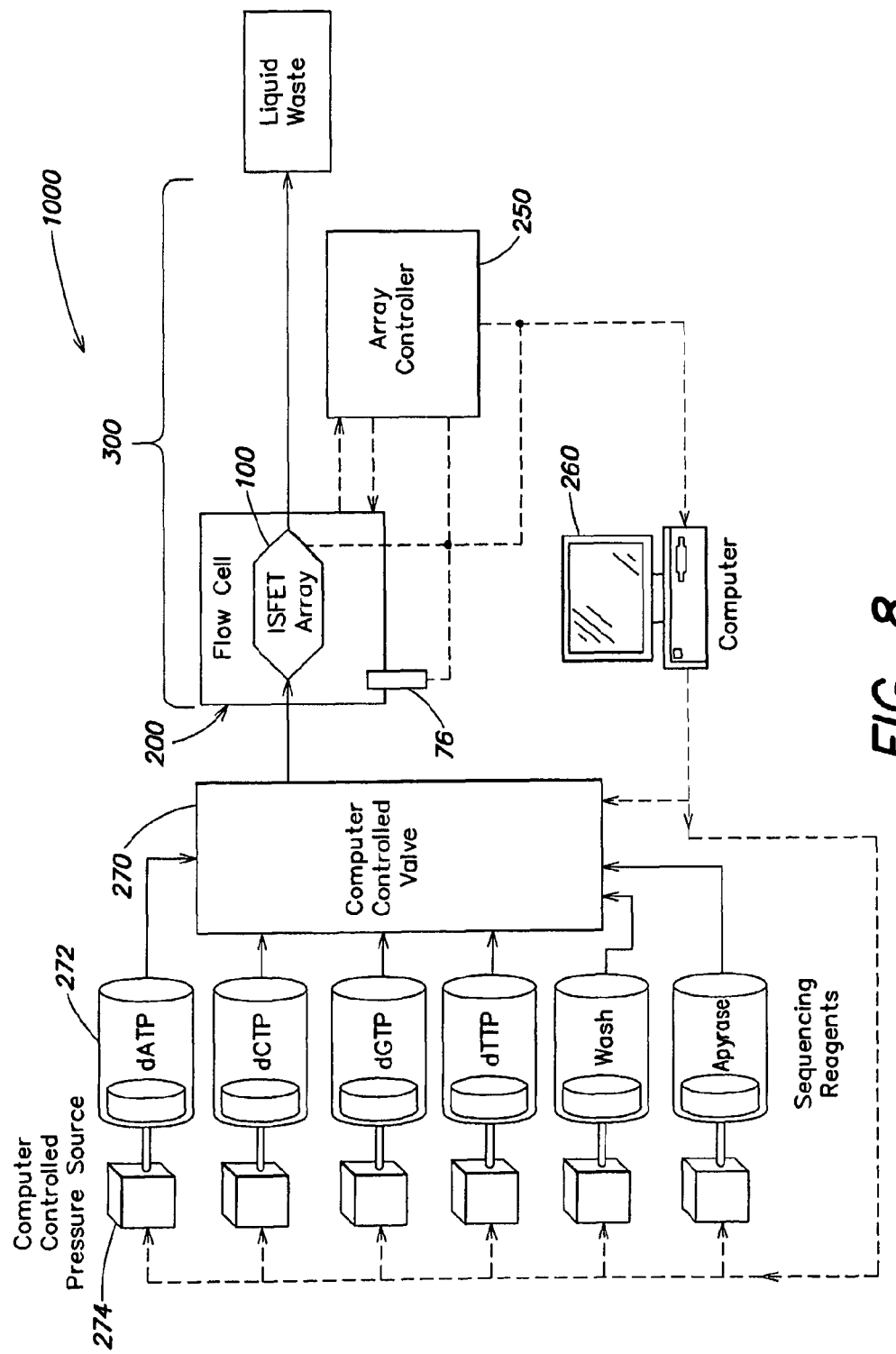
FIG. 8 generally illustrates a nucleic acid processing system comprising a large scale chemFET array, according to one inventive embodiment of the present disclosure.

FIG. 8 generally illustrates a nucleic acid processing system 1000 comprising a large scale chemFET array, according to one inventive embodiment of the present disclosure. An example of a nucleic acid processing system is a nucleic acid sequencing system. In the discussion that follows, the chemFET sensors of the array are described for purposes of illustration as ISFETs configured for sensitivity to static and/or dynamic ion concentration, including but not limited to hydrogen ion concentration and/or concentration of other ionic species involved in nucleic acid processing. However, it should be appreciated that the present disclosure is not limited in this respect, and that in any of the embodiments discussed herein in which ISFETs are employed as an illustrative example, other types of chemFETs may be similarly employed in alternative embodiments, as discussed in further detail below. Similarly it should be appreciated that various aspects and embodiments of the invention may employ ISFETs as sensors yet detect one or more ionic species that are not hydrogen ions.

The system 1000 includes a semiconductor/microfluidics hybrid structure 300 comprising an ISFET sensor array 100 and a microfluidics flow cell 200. In one aspect, the flow cell 200 may comprise a number of wells (not shown in FIG. 8) disposed above corresponding sensors of the ISFET array 100. In another aspect, the flow cell 200 is configured to facilitate the sequencing of one or more identical template nucleic acids disposed in the flow cell via the controlled and ordered admission (or introduction) to the flow cell of a number of sequencing reagents 272 (e.g., bases dATP, dCTP, dGTP, dTTP, generically referred to herein as dNTP, divalent cations such as but not limited to Mg$^{2+}$, wash solutions, and the like).

As illustrated in FIG. 8, the admission of the sequencing reagents to the flow cell 200 may be accomplished via one or more valves 270 and one or more pumps 274 that are controlled by computer 260. A number of techniques may be used to admit (i.e., introduce) the various processing materials (i.e., solutions, samples, reaction reagents, wash solutions, and the like) to the wells of such a flow cell. As illustrated in FIG. 8, reagents including bases may be admitted to the flow cell (e.g., via the computer controlled valve 270 and pumps 274) from which they diffuse into the wells, or reagents may be added to the flow cell by other means such as an ink jet. In yet another example, the flow cell 200 may not contain any wells, and diffusion properties of the reagents may be exploited to limit cross-talk between respective sensors of the ISFET array 100.

As will be discussed in greater detail herein, various embodiments of the sequencing methods provided in accordance with the invention use beads having attached to their surface multiple identical copies of a template nucleic acid. Such beads are generally referred to herein as "loaded" with nucleic acid. Preferably, each reaction well comprises only a single bead. The nucleic acid loaded beads, of which there may be tens, hundreds, thousands, or more, first enter the flow cell and then individual beads enter individual wells. The beads may enter the wells passively or otherwise. For example, the beads may enter the wells through gravity without any applied external force. The beads may enter the wells through an applied external force including but not limited to a magnetic force or a centrifugal force. In some embodiments, if an external force is applied, it is applied in a direction that is parallel to the well height/depth rather than transverse to the well height/depth, with the aim being to "capture" as many beads as possible. Preferably, the wells (or well arrays) are not agitated, as for example may occur through an applied external force that is perpendicular to the well height/depth. Moreover, once the wells are so loaded, they are not subjected to any other force that could dislodge the beads from the wells.

Furthermore, as will be discussed herein, in addition to the nucleic acid loaded beads, each well may also comprise a plurality of smaller beads, referred to herein as "packing beads". The packing beads may be composed of any inert material that does not interact or interfere with analytes, reagents, reaction parameters, and the like, present in the wells. Packing beads may be positioned between the chemFET surface and the nucleic acid loaded bead, in which case they may be introduced into the wells before the nucleic acid loaded beads. Alternatively, they may be positioned all around the nucleic acid loaded beads, in which case they may be added to the wells before, during and/or after the nucleic acid loaded beads. In still other embodiments, the majority of the packing beads may be positioned on top of the nucleic acid loaded beads, in which case they may be added to the wells after the nucleic acid loaded beads.

Packing beads may serve one or more various functions. For example, the packing beads may act to minimize or prevent altogether dislodgement of nucleic acid loaded beads from wells, particularly if some fraction of them are positioned on top of the nucleic acid loaded beads. The packing beads may act to decrease the diffusion rate of one or more component in the solution in the well, including but not limited to PPi and unincorporated nucleotides. In some embodiments, the packing beads are paramagnetic beads. Packing beads are commercially available from sources such as Bangs Laboratories.

Diffusion may also be impacted by including in the reaction chambers viscosity increasing agents. An example of such an agent is a polymer that is not a nucleic acid (i.e., a non-nucleic acid polymer). The polymer may be naturally or non-naturally occurring, and it may be of any nature provided it does not interfere with nucleotide incorporation and detection thereof except for slowing the diffusion of PPi, unincorporated nucleotides, and/or other reaction byproducts or reagents, towards the reaction chamber bottom. An example of a suitable polymer is polyethylene glycol (PEG). Other examples include PEA, dextrans, acrylamides, celluloses (e.g. methyl cellulose), and the like. The polymer may be free in solution or it may be immobilized (covalently or non-covalently) to one or more sides of the reaction chamber, to the capture bead, and/or to any packing beads that may be present. Non-covalent attachment may be accomplished via a biotin-avidin interaction.

In still other sequencing embodiments, instead of employing capture beads, the wells can be coated with one or more nucleic acids, including for example a pair of primer nucleic acids, and the template nucleic acid having adaptor nucleotide sequences complementary to the primer nucleotide sequence may be introduced into the wells. These and other agents useful in immobilizing analytes or template nucleic acids may be provided to the sensor array 100, to individual dies as part of the chip packaging, or to wells immediately before the processing of a sample). Other methods involving solgels may be used to immobilize agents such as nucleic acids near the surface of the ISFET array 100.

As will be discussed in greater detail herein, in some aspects of the sequencing methods contemplated by the invention, the template nucleic acid may be amplified prior to or after placement in the well. Various methods exist to amplify nucleic acids. Thus, in one aspect, once a template nucleic acid is loaded into a well of the flow cell 200, amplification may be performed in the well, the resulting amplified product denatured, and sequencing-by-synthesis or then performed. Amplification methods include but are not limited to bridge amplification, rolling circle amplification, or other strategies using isothermal or non-isothermal amplification techniques.

In sum, the flow cell 200 in the system of FIG. 8 may be configured in a variety of manners to provide one or more analytes (or one or more reaction solutions) in proximity to the ISFET array 100. For example, a template nucleic acid may be directly attached or applied in suitable proximity to one or more pixels of the sensor array 100, or on a support material (e.g., one or more "beads") located above the sensor array. Processing reagents (e.g., enzymes such as polymerases) can also be placed on the sensors directly, or on one or more solid supports in proximity to the sensors. It is to be understood that the device may be used without wells or beads for a number of biosensor applications involving the detection and/or measurement of at least one sensor-detectable product (e.g., ion concentration change).

In the system 1000 of FIG. 8, according to one embodiment the ISFET sensor array 100 monitors ionic species, and in particular, changes in the levels/amounts and/or concentration of ionic species. In important embodiments, the species are those that result from a nucleic acid synthesis or sequencing reaction. One particularly important ionic species is the PPi that is released as a result of nucleotide incorporation. Another important species is the excess nucleotides added to and remaining in the reaction chamber once the synthesis or sequencing reaction is complete. Such nucleotides are referred to herein as "unincorporated nucleotides."

As will be discussed in greater detail herein, various embodiments of the present invention may relate to monitoring/measurement techniques that involve the static and/or dynamic responses of an ISFET. In one embodiment relating to detection of nucleotide incorporation during a nucleic acid synthesis or sequencing reaction, detection/measurement techniques particularly rely on the transient or dynamic response of an ISFET (ion-step response, or "ion pulse" output), as discussed above in connection with FIG. 2A, to detect concentration changes of various ionic species relating to a nucleic acid synthesis or sequencing reaction. Although the particular example of a nucleic acid synthesis or sequencing reaction is provided to illustrate the transient or dynamic response of an ISFET, it should be appreciated that according to other embodiments, the transient or dynamic response of an ISFET as discussed below may be exploited for monitoring/sensing other types of chemical and/or biological activity beyond the specific example of a nucleic acid synthesis or sequencing reaction.

In one exemplary implementation, beyond the step-wise or essentially instantaneous pH changes in the analyte solution contemplated by prior research efforts, detection/measurement techniques relying on the dynamic response of an ISFET according to some embodiments of the present invention are based at least in part on the differential diffusion of various ionic species proximate to the analyte/passivation layer interface of the ISFET(s) (e.g., at the bottom of a reaction well over an ISFET). In particular, Applicants have recognized and appreciated that if a given stimulus constituted by a change in ionic strength proximate to the analyte/passivation layer interface, due to the appropriate diffusion of respective species of interest, occurs at a rate that is significantly faster than the ability of the passivation layer to adjust its surface charge density in response to the stimulus of the concentration change (e.g., faster than a characteristic response time constant $\tau$ associated with the passivation layer surface), a step-wise or essentially instantaneous change in ionic strength is not necessarily required to observe an ion pulse output from the ISFET. This principle is applicable not only to the example of DNA sequencing, but also to other types of chemical and chemical reaction sensing, as well.

For purposes of the present disclosure, the pulse response of an ISFET to a stimulus constituted by any significant change in ionic strength in the analyte solution that occurs on a sufficiently fast time scale is referred to as an "ion pulse," wherein the amplitude of the pulse is described by Eq. (17) above, and wherein the width and shape of the pulse (rise and decay of the pulse over time) relate to the diffusion parameters associated with the ion species giving rise to the change in ionic strength and the equilibrium reaction kinetics at the analyte/passivation layer interface (as reflected in one or more characteristic time constants $\tau$, as discussed above in connection with Eq. (18)). In various embodiments discussed herein, one or more ion pulses due to concentration changes of ionic species proximate to the analyte/passivation layer surface may be observed in an ISFET output signal if such concentration changes occur at a rate that is faster than the ability of the passivation layer to adjust its surface charge density in response to the stimulus of the concentration change (e.g., ionic strength changes occur in a time t<<τ). Again, from the foregoing, it should be appreciated that stepwise or instantaneous changes in ionic strength (e.g., a high flow rate directed normal to the ISFET passivation layer surface) is not required to observe an ion pulse output from the ISFET.

More specifically, with reference again to Eqs. (10) and (11) (assuming the applicability of the Debye theory in a regime of relatively lower ionic strengths, e.g., <1 mole/liter), consider that an ISFET re-equilibrates to the same surface potential after a change in ionic strength. This suggests that if the Debye screening length changes to $\lambda'$, the surface charge density changes by the opposite amount to keep the surface potential constant, i.e.:

$$\sigma' = \frac{\sigma\lambda}{\lambda'}. \quad (20)$$

As discussed above in connection with Eq. (18), the surface charge density σ may be described approximately as an exponential function of time with time constant τ. Accordingly, if there is a time-varying Debye screening length λ(t) due to a time varying ionic strength I(t) in the analyte solution (see Eqs. (12) and (13)), the surface charge density obeys the differential equation:

$$\frac{d\sigma}{dt} = -\frac{\left[\sigma - \frac{\sigma(0)\lambda(0)}{\lambda(t)}\right]}{\tau}. \quad (21)$$

From Eq. (21), it may be observed that the surface charge density is continuously trying to get back to a value that gives the initial surface potential as the Debye screening length changes with time. The surface potential as a function of time may be expressed in terms of the Debye screening length. from Eqs. (10) and (11), as:

$$\Psi_0(t) = \frac{-\lambda(t)\sigma(t)}{k\varepsilon_0}. \quad (22)$$

Introducing a new variable g(t) that includes σ(t) and referring to Eq. (12), Eq. (22) may be rewritten in terms of a time varying ionic strength I(t) as:

$$\Psi_0(t) = \frac{g(t)}{\sqrt{I(t)}}, \quad (23)$$

from which is obtained:

$$\frac{dg}{dt} = -\frac{\left[g - \frac{g(0)\sqrt{I(t)}}{\sqrt{I(0)}}\right]}{\tau}. \quad (24)$$

Eqs. (23) and (24) show that the generation and overall profile of an ion pulse in an ISFET output signal depends both on the time constant τ associated with the surface kinetics of the analyte/passivation layer interface and the ionic strength as a function of time I(t), which is given by the concentrations of respective ionic species in the reaction well as they change over time due to reaction and diffusion. As noted above, from the foregoing, Applicants have recognized and appreciated that as long as I(t) varies at a rate that is faster than the ability of the surface charge density to re-equilibrate (as characterized by the time constant τ), an ion pulse output may be observed, wherein the profile of the onset of the pulse is determined primarily by I(t) and the decay profile of the pulse is determined primarily by the time constant τ. Again, the foregoing analysis applies generally to virtually any ion species present in the analyte solution and, accordingly, the transient or dynamic response of an ISFET may be exploited to monitor a variety of chemical and/or biological activity.

Figure 8A:
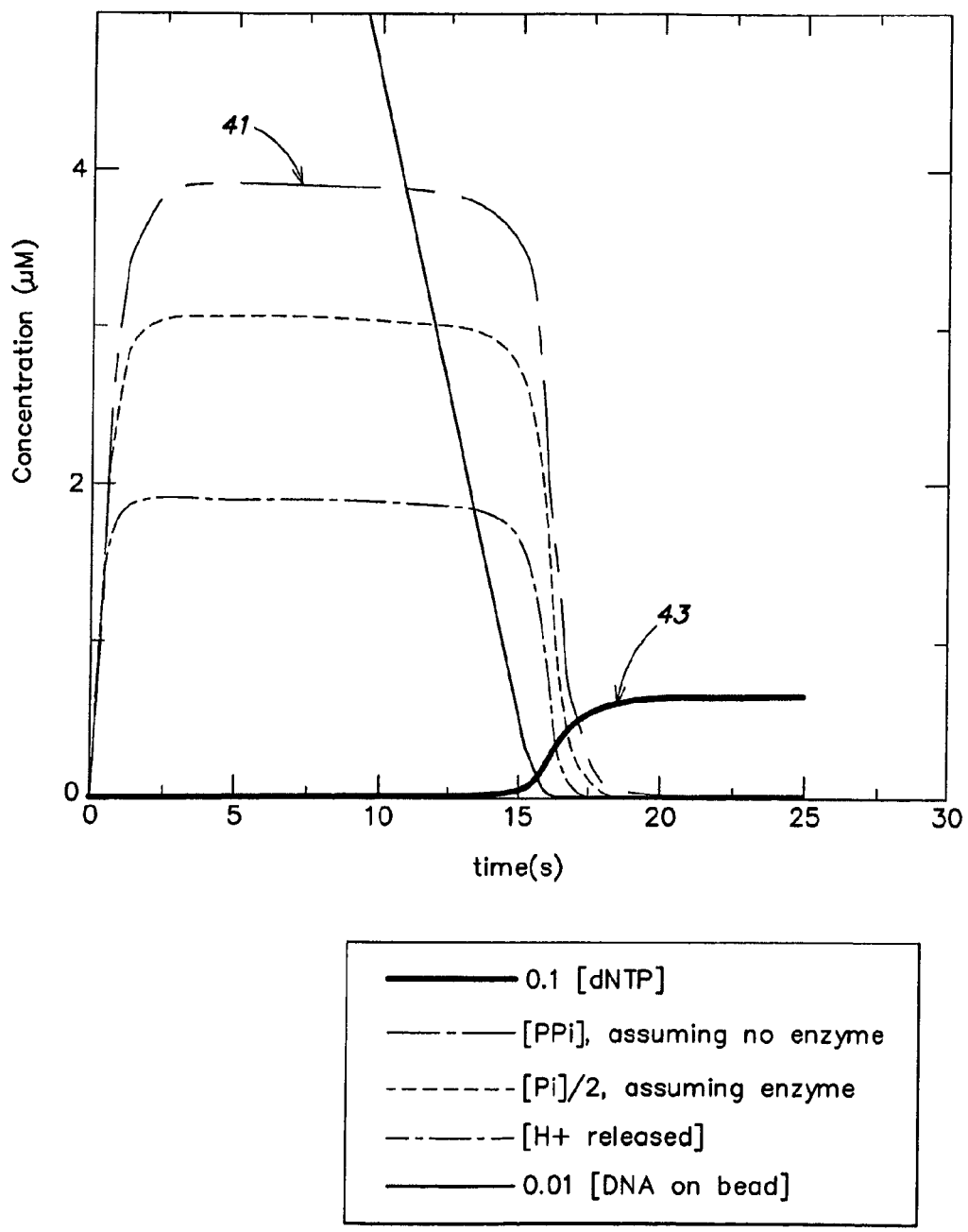
FIG. 8A is a graph illustrating plots of ionized species concentration in proximity of an analyte/passivation layer interface of a chemFET as a function of time for an exemplary nucleic acid sequencing/synthesis reaction according to one embodiment of the present invention.
Figure 8B:
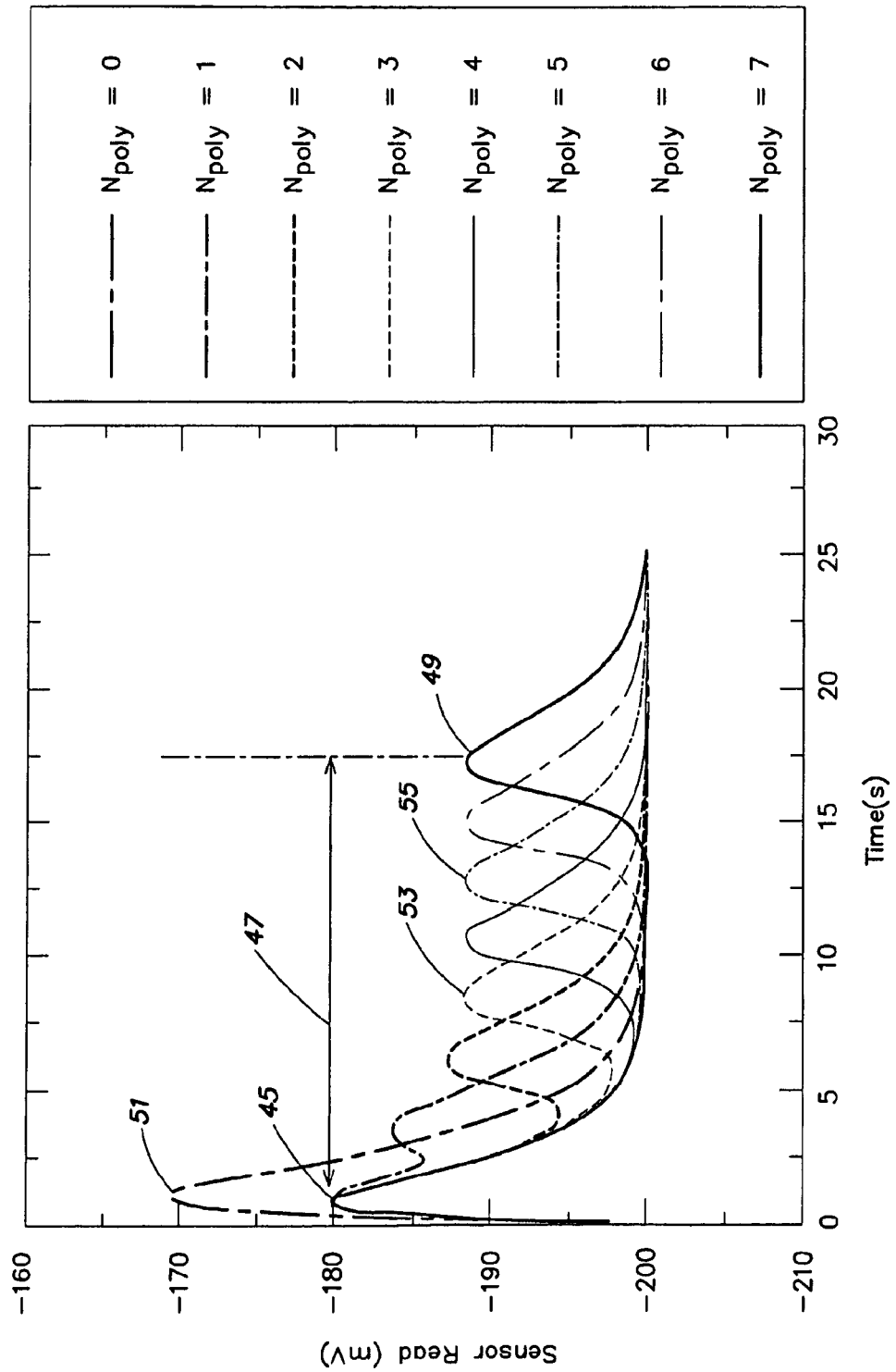
FIG. 8B is a graph illustrating multiple plots of chemFET output voltage as a function of time for exemplary nucleic acid sequencing/synthesis reactions similar to those profiled in FIG. 8A, according to one embodiment of the present invention.

With respect to the specific example of a nucleic acid synthesis or sequencing reaction, in one embodiment an exemplary ISFET of the array 100 may be employed to provide an output signal that includes one or more ion pulses in response to addition of synthesis or sequencing reagents to a corresponding reaction well associated with the ISFET and containing a previously loaded template. With reference to FIGS. 8A and 8B, in an exemplary method according to this embodiment, known nucleotides (i.e., dNTP, where N refers to one of A, C, G, or T) are introduced into a reaction well with appropriate diffusion parameters (discussed further below) in order to initiate the synthesis or sequencing reaction, and the number of ion pulses and the time interval between successive pulses (if multiple pulses are generated) detected in the ISFET output signal provide valuable information about nucleotide incorporation.

More specifically, in a method according to one embodiment for detecting nucleotide incorporation, if one or more of the nucleotides introduced into a reaction well are incorporated upon their introduction, PPi is generated. FIG. 8A is a graph showing the concentration (in μM) of various ionic species as a function of time in the analyte proximate the ISFET analyte/passivation layer interface during a nucleic acid synthesis or sequencing reaction in one exemplary implementation. In the particular example shown in FIG. 8A, the plot 41 indicates PPi concentration as a function of time, and the plot 43 indicates dNTP concentration as a function of time (in seconds). With time t=0 seconds corresponding essentially to an initial concentration increase of PPi, and with particular diffusion parameters for the species of interest, it may be observed that at approximately 15 sec<t<17.5 sec the concentration of PPi suddenly decreases and there is a corresponding increase in the concentration of dNTP. For purposes of the present discussion, each incorporation of a given nucleotide type dNTP upon admission to a reaction well is referred to as an "incorporation event." In the example of FIG. 8A, as discussed further below, multiple incorporation events occur during the time period 0<t<17.5 in which the PPi concentration is elevated.

FIG. 8B is a graph illustrating multiple plots of ISFET output voltage as a function of time for exemplary nucleic acid sequencing/synthesis reactions similar to those profiled in FIG. 8A. With reference to Table 1 above, and Eqs. (3), (4), (5) and (16), it may be appreciated that based on a passivation layer of either silicon dioxide or silicon nitride, for example, and an analyte pH of approximately 8-9, a "baseline" ISFET output voltage on the order of approximately −200 mV is to be expected, as illustrated in FIG. 8B. Given appropriate diffusion parameters of the ionic species involved, the initial generation of PPi proximate to the analyte/passivation layer interface of the ISFET due to one or more incorporation events constitutes a sufficiently fast ionic strength change stimulus I(t), thereby causing a change in the surface potential $\Psi_0$ according to Eq. (23) above and a corresponding change in the ISFET output signal given by Eqs. (3), (4) and (5) above, resulting in an ion pulse in the ISFET output signal. Stated differently, irrespective of the duration of PPi generation due to one or more incorporation events, following initial PPi generation constituting a sufficiently fast stimulus, the analyte/passivation layer interface returns to some steady-state equilibrium, thereby completing the transient response to the initial stimulus and giving rise to a pulse in the ISFET signal, examples of which are illustrated in FIG. 8B. It may be observed generally from FIG. 8B that in one exemplary implementation, the time constant $\tau$ for the decay profile a given ion pulse may be on the order of approximately 2 to 2.5 seconds. However, it should be appreciated that various embodiments of the present invention are not limited to this illustrative example, as the time constant $\tau$ may depend at least in part on material-dependent properties of a given passivation layer as well as the bulk pH of the analyte solution (e.g., as discussed above in connection with Eq. (19)).

In FIG. 8B, a number of different plots for an ISFET output signal as a function of time are indicated, with the legend employing the notation $N_{poly}=x$ (x=0, 1, 2, . . . 7) to indicate the number of incorporation events giving rise to the indicated output signal. All of the plots of output signals corresponding to one or more incorporation events ($N_{poly} \neq 0$) include two pulses whose respective peaks are separated by some time interval. For example, the plot of the output signal including the pulses 45 and 49 separated by the time interval 47 corresponds to the concentration changes illustrated in FIG. 8A and is labeled with the legend notation $N_{poly}=7$, indicating that the time interval 47 in this exemplary implementation represents seven incorporation events.

More specifically, in an exemplary method to detect nucleotide incorporation, if PPi is generated pursuant to one or more incorporation events, at some point incorporation ceases, PPi is no longer generated, and the concentration of unincorporated nucleotide (dNTP) increases, as shown in FIG. 8A by the plot 43. If diffusion parameters are such that the increased concentration of dNTP occurs after completion of the ion pulse due to PPi (i.e., after the analyte/passivation layer interface has reached steady state following the initial PPi stimulus), this increased concentration of unincorporated nucleotide constitutes a second ion stimulus that generates a second ion pulse in the ISFET output signal; again, using the illustrative example of concentration changes shown in FIG. 8A corresponding to seven incorporation events, the plot $N_{p01}=7$ in FIG. 8B includes a first ion pulse 45 corresponding to initial PPi generation, and a second pulse 49 corresponding to the increased concentration of dNTP once incorporation events cease, whose respective peaks are separated by the time interval 47.

More generally, Applicants have recognized and appreciated that for any of the ISFET output signals in FIG. 8B including multiple pulses separated by some time interval, the interval of time between a first ion pulse due to PPi generation and a second ion pulse due to increased concentration of unincorporated nucleotide relates at least in part to the number of incorporation events. As discussed further below, this time interval also may relate at least in part to other parameters including, but not limited to, dimensions of the reaction well, packing density within the well, kinetics of the nucleotide sequencing or synthesis reaction, diffusion coefficients of the involved species, nucleotide concentration, and initial amount of DNA. In addition to the output signal associated with the legend $N_{poly}=7$ in FIG. 8B, for purposes of further illustration a number of other pulses are labeled in FIG. 8B; in particular, the pulse 53 constitutes the second of two pulses in an output signal labeled as $N_{poly}=3$ (i.e., the time interval between the pulse 45 and the pulse 53 corresponds to three incorporation events), and the pulse 55 constitutes the second of two pulses in an output signal labeled as $N_{poly}=5$ (i.e., the time interval between the pulse 45 and the pulse 55 corresponds to five incorporation events).

In another aspect of the foregoing method for detecting nucleotide incorporation, if no nucleotides are incorporated upon introduction of a given nucleotide dNTP into a well, no PPi is generated, and the first and only ion stimulus to the ISFET associated with the well is the rise in concentration of dNTP as it is admitted to the well. As a result, only a single ion pulse is generated, again assuming appropriate diffusion parameters for the dNTP. This situation is illustrated by the output signal labeled as $N_{poly}=0$ in FIG. 8B, which includes only a single pulse 51 in the output signal.

Accordingly, the above-described method provides for significant characterization of the nucleic acid synthesis or sequencing reaction as follows:

1) If only a single ion pulse is present in the ISFET output signal, there is no incorporation of the nucleotide introduced to a reaction well (i.e., only dNTP stimulus);
2) If two successive ion pulses are present in the ISFET output signal, there is incorporation of the nucleotide introduced to the reaction well (i.e., PPi stimulus followed by dNTP stimulus); and
3) The time interval between two successive ion pulses is a function of the number of incorporation events.

In various exemplary implementations of methods pursuant to the various concepts discussed immediately above for nucleotide incorporation detection, it should be appreciated that merely determining whether one or two pulses are present in an ISFET output signal provides useful information regarding nucleotide incorporation. Hence, not all methods according to the present invention need also analyze the time interval between multiple pulses, if present. Again, however, this time interval provides additional useful information relating to the number of incorporation events, and indeed some exemplary implementations analyze not only the number of pulses present in an ISFET output signal but the timing between pulses, in some instances taking into consideration the various diffusion parameters involved for the respective species giving rise to one or more ion pulses.

Regarding the method for nucleotide incorporation detection discussed above, and with reference again to Eq. (17) above, Applicants have recognized and appreciated that various parameters of a nucleic acid synthesis or sequencing reaction may be improved and/or optimized to increase the signal-to-noise ratio (SNR) associated with a given ion pulse in an ISFET output signal (e.g., increase the amplitude $\Delta\Psi_0$ of the ion pulse).

First, it may be appreciated from Eq. (17) that a higher initial equilibrium surface potential $\Psi_1$, (e.g., the steady state surface potential in the presence of a wash buffer before introduction of a given nucleotide dNTP to a reaction well), generally results in a higher amplitude $\Delta\Psi_0$ for an ion pulse. In one aspect, with reference again to Eq. (16), Applicants have appreciated that a higher $\Psi_1$ is facilitated by the selection of a wash buffer having a pH that is significantly different than the $pH_{pzc}$ of the ISFET's passivation layer (i.e., the bulk analyte pH that results in zero charge density at the passivation layer surface). Hence, in various implementations, wash buffers may be appropriately selected based on the type of material employed for the passivation layer.

From Eq. (15), Applicants also have appreciated that a relatively high pH sensitivity ($\Delta\Psi_0/\Delta pH$) of the ISFET also may contribute to a higher $\Psi_1$; in this manner, as discussed above in connection with Eq. (15), a passivation layer material with a large intrinsic buffering capacity $\beta_{int}$ may be desirable, as the dimensionless sensitivity factor $\alpha$ given in Eq. (15) is increased by a large $\beta_{int}$. It should also be appreciated in this regard, however, that a high sensitivity to pH is not necessarily a requirement in the nucleotide incorporation detection method according to the specific embodiment described above, as the method is predicated primarily on detection of PPi and dNTP concentration changes, and not measurement of hydrogen ion concentration per se. This situation underscores the applicability to the method described above of various ISFET array optimization techniques discussed herein based on a consideration of a more limited pH measurement range and reduced linearity requirements (e.g., in consideration of the MOSFET body effect). Of course, methods according to other embodiments of the invention discussed herein indeed may rely on hydrogen ion concentration and concentration changes as reaction indicators. In any case, as noted above, Applicants have appreciated that a relatively high pH sensitivity of the ISFET, even over a significantly limited pH range, may in some instances facilitate an increased amplitude $\Delta\Psi_0$ for an ion pulse and hence an increased SNR of the ISFET output signal.

Additionally, Applicants have appreciated from Eq. (17) that reducing or minimizing the initial double layer capacitance $C_{dl,1}$ due to the initial ionic strength in the analyte solution (i.e., arising from the wash buffer, prior to introduction of dNTP), and/or increasing or maximizing the subsequent double layer capacitance $C_{dl,2}$ arising from the concentration change stimulus (i.e., PPi generation or dNTP increase), also results in a higher amplitude $\Delta\Psi_0$ for an ion pulse. Accordingly, in various implementations, low ionic strength buffers may be appropriately selected to facilitate an increased amplitude $\Delta\Psi_0$ for an ion pulse and hence an increased SNR of the ISFET output signal.

With respect to time resolution, as alluded to above, some aspect of pulse shape as well as the time interval between any two pulses is a function of the time and rate at which various ionic species of interest are generated proximate to the ISFET's analyte/passivation layer interface. Examples of significant parameters in these respects include, but are not limited to, the flow rate at which various constituents of the analyte solution (e.g., various reagents) are admitted to the reaction well, respective and/or collective concentration of various species, amount of template material present in the well, kinetics of the nucleic acid sequencing or synthesis reactions that may occur in the well, and various factors that affect diffusion of species in the reaction well (e.g., diffusion coefficients of various species, geometry/dimensions of the reaction well, presence and size of packing beads, additives to the analyte solution that affect density). Parameters generally relating to time resolution of one or more ion pulses in an ISFET output signal are discussed in greater detail below.

As noted above, the ISFET may be employed to measure steady state pH values, since in some embodiments pH change is proportional to the number of nucleotides incorporated into the newly synthesized nucleic acid strand. In other embodiments discussed in greater detail below, the FET sensor array may be particularly configured for sensitivity to other analytes that may provide relevant information about the chemical reactions of interest. An example of such a modification or configuration is the use of analyte-specific receptors to bind the analytes of interest, as discussed in greater detail herein.

Via an array controller 250 (also under operation of the computer 260), the ISFET array may be controlled so as to acquire data (e.g., output signals of respective ISFETs of the array) relating to analyte detection and/or measurements, and collected data may be processed by the computer 260 to yield meaningful information associated with the processing (including sequencing) of the template nucleic acid.

With respect to the ISFET array 100 of the system 1000 shown in FIG. 8, in one embodiment the array 100 is implemented as an integrated circuit designed and fabricated using standard CMOS processes (e.g., 0.35 micrometer process, 0.18 micrometer process), comprising all the sensors and electronics needed to monitor/measure one or more analytes and/or reactions. With reference again to FIG. 1, one or more reference electrodes 76 to be employed in connection with the ISFET array 100 may be placed in the flow cell 200 (e.g., disposed in "unused" wells of the flow cell) or otherwise exposed to a reference (e.g., one or more of the sequencing reagents 172) to establish a base line against which changes in analyte concentration proximate to respective ISFETs of the array 100 are compared. The reference electrode(s) 76 may be electrically coupled to the array 100, the array controller 250 or directly to the computer 260 to facilitate analyte measurements based on voltage signals obtained from the array 100; in some implementations, the reference electrode(s) may be coupled to an electric ground or other predetermined potential, or the reference electrode voltage may be measured with respect to ground, to establish an electric reference for ISFET output signal measurements, as discussed further below.

The ISFET array 100 is not limited to any particular size, as one- or two-dimensional arrays, including but not limited to as few as two to 256 pixels (e.g., 16 by 16 pixels in a two-dimensional implementation) or as many as 54 mega-pixels (e.g., 7400 by 7400 pixels in a two-dimensional implementation) or even greater may be fabricated and employed for various chemical/biological analysis purposes pursuant to the concepts disclosed herein. In one embodiment of the exemplary system shown in FIG. 8, the individual ISFET sensors of the array may be configured for sensitivity to PPi, unincorporated nucleotides, hydrogen ions, and the like; however, it should also be appreciated that the present disclosure is not limited in this respect, as individual sensors of an ISFET sensor array may be particularly configured for sensitivity to other types of ion concentrations for a variety of applications (materials sensitive to other ions such as sodium, silver, iron, bromine, iodine, calcium, and nitrate, for example, are known).

More generally, a chemFET array according to various embodiments of the present disclosure may be configured for sensitivity to any one or more of a variety of analytes. In one embodiment, one or more chemFETs of an array may be particularly configured for sensitivity to one or more analytes and/or one or more binding events, and in other embodiments different chemFETs of a given array may be configured for sensitivity to different analytes. For example, in one embodiment, one or more sensors (pixels) of the array may include a first type of chemFET configured to be sensitive to a first analyte, and one or more other sensors of the array may include a second type of chemFET configured to be sensitive to a second analyte different from the first analyte. In one exemplary implementation, both a first and a second analyte may indicate a particular reaction such as for example nucleotide incorporation in a sequencing-by-synthesis method. Of course, it should be appreciated that more than two different types of chemFETs may be employed in any given array to detect and/or measure different types of analytes and/or other reactions. In general, it should be appreciated in any of the embodiments of sensor arrays discussed herein that a given sensor array may be "homogeneous" and include chemFETs of substantially similar or identical types to detect and/or measure a same type of analyte (e.g., pH or other ion concentration), or a sensor array may be "heterogeneous" and include chemFETs of different types to detect and/or measure different analytes. For simplicity of discussion, again the example of an ISFET is discussed below in various embodiments of sensor arrays, but the present disclosure is not limited in this respect, and several other options for analyte sensitivity are discussed in further detail below (e.g., in connection with FIG. 11A).

The chemFET arrays configured for sensitivity to any one or more of a variety of analytes may be disposed in electronic chips, and each chip may be configured to perform one or more different biological reactions. The electronic chips can be connected to the portions of the above-described system which read the array output by means of pins coded in a manner such that the pins convey information to the system as to characteristics of the array and/or what kind of biological reaction(s) is(are) to be performed on the particular chip.

In one embodiment, the invention encompasses an electronic chip configured for conducting biological reactions thereon, comprising one or more pins for delivering information to a circuitry identifying a characteristic of the chip and/or a type of reaction to be performed on the chip. Such t may include, but are not limited to, a short nucleotide polymorphism detection, short tandem repeat detection, or sequencing.

In another embodiment, the invention encompasses a system adapted to performing more than one biological reaction on a chip comprising: a chip receiving module adapted for receiving the chip; and a receiver for detecting information from the electronic chip, wherein the information determines a biological reaction to be performed on the chip. Typically, the system further comprises one or more reagents to perform the selected biological reaction.

In another embodiment, the invention encompasses an apparatus for sequencing a polymer template comprising: at least one integrated circuit that is configured to relay information about spatial location of a reaction chamber, type of monomer added to the spatial location, time required to complete reaction of a reagent comprising a plurality of the monomers with an elongating polymer.

In exemplary implementations based on 0.35 micrometer CMOS processing techniques (or CMOS processing techniques capable of smaller feature sizes), each pixel of the ISFET array 100 may include an ISFET and accompanying enable/select components, and may occupy an area on a surface of the array of approximately ten micrometers by ten micrometers (i.e., 100 micrometers$^2$) or less; stated differently, arrays having a pitch (center of pixel-to-center of pixel spacing) on the order of 10 micrometers or less may be realized. An array pitch on the order of 10 micrometers or less using a 0.35 micrometer CMOS processing technique constitutes a significant improvement in terms of size reduction with respect to prior attempts to fabricate ISFET arrays, which resulted in pixel sizes on the order of at least 12 micrometers or greater.

More specifically, in some embodiments discussed further below based on the inventive concepts disclosed herein, an array pitch of approximately nine (9) micrometers allows an ISFET array including over 256,000 pixels (e.g., a 512 by 512 array), together with associated row and column select and bias/readout electronics, to be fabricated on a 7 millimeter by 7 millimeter semiconductor die, and a similar sensor array including over four million pixels (e.g., a 2048 by 2048 array yielding over 4 Mega-pixels) to be fabricated on a 21 millimeter by 21 millimeter die. In other examples, an array pitch of approximately 5 micrometers allows an ISFET array including approximately 1.55 Mega-pixels (e.g., a 1348 by 1152 array) and associated electronics to be fabricated on a 9 millimeter by 9 millimeter die, and an ISFET sensor array including over 14 Mega-pixels and associated electronics on a 22 millimeter by 20 millimeter die. In yet other implementations, using a CMOS fabrication process in which feature sizes of less than 0.35 micrometers are possible (e.g., 0.18 micrometer CMOS processing techniques), ISFET sensor arrays with a pitch significantly below 5 micrometers may be fabricated (e.g., array pitch of 2.6 micrometers or pixel area of less than 8 or 9 micrometers$^2$), providing for significantly dense ISFET arrays. Of course, it should be appreciated that pixel sizes greater than 10 micrometers (e.g., on the order of approximately 20, 50, 100 micrometers or greater) may be implemented in various embodiments of chemFET arrays according to the present disclosure also.

As will be understood by those of skill in the art, the ability to miniaturize sequencing reactions reduces the time, cost and labor involved in sequencing of large genomes (such as the human genome).

In other aspects of the system shown in FIG. 8, one or more array controllers 250 may be employed to operate the ISFET array 100 (e.g., selecting/enabling respective pixels of the array to obtain output signals representing analyte measurements). In various implementations, one or more components constituting one or more array controllers may be implemented together with pixel elements of the arrays themselves, on the same integrated circuit (IC) chip as the array but in a different portion of the IC chip, or off-chip. In connection with array control, analog-to-digital conversion of ISFET output signals may be performed by circuitry implemented on the same integrated circuit chip as the ISFET array, but located outside of the sensor array region (locating the analog to digital conversion circuitry outside of the sensor array region allows for smaller pitch and hence a larger number of sensors, as well as reduced noise). In various exemplary implementations discussed further below, analog-to-digital conversion can be 4-bit, 8-bit, 12-bit, 16-bit or other bit resolutions depending on the signal dynamic range required.

As used herein, an array is planar arrangement of elements such as sensors or wells. The array may be one or two dimensional. A one dimensional array is an array having one column (or row) of elements in the first dimension and a plurality of columns (or rows) in the second dimension. An example of a one dimensional array is a 1×5 array. A two dimensional array is an array having a plurality of columns (or rows) in both the first and the second dimension. The number of columns (or rows) in the first and second dimensions may or may not be the same. An example of a two dimensional array is a 5×10 array.

Having provided a general overview of the role of a chemFET (e.g., ISFET) array 100 in an exemplary system 1000 for measuring one or more analytes, following below are more detailed descriptions of exemplary chemFET arrays according to various inventive embodiments of the present disclosure that may be employed in a variety of applications. Again, for purposes of illustration, chemFET arrays according to the present disclosure are discussed below using the particular example of an ISFET array, but other types of chemFETs may be employed in alternative embodiments. Also, again, for purposes of illustration, chemFET arrays are discussed in the context of nucleic acid sequencing applications, however, the invention is not so limited and rather contemplates a variety of applications for the chemFET arrays described herein.

As noted above, various inventive embodiments disclosed herein specifically improve upon the ISFET array design of Milgrew et al. discussed above in connection with FIGS. 1-7, as well as other prior ISFET array designs, so as to significantly reduce pixel size and array pitch, and thereby increase the number of pixels of an ISFET array for a given semiconductor die size (i.e., increase pixel density). In some implementations, an increase in pixel density is accomplished while at the same time increasing the signal-to-noise ratio (SNR) of output signals corresponding to respective measurements relating to one or more analytes and the speed with which such output signals may be read from the array. In particular, Applicants have recognized and appreciated that by relaxing requirements for ISFET linearity and focusing on a more limited signal output/measurement range (e.g., signal outputs corresponding to a pH range of from approximately 7 to 9 or smaller rather than 1 to 14, as well as output signals that may not necessarily relate significantly to pH changes in sample), individual pixel complexity and size may be significantly reduced, thereby facilitating the realization of very large scale dense ISFET arrays.

Figure 9:
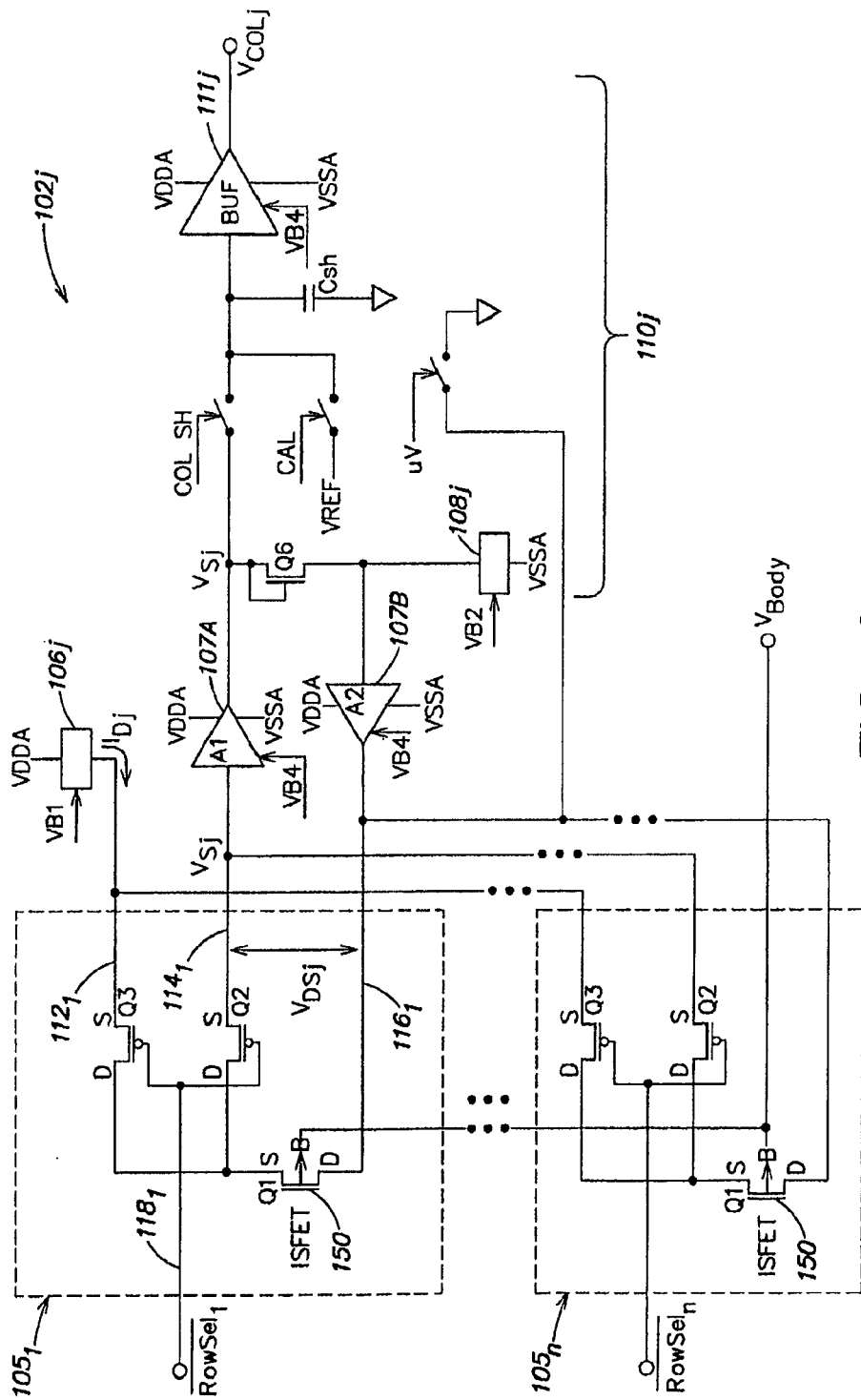
FIG. 9 illustrates one column of an chemFET array similar to that shown in FIG. 8, according to one inventive embodiment of the present disclosure.

To this end, FIG. 9 illustrates one column $102_j$ of an ISFET array 100, according to one inventive embodiment of the present disclosure, in which ISFET pixel design is appreciably simplified to facilitate small pixel size. The column $102_j$ includes n pixels, the first and last of which are shown in FIG. 9 as the pixels $105_1$ and $105_n$. As discussed further below in connection with FIG. 13, a complete two-dimensional ISFET array 100 based on the column design shown in FIG. 9 includes m such columns $102_j$ (j=1, 2, 3, . . . m) with successive columns of pixels generally arranged side by side. Of course, the ISFETs may be arrayed in other than a row-column grid, such as in a honeycomb pattern.

In one aspect of the embodiment shown in FIG. 9, each pixel $105_1$ through $105_n$ of the column $102_j$ includes only three components, namely, an ISFET 150 (also labeled as Q1) and two MOSFET switches Q2 and Q3. The MOSFET switches Q2 and Q3 are both responsive to one of n row select signals ($\overline{RowSel_1}$ through $\overline{RowSel_n}$, logic low active) so as to enable or select a given pixel of the column $102_j$. Using pixel $105_1$ as an example that applies to all pixels of the column, the transistor switch Q3 couples a controllable current source $106_j$ via the line $112_1$ to the source of the ISFET 150 upon receipt of the corresponding row select signal via the line $118_1$. The transistor switch Q2 couples the source of the ISFET 150 to column bias/readout circuitry $110_j$ via the line $114_1$ upon receipt of the corresponding row select signal. The drain of the ISFET 150 is directly coupled via the line $116_1$ to the bias/readout circuitry $110_j$. Thus, only four signal lines per pixel, namely the lines $112_1$, $114_1$, $116_1$ and $118_1$, are required to operate the three components of the pixel $105_1$. In an array of m columns, a given row select signal is applied simultaneously to one pixel of each column (e.g., at same positions in respective columns).

Figure 3:
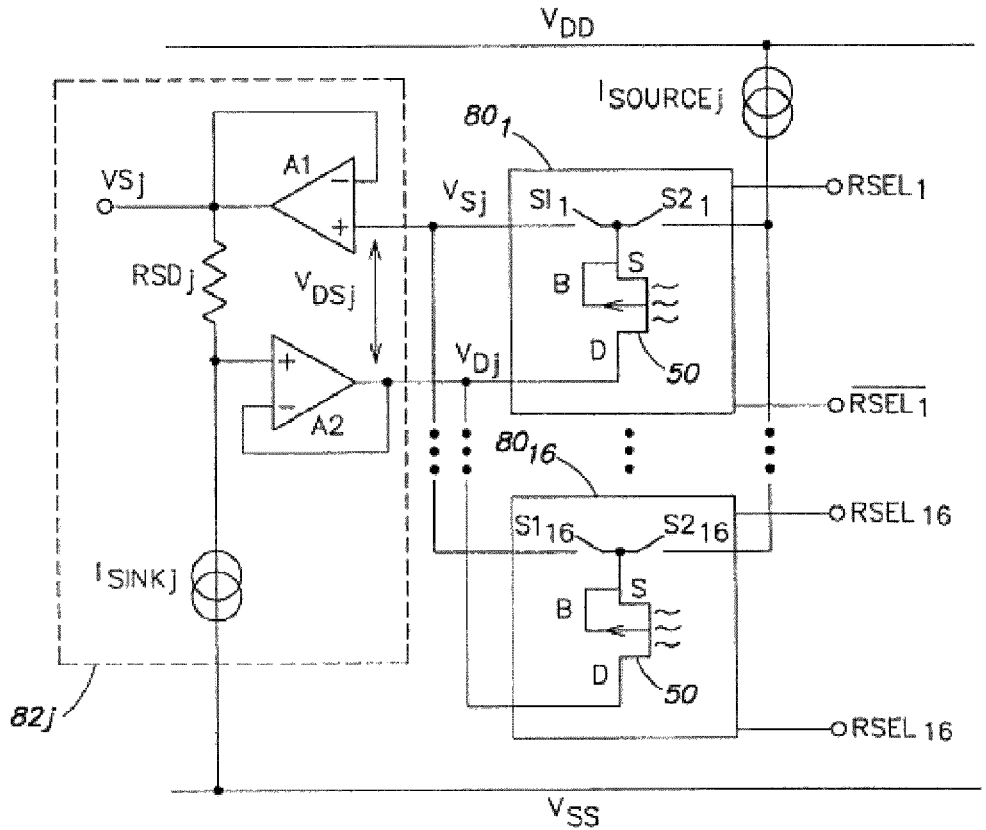
FIG. 3 illustrates one column of a two-dimensional ISFET array based on the ISFET shown in FIG. 1.

As illustrated in FIG. 9, the design for the column $102_j$ according to one embodiment is based on general principles similar to those discussed above in connection with the column design of Milgrew et al. shown FIG. 3. In particular, the ISFET of each pixel, when enabled, is configured with a constant drain current $I_{Dj}$ and a constant drain-to-source voltage $V_{DSj}$ to obtain an output signal $V_{Sj}$ from an enabled pixel according to Eq. (3) above. To this end, the column $102_j$ includes a controllable current source $106_j$, coupled to an analog circuitry positive supply voltage VDDA and responsive to a bias voltage VB1, that is shared by all pixels of the column to provide a constant drain current $I_{Dj}$ to the ISFET of an enabled pixel. In one aspect, the current source $106_j$ is implemented as a current mirror including two long-channel length and high output impedance MOSFETs. The column also includes bias/readout circuitry $110_j$ that is also shared by all pixels of the column to provide a constant drain-to-source voltage to the ISFET of an enabled pixel. The bias/readout circuitry 110 is based on a Kelvin Bridge configuration and includes two operational amplifiers 107A (A1) and 107B (A2) configured as buffer amplifiers and coupled to analog circuitry positive supply voltage VDDA and the analog supply voltage ground VSSA. The bias/readout circuitry also includes a controllable current sink $108_j$ (similar to the current source $106j$) coupled to the analog ground VSSA and responsive to a bias voltage VB2, and a diode-connected MOSFET Q6. The bias voltages VB1 and VB2 are set/controlled in tandem to provide a complimentary source and sink current. The voltage developed across the diode-connected MOSFET Q6 as a result of the current drawn by the current sink $108_j$ is forced by the operational amplifiers to appear across the drain and source of the ISFET of an enabled pixel as a constant drain-source voltage $V_{DSj}$.

By employing the diode-connected MOSFET Q6 in the bias/readout circuitry 110 of FIG. 9, rather than the resistor $R_{SDj}$ as shown in the design of Milgrew et al. illustrated in FIG. 3, a significant advantage is provided in a CMOS fabrication process; specifically, matching resistors can be fabricated with error tolerances generally on the order of ±20%, whereas MOSFET matching in a CMOS fabrication process is on the order of ±1% or better. The degree to which the component responsible for providing a constant ISFET drain-to-source voltage $V_{DSj}$ can be matched from column to column significantly affects measurement accuracy (e.g., offset) from column to column. Thus, employing the MOSFET Q6 rather than a resistor appreciably mitigates measurement offsets from column-to-column. Furthermore, whereas the thermal drift characteristics of a resistor and an ISFET may be appreciably different, the thermal drift characteristics of a MOSFET and ISFET are substantially similar, if not virtually identical; hence, any thermal drift in MOSFET Q6 virtually cancels any thermal drift from ISFET Q1, resulting in greater measurement stability with changes in array temperature.

In FIG. 9, the column bias/readout circuitry $110j$ also includes sample/hold and buffer circuitry to provide an output signal $V_{COLj}$ from the column. In particular, after one of the pixels $105_1$ through $105_n$ is enabled or selected via the transistors Q2 and Q3 in each pixel, the output of the amplifier 107A (A1), i.e., a buffered $V_{Sj}$, is stored on a column sample and hold capacitor $C_{sh}$, via operation of a switch (e.g., a transmission gate) responsive to a column sample and hold signal COL SH. Examples of suitable capacitances for the sample and hold capacitor include, but are not limited to, a range of from approximately 500 fF to 2 pF. The sampled voltage is buffered via a column output buffer amplifier 111j (BUF) and provided as the column output signal $V_{COLj}$. As also shown in FIG. 9, a reference voltage VREF may be applied to the buffer amplifier 111j, via a switch responsive to a control signal CAL, to facilitate characterization of column-to-column non-uniformities due to the buffer amplifier 111j and thus allow post-read data correction.

Figure 9A:
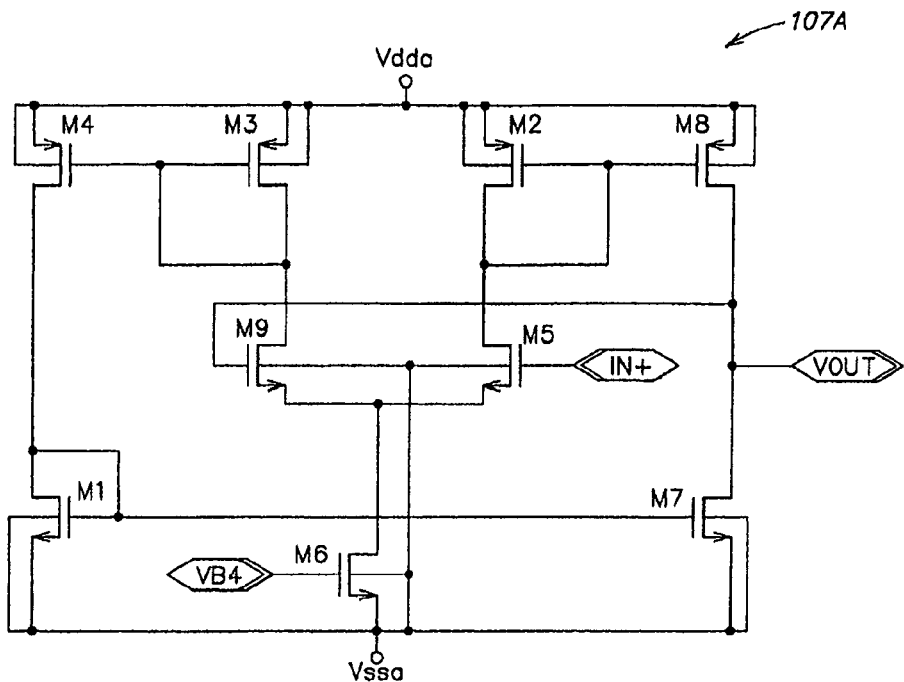
FIG. 9A illustrates a circuit diagram for an exemplary amplifier employed in the array column shown in FIG. 9.
Figure 9B:
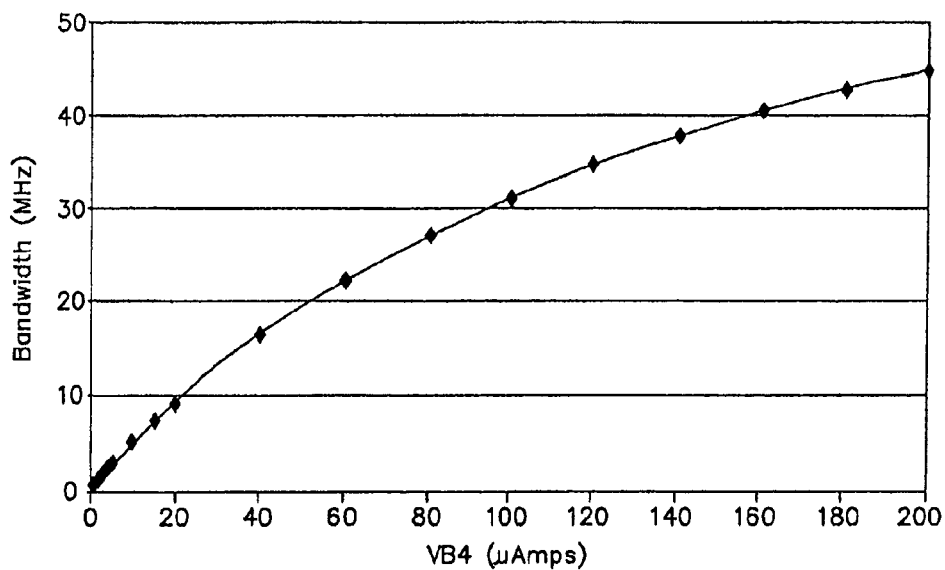
FIG. 9B is a graph of amplifier bias vs. bandwidth, according to one inventive embodiment of the present disclosure.

FIG. 9A illustrates an exemplary circuit diagram for one of the amplifiers 107A of the bias/readout circuitry 110j (the amplifier 107B is implemented identically), and FIG. 9B is a graph of amplifier bias vs. bandwidth for the amplifiers 107A and 107B. As shown in FIG. 9A, the amplifier 107A employs an arrangement of multiple current mirrors based on nine MOSFETs (M1 through M9) and is configured as a unity gain buffer, in which the amplifier's inputs and outputs are labeled for generality as IN+ and VOUT, respectively. The bias voltage VB4 (representing a corresponding bias current) controls the transimpedance of the amplifier and serves as a bandwidth control (i.e., increased bandwidth with increased current).

With reference again to FIG. 9, due to the sample and hold capacitor $C_{sh}$, the output of the amplifier 107A essentially drives a filter when the sample and hold switch is closed. Accordingly, to achieve appreciably high data rates, the bias voltage VB4 may be adjusted to provide higher bias currents and increased amplifier bandwidth. From FIG. 9B, it may be observed that in some exemplary implementations, amplifier bandwidths of at least 40 MHz and significantly greater may be realized. In some implementations, amplifier bandwidths as high as 100 MHz may be appropriate to facilitate high data acquisition rates and relatively lower pixel sample or "dwell" times (e.g., on the order of 10 to 20 microseconds).

In another aspect of the embodiment shown in FIG. 9, unlike the pixel design of Milgrew et al. shown in FIG. 3, the pixels $105_1$ through $105_n$ do not include any transmission gates or other devices that require both n-channel and p-channel FET components; in particular, the pixels $105_1$ through $105_n$ of this embodiment include only FET devices of a same type (i.e., only n-channel or only p-channel). For purposes of illustration, the pixels $105_1$ and $105_n$ illustrated in FIG. 9 are shown as comprising only p-channel components, i.e., two p-channel MOSFETs Q2 and Q3 and a p-channel ISFET 150. By not employing a transmission gate to couple the source of the ISFET to the bias/readout circuitry $110_j$, some dynamic range for the ISFET output signal (i.e., the ISFET source voltage $V_S$) may be sacrificed. However, Applicants have recognized and appreciated that by potentially foregoing some output signal dynamic range (and thereby potentially limiting measurement range for a given static and/or dynamic chemical property, such as pH or concentration changes of other ion species), the requirement of different type FET devices (both n-channel and p-channel) in each pixel may be eliminated and the pixel component count reduced. As discussed further below in connection with FIGS. 10-12, this significantly facilitates pixel size reduction. Thus, in one aspect, there is a beneficial tradeoff between reduced dynamic range and smaller pixel size.

In yet another aspect of the embodiment shown in FIG. 9, unlike the pixel design of Milgrew et al., the ISFET 150 of each pixel $105_1$ through $105_n$ does not have its body connection tied to its source (i.e., there is no electrical conductor coupling the body connection and source of the ISFET such that they are forced to be at the same electric potential during operation). Rather, the body connections of all ISFETs of the array are tied to each other and to a body bias voltage $V_{BODY}$. While not shown explicitly in FIG. 9, the body connections for the MOSFETs Q2 and Q3 likewise are not tied to their respective sources, but rather to the body bias voltage $V_{BODY}$. In one exemplary implementation based on pixels having all p-channel components, the body bias voltage $V_{BODY}$ is coupled to the highest voltage potential available to the array (e.g., VDDA), as discussed further below in connection with FIG. 17.

By not tying the body connection of each ISFET to its source, the possibility of some non-zero source-to-body voltage $V_{SB}$ may give rise to the "body effect," as discussed above in connection with FIG. 1, which affects the threshold voltage $V_{TH}$ of the ISFET according to a nonlinear relationship (and thus, according to Eqs. (3), (4) and (5) may affect detection and/or measurement of analyte activity giving rise to surface potential changes at the analyte/passivation layer interface). However, Applicants have recognized and appreciated that by focusing on a reduced ISFET output signal dynamic range, any body effect that may arise in the ISFET from a non-zero source-to-body voltage may be relatively minimal. Thus, any measurement nonlinearity that may result over the reduced dynamic range may be ignored as insignificant or taken into consideration and compensated (e.g., via array calibration and data processing techniques, as discussed further below in connection with FIG. 17). Applicants have also recognized and appreciated that by not tying each ISFET source to its body connection, all of the FETs constituting the pixel may share a common body connection, thereby further facilitating pixel size reduction, as discussed further below in connection with FIGS. 10-12. Accordingly, in another aspect, there is a beneficial tradeoff between reduced linearity and smaller pixel size.

Figure 10:
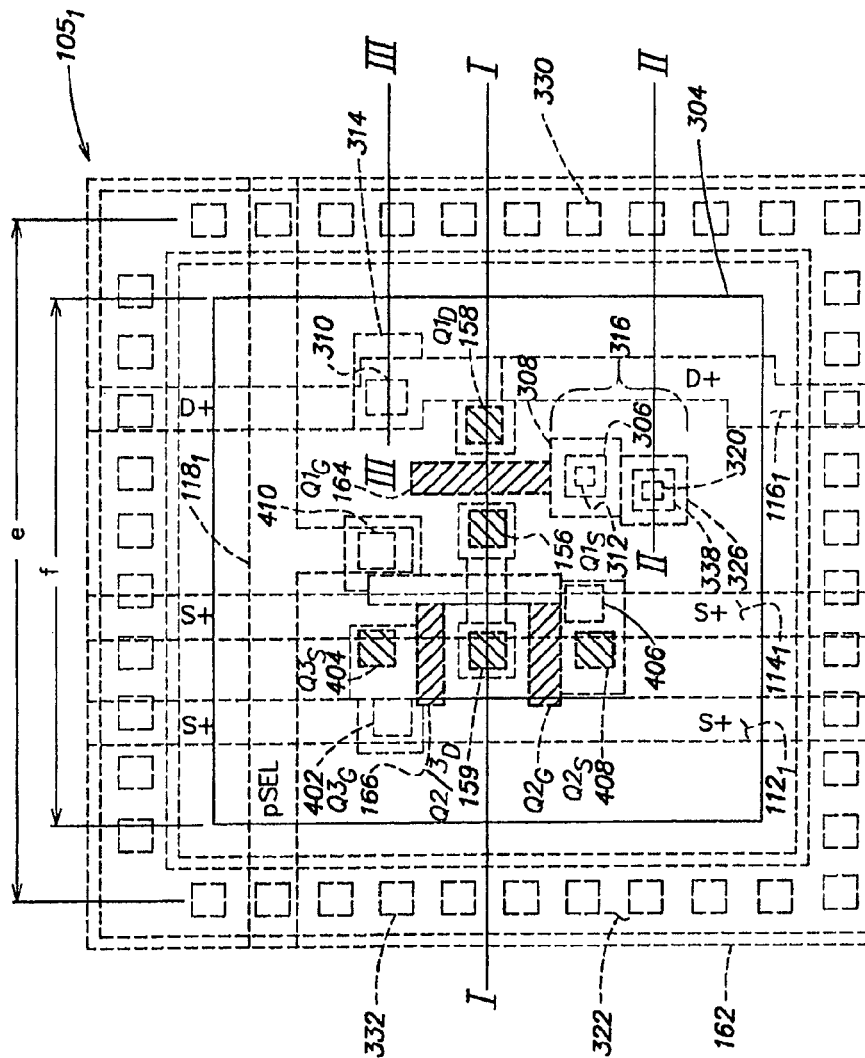
FIG. 10 illustrates a top view of a chip layout design for a pixel of the column of an chemFET array shown in FIG. 9, according to one inventive embodiment of the present disclosure.
Figures 1, 10:
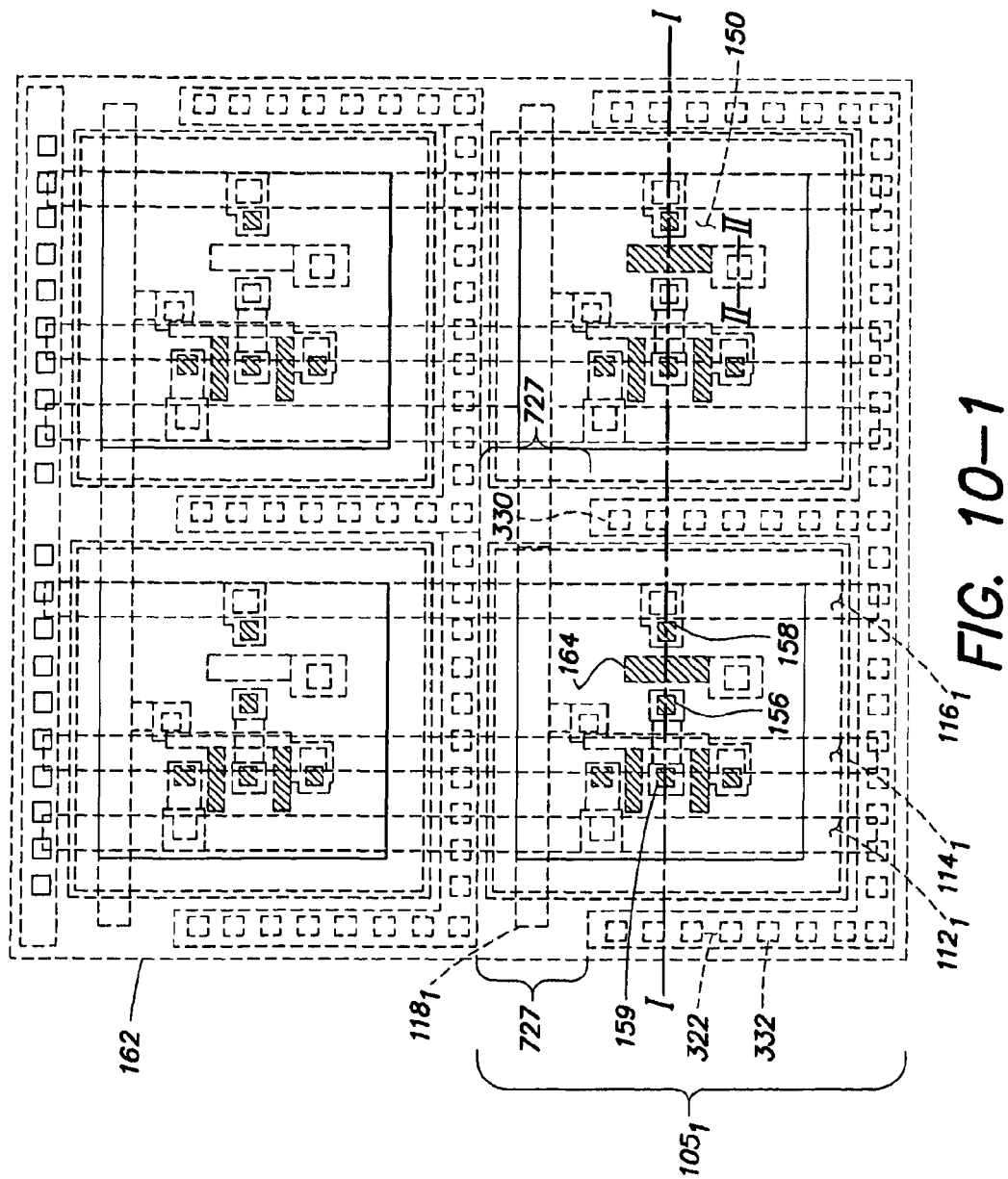
Figure 11A:
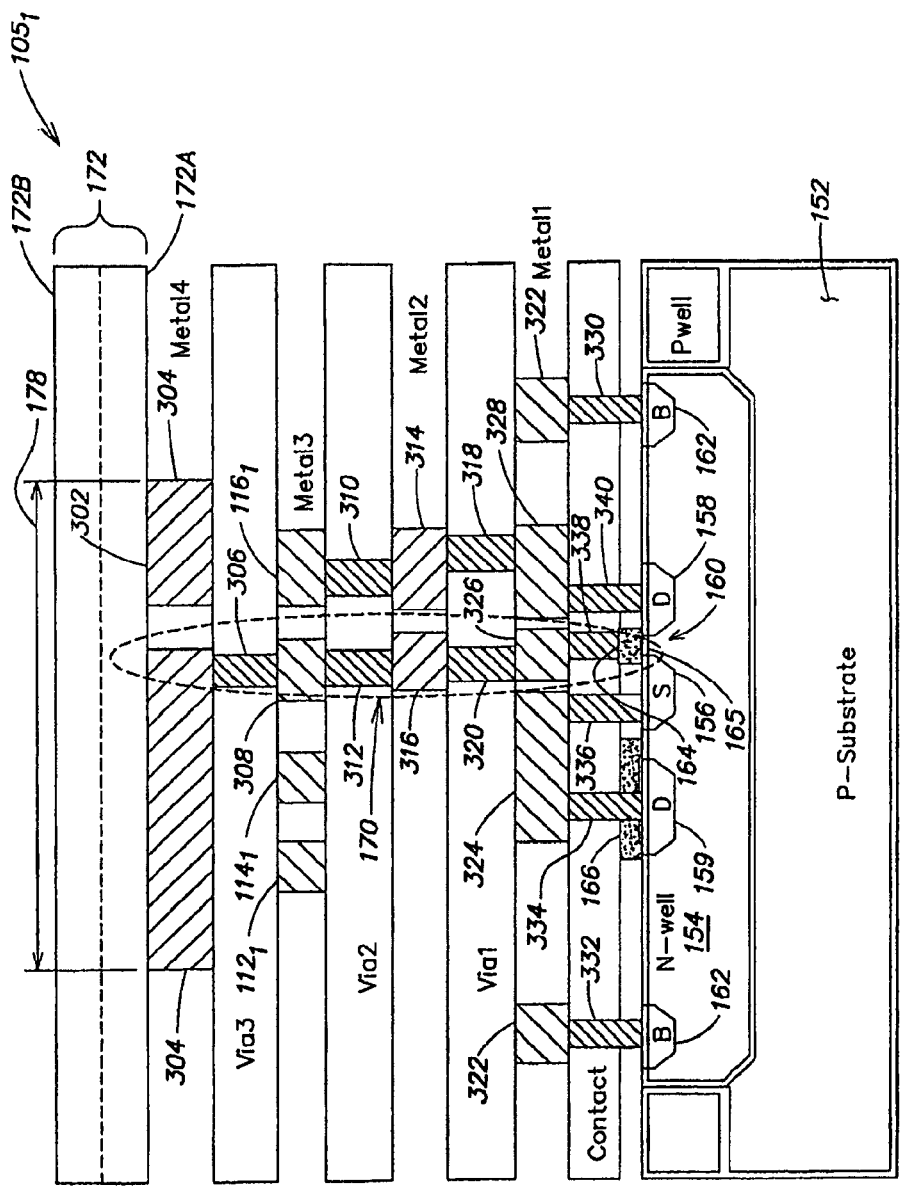
FIG. 11A shows a composite cross-sectional view along the line I-I of the pixel shown in FIG. 10, including additional elements on the right half of FIG. 10 between the lines II-II and III-III, illustrating a layer-by-layer view of the pixel fabrication according to one inventive embodiment of the present disclosure.

FIG. 10 illustrates a top view of a chip layout design for the pixel $105_1$ shown in FIG. 9, according to one inventive embodiment of the present disclosure. FIG. 11A shows a composite cross-sectional view along the line I-I of the pixel shown in FIG. 10, including additional elements on the right half of FIG. 10 between the lines II-II and III-III, illustrating a layer-by-layer view of the pixel fabrication, and FIGS. 12A through 12L provide top views of each of the fabrication layers shown in FIG. 11A (the respective images of FIGS. 12A through 12L are superimposed one on top of another to create the pixel chip layout design shown in FIG. 10). In one exemplary implementation, the pixel design illustrated in FIGS. 10-12 may be realized using a standard 4-metal, 2-poly, 0.35 micrometer CMOS process to provide a geometrically square pixel having a dimension "e" as shown in FIG. 10 of approximately 9 micrometers, and a dimension "f" corresponding to the ISFET sensitive area of approximately 7 micrometers.

In the top view of FIG. 10, the ISFET 150 (labeled as Q1 in FIG. 10) generally occupies the right center portion of the pixel illustration, and the respective locations of the gate, source and drain of the ISFET are indicated as $Q1_G$, $Q1_S$ and $Q1_D$. The MOSFETs Q2 and Q3 generally occupy the left center portion of the pixel illustration; the gate and source of the MOSFET Q2 are indicated as $Q2_G$ and $Q2_S$, and the gate and source of the MOSFET Q3 are indicated as $Q3_G$ and $Q3_S$. In one aspect of the layout shown in FIG. 10, the MOSFETs Q2 and Q3 share a drain, indicated as $Q2/3_D$. In another aspect, it may be observed generally from the top view of FIG. 10 that the ISFET is formed such that its channel lies along a first axis of the pixel (e.g., parallel to the line I-I), while the MOSFETs Q2 and Q3 are formed such that their channels lie along a second axis perpendicular to the first axis. FIG. 10 also shows the four lines required to operate the pixel, namely, the line $112_1$ coupled to the source of Q3, the line $114_1$ coupled to the source of Q2, the line $116_1$ coupled to the drain of the ISFET, and the row select line $118_1$ coupled to the gates of Q2 and Q3. With reference to FIG. 9, it may be appreciated that all pixels in a given column share the lines 112, 114 and 116 (e.g., running vertically across the pixel in FIG. 10), and that all pixels in a given row share the line 118 (e.g., running horizontally across the pixel in FIG. 10); thus, based on the pixel design of FIG. 9 and the layout shown in FIG. 10, only four metal lines need to traverse each pixel.

With reference now to the cross-sectional view of FIG. 11A, highly doped p-type regions 156 and 158 (lying along the line I-I in FIG. 10) in n-well 154 constitute the source (S) and drain (D) of the ISFET, between which lies a region 160 of the n-well in which the ISFETs p-channel is formed below the ISFETs polysilicon gate 164 and a gate oxide 165. According to one aspect of the inventive embodiment shown in FIGS. 10 and 11, all of the FET components of the pixel $105_1$ are fabricated as p-channel FETs in the single n-type well 154 formed in a p-type semiconductor substrate 152. This is possible because, unlike the design of Milgrew et al., 1) there is no requirement for a transmission gate in the pixel; and 2) the ISFETs source is not tied to the n-well's body connection. More specifically, highly doped n-type regions 162 provide a body connection (B) to the n-well 154 and, as shown in FIG. 10, the body connection B is coupled to a metal conductor 322 around the perimeter of the pixel 105$_1$. However, the body connection is not directly electrically coupled to the source region 156 of the ISFET (i.e., there is no electrical conductor coupling the body connection and source such that they are forced to be at the same electric potential during operation), nor is the body connection directly electrically coupled to the gate, source or drain of any component in the pixel. Thus, the other p-channel FET components of the pixel, namely Q2 and Q3, may be fabricated in the same n-well 154.

In the composite cross-sectional view of FIG. 11A, a highly doped p-type region 159 is also visible (lying along the line I-I in FIG. 10), corresponding to the shared drain (D) of the MOSFETs Q2 and Q3. For purposes of illustration, a polysilicon gate 166 of the MOSFET Q3 also is visible in FIG. 11A, although this gate does not lie along the line I-I in FIG. 10, but rather "behind the plane" of the cross-section along the line I-I. However, for simplicity, the respective sources of the MOSFETs Q2 and Q3 shown in FIG. 10, as well as the gate of Q2, are not visible in FIG. 11A, as they lie along the same axis (i.e., perpendicular to the plane of the figure) as the shared drain (if shown in FIG. 11A, these elements would unduly complicate the composite cross-sectional view of FIG. 11A).

Above the substrate, gate oxide, and polysilicon layers shown in FIG. 11A, a number of additional layers are provided to establish electrical connections to the various pixel components, including alternating metal layers and oxide layers through which conductive vias are formed. Pursuant to the example of a 4-Metal CMOS process, these layers are labeled in FIG. 11A as "Contact," "Metal1," "Via1," "Metal2," "Via2," "Metal3," "Via3," and "Metal4." (Note that more or fewer metal layers may be employed.) To facilitate an understanding particularly of the ISFET electrical connections, the composite cross-sectional view of FIG. 11A shows additional elements of the pixel fabrication on the right side of the top view of FIG. 10 between the lines II-II and III-III. With respect to the ISFET electrical connections, the topmost metal layer 304 corresponds to the ISFETs sensitive area 178, above which is disposed an analyte-sensitive passivation layer 172. The topmost metal layer 304, together with the ISFET polysilicon gate 164 and the intervening conductors 306, 308, 312, 316, 320, 326 and 338, form the ISFETs "floating gate" structure 170, in a manner similar to that discussed above in connection with a conventional ISFET design shown in FIG. 1. An electrical connection to the ISFETs drain is provided by the conductors 340, 328, 318, 314 and 310 coupled to the line 116$_1$. The ISFETs source is coupled to the shared drain of the MOSFETs Q2 and Q3 via the conductors 334 and 336 and the conductor 324 (which lies along the line I-I in FIG. 10). The body connections 162 to the n-well 154 are electrically coupled to a metal conductor 322 around the perimeter of the pixel on the "Metal1" layer via the conductors 330 and 332.

As indicated above, FIGS. 12A through 12L provide top views of each of the fabrication layers shown in FIG. 11A (the respective images of FIGS. 12A through 12L are superimposed one on top of another to create the pixel chip layout design shown in FIG. 10). In FIG. 12, the correspondence between the lettered top views of respective layers and the cross-sectional view of FIG. 11A is as follows: A) n-type well 154; B) Implant; C) Diffusion; D) polysilicon gates 164 (ISFET) and 166 (MOSFETs Q2 and Q3); E) contacts; F) Metal1; G) Via1; H) Metal2; I) Via2; J) Metal3; K) Via3; L) Metal4 (top electrode contacting ISFET gate). The various reference numerals indicated in FIGS. 12A through 12L correspond to the identical features that are present in the composite cross-sectional view of FIG. 11A.

Applicants have recognized and appreciated that, at least in some applications, pixel capacitance may be a salient parameter for some type of analyte measurements. Accordingly, in another embodiment related to pixel layout and design, various via and metal layers may be reconfigured so as to at least partially mitigate the potential for parasitic capacitances to arise during pixel operation. For example, in one such embodiment, pixels are designed such that there is a greater vertical distance between the signal lines 112$_1$, 114$_1$, 116$_1$ and 118$_1$, and the topmost metal layer 304 constituting the floating gate structure 170.

In the embodiment described immediately above, with reference again to FIG. 11A, it may be readily observed that the topmost metal layer 304 is formed in the Metal4 layer (also see FIG. 12L), and the signal lines 112$_1$, 114$_1$, and 116$_1$ are formed in the Metal3 layer (also see FIG. 12J). Also, while not visible in the view of FIG. 11A, it may be observed from FIG. 12H that the signal line 118$_1$ is formed in the Metal2 layer. As one or more of these signals may be grounded from time to time during array operation, a parasitic capacitance may arise between any one or more of these signal lines and metal layer 304. By increasing a distance between these signal lines and the metal layer 304, such parasitic capacitance may be reduced.

Figure 12:
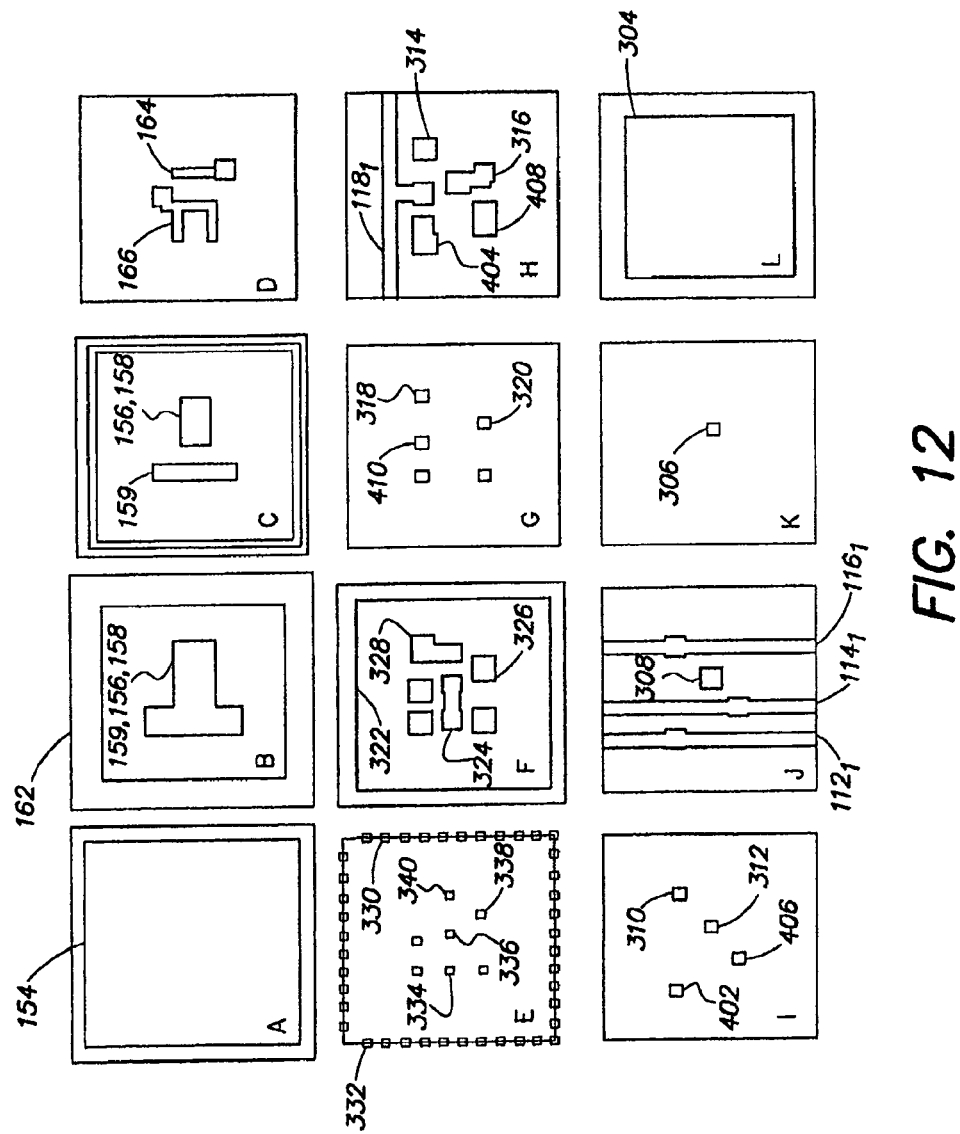
Figures 1, 12:
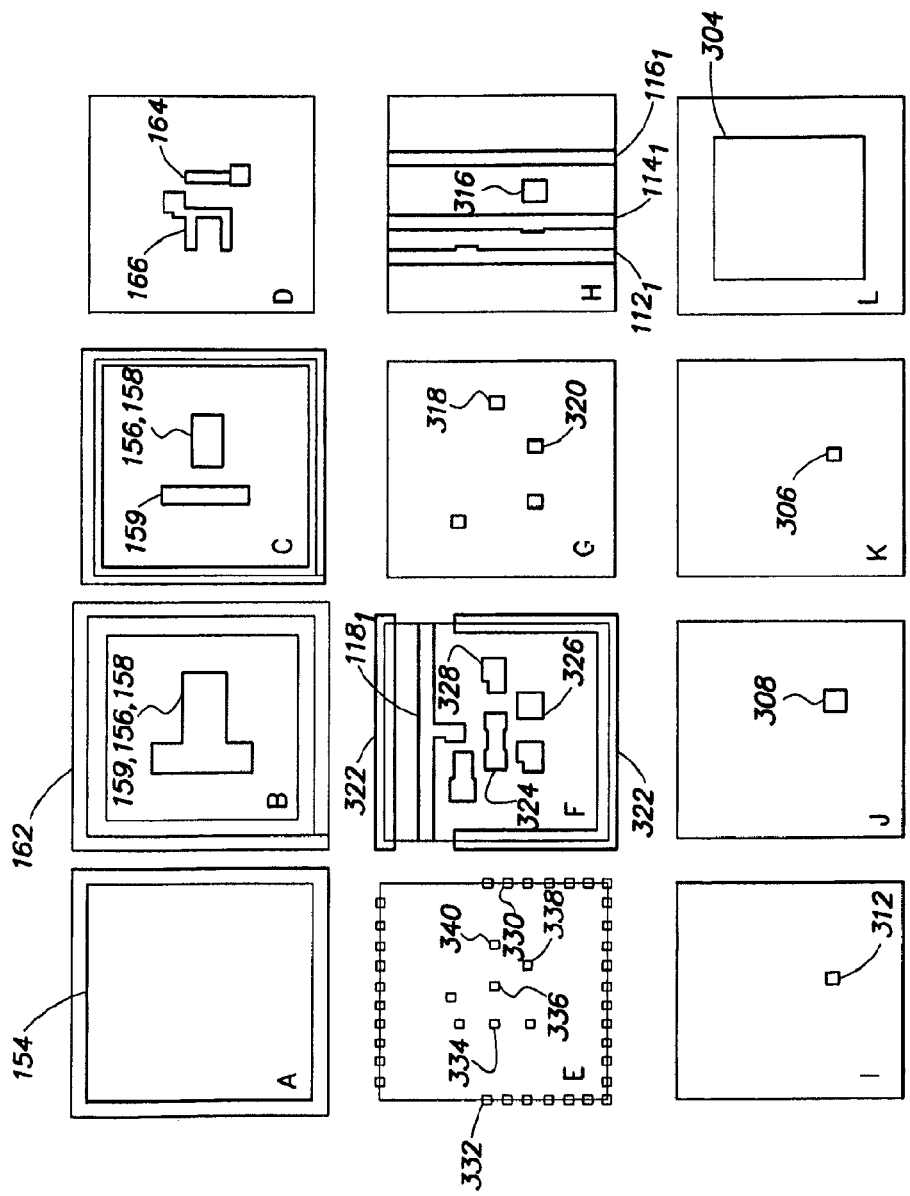

To this end, in another embodiment some via and metal layers are reconfigured such that the signal lines 112$_1$, 114$_1$, 116$_1$ and 118$_1$ are implemented in the Metal1 and Metal2 layers, and the Metal3 layer is used only as a jumper between the Metal2 layer component of the floating gate structure 170 and the topmost metal layer 304, thereby ensuring a greater distance between the signal lines and the metal layer 304. FIG. 10-1 illustrates a top view of a such a chip layout design for a cluster of four neighboring pixels of an chemFET array shown in FIG. 9, with one particular pixel 105$_1$ identified and labeled. FIG. 11A-1 shows a composite cross-sectional view of neighboring pixels, along the line I-I of the pixel 105$_1$ shown in FIG. 10-1, including additional elements between the lines II-II, illustrating a layer-by-layer view of the pixel fabrication, and FIGS. 12-1A through 12-1L provide top views of each of the fabrication layers shown in FIG. 11A-1 (the respective images of FIGS. 12-1A through 12-1L are superimposed one on top of another to create the pixel chip layout design shown in FIG. 10-1).

In FIG. 10-1, it may be observed that the pixel top view layout is generally similar to that shown in FIG. 10. For example, in the top view, the ISFET 150 generally occupies the right center portion of each pixel, and the MOSFETs Q2 and Q3 generally occupy the left center portion of the pixel illustration. Many of the component labels included in FIG. 10 are omitted from FIG. 10-1 for clarity, although the ISFET polysilicon gate 164 is indicated in the pixel 105$_1$ for orientation. FIG. 10-1 also shows the four lines (112$_1$, 114$_1$, 116$_1$ and 118$_1$) required to operate the pixel. One noteworthy difference between FIG. 10 and FIG. 10-1 relates to the metal conductor 322 (located on the Metal1 layer) which provides an electrical connection to the body region 162; namely, in FIG. 10, the conductor 322 surrounds a perimeter of the pixel, whereas in FIG. 10-1, the conductor 322 does not completely surround a perimeter of the pixel but includes discontinuities 727. These discontinuities 727 permit the line 118$_1$ to also be fabricated on the Metal1 layer and traverse the pixel to connect to neighboring pixels of a row.

With reference now to the cross-sectional view of FIG. 11A-1, three adjacent pixels are shown in cross-section, with the center pixel corresponding to the pixel $105_1$ in FIG. 10-1 for purposes of discussion. As in the embodiment of FIG. 11A, all of the FET components of the pixel $105_1$ are fabricated as p-channel FETs in the single n-type well 154. Additionally, as in FIG. 11A, in the composite cross-sectional view of FIG. 11A-1 the highly doped p-type region 159 is also visible (lying along the line I-I in FIG. 10-1), corresponding to the shared drain (D) of the MOSFETs Q2 and Q3. For purposes of illustration, the polysilicon gate 166 of the MOSFET Q3 also is visible in FIG. 11A-1, although this gate does not lie along the line I-I in FIG. 10-1, but rather "behind the plane" of the cross-section along the line I-I. However, for simplicity, the respective sources of the MOSFETs Q2 and Q3 shown in FIG. 10-1, as well as the gate of Q2, are not visible in FIG. 11A-1, as they lie along the same axis (i.e., perpendicular to the plane of the figure) as the shared drain. Furthermore, to facilitate an understanding of the ISFET floating gate electrical connections, the composite cross-sectional view of FIG. 11A-1 shows additional elements of the pixel fabrication between the lines II-II of FIG. 10-1.

More specifically, as in the embodiment of FIG. 11A, the topmost metal layer 304 corresponds to the ISFETs sensitive area 178, above which is disposed an analyte-sensitive passivation layer 172. The topmost metal layer 304, together with the ISFET polysilicon gate 164 and the intervening conductors 306, 308, 312, 316, 320, 326 and 338, form the ISFETs floating gate structure 170. However, unlike the embodiment of FIG. 11A, an electrical connection to the ISFETs drain is provided by the conductors 340, 328, and 318, coupled to the line $116_1$ which is formed in the Metal2 layer rather than the Metal3 layer. Additionally, the lines $112_1$ and $114_1$ also are shown in FIG. 11A-1 as formed in the Metal2 layer rather than the Metal3 layer. The configuration of these lines, as well as the line $118_1$, may be further appreciated from the respective images of FIGS. 12-1A through 12-1L (in which the correspondence between the lettered top views of respective layers and the cross-sectional view of FIG. 11A-1 is the same as that described in connection with FIGS. 12A-12L); in particular, it may be observed in FIG. 12-1F that the line $118_1$, together with the metal conductor 322, is formed in the Metal1 layer, and it may be observed that the lines $112_1$, $114_1$ and $116_1$ are formed in the Metal2 layer, leaving only the jumper 308 of the floating gate structure 170 in the Metal3 layer shown in FIG. 12-1J.

Accordingly, by consolidating the signal lines $112_1$, $114_1$, $116_1$ and $118_1$ to the Metal1 and Metal2 layers and thereby increasing the distance between these signal lines and the topmost layer 304 of the floating gate structure 170 in the Metal4 layer, parasitic capacitances in the ISFET may be at least partially mitigated. It should be appreciated that this general concept (e.g., including one or more intervening metal layers between signal lines and topmost layer of the floating gate structure) may be implemented in other fabrication processes involving greater numbers of metal layers. For example, distance between pixel signal lines and the topmost metal layer may be increased by adding additional metal layers (more than four total metal layers) in which only jumpers to the topmost metal layer are formed in the additional metal layers. In particular, a six-metal-layer fabrication process may be employed, in which the signal lines are fabricated using the Metal1 and Metal2 layers, the topmost metal layer of the floating gate structure is formed in the Metal6 layer, and jumpers to the topmost metal layer are formed in the Metal3, Metal4 and Metal5 layers, respectively (with associated vias between the metal layers). In another exemplary implementation based on a six-metal-layer fabrication process, the general pixel configuration shown in FIGS. 10, 11A, and 12A-12L may be employed (signal lines on Metal2 and Metal 3 layers), in which the topmost metal layer is formed in the Metal6 layer and jumpers are formed in the Metal4 and Metal5 layers, respectively.

In yet another aspect relating to reduced capacitance, a dimension "f" of the topmost metal layer 304 (and thus the ISFET sensitive area 178) may be reduced so as to reduce cross-capacitance between neighboring pixels. As may be observed in FIG. 11A-1 (and as discussed further below in connection with other embodiments directed to well fabrication above an ISFET array), the well 725 may be fabricated so as to have a tapered shape, such that a dimension "g" at the top of the well is smaller than the pixel pitch "e" but yet larger than a dimension "f" at the bottom of the well. Based on such tapering, the topmost metal layer 304 also may be designed with the dimension "f" rather than the dimension "g" so as to provide for additional space between the top metal layers of neighboring pixels. In some illustrative non-limiting implementations, for pixels having a dimension "e" on the order of 9 micrometers the dimension "f" may be on the order of 6 micrometers (as opposed to 7 micrometers, as discussed above), and for pixels having a dimension "e" on the order of 5 micrometers the dimension "f" may be on the order of 3.5 micrometers.

Thus, the pixel chip layout designs respectively shown in FIGS. 10, 11A, and 12A through 12L, and FIGS. 10-1, 11A-1, and 12-1A through 12-1L, illustrate that according to various embodiments FET devices of a same type may be employed for all components of a pixel, and that all components may be implemented in a single well. This dramatically reduces the area required for the pixel, thereby facilitating increased pixel density in a given area.

In one exemplary implementation, the gate oxide 165 for the ISFET may be fabricated to have a thickness on the order of approximately 75 Angstroms, giving rise to a gate oxide capacitance per unit area $C_{ox}$ of 4.5 fF/$\mu m^2$. Additionally, the polysilicon gate 164 may be fabricated with dimensions corresponding to a channel width W of 1.2 μm and a channel length L of from 0.35 to 0.6 μm (i.e., W/L ranging from approximately 2 to 3.5), and the doping of the region 160 may be selected such that the carrier mobility for the p-channel is 190 cm$^2$/V·s (i.e., 1.9E10 μm$^2$/V·s). From Eq. (2) above, this results in an ISFET transconductance parameter β on the order of approximately 170 to 300 μA/V$^2$. In other aspects of this exemplary implementation, the analog supply voltage VDDA is 3.3 Volts, and VB1 and VB2 are biased so as to provide a constant ISFET drain current $I_D$; on the order of 5 μA (in some implementations, VB1 and VB2 may be adjusted to provide drain currents from approximately 1 μA to 20 μA). Additionally, the MOSFET Q6 (see bias/readout circuitry 110j in FIG. 9) is sized to have a channel width to length ratio (e.g., W/L of approximately 50) such that the voltage across Q6, given $I_{Dj}$ of 5 μA, is 800 mV (i.e., $V_{DSj}$=800 mV). From Eq. (3), based on these exemplary parameters, this provides for pixel output voltages $V_{Sj}$ over a range of approximately 0.5 to 2.5 Volts for ISFET threshold voltage changes over a range of approximately 0 to 2 Volts.

With respect to the analyte-sensitive passivation layer 172 shown in FIG. 11A, in exemplary CMOS implementations the passivation layer may be significantly sensitive to the concentration of various ion species, including hydrogen, and may include silicon nitride ($Si_3N_4$) and/or silicon oxynitride ($Si_2N_2O$). In conventional CMOS processes, a passivation layer may be formed by one or more successive depositions of these materials, and is employed generally to treat or coat devices so as to protect against contamination and increase electrical stability. The material properties of silicon nitride and silicon oxynitride are such that a passivation layer comprising these materials provides scratch protection and serves as a significant barrier to the diffusion of water and sodium, which can cause device metallization to corrode and/or device operation to become unstable. A passivation layer including silicon nitride and/or silicon oxynitride also provides ion-sensitivity in ISFET devices, in that the passivation layer contains surface groups that may donate or accept protons from an analyte solution with which they are in contact, thereby altering the surface potential and the device threshold voltage $V_{TH}$, as discussed above in connection with FIGS. 1 and 2A.

For CMOS processes involving aluminum as the metal (which has a melting point of approximately 650 degrees Celsius), a silicon nitride and/or silicon oxynitride passivation layer generally is formed via plasma-enhanced chemical vapor deposition (PECVD), in which a glow discharge at 250-350 degrees Celsius ionizes the constituent gases that form silicon nitride or silicon oxynitride, creating active species that react at the wafer surface to form a laminate of the respective materials. In one exemplary process, a passivation layer having a thickness on the order of approximately 1.0 to 1.5 µm may be formed by an initial deposition of a thin layer of silicon oxynitride (on the order of 0.2 to 0.4 µm) followed by a slighting thicker deposition of silicon oxynitride (on the order of 0.5 µm) and a final deposition of silicon nitride (on the order of 0.5 µm). Because of the low deposition temperature involved in the PECVD process, the aluminum metallization is not adversely affected.

However, Applicants have recognized and appreciated that while a low-temperature PECVD process provides adequate passivation for conventional CMOS devices, the low-temperature process results in a generally low-density and somewhat porous passivation layer, which in some cases may adversely affect ISFET threshold voltage stability. In particular, during ISFET device operation, a low-density porous passivation layer over time may absorb and become saturated with ions from the solution, which may in turn cause an undesirable time-varying drift in the ISFETs threshold voltage $V_{TH}$, making accurate measurements challenging.

In view of the foregoing, in one embodiment a CMOS process that uses tungsten metal instead of aluminum may be employed to fabricate ISFET arrays according to the present disclosure. The high melting temperature of Tungsten (above 3400 degrees Celsius) permits the use of a higher temperature low pressure chemical vapor deposition (LPCVD) process (e.g., approximately 700 to 800 degrees Celsius) for a silicon nitride or silicon oxynitride passivation layer. The LPCVD process typically results in significantly more dense and less porous films for the passivation layer, thereby mitigating the potentially adverse effects of ion absorption from the analyte solution leading to ISFET threshold voltage drift.

In yet another embodiment in which an aluminum-based CMOS process is employed to fabricate ISFET arrays according to the present disclosure, the passivation layer 172 shown in FIG. 11A may comprise additional depositions and/or materials beyond those typically employed in a conventional CMOS process. For example, the passivation layer 172 may include initial low-temperature plasma-assisted depositions (PECVD) of silicon nitride and/or silicon oxynitride as discussed above; for purposes of the present discussion, these conventional depositions are illustrated in FIG. 11A as a first portion 172A of the passivation layer 172. In one embodiment, following the first portion 172A, one or more additional passivation materials are disposed to form at least a second portion 172B to increase density and reduce porosity of (and absorption by) the overall passivation layer 172. While one additional portion 172B is shown primarily for purposes of illustration in FIG. 11A, it should be appreciated that the disclosure is not limited in this respect, as the overall passivation layer 172 may comprise two or more constituent portions, in which each portion may comprise one or more layers/depositions of same or different materials, and respective portions may be configured similarly or differently.

Examples of materials suitable for the second portion 172B (or other additional portions) of the passivation layer 172 include, but are not limited to, silicon nitride, silicon oxynitride, aluminum oxide ($Al_2O_3$), tantalum oxide ($Ta_3O_5$), tin oxide ($SnO_2$) and silicon dioxide ($SiO_2$). In one aspect, the second portion 172B (or other additional portions) may be deposited via a variety of relatively low-temperature processes including, but not limited to, RF sputtering, DC magnetron sputtering, thermal or e-beam evaporation, and ion-assisted depositions. In another aspect, a pre-sputtering etch process may be employed, prior to deposition of the second portion 172B, to remove any native oxide residing on the first portion 172A (alternatively, a reducing environment, such as an elevated temperature hydrogen environment, may be employed to remove native oxide residing on the first portion 172A). In yet another aspect, a thickness of the second portion 172B may be on the order of approximately 0.04 µm to 0.06 µm (400 to 600 Angstroms) and a thickness of the first portion may be on the order of 1.0 to 1.5 µm, as discussed above. In some exemplary implementations, the first portion 172A may include multiple layers of silicon oxynitride and silicon nitride having a combined thickness of 1.0 to 1.5 µm, and the second portion 172B may include a single layer of either aluminum oxide or tantalum oxide having a thickness of approximately 400 to 600 Angstroms. Again, it should be appreciated that the foregoing exemplary thicknesses are provided primarily for purposes of illustration, and that the disclosure is not limited in these respects.

It has been found according to the invention that hydrogen ion sensitive passivation layers are also sensitive to other analytes including but not limited to PPi and unincorporated nucleotide triphosphates. As an example, a silicon nitride passivation layer is able to detect changes in the concentration of PPi and nucleotide triphosphates. The ability to measure the concentration change of these analytes using the same chemFET greatly facilitates the ability to sequence a nucleic acid using a single array, thereby simplifying the sequencing method.

Thus it is to be understood that the chemFET arrays described herein may be used to detect and/or measure various analytes and, by doing so, may monitor a variety of reactions and/or interactions. It is also to be understood that the discussion herein relating to hydrogen ion detection (in the form of a pH change) is for the sake of convenience and brevity and that static or dynamic levels/concentrations of other analytes (including other ions) can be substituted for hydrogen in these descriptions. In particular, sufficiently fast concentration changes of any one or more of various ion species present in the analyte may be detected via the transient or dynamic response of a chemFET, as discussed above in connection with FIG. 2A. As also discussed above in connection with the Site-Dissociation (or Site-Binding) model for the analyte/passivation layer interface, it should be appreciated that various parameters relating to the equilibrium reactions at the analyte/passivation layer interface (e.g., rate constants for forward and backward equilibrium reactions, total number of proton donor/acceptor sites per unit area on the passivation layer surface, intrinsic buffering capacity, pH at point of zero charge) are material dependent properties and thus are affected by the choice of materials employed for the passivation layer.

The chemFETs, including ISFETs, described herein are capable of detecting any analyte that is itself capable of inducing a change in electric field when in contact with or otherwise sensed or detected by the chemFET surface. The analyte need not be charged in order to be detected by the sensor. For example, depending on the embodiment, the analyte may be positively charged (i.e., a cation), negatively charged (i.e., an anion), zwitterionic (i.e., capable of having two equal and opposite charges but being neutral overall), and polar yet neutral. This list is not intended as exhaustive as other analyte classes as well as species within each class will be readily contemplated by those of ordinary skill in the art based on the disclosure provided herein.

In the broadest sense of the invention, the passivation layer may or may not be coated and the analyte may or may not interact directly with the passivation layer. As an example, the passivation layer may be comprised of silicon nitride and the analyte may be something other than hydrogen ions. As a specific example, the passivation layer may be comprised of silicon nitride and the analyte may be PPi. In these instances, PPi is detected directly (i.e., in the absence of PPi receptors attached to the passivation layer either directly or indirectly).

If the analyte being detected is hydrogen (or alternatively hydroxide), then it is preferable to use weak buffers so that changes in either ionic species can be detected at the passivation layer. If the analyte being detected is something other than hydrogen (or hydroxide) but there is some possibility of a pH change in the solution during the reaction or detection step, then it is preferable to use a strong buffer so that changes in pH do not interfere with the detection of the analyte. A buffer is an ionic molecule (or a solution comprising an ionic molecule) that resists to varying extents changes in pH. Some buffers are able to neutralize acids or bases added to or generated in a solution, resulting in no effective pH change in the solution. It is to be understood that any buffer is suitable provided it has a pKa in the desired range. For some embodiments, a suitable buffer is one that functions in about the pH range of 6 to 9, and more preferably 6.5 to 8.5. In other embodiments, a suitable buffer is one that functions in about the pH range of 7-10, including 8.5-9.5.

The strength of a buffer is a relative term since it depends on the nature, strength and concentration of the acid or base added to or generated in the solution of interest. A weak buffer is a buffer that allows detection (and therefore is not able to otherwise control) pH changes of about at least +/−0.005, about at least +/−0.01, about at least +/−0.015, about at least +/−0.02, about at least +/−0.03, about at least +/−0.04, about at least +/−0.05, about at least +/−0.10, about at least +/−0.15, about at least +/−0.20, about at least +/−0.25, about at least +/−0.30, about at least +/−0.35, about at least +/−0.45, about at least +/−0.50, or more. In some embodiments, the pH change is on the order of about 0.005 (e.g., per nucleotide incorporation) and is preferably an increase in pH. A strong buffer is a buffer that controls pH changes of about at least +/−0.005, about at least +/−0.01, about at least +/−0.015, about at least +/−0.02, about at least +/−0.03, about at least +/−0.04, about at least +/−0.05, about at least +/−0.10, about at least +/−0.15, about at least +/−0.20, about at least +/−0.25, about at least +/−0.30, about at least +/−0.35, about at least +/−0.45, about at least +/−0.50, or more. Buffer strength can be varied by varying the concentration of the buffer species itself. Thus low concentration buffers can be low strength buffers. Examples include those having less than 1 mM (e.g., 50-100 µM) buffer species. A non-limiting example of a weak buffer suitable for the sequencing reactions described herein wherein pH change is the readout is 0.1 mM Tris or Tricine. Examples of suitable weak buffers are provided in the Examples and are also known in the art. Higher concentration buffers can be stronger buffers. Examples include those having 1-25 mM buffer species. A non-limiting example of a strong buffer suitable for the sequencing reactions described herein wherein PPi and/or nucleotide triphosphates are read directly is 1, 5 or 25 mM (or more) Tris or Tricine. One of ordinary skill in the art will be able to determine the optimal buffer for use in the reactions and detection methods encompassed by the invention.

In some embodiments, the passivation layer and/or the layers and/or molecules coated thereon dictate the analyte specificity of the array readout.

Detection of hydrogen ions (in the form of pH), and other analytes as determined by the invention, can be carried out using a passivation layer made of silicon nitride ($Si_3N_4$), silicon oxynitride ($Si_2N_2O$), silicon oxide ($SiO_2$), aluminum oxide ($Al_2O_3$), tantalum pentoxide ($Ta_2O_5$), tin oxide or stannic oxide ($SnO_2$), and the like.

The passivation layer can also detect other ion species directly including but not limited to calcium, potassium, sodium, iodide, magnesium, chloride, lithium, lead, silver, cadmium, nitrate, phosphate, dihydrogen phosphate, and the like.

In some embodiments, the passivation layer is coated with a receptor for the analyte of interest. Preferably, the receptor binds selectively to the analyte of interest or in some instances to a class of agents to which the analyte belongs. As used herein, a receptor that binds selectively to an analyte is a molecule that binds preferentially to that analyte (i.e., its binding affinity for that analyte is greater than its binding affinity for any other analyte). Its binding affinity for the analyte of interest may be 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 100-fold or more than its binding affinity for any other analyte. In addition to its relative binding affinity, the receptor must also have an absolute binding affinity that is sufficiently high to efficiently bind the analyte of interest (i.e., it must have a sufficient sensitivity). Receptors having binding affinities in the picomolar to micromolar range are suitable. Preferably such interactions are reversible.

The receptor may be of any nature (e.g., chemical, nucleic acid, peptide, lipid, combinations thereof and the like). In such embodiments, the analyte too may be of any nature provided there exists a receptor that binds to it selectively and in some instances specifically. It is to be understood however that the invention further contemplates detection of analytes in the absence of a receptor. An example of this is the detection of PPi and Pi by the passivation layer in the absence of PPi or Pi receptors.

In one aspect, the invention contemplates receptors that are ionophores. As used herein, an ionophore is a molecule that binds selectively to an ionic species, whether anion or cation. In the context of the invention, the ionophore is the receptor and the ion to which it binds is the analyte. Ionophores of the invention include art-recognized carrier ionophores (i.e., small lipid-soluble molecules that bind to a particular ion) derived from microorganisms. Various ionophores are commercially available from sources such as Calbiochem.

Detection of some ions can be accomplished through the use of the passivation layer itself or through the use of receptors coated onto the passivation layer. For example, potassium can be detected selectively using polysiloxane, valinomycin, or salinomycin; sodium can be detected selectively using monensin, nystatin, or SQI-Pr; calcium can be detected selectively using ionomycin, calcimycine (A23187), or CA 1001 (ETH 1001).

Receptors able to bind more than one ion can also be used in some instances. For example, beauvericin can be used to detect calcium and/or barium ions, nigericin can be used to detect potassium, hydrogen and/or lead ions, and gramicidin can be used to detect hydrogen, sodium and/or potassium ions. One of ordinary skill in the art will recognize that these compounds can be used in applications in which single ion specificity is not required or in which it is unlikely (or impossible) that other ions which the compounds bind will be present or generated. Similarly, receptors that bind multiple species of a particular genus may also be useful in some embodiments including those in which only one species within the genus will be present or in which the method does not require distinction between species.

As another example, receptors for neurotoxins are described in Simonian Electroanalysis 2004, 16: 1896-1906.

Figures 1, 11A:
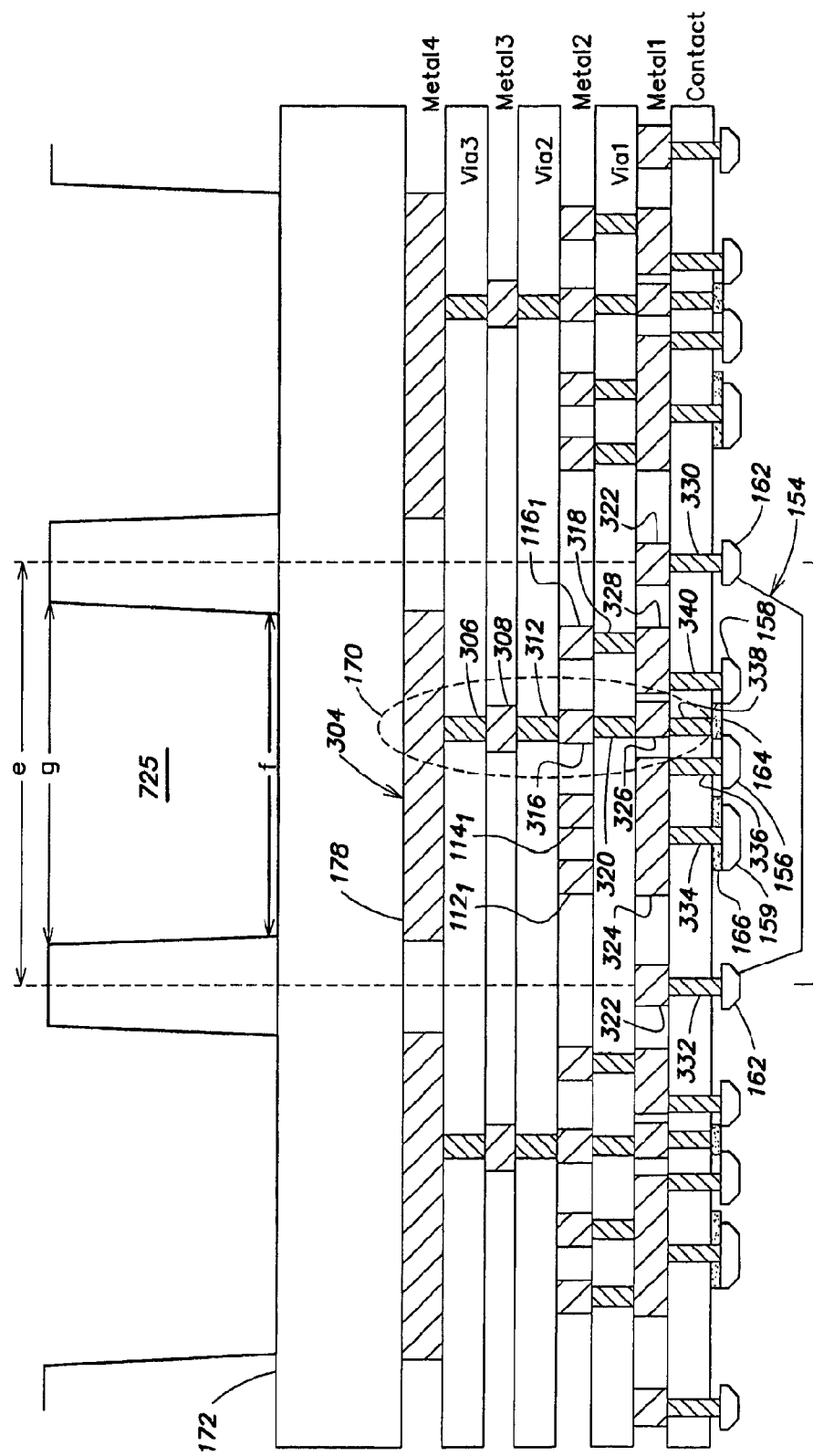
Figure 11E:
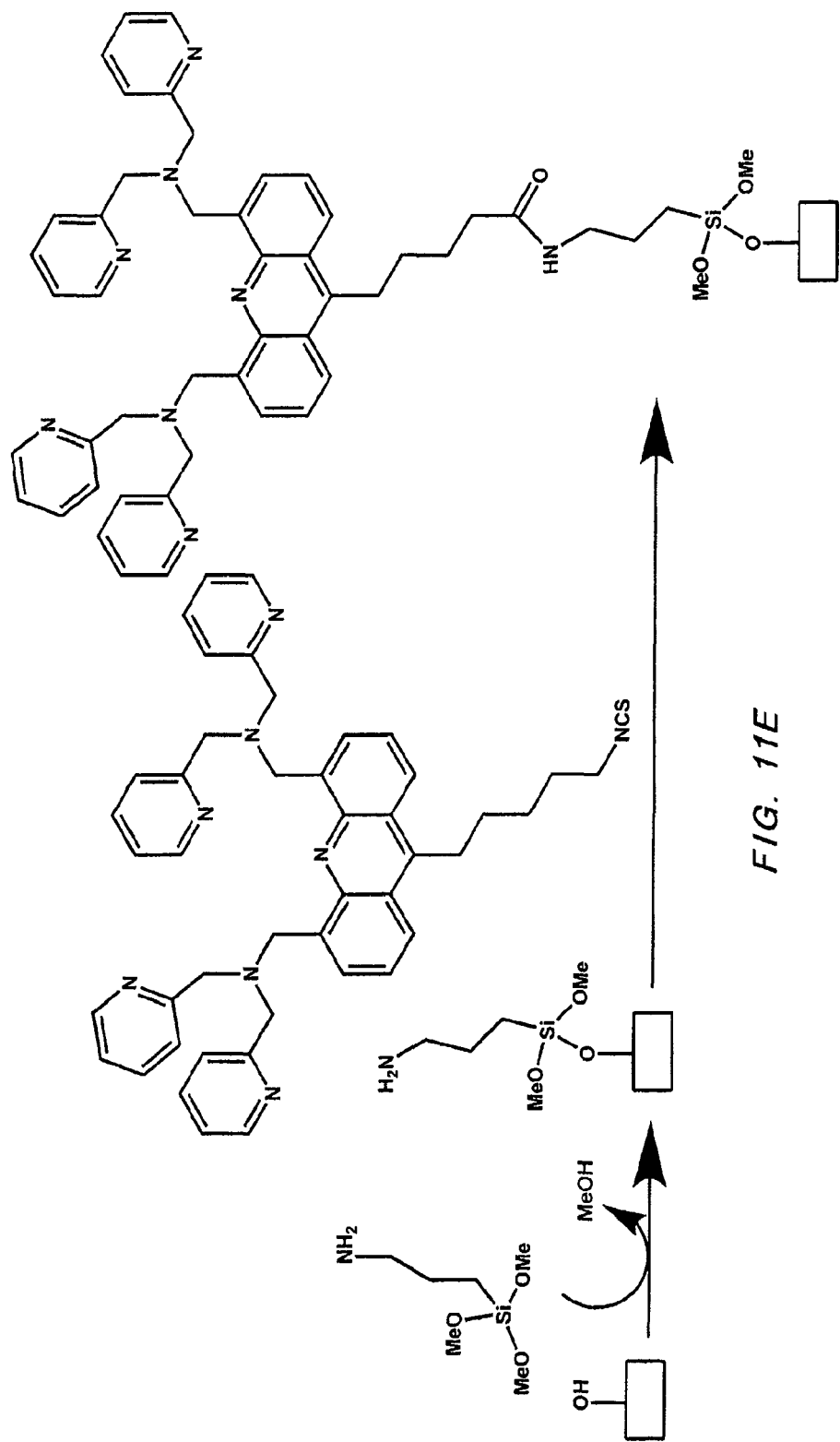
FIG. 11E is a schematic of attachment of compound 7 from FIG. 11B(3) to a metal oxide surface.

In other embodiments, including but not limited to nucleic acid sequencing applications, receptors that bind selectively to PPi can be used. Examples of PPi receptors include those compounds shown in FIGS. 11B(1)-(3) (compounds 1-10). Compound 1 is described in Angew, Chem Int (Ed 2004) 43:4777-4780 and US 2005/0119497 A1 and is referred to as p-naphthyl-bis[(bis(2-pyridylmethyl)amino)methyl]phenol. Compound 2 is described in J Am Chem Soc 2003 125:7752-7753 and US 2005/0119497 A1 and is referred to as p-(p-nitrophenylazo)-bis[(bis(2-pyridylmethyl-1)amino)methyl]phenol (or its dinuclear Zn complex). Synthesis schemes for compounds 1 and 2 are shown provided in US 2005/0119497 A1. Compound 3 is described in by Lee et al. Organic Letters 2007 9(2):243-246, and Sensors and Actuators B 1995 29:324-327. Compound 4 is described in Angew, Chem Int (Ed 2002) 41(20):3811-3814. Exemplary syntheses for compounds 7, 8 and 9 are shown in FIGS. 11C(1)-(3). Compound 5 is described in WO 2007/002204 and is referred to therein as bis-$Zn^{2+}$-dipicolylamine ($Zn^{2+}$-DPA). Compound 6 is illustrated in FIG. 11B(3) bound to PPi. (McDonough et al. Chem. Commun. 2006 2971-2973.) Attachment of compound 7 to a metal oxide surface is shown in FIG. 11E.

Receptors may be attached to the passivation layer covalently or non-covalently. Covalent attachment of a receptor to the passivation layer may be direct or indirect (e.g., through a linker). FIGS. 11D(1) and (2) illustrate the use of silanol chemistry to covalently bind receptors to the passivation layer. Receptors may be immobilized on the passivation layer using for example aliphatic primary amines (bottom left panel) or aryl isothiocyanates (bottom right panel). In these and other embodiments, the passivation layer which itself may be comprised of silicon nitride, aluminum oxide, silicon oxide, tantalum pentoxide, or the like, is bonded to a silanation layer via its reactive surface groups. For greater detail on silanol chemistry for covalent attachment to the FET surface, reference can be made to at least the following publications: for silicon nitride, see Sensors and Actuators B 1995 29:324-327, Jpn J Appl Phys 1999 38:3912-3917 and Langmuir 2005 21:395-402; for silicon oxide, see Protein Sci 1995 4:2532-2544 and Am Biotechnol Lab 2002 20(7):16-18; and for aluminum oxide, see Colloids and Surfaces 1992 63:1-9, Sensors and Actuators B 2003 89:40-47, and Bioconjugate Chem 1997 8:424-433. The receptor is then conjugated to the silanation layer reactive groups. This latter binding can occur directly or indirectly through the use of a bifunctional linker, as illustrated in FIGS. 11D(1) and (2).

A bifunctional linker is a compound having at least two reactive groups to which two entities may be bound. In some instances, the reactive groups are located at opposite ends of the linker. In some embodiments, the bifunctional linker is a universal bifunctional linker such as that shown in FIGS. 11D(1) and (2). A universal linker is a linker that can be used to link a variety of entities. It should be understood that the chemistries shown in FIGS. 11D(1) and (2) are meant to be illustrative and not limiting.

The bifunctional linker may be a homo-bifunctional linker or a hetero-bifunctional linker, depending upon the nature of the molecules to be conjugated. Homo-bifunctional linkers have two identical reactive groups. Hetero-bifunctional linkers are have two different reactive groups. Various types of commercially available linkers are reactive with one or more of the following groups: primary amines, secondary amines, sulphydryls, carboxyls, carbonyls and carbohydrates. Examples of amine-specific linkers are bis(sulfosuccinimidyl) suberate, bis[2-(succinimidooxycarbonyloxy)ethyl]sulfone, disuccinimidyl suberate, disuccinimidyl tartarate, dimethyl adipimate.2HCl, dimethyl pimelimidate.2HCl, dimethyl suberimidate.2HCl, and ethylene glycolbis-[succinimidyl-[succinate]]. Linkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido) butyl]-3'-[2'-pyridyldithio]propionamide. Linkers preferentially reactive with carbohydrates include azidobenzoyl hydrazine. Linkers preferentially reactive with carboxyl groups include 4-[p-azidosalicylamido]butylamine.

Heterobifunctional linkers that react with amines and sulfhydryls include N-succinimidyl-3-[2-pyridyldithio]propionate, succinimidyl[4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional linkers that react with carboxyl and amine groups include 1-ethyl-3-[3-dimethylaminopropyl]-carbodiimide hydrochloride. Heterobifunctional linkers that react with carbohydrates and sulfhydryls include 4-[N-maleimidomethyl]-cyclohexane-1-carboxylhydrazide.2HCl, 4-(4-N-maleimidophenyl)-butyric acid hydrazide.2HCl, and 3-[2-pyridyldithio]propionyl hydrazide.

Alternatively, receptors may be non-covalently coated onto the passivation layer. Non-covalent deposition of the receptor onto the passivation layer may involve the use of a polymer matrix. The polymer may be naturally occurring or non-naturally occurring and may be of any type including but not limited to nucleic acid (e.g., DNA, RNA, PNA, LNA, and the like, or mimics, derivatives, or combinations thereof), amino acid (e.g., peptides, proteins (native or denatured), and the like, or mimics, derivatives, or combinations thereof, lipids, polysaccharides, and functionalized block copolymers. The receptor may be adsorbed onto and/or entrapped within the polymer matrix. The nature of the polymer will depend on the nature of the receptor being used and/or analyte being detected.

Alternatively, the receptor may be covalently conjugated or crosslinked to the polymer (e.g., it may be "grafted" onto a functionalized polymer).

An example of a suitable peptide polymer is poly-lysine (e.g., poly-L-lysine). Examples of other polymers include block copolymers that comprise polyethylene glycol (PEG), polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, polyvinyl chloride, polystyrene, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), poly(lactide-glycolide), copolyoxalates, polycaprolactones, polyesteramides, polyorthoesters, polyhydroxybutyric acid, polyanhydrides, poly(styrene-b-isobutylene-b-styrene) (SIBS) block copolymer, ethylene vinyl acetate, poly(meth)acrylic acid, polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, albumin and other hydrophilic proteins, zein and other prolamines and hydrophobic proteins, copolymers and mixtures thereof, and chemical derivatives thereof including substitutions and/or additions of chemical groups, for example, alkyl, alkylene, hydroxylations, oxidations, and other modifications routinely made by those skilled in the art.

Another issue that relates to ISFET threshold voltage stability and/or predictability involves trapped charge that may accumulate (especially) on metal layers of CMOS-fabricated devices as a result of various processing activities during or following array fabrication (e.g., back-end-of-line processing such as plasma metal etching, wafer cleaning, dicing, packaging, handling, etc.). In particular, with reference to FIG. 11A, trapped charge may in some instances accumulate on one or more of the various conductors 304, 306, 308, 312, 316, 320, 326, 338, and 164 constituting the ISFETs floating gate structure 170. This phenomenon also is referred to in the relevant literature as the "antenna effect."

One opportunity for trapped charge to accumulate includes plasma etching of the topmost metal layer 304. Applicants have recognized and appreciated that other opportunities for charge to accumulate on one or more conductors of the floating gate structure or other portions of the FETs includes wafer dicing, during which the abrasive process of a dicing saw cutting through a wafer generates static electricity, and/or various post-processing wafer handling/packaging steps, such as die-to-package wire bonding, where in some cases automated machinery that handles/transports wafers may be sources of electrostatic discharge (ESD) to conductors of the floating gate structure. If there is no connection to the silicon substrate (or other semi-conductor substrate) to provide an electrical path to bleed off such charge accumulation, charge may build up to the point of causing undesirable changes or damage to the gate oxide 165 (e.g., charge injection into the oxide, or low-level oxide breakdown to the underlying substrate). Trapped charge in the gate oxide or at the gate oxide-semiconductor interface in turn can cause undesirable and/or unpredictable variations in ISFET operation and performance, such as fluctuations in threshold voltage.

In view of the foregoing, other inventive embodiments of the present disclosure are directed to methods and apparatus for improving ISFET performance by reducing trapped charge or mitigating the antenna effect. In one embodiment, trapped charge may be reduced after a sensor array has been fabricated, while in other embodiments the fabrication process itself may be modified to reduce trapped charge that could be induced by some conventional process steps. In yet other embodiments, both "during fabrication" and "post fabrication" techniques may be employed in combination to reduce trapped charge and thereby improve ISFET performance.

With respect to alterations to the fabrication process itself to reduce trapped charge, in one embodiment the thickness of the gate oxide 165 shown in FIG. 11A may be particularly selected so as to facilitate bleeding of accumulated charge to the substrate; in particular, a thinner gate oxide may allow a sufficient amount of built-up charge to pass through the gate oxide to the substrate below without becoming trapped. In another embodiment based on this concept, a pixel may be designed to include an additional "sacrificial" device, i.e., another transistor having a thinner gate oxide than the gate oxide 165 of the ISFET. The floating gate structure of the ISFET may then be coupled to the gate of the sacrificial device such that it serves as a "charge bleed-off transistor." Of course, it should be appreciated that some trade-offs for including such a sacrificial device include an increase in pixel size and complexity.

In another embodiment, the topmost metal layer 304 of the ISFETs floating gate structure 170 shown in FIG. 11A may be capped with a dielectric prior to plasma etching to mitigate trapped charge. As discussed above, charge accumulated on the floating gate structure may in some cases be coupled from the plasma being used for metal etching. Typically, a photoresist is applied over the metal to be etched and then patterned based on the desired geometry for the underlying metal. In one exemplary implementation, a capping dielectric layer (e.g., an oxide) may be deposited over the metal to be etched, prior to the application of the photoresist, to provide an additional barrier on the metal surface against charge from the plasma etching process. In one aspect, the capping dielectric layer may remain behind and form a portion of the passivation layer 172.

In yet another embodiment, the metal etch process for the topmost metal layer 304 may be modified to include wet chemistry or ion-beam milling rather than plasma etching. For example, the metal layer 304 could be etched using an aqueous chemistry selective to the underlying dielectric (e.g., see website for Transene relating to aluminum, which is hereby incorporated herein by reference). Another alternative approach employs ion-milling rather than plasma etching for the metal layer 304. Ion-milling is commonly used to etch materials that cannot be readily removed using conventional plasma or wet chemistries. The ion-milling process does not employ an oscillating electric field as does a plasma, so that charge build-up does not occur in the metal layer(s). Yet another metal etch alternative involves optimizing the plasma conditions so as to reduce the etch rate (i.e. less power density).

In yet another embodiment, architecture changes may be made to the metal layer to facilitate complete electrical isolation during definition of the floating gate. In one aspect, designing the metal stack-up so that the large area ISFET floating gate is not connected to anything during its final definition may require a subsequent metal layer serving as a "jumper" to realize the electrical connection to the floating gate of the transistor. This "jumper" connection scheme prevents charge flow from the large floating gate to the transistor. This method may be implemented as follows (M=metal layer): i) M1 contacting Poly gate electrode; ii) M2 contacting M1; iii) M3 defines floating gate and separately connects to M2 with isolated island; iv) M4 jumper, having very small area being etched over the isolated islands and connections to floating gate M3, connects the M3 floating gate to the M1/M2/M3 stack connected to the Poly gate immediately over the transistor active area; and v) M3 to M4 interlayer dielectric is removed only over the floating gate so as to expose the bare M3 floating gate. In the method outlined immediately above, step v) need not be done, as the ISFET architecture according to some embodiments discussed above leaves the M4 passivation in place over the M4 floating gate. In one aspect, removal may nonetheless improve ISFET performance in other ways (i.e. sensitivity). In any case, the final sensitive passivation layer may be a thin sputter-deposited ion-sensitive metal-oxide layer. It should be appreciated that the over-layer jumpered architecture discussed above may be implemented in the standard CMOS fabrication flow to allow any of the first three metal layers to be used as the floating gates (i.e. M1, M2 or M3).

With respect to post-fabrication processes to reduce trapped charge, in one embodiment a "forming gas anneal" may be employed as a post-fabrication process to mitigate potentially adverse effects of trapped charge. In a forming gas anneal, CMOS-fabricated ISFET devices are heated in a hydrogen and nitrogen gas mixture. The hydrogen gas in the mixture diffuses into the gate oxide 165 and neutralizes certain forms of trapped charges. In one aspect, the forming gas anneal need not necessarily remove all gate oxide damage that may result from trapped charges; rather, in some cases, a partial neutralization of some trapped charge is sufficient to significantly improve ISFET performance. In exemplary annealing processes according to the present disclosure, ISFETs may be heated for approximately 30 to 60 minutes at approximately 400 to 425 degrees Celsius in a hydrogen/nitrogen mixture that includes 10% to 15% hydrogen. In one particular implementation, annealing at 425 degrees Celsius at 30 minutes in a hydrogen/nitrogen mixture that includes 10% hydrogen is observed to be particularly effective at improving ISFET performance. For aluminum CMOS processes, the temperature of the anneal should be kept at or below 450 degrees Celsius to avoid damaging the aluminum metallurgy. In another aspect of an annealing process according to the present disclosure, the forming gas anneal is performed after wafers of fabricated ISFET arrays are diced, so as to ensure that damage due to trapped charge induced by the dicing process itself, and/or other pre-dicing processing steps (e.g., plasma etching of metals) may be effectively ameliorated. In yet another aspect, the forming gas anneal may be performed after die-to-package wirebonding to similarly ameliorate damage due to trapped charge. At this point in the assembly process, a diced array chip is typically in a heat and chemical resistant ceramic package, and low-tolerance wirebonding procedures as well as heat-resistant die-to-package adhesives may be employed to withstand the annealing procedure. Thus, in one exemplary embodiment, the invention encompasses a method for manufacturing an array of FETs, each having or coupled to a floating gate having a trapped charge of zero or substantially zero comprising: fabricating a plurality of FETs in a common semiconductor substrate, each of a plurality of which is coupled to a floating gate; applying a forming gas anneal to the semiconductor prior to a dicing step; dicing the semiconductor; and applying a forming gas anneal to the semiconductor after the dicing step. Preferably, the semiconductor substrate comprises at least 100,000 FETs. Preferably, the plurality of FETs are chemFETs. The method may further comprise depositing a passivation layer on the semiconductor, depositing a polymeric, glass, ion-reactively etchable or photodefineable material layer on the passivation layer and etching the polymeric, glass ion-reactively etchable or photodefineable material to form an array of reaction chambers in the glass layer.

In yet other processes for mitigating potentially adverse effects of trapped charge according to embodiments of the present disclosure, a variety of "electrostatic discharge (ESD)-sensitive protocols" may be adopted during any of a variety of wafer post-fabrication handling/packaging steps. For example, in one exemplary process, anti-static dicing tape may be employed to hold wafer substrates in place (e.g., during the dicing process). Also, although high-resistivity (e.g., 10 MΩ) deionized water conventionally is employed in connection with cooling of dicing saws, according to one embodiment of the present disclosure less resistive/more conductive water may be employed for this purpose to facilitate charge conduction via the water; for example, deionized water may be treated with carbon dioxide to lower resistivity and improve conduction of charge arising from the dicing process. Furthermore, conductive and grounded die-ejection tools may be used during various wafer dicing/handling/packaging steps, again to provide effective conduction paths for charge generated during any of these steps, and thereby reduce opportunities for charge to accumulate on one or more conductors of the floating gate structure of respective ISFETs of an array.

In yet another embodiment involving a post-fabrication process to reduce trapped charge, the gate oxide region of an ISFET may be irradiated with UV radiation. With reference again to FIG. 11A, in one exemplary implementation based on this embodiment, an optional hole or window 302 is included during fabrication of an ISFET array in the top metal layer 304 of each pixel of the array, proximate to the ISFET floating gate structure. This window is intended to allow UV radiation, when generated, to enter the ISFETs gate region; in particular, the various layers of the pixel $105_1$, as shown in FIGS. 11 and 12 A-L, are configured such that UV radiation entering the window 302 may impinge in an essentially unobstructed manner upon the area proximate to the polysilicon gate 164 and the gate oxide 165.

To facilitate a UV irradiation process to reduce trapped charge, Applicants have recognized and appreciated that materials other than silicon nitride and silicon oxynitride generally need to be employed in the passivation layer 172 shown in FIG. 11A, as silicon nitride and silicon oxynitride significantly absorb UV radiation. In view of the foregoing, these materials need to be substituted with others that are appreciably transparent to UV radiation, examples of which include, but are not limited to, phosphosilicate glass (PSG) and boron-doped phosphosilicate glass (BPSG). PSG and BPSG, however, are not impervious to hydrogen and hydroxyl ions; accordingly, to be employed in a passivation layer of an ISFET designed for pH sensitivity, PSG and BPSG may be used together with an ion-impervious material that is also significantly transparent to UV radiation, such as aluminum oxide ($Al_2O_3$), to form the passivation layer. For example, with reference again to FIG. 11A, PSG or BPSG may be employed as a substitute for silicon nitride or silicon oxynitride in the first portion 172A of the passivation layer 172, and a thin layer (e.g., 400 to 600 Angstroms) of aluminum oxide may be employed in the second portion 172B of the passivation layer 172 (e.g., the aluminum oxide may be deposited using a post-CMOS lift-off lithography process).

In another aspect of an embodiment involving UV irradiation, each ISFET of a sensor array must be appropriately biased during a UV irradiation process to facilitate reduction of trapped charge. In particular, high energy photons from the UV irradiation, impinging upon the bulk silicon region 160 in which the ISFET conducting channel is formed, create electron-hole pairs which facilitate neutralization of trapped charge in the gate oxide as current flows through the ISFETs conducting channel. To this end, an array controller, discussed further below in connection with FIG. 17, generates appropriate signals for biasing the ISFETs of the array during a UV irradiation process. In particular, with reference again to FIG. 9, each of the signals $\overline{RowSel_1}$ through $\overline{RowSel_n}$ is generated so as to enable/select (i.e., turn on) all rows of the sensor array at the same time and thereby couple all of the ISFETs of the array to respective controllable current sources $106_j$ in each column. With all pixels of each column simultaneously selected, the current from the current source 106 of a given column is shared by all pixels of the column. The column amplifiers 107A and 107B are disabled by removing the bias voltage VB4, and at the same time the output of the amplifier 107B, connected to the drain of each ISFET in a given column, is grounded via a switch responsive to a control signal "UV." Also, the common body voltage $V_{BODY}$ for all ISFETs of the array is coupled to electrical ground (i.e., $V_{BODY}=0$ Volts) (as discussed above, during normal operation of the array, the body bias voltage $V_{BODY}$ is coupled to the highest voltage potential available to the array, e.g., VDDA). In one exemplary procedure, the bias voltage VB1 for all of the controllable current sources 106 is set such that each pixel's ISFET conducts approximately 1 µA of current. With the ISFET array thusly biased, the array then is irradiated with a sufficient dose of UV radiation (e.g., from an EPROM eraser generating approximately 20 milliWatts/cm$^2$ of radiation at a distance of approximately one inch from the array for approximately 1 hour). After irradiation, the array may be allowed to rest and stabilize over several hours before use for measurements of chemical properties such as ion concentration.

Utilizing at least one of the above-described techniques for reducing trapped charge, we have been able to fabricate FETs floating gates having a trapped charge of zero or substantially zero. Thus, in some embodiments, an aspect of the invention encompasses a floating gate having a surface area of about 4 µm$^2$ to about 50 µm$^2$ having baseline threshold voltage and preferably a trapped charge of zero or substantially zero. Preferably the FETs are chemFETs. The trapped charge should be kept to a level that does not cause appreciable variations from FET to FET across the array, as that would limit the dynamic range of the devices, consistency of measurements, and otherwise adversely affect performance.

Figure 13:
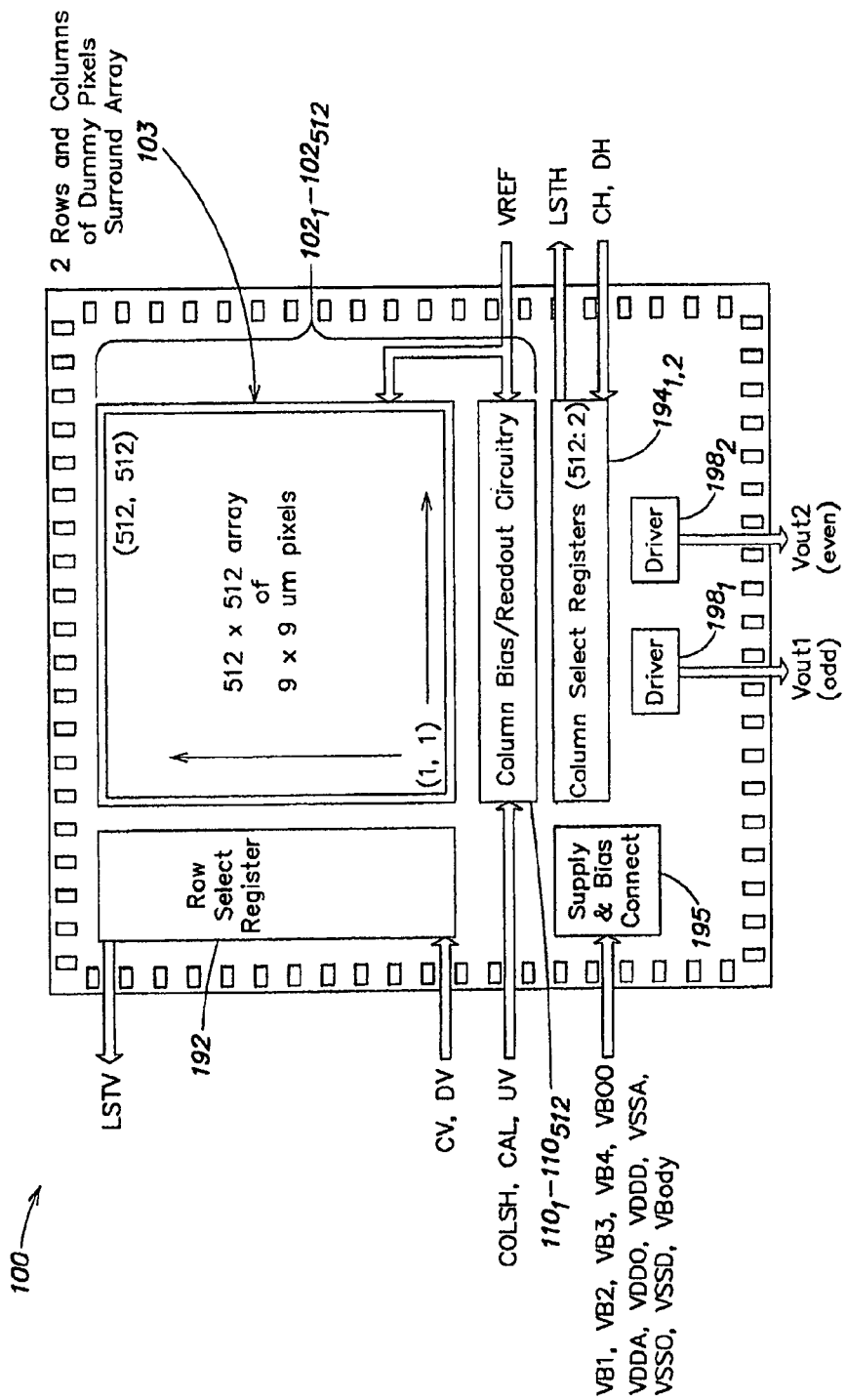
FIG. 13 illustrates a block diagram of an exemplary CMOS IC chip implementation of an chemFET sensor array similar to that shown in FIG. 8, based on the column and pixel designs shown in FIGS. 9-12, according to one inventive embodiment of the present disclosure.

FIG. 13 illustrates a block diagram of an exemplary CMOS IC chip implementation of an ISFET sensor array 100 based on the column and pixel designs discussed above in connection with FIGS. 9-12, according to one embodiment of the present disclosure. In one aspect of this embodiment, the array 100 includes 512 columns $102_1$ through $102_{512}$ with corresponding column bias/readout circuitry $110_1$ through $110_{512}$ (one for each column, as shown in FIG. 9), wherein each column includes 512 geometrically square pixels $105_1$ through $105_{512}$, each having a size of approximately 9 micrometers by 9 micrometers (i.e., the array is 512 columns by 512 rows). In another aspect, the entire array (including pixels together with associated row and column select circuitry and column bias/readout circuitry) may be fabricated on a semiconductor die as an application specific integrated circuit (ASIC) having dimensions of approximately 7 millimeters by 7 millimeters. While an array of 512 by 512 pixels is shown in the embodiment of FIG. 13, it should be appreciated that arrays may be implemented with different numbers of rows and columns and different pixel sizes according to other embodiments, as discussed further below in connection with FIGS. 19-23.

Also, as discussed above, it should be appreciated that arrays according to various embodiments of the present invention may be fabricated according to conventional CMOS fabrications techniques, as well as modified CMOS fabrication techniques (e.g., to facilitate realization of various functional aspects of the chemFET arrays discussed herein, such as additional deposition of passivation materials, process steps to mitigate trapped charge, etc.) and other semiconductor fabrication techniques beyond those conventionally employed in CMOS fabrication. Additionally, various lithography techniques may be employed as part of an array fabrication process. For example, in one exemplary implementation, a lithography technique may be employed in which appropriately designed blocks are "stitched" together by overlapping the edges of a step and repeat lithography exposures on a wafer substrate by approximately 0.2 micrometers. In a single exposure, the maximum die size typically is approximately 21 millimeters by 21 millimeters. By selectively exposing different blocks (sides, top & bottoms, core, etc.) very large chips can be defined on a wafer (up to a maximum, in the extreme, of one chip per wafer, commonly referred to as "wafer scale integration").

In one aspect of the array 100 shown in FIG. 13, the first and last two columns $102_1$, $102_2$, $102_{511}$ and $102_{512}$, as well as the first two pixels $105_1$ and $105_2$ and the last two pixels $105_{511}$ and $105_{512}$ of each of the columns $102_3$ through $102_{510}$ (e.g., two rows and columns of pixels around a perimeter of the array) may be configured as "reference" or "dummy" pixels 103. With reference to FIG. 11A, for the dummy pixels of an array, the topmost metal layer 304, of each dummy pixel's ISFET (coupled ultimately to the ISFETs polysilicon gate 164) is tied to the same metal layer of other dummy pixels and is made accessible as a terminal of the chip, which in turn may be coupled to a reference voltage VREF. As discussed above in connection with FIG. 9, the reference voltage VREF also may be applied to the bias/readout circuitry of respective columns of the array. In some exemplary implementations discussed further below, preliminary test/evaluation data may be acquired from the array based on applying the reference voltage VREF and selecting and reading out dummy pixels, and/or reading out columns based on the direct application of VREF to respective column buffers (e.g., via the CAL signal), to facilitate offset determination (e.g., pixel-to-pixel and column-to-column variances) and array calibration.

In yet another implementation of an array similar to that shown in FIG. 13, rather than reserving the first and last two columns of 512 columns and the first and last two pixels of each column of 512 pixels as reference pixels, the array may be fabricated to include an additional two rows/columns of reference pixels surrounding a perimeter of a 512 by 512 region of active pixels, such that the total size of the array in terms of actual pixels is 516 by 516 pixels. As arrays of various sizes and configurations are contemplated by the present disclosure, it should be appreciated that the foregoing concept may be applied to any of the other array embodiments discussed herein. For purposes of the discussion immediately below regarding the exemplary array 100 shown in FIG. 13, a total pixel count for the array of 512 by 512 pixels is considered.

In FIG. 13, various power supply and bias voltages required for array operation (as discussed above in connection with FIG. 9) are provided to the array via electrical connections (e.g., pins, metal pads) and labeled for simplicity in block 195 as "supply and bias connections." The array 100 of FIG. 13 also includes a row select shift register 192, two sets of column select shift registers $194_{1,2}$ and two output drivers $198_1$ and $198_2$ to provide two parallel array output signals, Vout1 and Vout2, representing sensor measurements (i.e., collections of individual output signals generated by respective ISFETs of the array). The various power supply and bias voltages, control signals for the row and column shift registers, and control signals for the column bias/readout circuitry shown in FIG. 13 are provided by an array controller, as discussed further below in connection with FIG. 17, which also reads the array output signals Vout1 and Vout2 (and other optional status/diagnostic signals) from the array 100. In another aspect of the array embodiment shown in FIG. 13, configuring the array such that multiple regions (e.g., multiple columns) of the array may be read at the same time via multiple parallel array output signals (e.g., Vout1 and Vout2) facilitates increased data acquisition rates, as discussed further below in connection with FIGS. 17 and 18. While FIG. 13 illustrates an array having two column select registers and parallel array output signals Vout1 and Vout2 to acquire data simultaneously from two columns at a time, it should be appreciated that, in other embodiments, arrays according to the present disclosure may be configured to have only one measurement signal output, or more than two measurement signal outputs; in particular, as discussed further below in connection with FIGS. 19-23, more dense arrays according to other inventive embodiments may be configured to have four our more parallel measurement signal outputs and simultaneously enable different regions of the array to provide data via the four or more outputs.

Figure 14:
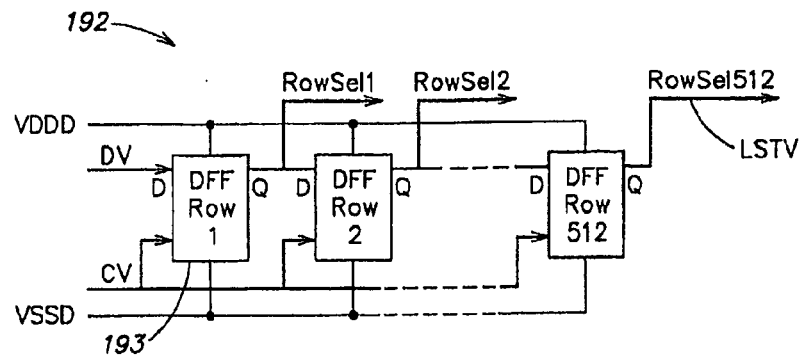
FIG. 14 illustrates a row select shift register of the array shown in FIG. 13, according to one inventive embodiment of the present disclosure.
Figure 15:
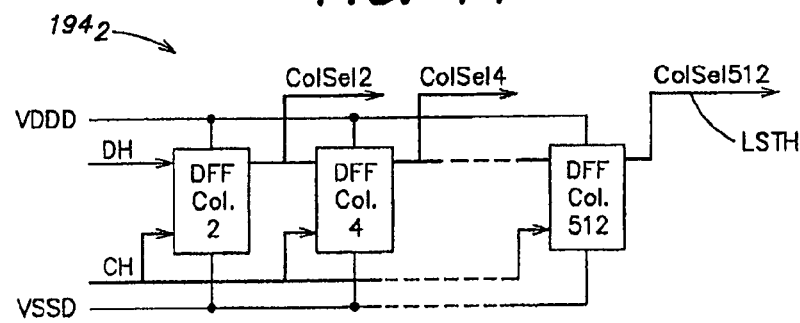
FIG. 15 illustrates one of two column select shift registers of the array shown in FIG. 13, according to one inventive embodiment of the present disclosure.
Figure 16:
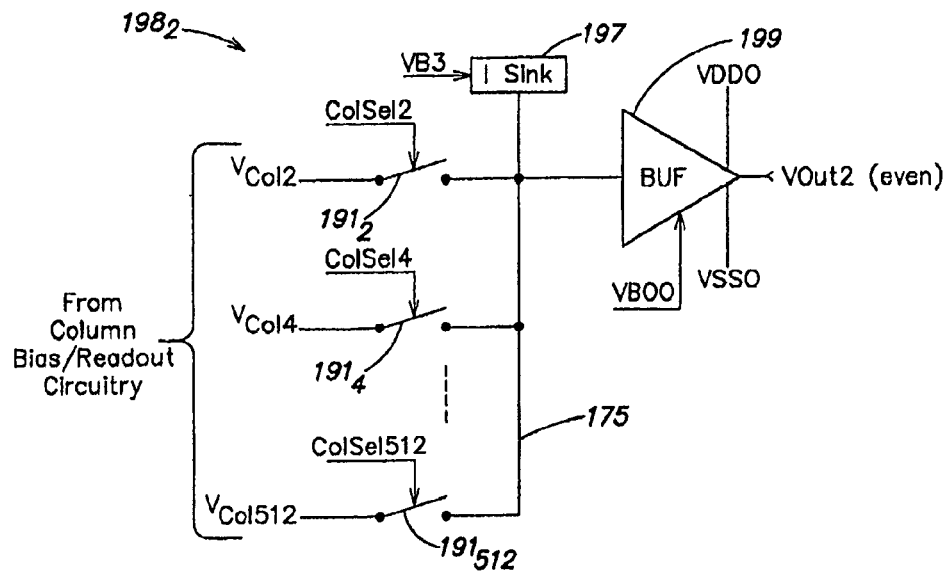
FIG. 16 illustrates one of two output drivers of the array shown in FIG. 13, according to one inventive embodiment of the present disclosure.

FIG. 14 illustrates the row select shift register 192, FIG. 15 illustrates one of the column select shift registers $194_2$ and FIG. 16 illustrates one of the output drivers $198_2$ of the array 100 shown in FIG. 13, according to one exemplary implementation. As shown in FIGS. 14 and 15, the row and column select shift registers are implemented as a series of D-type flip-flops coupled to a digital circuitry positive supply voltage VDDD and a digital supply ground VSSD. In the row and column shift registers, a data signal is applied to a D-input of first flip-flop in each series and a clock signal is applied simultaneously to a clock input of all of the flip-flops in the series. For each flip-flop, a "Q" output reproduces the state of the D-input upon a transition (e.g., falling edge) of the clock signal. With reference to FIG. 14, the row select shift register 192 includes 512 D-type flip-flops, in which a first flip-flop 193 receives a vertical data signal DV and all flip-flops receive a vertical clock signal CV. A "Q" output of the first flip-flop 193 provides the first row select signal $RowSel_1$ and is coupled to the D-input of the next flip-flop in the series. The Q outputs of successive flip-flops are coupled to the D-inputs of the next flip-flop in the series and provide the row select signals $RowSel_2$ through $RowSel_{512}$ with successive falling edge transitions of the vertical clock signal CV, as discussed further below in connection with FIG. 18. The last row select signal $RowSel_{512}$ also may be taken as an optional output of the array 100 as the signal LSTV (Last STage Vertical), which provides an indication (e.g., for diagnostic purposes) that the last row of the array has been selected. While not shown explicitly in FIG. 14, each of the row select signals $RowSel_1$ through $RowSel_{512}$ is applied to a corresponding inverter, the output of which is used to enable a given pixel in each column (as illustrated in FIG. 9 by the signals $\overline{RowSel_1}$ through $\overline{RowSel_n}$).

Regarding the column select shift registers $194_1$ and $194_2$, these are implemented in a manner similar to that of the row select shift registers, with each column select shift register comprising 256 series-connected flip-flops and responsible for enabling readout from either the odd columns of the array or the even columns of the array. For example, FIG. 15 illustrates the column select shift register $194_2$, which is configured to enable readout from all of the even numbered columns of the array in succession via the column select signals $ColSel_2$, $ColSel_4$, . . . $ColSel_{512}$, whereas another column select shift register $194_1$ is configured to enable readout from all of the odd numbered columns of the array in succession (via column select signals $ColSel_1$, $ColSel_3$, . . . $ColSel_{511}$). Both column select shift registers are controlled simultaneously by the horizontal data signal DH and the horizontal clock signal CH to provide the respective column select signals, as discussed further below in connection with FIG. 18. As shown in FIG. 15, the last column select signal $ColSel_{512}$ also may be taken as an optional output of the array 100 as the signal LSTH (Last STage Horizontal), which provides an indication (e.g., for diagnostic purposes) that the last column of the array has been selected.

With reference again for the moment to FIG. 7, Applicants have recognized and appreciated that an implementation for array row and column selection based on shift registers, as discussed above in connection with FIGS. 13-15, is a significant improvement to the row and column decoder approach employed in various prior art ISFET array designs, including the design of Milgrew et al. shown in FIG. 7. In particular, regarding the row decoder 92 and the column decoder 94 shown in FIG. 7, the complexity of implementing these components in an integrated circuit array design increases dramatically as the size of the array is increased, as additional inputs to both decoders are required. For example, an array having 512 rows and columns as discussed above in connection with FIG. 13 would require nine inputs ($2^9$=512) per row and column decoder if such a scheme were employed for row and column selection; similarly, arrays having 7400 rows and 7400 columns, as discussed below in connection with other embodiments, would require 13 inputs ($2^{13}$=8192) per row and column decoder. In contrast, the row and column select shift registers shown in FIGS. 14 and 15 require no additional input signals as array size is increased, but rather additional D-type flip-flops (which are routinely implemented in a CMOS process). Thus, the shift register implementations shown in FIGS. 14 and 15 provide an easily scalable solution to array row and column selection.

In the embodiment of FIG. 13, the "odd" column select shift register $194_1$ provides odd column select signals to an "odd" output driver $198_1$ and the even column select shift register $194_2$ provides even column select signals to an "even" output driver $198_2$. Both output drivers are configured similarly, and an example of the even output driver $198_2$ is shown in FIG. 16. In particular, FIG. 16 shows that respective even column output signals $V_{COL2}$, $V_{COL4}$, . . . $V_{COL512}$ (refer to FIG. 9 for the generic column signal output $V_{COLj}$) are applied to corresponding switches $191_2$, $191_4$, . . . $191_{512}$, responsive to the even column select signals $ColSel_2$, $ColSel_4$, . . . $ColSel_{512}$ provided by the column select register $194_2$, to successively couple the even column output signals to the input of a buffer amplifier 199 (BUF) via a bus 175. In FIG. 16, the buffer amplifier 199 receives power from an output buffer positive supply voltage VDDO and an output buffer supply ground VSSO, and is responsive to an output buffer bias voltage VBO0 to set a corresponding bias current for the buffer output. Given the high impedance input of the buffer amplifier 199, a current sink 197 responsive to a bias voltage VB3 is coupled to the bus 175 to provide an appropriate drive current (e.g., on the order of approximately 100 µA) for the output of the column output buffer (see the buffer amplifier 111$j$ of FIG. 9) of a selected column. The buffer amplifier 199 provides the output signal Vout2 based on the selected even column of the array; at the same time, with reference to FIG. 13, a corresponding buffer amplifier of the "odd" output driver 198$_1$ provides the output signal Vout1 based on a selected odd column of the array.

In one exemplary implementation, the switches of both the even and odd output drivers 198$_1$ and 198$_2$ (e.g., the switches 191$_2$, 191$_4$, . . . 191$_{512}$ shown in FIG. 16) may be implemented as CMOS-pair transmission gates (including an n-channel MOSFET and a p-channel MOSFET; see FIG. 4), and inverters may be employed so that each column select signal and its complement may be applied to a given transmission gate switch 191 to enable switching. Each switch 191 has a series resistance when enabled or "on" to couple a corresponding column output signal to the bus 175; likewise, each switch adds a capacitance to the bus 175 when the switch is off A larger switch reduces series resistance and allows a higher drive current for the bus 175, which generally allows the bus 175 to settle more quickly; on the other hand, a larger switch increases capacitance of the bus 175 when the switch is off, which in turn increases the settling time of the bus 175. Hence, there is a trade-off between switch series resistance and capacitance in connection with switch size.

The ability of the bus 175 to settle quickly following enabling of successive switches in turn facilitates rapid data acquisition from the array. To this end, in some embodiments the switches 191 of the output drivers 198$_1$ and 198$_2$ are particularly configured to significantly reduce the settling time of the bus 175. Both the n-channel and the p-channel MOSFETs of a given switch add to the capacitance of the bus 175; however, n-channel MOSFETs generally have better frequency response and current drive capabilities than their p-channel counterparts. In view of the foregoing, Applicants have recognized and appreciated that some of the superior characteristics of n-channel MOSFETs may be exploited to improve settling time of the bus 175 by implementing "asymmetric" switches in which respective sizes for the n-channel MOSFET and p-channel MOSFET of a given switch are different.

For example, in one embodiment, with reference to FIG. 16, the current sink 197 may be configured such that the bus 175 is normally "pulled down" when all switches 191$_2$, 191$_4$, . . . 191$_{512}$ are open or off (not conducting). Given a somewhat limited expected signal dynamic range for the column output signals based on ISFET measurements, when a given switch is enabled or on (conducting), in many instances most of the conduction is done by the n-channel MOSFET of the CMOS-pair constituting the switch. Accordingly, in one aspect of this embodiment, the n-channel MOSFET and the p-channel MOSFET of each switch 191 are sized differently; namely, in one exemplary implementation, the n-channel MOSFET is sized to be significantly larger than the p-channel MOSFET. More specifically, considering equally-sized n-channel and p-channel MOSFETs as a point of reference, in one implementation the n-channel MOSFET may be increased to be about 2 to 2.5 times larger, and the p-channel MOSFET may be decreased in size to be about 8 to 10 times smaller, such that the n-channel MOSFET is approximately 20 times larger than the p-channel MOSFET. Due to the significant decrease in size of the p-channel MOSFET and the relatively modest increase in size of the n-channel MOSFET, the overall capacitance of the switch in the off state is notably reduced, and there is a corresponding notable reduction in capacitance for the bus 175; at the same time, due to the larger n-channel MOSFET, there is a significant increase in current drive capability, frequency response and transconductance of the switch, which in turn results in a significant reduction in settling time of the bus 175.

While the example above describes asymmetric switches 191 for the output drivers 198$_1$ and 198$_2$ in which the n-channel MOSFET is larger than the p-channel MOSFET, it should be appreciated that in another embodiment, the converse may be implemented, namely, asymmetric switches in which the p-channel MOSFET is larger than the n-channel MOSFET. In one aspect of this embodiment, with reference again to FIG. 16, the current sink 197 may alternatively serve as a source of current to appropriately drive the output of the column output buffer (see the buffer amplifier 111$j$ of FIG. 9) of a selected column, and be configured such that the bus 175 is normally "pulled up" when all switches 191$_2$, 191$_4$, . . . 191$_{512}$ are open or off (not conducting). In this situation, most of the switch conduction may be accomplished by the p-channel MOSFET of the CMOS-pair constituting the switch. Benefits of reduced switch capacitance (and hence reduced bus capacitance) may be realized in this embodiment, although the overall beneficial effect of reduced settling time for the bus 175 may be somewhat less than that described previously above, due to the lower frequency response of p-channel MOSFETs as compared to n-channel MOSFETs. Nevertheless, asymmetric switches based on larger p-channel MOSFETs may still facilitate a notable reduction in bus settling time, and may also provide for circuit implementations in which the column output buffer amplifier (111$j$ of FIG. 9) may be a body-tied source follower with appreciably increased gain.

In yet another embodiment directed to facilitating rapid settling of the bus 175 shown in FIG. 16, it may be appreciated that fewer switches 191 coupled to the bus 175 results in a smaller bus capacitance. With this in mind, and with reference again to FIG. 13, in yet another embodiment, more than two output drivers 198$_1$ and 198$_2$ may be employed in the ISFET array 100 such that each output driver handles a smaller number of columns of the array. For example, rather than having all even columns handled by one driver and all odd columns handled by another driver, the array may include four column select registers 194$_{1,2,3,4}$ and four corresponding output drivers 198$_{1,2,3,4}$ such that each output driver handles one-fourth of the total columns of the array, rather than one-half of the columns. In such an implementation, each output driver would accordingly have half the number of switches 191 as compared with the embodiment discussed above in connection with FIG. 16, and the bus 175 of each output driver would have a corresponding lower capacitance, thereby improving bus settling time. While four output drivers are discussed for purposes of illustration in this example, it should be appreciated that the present disclosure is not limited in this respect, and virtually any number of output drivers greater than two may be employed to improve bus settling time in the scenario described above. Other array embodiments in which more than two output drivers are employed to facilitate rapid data acquisition from the array are discussed in greater detail below (e.g., in connection with FIGS. 19-23).

For purposes of illustration, the bus 175 may have a capacitance in the range of approximately 5 pF to 20 pF in any of the embodiments discussed immediately above (e.g. symmetric switches, asymmetric switches, greater numbers of output drivers, etc.). Of course, it should be appreciated that the capacitance of the bus 175 is not limited to these exemplary values, and that other capacitance values are possible in different implementations of an array according to the present disclosure.

In one aspect of the array design discussed above in connection with FIGS. 13-16, separate analog supply voltage connections (for VDDA, VSSA), digital supply voltage connections (for VDDD, VSSD) and output buffer supply voltage connections (for VDDO, VSSO) are provided on the array to facilitate noise isolation and reduce signal cross-talk amongst various array components, thereby increasing the signal-to-noise ratio (SNR) of the output signals Vout1 and Vout2. In one exemplary implementation, the positive supply voltages VDDA, VDDD and VDDO each may be approximately 3.3 Volts. In another aspect, these voltages respectively may be provided "off chip" by one or more programmable voltage sources, as discussed further below in connection with FIG. 17.

Figure 17:
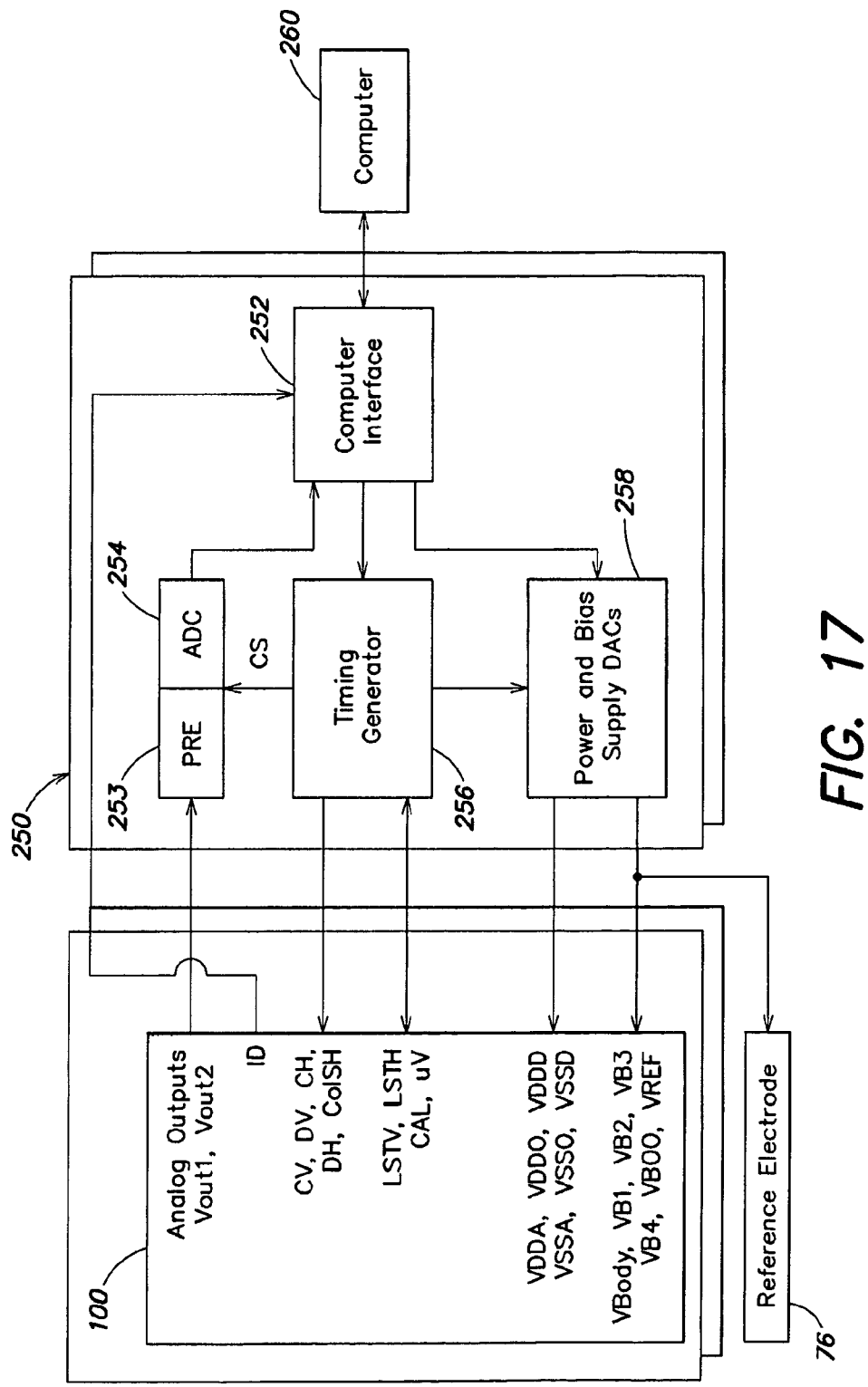
FIG. 17 illustrates a block diagram of the chemFET sensor array of FIG. 13 coupled to an array controller, according to one inventive embodiment of the present disclosure.

FIG. 17 illustrates a block diagram of the sensor array 100 of FIG. 13 coupled to an array controller 250, according to one inventive embodiment of the present disclosure. In various exemplary implementations, the array controller 250 may be fabricated as a "stand alone" controller, or as one or more computer compatible "cards" forming part of a computer 260, as discussed above in connection with FIG. 8. In one aspect, the functions of the array controller 250 may be controlled by the computer 260 through an interface block 252 (e.g., serial interface, via USB port or PCI bus, Ethernet connection, etc.), as shown in FIG. 17. In one embodiment, all or a portion of the array controller 250 is fabricated as one or more printed circuit boards, and the array 100 is configured to plug into one of the printed circuit boards, similar to a conventional IC chip (e.g., the array 100 is configured as an ASIC that plugs into a chip socket, such as a zero-insertion-force or "ZIF" socket, of a printed circuit board). In one aspect of such an embodiment, an array 100 configured as an ASIC may include one or more pins/terminal connections dedicated to providing an identification code, indicated as "ID" in FIG. 17, that may be accessed/read by the array controller 250 and/or passed on to the computer 260. Such an identification code may represent various attributes of the array 100 (e.g., size, number of pixels, number of output signals, various operating parameters such as supply and/or bias voltages, etc.) and may be processed to determine corresponding operating modes, parameters and or signals provided by the array controller 250 to ensure appropriate operation with any of a number of different types of arrays 100. In one exemplary implementation, an array 100 configured as an ASIC may be provided with three pins dedicated to an identification code, and during the manufacturing process the ASIC may be encoded to provide one of three possible voltage states at each of these three pins (i.e., a tri-state pin coding scheme) to be read by the array controller 250, thereby providing for 27 unique array identification codes. In another aspect of this embodiment, all or portions of the array controller 250 may be implemented as a field programmable gate array (FPGA) configured to perform various array controller functions described in further detail below.

Generally, the array controller 250 provides various supply voltages and bias voltages to the array 100, as well as various signals relating to row and column selection, sampling of pixel outputs and data acquisition. In particular, the array controller 250 reads one or more analog output signals (e.g., Vout1 and Vout2) including multiplexed respective pixel voltage signals from the array 100 and then digitizes these respective pixel signals to provide measurement data to the computer 260, which in turn may store and/or process the data. In some implementations, the array controller 250 also may be configured to perform or facilitate various array calibration and diagnostic functions, and an optional array UV irradiation treatment as discussed above in connection with FIG. 11A.

As illustrated in FIG. 17, the array controller 250 generally provides to the array 100 the analog supply voltage and ground (VDDA, VSSA), the digital supply voltage and ground (VDDD, VSSD), and the buffer output supply voltage and ground (VDDO, VSSO). In one exemplary implementation, each of the supply voltages VDDA, VDDD and VDDO is approximately 3.3 Volts. In another implementation, the supply voltages VDDA, VDDD and VDDO may be as low as approximately 1.8 Volts. As discussed above, in one aspect each of these power supply voltages is provided to the array 100 via separate conducting paths to facilitate noise isolation. In another aspect, these supply voltages may originate from respective power supplies/regulators, or one or more of these supply voltages may originate from a common source in a power supply 258 of the array controller 250. The power supply 258 also may provide the various bias voltages required for array operation (e.g., VB1, VB2, VB3, VB4, VBO0, $V_{BODY}$) and the reference voltage VREF used for array diagnostics and calibration.

In another aspect, the power supply 258 includes one or more digital-to-analog converters (DACs) that may be controlled by the computer 260 to allow any or all of the bias voltages, reference voltage, and supply voltages to be changed under software control (i.e., programmable bias settings). For example, a power supply 258 responsive to computer control (e.g., via software execution) may facilitate adjustment of one or more of the supply voltages (e.g., switching between 3.3 Volts and 1.8 Volts depending on chip type as represented by an identification code), and or adjustment of one or more of the bias voltages VB1 and VB2 for pixel drain current, VB3 for column bus drive, VB4 for column amplifier bandwidth, and VBO0 for column output buffer current drive. In some aspects, one or more bias voltages may be adjusted to optimize settling times of signals from enabled pixels. Additionally, the common body voltage $V_{BODY}$ for all ISFETs of the array may be grounded during an optional post-fabrication UV irradiation treatment to reduce trapped charge, and then coupled to a higher voltage (e.g., VDDA) during diagnostic analysis, calibration, and normal operation of the array for measurement/data acquisition. Likewise, the reference voltage VREF may be varied to facilitate a variety of diagnostic and calibration functions.

As also shown in FIG. 17, the reference electrode 76 which is typically employed in connection with an analyte solution to be measured by the array 100 (as discussed above in connection with FIG. 1), may be coupled to the power supply 258 to provide a reference potential for the pixel output voltages. For example, in one implementation the reference electrode 76 may be coupled to a supply ground (e.g., the analog ground VSSA) to provide a reference for the pixel output voltages based on Eq. (3) above. In other exemplary implementations, the reference electrode voltage may be set by placing a solution/sample of interest having a known pH level in proximity to the sensor array 100 and adjusting the reference electrode voltage until the array output signals Vout1 and Vout2 provide pixel voltages at a desired reference level, from which subsequent changes in pixel voltages reflect local changes in pH with respect to the known reference pH level. In general, it should be appreciated that a voltage associated with the reference electrode 76 need not necessarily be identical to the reference voltage VREF discussed above (which may be employed for a variety of array diagnostic and calibration functions), although in some implementations the reference voltage VREF provided by the power supply 258 may be used to set the voltage of the reference electrode 76.

Regarding data acquisition from the array 100, in one embodiment the array controller 250 of FIG. 17 may include one or more preamplifiers 253 to further buffer one or more output signals (e.g., Vout1 and Vout2) from the sensor array and provide selectable gain. In one aspect, the array controller 250 may include one preamplifier for each output signal (e.g., two preamplifiers for two analog output signals). In other aspects, the preamplifiers may be configured to accept input voltages from 0.0 to 1.8 Volts or 0.0 to 3.3 Volts, may have programmable/computer selectable gains (e.g., 1, 2, 5, 10 and 20) and low noise outputs (e.g., <10 nV/sqrtHz), and may provide low pass filtering (e.g., bandwidths of 5 MHz and 25 MHz). With respect to noise reduction and increasing signal-to-noise ratio, in one implementation in which the array 100 is configured as an ASIC placed in a chip socket of a printed circuit board containing all or a portion of the array controller 250, filtering capacitors may be employed in proximity to the chip socket (e.g., the underside of a ZIF socket) to facilitate noise reduction. In yet another aspect, the preamplifiers may have a programmable/computer selectable offset for input and/or output voltage signals to set a nominal level for either to a desired range.

The array controller 250 of FIG. 17 also comprises one or more analog-to-digital converters 254 (ADCs) to convert the sensor array output signals Vout1 and Vout2 to digital outputs (e.g., 10-bit or 12-bit) so as to provide data to the computer 260. In one aspect, one ADC may be employed for each analog output of the sensor array, and each ADC may be coupled to the output of a corresponding preamplifier (if preamplifiers are employed in a given implementation). In another aspect, the ADC(s) may have a computer-selectable input range (e.g., 50 mV, 200 mV, 500 mV, 1V) to facilitate compatibility with different ranges of array output signals and/or preamplifier parameters. In yet other aspects, the bandwidth of the ADC(s) may be greater than 60 MHz, and the data acquisition/conversion rate greater than 25 MHz (e.g., as high as 100 MHz or greater).

In the embodiment of FIG. 17, ADC acquisition timing and array row and column selection may be controlled by a timing generator 256. In particular, the timing generator provides the digital vertical data and clock signals (DV, CV) to control row selection, the digital horizontal data and clock signals (DH, CH) to control column selection, and the column sample and hold signal COL SH to sample respective pixel voltages for an enabled row, as discussed above in connection with FIG. 9. The timing generator 256 also provides a sampling clock signal CS to the ADC(s) 254 so as to appropriately sample and digitize consecutive pixel values in the data stream of a given array analog output signal (e.g., Vout1 and Vout2), as discussed further below in connection with FIG. 18. In some implementations, the timing generator 256 may be implemented by a microprocessor executing code and configured as a multi-channel digital pattern generator to provide appropriately timed control signals. In one exemplary implementation, the timing generator 256 may be implemented as a field-programmable gate array (FPGA).

Figure 18:
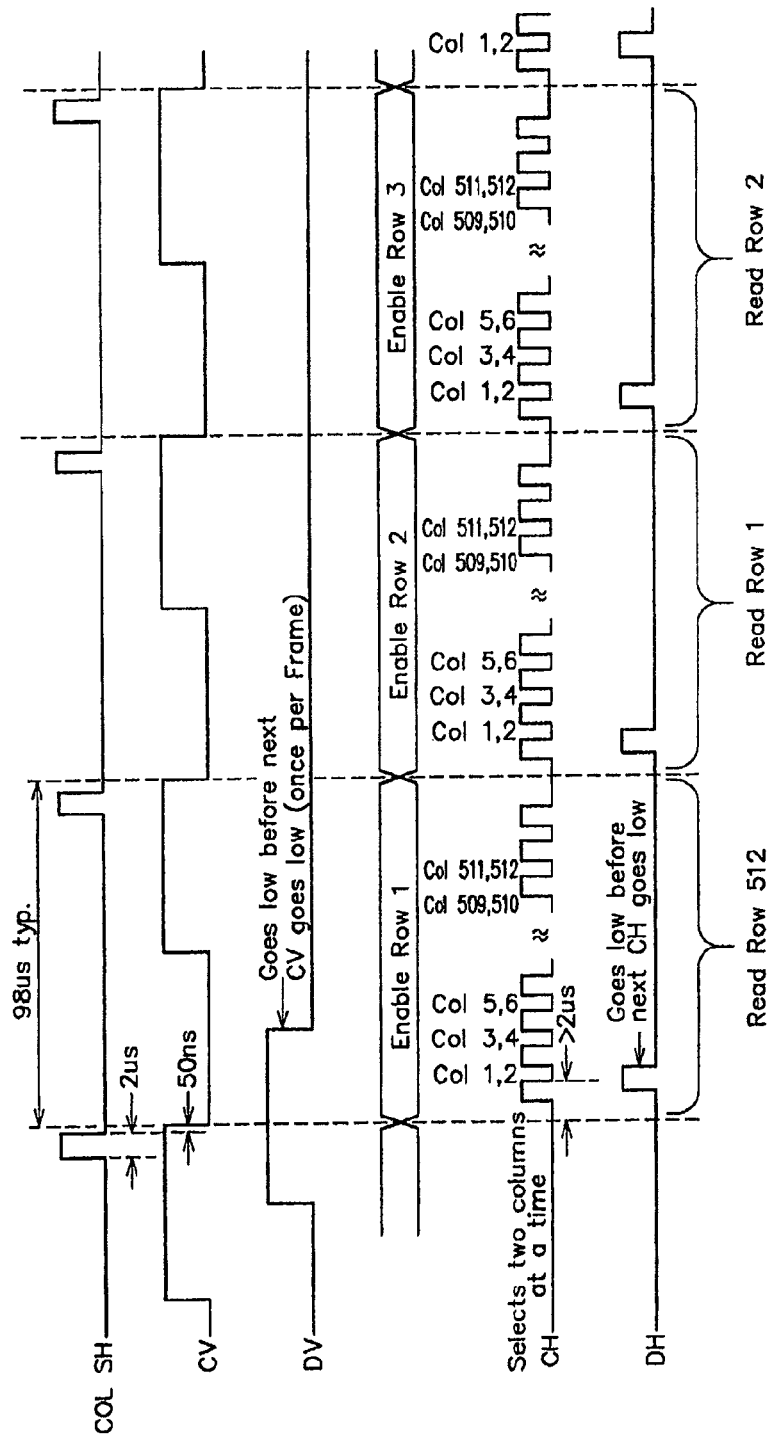
FIG. 18 illustrates an exemplary timing diagram for various signals provided by the array controller of FIG. 17, according to one inventive embodiment of the present disclosure.

FIG. 18 illustrates an exemplary timing diagram for various array control signals, as provided by the timing generator 256, to acquire pixel data from the sensor array 100. For purposes of the following discussion, a "frame" is defined as a data set that includes a value (e.g., pixel output signal or voltage $V_S$) for each pixel in the array, and a "frame rate" is defined as the rate at which successive frames may be acquired from the array. Thus, the frame rate corresponds essentially to a "pixel sampling rate" for each pixel of the array, as data from any given pixel is obtained at the frame rate.

In the example of FIG. 18, an exemplary frame rate of 20 frames/sec is chosen to illustrate operation of the array (i.e., row and column selection and signal acquisition); however, it should be appreciated that arrays and array controllers according to the present disclosure are not limited in this respect, as different frame rates, including lower frame rates (e.g., 1 to 10 frames/second) or higher frame rates (e.g., 25, 30, 40, 50, 60, 70 to 100 frames/sec., etc.), with arrays having the same or higher numbers of pixels, are possible. In some exemplary applications, a data set may be acquired that includes many frames over several seconds to conduct an experiment on a given analyte or analytes. Several such experiments may be performed in succession, in some cases with pauses in between to allow for data transfer/processing and/or washing of the sensor array ASIC and reagent preparation for a subsequent experiment.

For example, with respect to the method for detecting nucleotide incorporation, discussed above in connection with FIGS. 8, 8A and 8B, in which one or more ion pulses are generated in the output signal of a given ISFET pixel of the array during a nucleic acid synthesis or sequencing reaction in a reaction well above the ISFET, appropriate frame rates may be chosen to sufficiently sample the ISFET's output signal so as to effectively detect the presence of one or more pulses and the time interval between pulses. In some exemplary implementations, one or more ion pulses may be generated having a full-width at half-maximum (FWHM) on the order of approximately 1 second to approximately 2.5 seconds, and time intervals between successive pulse peaks (if multiple pulses are generated) on the order of approximately 1 to 20 seconds, depending on the number of nucleotide incorporation events. Given these exemplary values, a frame rate (or pixel sampling rate) of 20 Hz is sufficient to reliably resolve the one or more pulses in a given pixel's output signal. Again, the pulse characteristics and frame rate given in this example are provided primarily for purposes of illustration, and different pulse characteristics and frame rates may be involved in other implementations.

In one implementation, the array controller 250 controls the array 100 to enable rows successively, one at a time. For example, with reference again for the moment to FIG. 9, a first row of pixels is enabled via the row select signal $\overline{\text{RowSel}_1}$. The enabled pixels are allowed to settle for some time period, after which the COL SH signal is asserted briefly to close the sample/hold switch in each column and store on the column's sample/hold capacitor $C_{sh}$ the voltage value output by the first pixel in the column. This voltage is then available as the column output voltage $V_{COLj}$ applied to one of the two (odd and even column) array output drivers 198$_1$ and 198$_2$ (e.g., see FIG. 16). The COL SH signal is then de-asserted, thereby opening the sample/hold switches in each column and decoupling the column output buffer 111j from the column amplifiers 107A and 107B. Shortly thereafter, the second row of pixels is enabled via the row select signal $\overline{\text{RowSel}_2}$. During the time period in which the second row of pixels is allowed to settle, the column select signals are generated two at a time (one odd and one even; odd column select signals are applied in succession to the odd output driver, even column select signals are applied in succession to the even output driver) to read the column output voltages associated with the first row. Thus, while a given row in the array is enabled and settling, the previous row is being read out, two columns at a time. By staggering row selection and sampling/readout (e.g., via different vertical and horizontal clock signals and column sample/hold), and by reading multiple columns at a time for a given row, a frame of data may be acquired from the array in a significantly streamlined manner.

FIG. 18 illustrates the timing details of the foregoing process for an exemplary frame rate of 20 frames/sec. Given this frame rate and 512 rows in the array, each row must be read out in approximately 98 microseconds, as indicated by the vertical delineations in FIG. 18. Accordingly, the vertical clock signal CV has a period of 98 microseconds (i.e., a clock frequency of over 10 kHz), with a new row being enabled on a trailing edge (negative transition) of the CV signal. The left side of FIG. 18 reflects the beginning of a new frame cycle, at which point the vertical data signal DV is asserted before a first trailing edge of the CV signal and de-asserted before the next trailing edge of the CV signal (for data acquisition from successive frames, the vertical data signal is reasserted again only after row 512 is enabled). Also, immediately before each trailing edge of the CV signal (i.e., new row enabled), the COL SH signal is asserted for 2 microseconds, leaving approximately 50 nanoseconds before the trailing edge of the CV signal.

In FIG. 18, the first occurrence of the COL SH signal is actually sampling the pixel values of row 512 of the array. Thus, upon the first trailing edge of the CV signal, the first row is enabled and allowed to settle (for approximately 96 microseconds) until the second occurrence of the COL SH signal. During this settling time for the first row, the pixel values of row 512 are read out via the column select signals. Because two column select signals are generated simultaneously to read 512 columns, the horizontal clock signal CH must generate 256 cycles within this period, each trailing edge of the CH signal generating one odd and one even column select signal. As shown in FIG. 18, the first trailing edge of the CH signal in a given row is timed to occur two microseconds after the selection of the row (after deactivation of the COL SH signal) to allow for settling of the voltage values stored on the sample/hold capacitors $C_{sh}$ and provided by the column output buffers. It should be appreciated however that, in other implementations (e.g., as discussed below in connection with FIG. 18A), the time period between the first trailing edge of the CH signal and a trailing edge (i.e., deactivation) of the COL SH signal may be significantly less than two microseconds, and in some cases as small as just over 50 nanoseconds. Also for each row, the horizontal data signal DH is asserted before the first trailing edge of the CH signal and de-asserted before the next trailing edge of the CH signal. The last two columns (e.g., 511 and 512) are selected before the occurrence of the COL SH signal which, as discussed above, occurs approximately two microseconds before the next row is enabled. Thus, 512 columns are read, two at a time, within a time period of approximately 94 microseconds (i.e., 98 microseconds per row, minus two microseconds at the beginning and end of each row). This results in a data rate for each of the array output signals Vout1 and Vout2 of approximately 2.7 MHz.

Figure 18A:
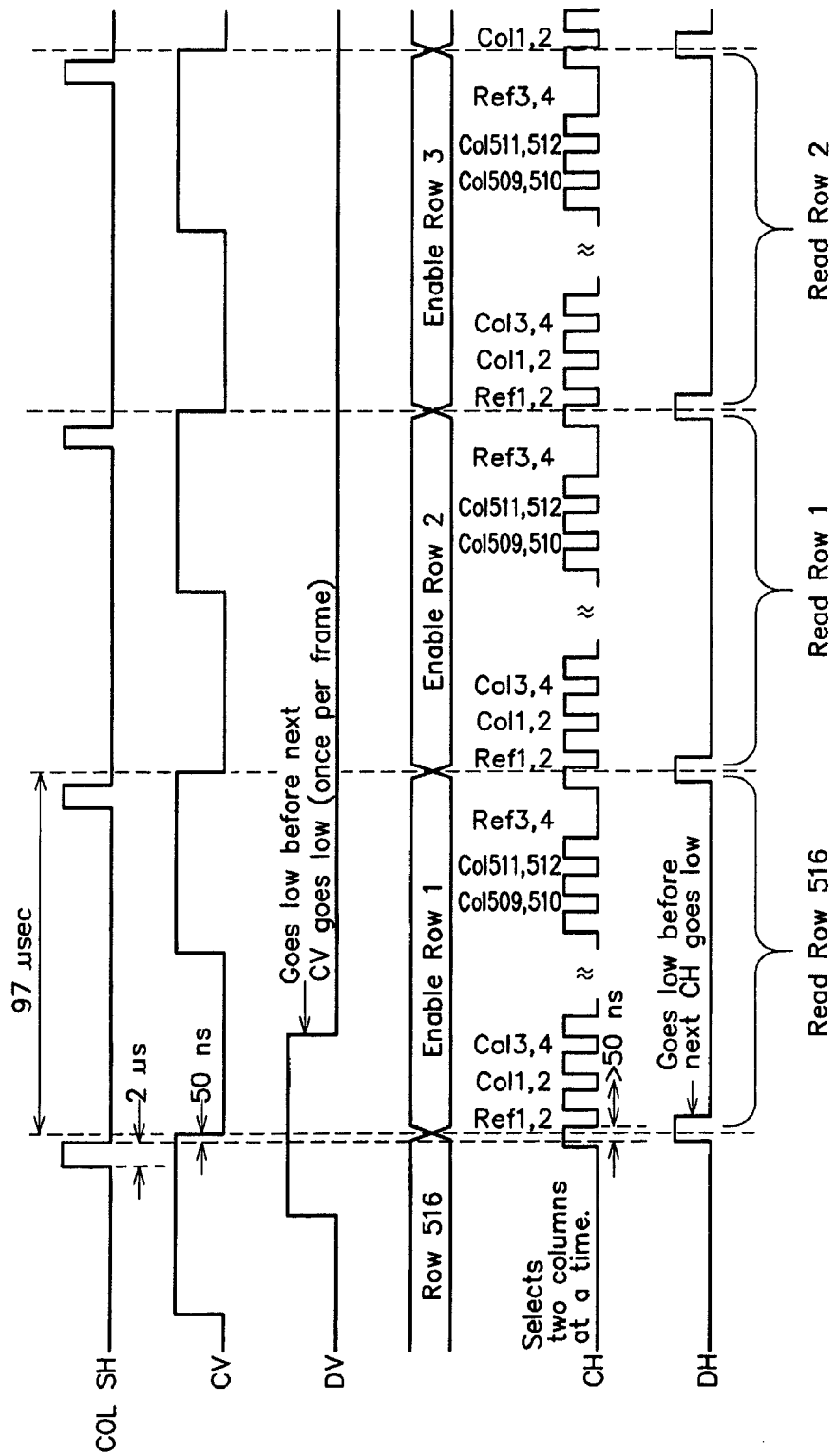
FIG. 18A illustrates another exemplary timing diagram for various signals provided by the array controller of FIG. 17, according to one inventive embodiment of the present disclosure.

FIG. 18A illustrates another timing diagram of a data acquisition process from an array 100 that is slightly modified from the timing diagram of FIG. 18. As discussed above in connection with FIG. 13, in some implementations an array similar to that shown in FIG. 13 may be configured to include a region of 512 by 512 "active" pixels that are surrounded by a perimeter of reference pixels (i.e., the first and last two rows and columns of the array), resulting in an array having a total pixel count of 516 by 516 pixels. Accordingly, given the exemplary frame rate of 20 frames/sec and 516 rows in the array, each row must be read out in approximately 97 microseconds, as indicated by the vertical delineations in FIG. 18A. Accordingly, the vertical clock signal CV has a slightly smaller period of 97 microseconds. Because two column select signals are generated simultaneously to read 516 columns, the horizontal clock signal CH must generate 258 cycles within this period, as opposed to the 256 cycles referenced in connection with FIG. 18. Accordingly, in one aspect illustrated in FIG. 18A, the first trailing edge of the CH signal in a given row is timed to occur just over 50 nanoseconds from the trailing edge (i.e., deactivation) of the COL SH signal, so as to "squeeze" additional horizontal clock cycles into a slightly smaller period of the vertical clock signal CV. As in FIG. 18, the horizontal data signal DH is asserted before the first trailing edge of the CH signal, and as such also occurs slightly earlier in the timing diagram of FIG. 18A as compared to FIG. 18. The last two columns (i.e., columns 515 and 516, labeled as "Ref3,4 in FIG. 18A) are selected before the occurrence of the COL SH signal which, as discussed above, occurs approximately two microseconds before the next row is enabled. Thus, 516 columns are read, two at a time, within a time period of approximately 95 microseconds (i.e., 97 microseconds per row, minus two microseconds at the end of each row and negligible time at the beginning of each row). This results in essentially the same data rate for each of the array output signals Vout1 and Vout2 provided by the timing diagram of FIG. 18, namely, approximately 2.7 MHz.

As discussed above in connection with FIG. 17, the timing generator 256 also generates the sampling clock signal CS to the ADC(s) 254 so as to appropriately sample and digitize consecutive pixel values in the data stream of a given array output signal. In one aspect, the sampling clock signal CS provides for sampling a given pixel value in the data stream at least once. Although the sampling clock signal CS is not shown in the timing diagrams of FIGS. 18 and 18A, it may be appreciated that in exemplary implementations the signal CS may essentially track the timing of the horizontal clock signal CH; in particular, the sampling clock signal CS may be coordinated with the horizontal clock signal CH so as to cause the ADC(s) to sample a pixel value immediately prior to a next pixel value in the data stream being enabled by CH, thereby allowing for as much signal settling time as possible prior to sampling a given pixel value. For example, the ADC(s) may be configured to sample an input pixel value upon a positive transition of CS, and respective positive transitions of CS may be timed by the timing generator 256 to occur immediately prior to, or in some cases essentially coincident with, respective negative transitions of CH, so as to sample a given pixel just prior to the next pixel in the data stream being enabled. In another exemplary implementation, the ADC(s) 254 may be controlled by the timing generator 256 via the sampling clock signal CS to sample the output signals Vout1 and Vout2 at a significantly higher rate to provide multiple digitized samples for each pixel measurement, which may then be averaged (e.g., the ADC data acquisition rate may be approximately 100 MHz to sample the 2.7 MHz array output signals, thereby providing as many as approximately 35-40 samples per pixel measurement).

Figure 18B:
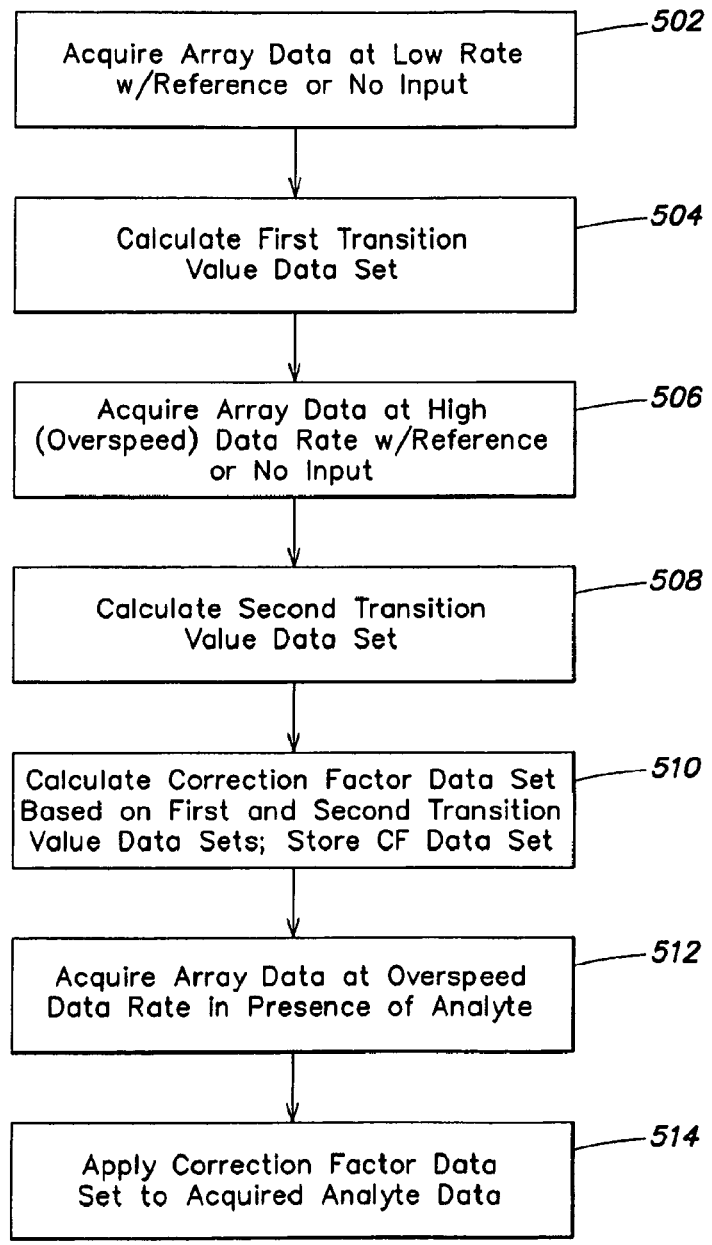
FIG. 18B shows a flow chart illustrating an exemplary method for processing and correction of array data acquired at high acquisition rates, according to one inventive embodiment of the present disclosure.

In one embodiment, once pixel values are sampled and digitized by the ADC(s) 254, the computer 260 may be programmed to process pixel data obtained from the array 100 and the array controller 250 so as to facilitate high data acquisition rates that in some cases may exceed a sufficient settling time for pixel voltages represented in a given array output signal. A flow chart illustrating an exemplary method according to one embodiment of the present invention that may be implemented by the computer 260 for processing and correction of array data acquired at high acquisition rates is illustrated in FIG. 18B. In various aspects of this embodiment, the computer 260 is programmed to first characterize a sufficient settling time for pixel voltages in a given array output signal, as well as array response at appreciably high operating frequencies, using a reference or "dry" input to the array (e.g., no analyte present). This characterization forms the basis for deriving correction factors that are subsequently applied to data obtained from the array at the high operating frequencies and in the presence of an analyte to be measured.

Figure 18C:
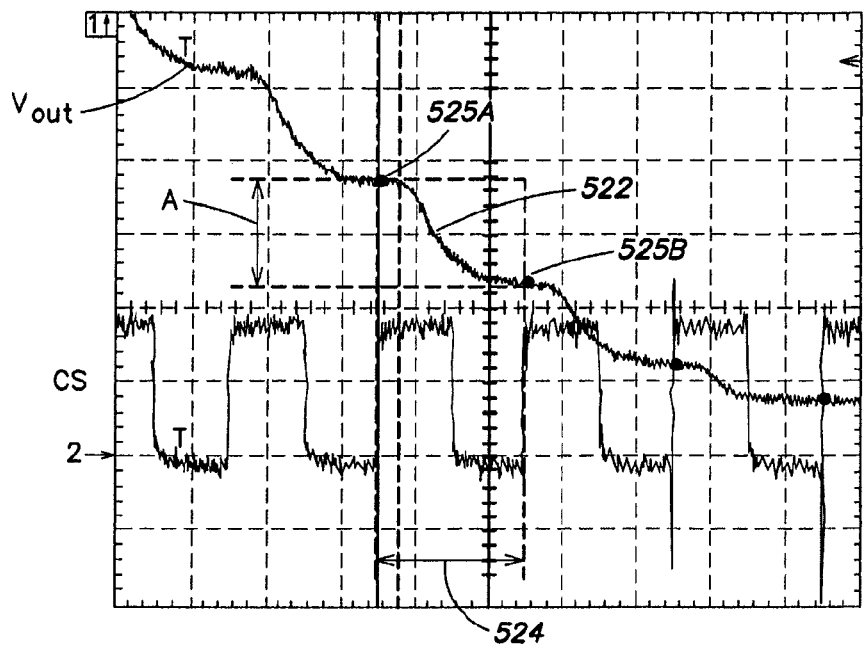
FIGS. 18C and 18D illustrate exemplary pixel voltages showing pixel-to-pixel transitions in a given array output signal, according to one embodiment of the present disclosure.
Figure 18D:
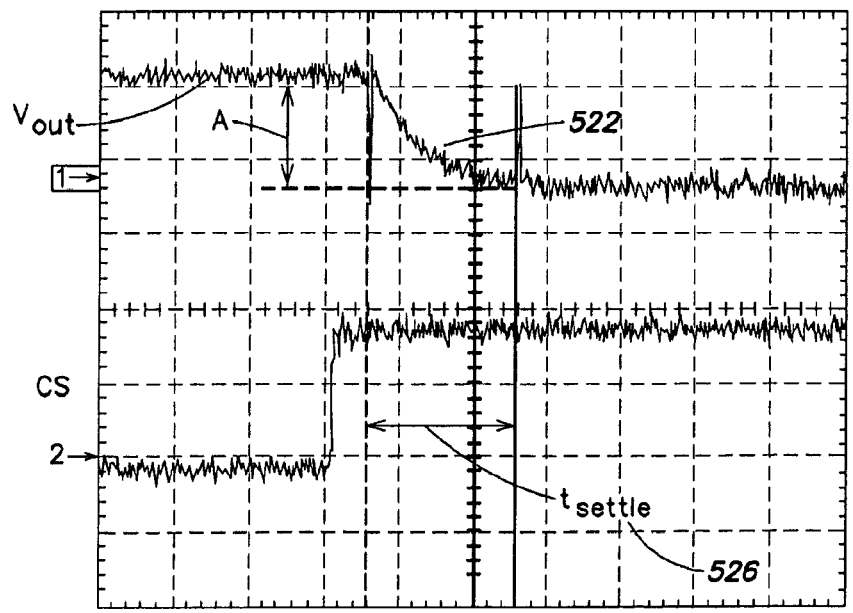

Regarding pixel settling time, with reference again to FIG. 16, as discussed above a given array output signal (e.g., Vout2 in FIG. 16) includes a series of pixel voltage values resulting from the sequential operation of the column select switches 191 to apply respective column voltages $V_{COLj}$ via the bus 175 to the buffer amplifier 199 (the respective column voltages $V_{COLj}$ in turn represent buffered versions of ISFET source voltages $V_{Sj}$). In some implementations, it is observed that voltage changes $\Delta V_{PIX}$ in the array output signal between two consecutive pixel reads is characterized as an exponential process given by $$\Delta V_{PIX}(t) = A(1 - e^{-t/k}), \quad (PP)$$

where A is the difference ($V_{COLj} - V_{COLj-1}$) between two pixel voltage values and k is a time constant associated with a capacitance of the bus 175. FIGS. 18C and 18D illustrate exemplary pixel voltages in a given array output signal Vout (e.g., one of Vout1 and Vout2) showing pixel-to-pixel transitions in the output signal as a function of time, plotted against exemplary sampling clock signals CS. In FIG. 18C, the sampling clock signal CS has a period 524, and an ADC controlled by CS samples a pixel voltage upon a positive transition of CS (as discussed above, in one implementation CS and CH have essentially a same period). FIG. 18C indicates two samples 525A and 525B, between which an exponential voltage transition 522 corresponding to $\Delta V_{PIX}(t)$, between a voltage difference A, may be readily observed.

For purposes of the present discussion, pixel "settling time" $t_{settle}$ is defined as the time t at which $\Delta V_{PIX}(t)$ attains a value that differs from it's final value by an amount that is equal to the peak noise level of the array output signal. If the peak noise level of the array output signal is denoted as $n_p$, then the voltage at the settling time $t_{settle}$ is given by $\Delta V_{PIX}(t_{settle}) = A[1 - (n_p/A)]$. Substituting in Eq. (PP) and solving for $t_{settle}$ yields $$t_{settle} = -k \ln\left(\frac{n_p}{A}\right). \quad (QQ)$$

FIG. 18D conceptually illustrates a pixel settling time $t_{settle}$ (reference numeral 526) for a single voltage transition 522 between two pixel voltages having a difference A, using a sampling clock signal CS having a sufficiently long period so as to allow for full settling. To provide some exemplary parameters for purposes of illustration, in one implementation a maximum value for A, representing a maximum range for pixel voltage transitions (e.g., consecutive pixels at minimum and maximum values), is on the order of approximately 250 mV. Additionally, a peak noise level $n_p$ of the array output signal is taken as approximately 100 μV, and the time constant k is taken as 5 nanoseconds. These values provide an exemplary settling time $t_{settle}$ of approximately 40 nanoseconds. If a maximum data rate of an array output signal is taken as the inverse of the settling time $t_{settle}$, a settling time of 40 nanoseconds corresponds to maximum data rate of 25 MHz. In other implementations, A may be on the order of 20 mV and the time constant k may be on the order of 15 nanoseconds, resulting in a settling time $t_{settle}$ of approximately 80 nanoseconds and a maximum data rate of 12.5 MHz. The values of k indicated above generally correspond to capacitances for the bus 175 in a range of approximately 5 pF to 20 pF. It should be appreciated that the foregoing values are provided primarily for purposes of illustration, and that various embodiments of the present invention are not limited to these exemplary values; in particular, arrays according to various embodiment of the present invention may have different pixel settling times $t_{settle}$ (e.g., in some cases less than 40 nanoseconds).

As indicated above, in one embodiment pixel data may be acquired from the array at data rates that exceed those dictated by the pixel settling time. FIG. 18B illustrates a flow chart for such a method according to one inventive embodiment of the present disclosure. In the method of FIG. 18B, sufficiently slow clock frequencies initially are chosen for the signals CV, CH and CS such that the resulting data rate per array output signal is equal to or lower than the reciprocal of the pixel settling time $t_{settle}$ to allow for fully settled pixel voltage values from pixel to pixel in a given output signal. With these clock frequencies, as indicated in block 502 of FIG. 18B, settled pixel voltage values are then acquired for the entire array in the absence of an analyte (or in the presence of a reference analyte) to provide a first "dry" or reference data image for the array. In block 504 of FIG. 18B, for each pixel voltage constituting the first data image, a transition value between the pixel's final voltage and the final voltage of the immediately preceding pixel in the corresponding output signal data stream (i.e., the voltage difference A) is collected and stored. The collection of these transition values for all pixels of the array provides a first transition value data set.

Subsequently, in block 506 of FIG. 18B, the clock frequencies for the signals CV, CH and CS are increased such that the resulting data rate per array output signal exceeds a rate at which pixel voltage values are fully settled (i.e., a data rate higher than the reciprocal of the settling time $t_{settle}$). For purposes of the present discussion, the data rate per array output signal resulting from the selection of such increased clock frequencies for the signals CV, CH and CS is referred to as an "overspeed data rate." Using the clock frequencies corresponding to the overspeed data rate, pixel voltage values are again obtained for the entire array in the absence of an analyte (or in the presence of the same reference analyte) to provide a second "dry" or reference data image for the array. In block 508 of FIG. 18B, a second transition value data set based on the second data image obtained at the overspeed data rate is calculated and stored, as described above for the first data image.

In block 510 of FIG. 18B, a correction factor for each pixel of the array is calculated based on the values stored in the first and second transition value data sets. For example, a correction factor for each pixel may be calculated as a ratio of its transition value from the first transition value data set and its corresponding transition value from the second transition value data set (e.g., the transition value from the first data set may be divided by the transition value from the second data set, or vice versa) to provide a correction factor data set which is then stored. As noted in blocks 512 and 514 of FIG. 18B, this correction factor data set may then be employed to process pixel data obtained from the array operated at clock frequencies corresponding to the overspeed data rate, in the presence of an actual analyte to be measured; in particular, data obtained from the array at the overspeed data rate in the presence of an analyte may be multiplied or divided as appropriate by the correction factor data set (e.g., each pixel multiplied or divided by a corresponding correction factor) to obtain corrected data representative of the desired analyte property to be measured (e.g., ion concentration). It should be appreciated that once the correction factor data set is calculated and stored, it may be used repeatedly to correct multiple frames of data acquired from the array at the overspeed data rate.

In addition to controlling the sensor array and ADCs, the timing generator 256 may be configured to facilitate various array calibration and diagnostic functions, as well as an optional UV irradiation treatment. To this end, the timing generator may utilize the signal LSTV indicating the selection of the last row of the array and the signal LSTH to indicate the selection of the last column of the array. The timing generator 256 also may be responsible for generating the CAL signal which applies the reference voltage VREF to the column buffer amplifiers, and generating the UV signal which grounds the drains of all ISFETs in the array during a UV irradiation process (see FIG. 9). The timing generator also may provide some control function over the power supply 258 during various calibration and diagnostic functions, or UV irradiation, to appropriately control supply or bias voltages; for example, during UV irradiation, the timing generator may control the power supply to couple the body voltage $V_{BODY}$ to ground while the UV signal is activated to ground the ISFET drains. With respect to array calibration and diagnostics, as well as UV irradiation, in some implementations the timing generator may receive specialized programs from the computer 260 to provide appropriate control signals. In one aspect, the computer 260 may use various data obtained from reference and/or dummy pixels of the array, as well as column information based on the application of the CAL signal and the reference voltage VREF, to determine various calibration parameters associated with a given array and/or generate specialized programs for calibration and diagnostic functions.

With respect to the computer interface 252 of the array controller 250, in one exemplary implementation the interface is configured to facilitate a data rate of approximately 200 MB/sec to the computer 260, and may include local storage of up to 400 MB or greater. The computer 260 is configured to accept data at a rate of 200 MB/sec, and process the data so as to reconstruct an image of the pixels (e.g., which may be displayed in false-color on a monitor). For example, the computer may be configured to execute a general-purpose program with routines written in C++ or Visual Basic to manipulate the data and display is as desired.

The systems described herein, when used for sequencing, typically involve a chemFET array supporting reaction chambers, the chemFETs being coupled to an interface capable of executing logic that converts the signals from the chemFETs into sequencing information.

In some embodiments, the invention encompasses logic (preferably computer executable logic) for polymer sequencing, comprising logic for determining ion pulses associated with an ionic interaction with a PPi or a dNTP or both. Typically, the logic converts characteristic(s) of the ion pulses into polymer sequencing information.

In some embodiments, the invention encompasses logic (preferably computer executable logic) comprising logic for determining a sequence of a nucleic acid template based on time between ion pulses or a characteristic of a single ion pulse. The logic may optionally further comprise logic for determining spatial location of the ion pulse on an array of chemFETs.

In some embodiments, the invention encompasses logic (preferably computer executable logic) comprising logic for determining a sequence of a nucleic acid template based on a duration of time it takes for a particular dNTP to be utilized in a sequencing reaction. Typically, the logic receives signal from one or more chemFETs. Preferably, the sequence is displayed in substantially real time.

In some embodiments, the invention encompasses logic (preferably computer executable logic) for processing ion pulses from an array of chemFETs to determine the sequence of a polymer of interest. The logic may optionally further comprise logic for file management, file storage, and visualization. The logic may also optionally further comprise logic for converting the ion pulses into nucleotide sequences. Preferably, the sequence is displayed in substantially real time.

The sequencing information obtained from the system may be delivered to a handheld computing device, such as a personal digital assistant. Thus, in one embodiment, the invention encompasses logic for displaying a complete genome of an organism on a handheld computing device. The invention also encompasses logic adapted for sending data from a chemFET array to a handheld computing device. Any of such logic may be computer-implemented.

Having discussed several aspects of an exemplary ISFET array and an array controller according to the present disclosure, FIGS. 19-23 illustrate block diagrams of alternative CMOS IC chip implementations of ISFET sensor arrays having greater numbers of pixels, according to yet other inventive embodiments. In one aspect, each of the ISFET arrays discussed further below in connection with FIGS. 19-23 may be controlled by an array controller similar to that shown in FIG. 17, in some cases with minor modifications to accommodate higher numbers of pixels (e.g., additional preamplifiers 253 and analog-to-digital converters 254).

Figure 19:
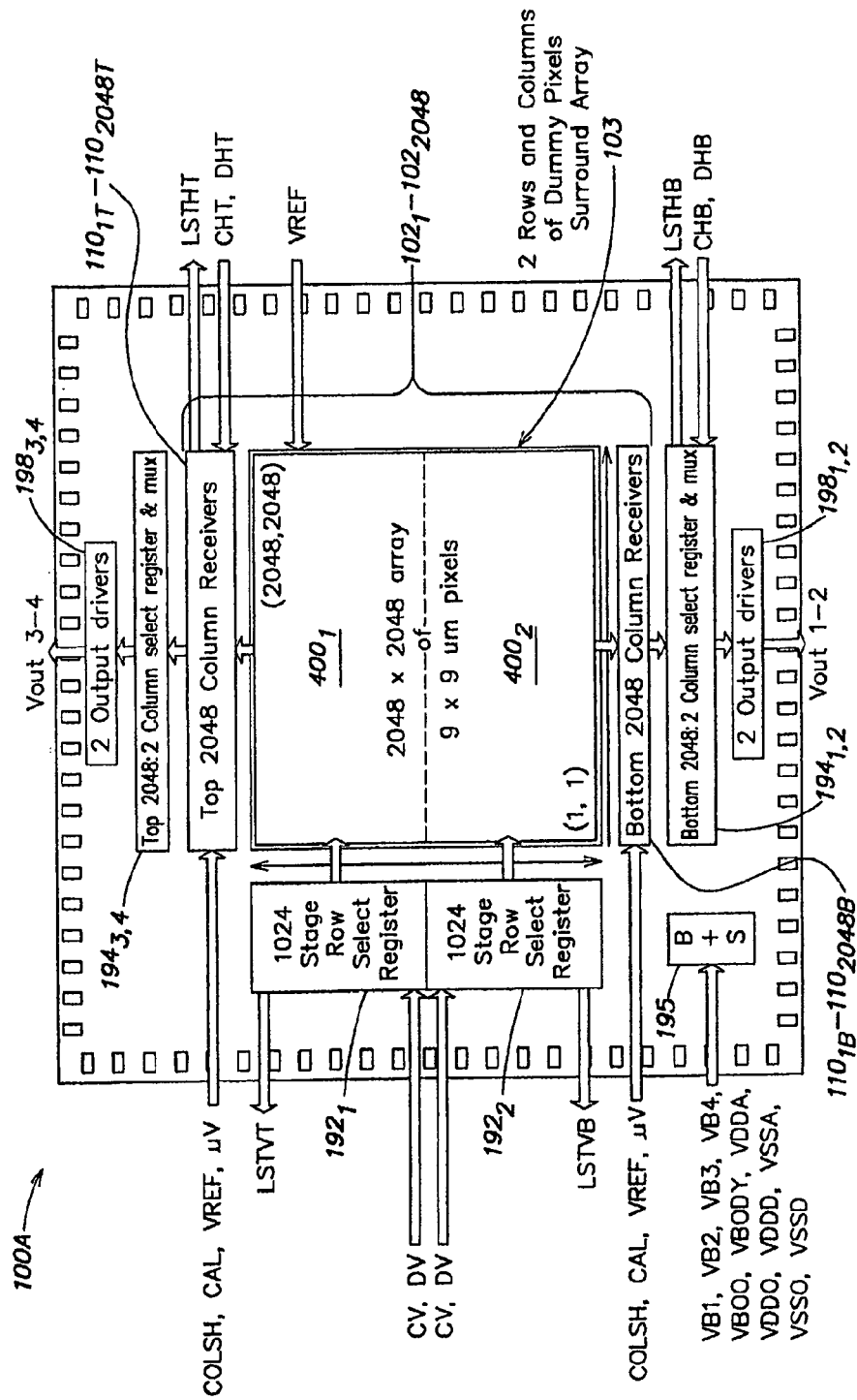
FIGS. 19-20 illustrate block diagrams of alternative CMOS IC chip implementations of chemFET sensor arrays, according to other inventive embodiments of the present disclosure.

FIG. 19 illustrates a block diagram of an ISFET sensor array 100A based on the column and pixel designs discussed above in connection with FIGS. 9-12 and a 0.35 micrometer CMOS fabrication process, according to one inventive embodiment. The array 100A includes 2048 columns $102_1$ through $102_{2048}$, wherein each column includes 2048 geometrically square pixels $105_1$ through $105_{2048}$, each having a size of approximately 9 micrometers by 9 micrometers. Thus, the array includes over four million pixels (>4 Mega-pixels) and, in one exemplary implementation, the complete array (ISFET pixels and associated circuitry) may be fabricated as an integrated circuit chip having dimensions of approximately 20.5 millimeters by 20.5 millimeters.

In one aspect of the embodiment shown in FIG. 19, the array 100A may be configured, at least in part, as multiple groups of pixels that may be respectively controlled. For example, each column of pixels may be divided into top and bottom halves, and the collection of pixels in respective top halves of columns form a first group $400_1$ of rows (e.g., a top group, rows 1-1024) and the collection of pixels in respective bottom halves of columns form a second group $400_2$ of rows (e.g., a bottom group, rows 1025-2048). In turn, each of the first and second (e.g., top and bottom) groups of rows is associated with corresponding row select registers, column bias/readout circuitry, column select registers, and output drivers. In this manner, pixel selection and data acquisition from each of the first and second groups of rows $400_1$ and $400_2$ is substantially similar to pixel selection and data acquisition from the entire array 100 shown in FIG. 13; stated differently, in one aspect, the array 100A of FIG. 19 substantially comprises two simultaneously controlled "sub-arrays" of different pixel groups to provide for significantly streamlined data acquisition from higher numbers of pixels.

In particular, FIG. 19 shows that row selection of the first group $400_1$ of rows may be controlled by a first row select register $192_1$, and row selection of the second group $400_2$ of rows may be controlled by a second row select register $192_2$. In one aspect, each of the row select registers $192_1$ and $192_2$ may be configured as discussed above in connection with FIG. 14 to receive vertical clock (CV) and vertical data (DV) signals and generate row select signals in response; for example the first row select register $192_1$ may generate the signals $\overline{RowSel_1}$ through $\overline{RowSel_{1024}}$ and the second row select register $192_2$ may generate the signals $\overline{RowSel_{1025}}$ through $\overline{RowSel_{2048}}$. In another aspect, both row select registers $192_1$ and $192_2$ may simultaneously receive common vertical clock and data signals, such that two rows of the array are enabled at any given time, one from the top group and another from the bottom group.

For each of the first and second groups of rows, the array 100A of FIG. 19 further comprises column bias/readout circuitry $110_{1T}$-$110_{2048T}$ (for the first row group $400_1$) and $110_{1B}$-$110_{2048B}$ (for the second row group $400_2$), such that each column includes two instances of the bias/readout circuitry $110j$ shown in FIG. 9. The array 100A also comprises two column select registers $192_{1,2}$ (odd and even) and two output drivers $198_{1,2}$ (odd and even) for the second row group $400_2$, and two column select registers $192_{3,4}$ (odd and even) and two output drivers $198_{3,4}$ (odd and even) for the first row group $400_1$ (i.e., a total of four column select registers and four output drivers). The column select registers receive horizontal clock signals (CHT and CHB for the first row group and second row group, respectively) and horizontal data signals (DHT and DHB for the first row group and second row group, respectively) to control odd and even column selection. In one implementation, the CHT and CHB signals may be provided as common signals, and the DHT and DHB may be provided as common signals, to simultaneously read out four columns at a time from the array (i.e., one odd and one even column from each row group); in particular, as discussed above in connection with FIGS. 13-18, two columns may be simultaneously read for each enabled row and the corresponding pixel voltages provided as two output signals. Thus, via the enablement of two rows at any given time, and reading of two columns per row at any given time, the array 100A may provide four simultaneous output signals Vout1, Vout2, Vout3 and Vout4.

In one exemplary implementation of the array 100A of FIG. 19, in which complete data frames (all pixels from both the first and second row groups $400_1$ and $400_2$) are acquired at a frame rate of 20 frames/sec, 1024 pairs of rows are successively enabled for periods of approximately 49 microseconds each. For each enabled row, 1024 pixels are read out by each column select register/output driver during approximately 45 microseconds (allowing 2 microseconds at the beginning and end of each row, as discussed above in connection with FIG. 18). Thus, in this example, each of the array output signals Vout1, Vout2, Vout3 and Vout4 has a data rate of approximately 23 MHz. Again, it should be appreciated that in other implementations, data may be acquired from the array 100A of FIG. 19 at frame rates other than 20 frames/sec (e.g., 50-100 frames/sec).

Like the array 100 of FIG. 13, in yet other aspects the array 100A of FIG. 19 may include multiple rows and columns of dummy or reference pixels 103 around a perimeter of the array to facilitate preliminary test/evaluation data, offset determination an/or array calibration. Additionally, various power supply and bias voltages required for array operation (as discussed above in connection with FIG. 9) are provided to the array 100A in block 195, in a manner similar to that discussed above in connection with FIG. 13.

Figure 20:
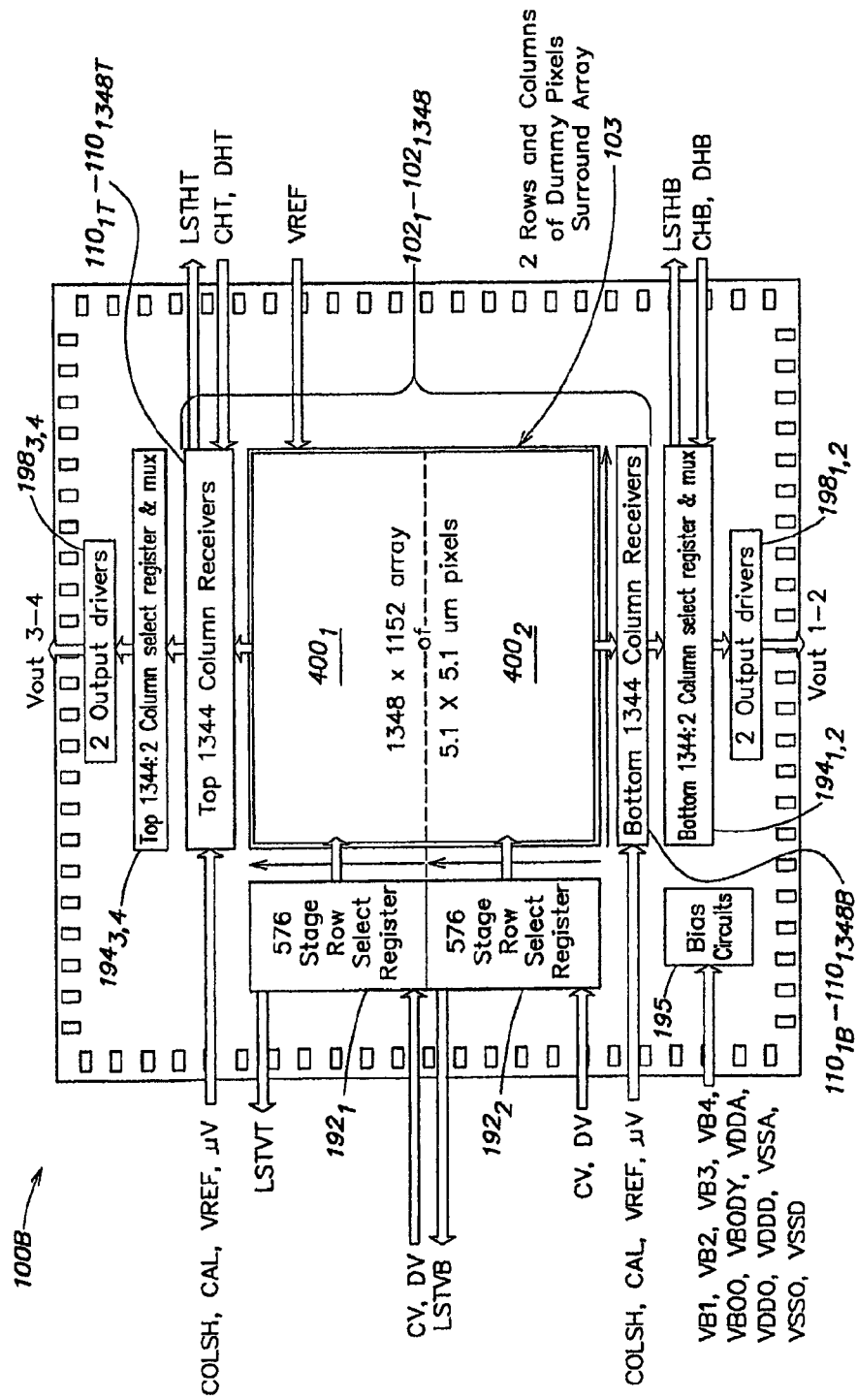
Figure 20A:
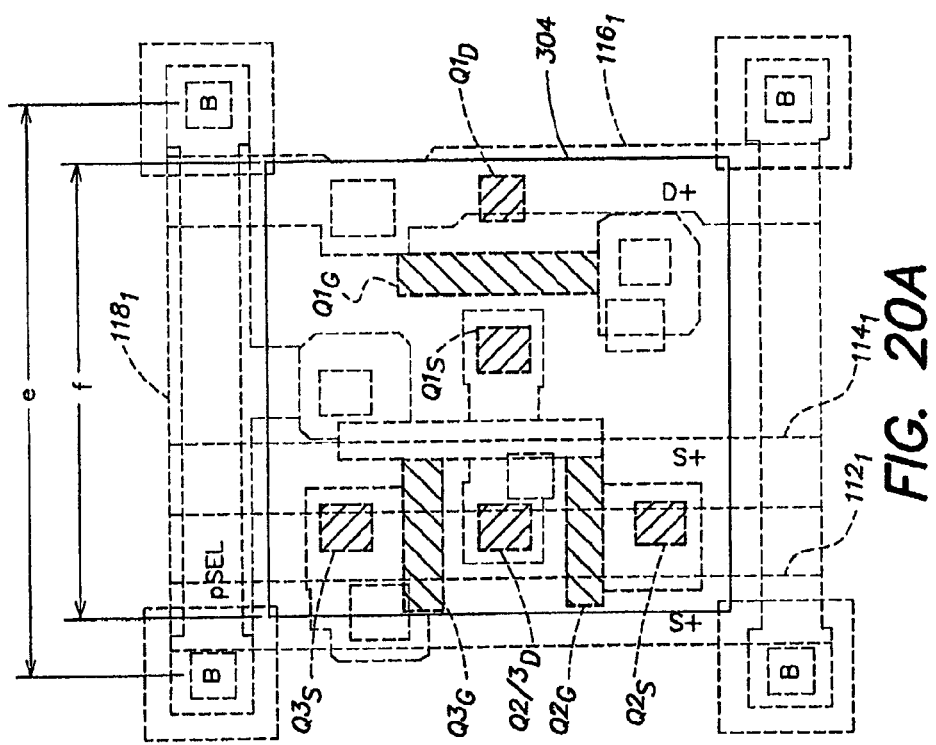
FIG. 20A illustrates a top view of a chip layout design for a pixel of the chemFET array shown in FIG. 20, according to another inventive embodiment of the present disclosure.

FIG. 20 illustrates a block diagram of an ISFET sensor array 100B based on a 0.35 micrometer CMOS fabrication process and having a configuration substantially similar to the array 100A discussed above in FIG. 19, according to yet another inventive embodiment. While the array 100B also is based generally on the column and pixel designs discussed above in connection with FIGS. 9-12, the pixel size/pitch in the array 100B is smaller than that of the pixel shown in FIG. 10. In particular, with reference again to FIGS. 10 and 11, the dimension "e" shown in FIG. 10 is substantially reduced in the embodiment of FIG. 20, without affecting the integrity of the active pixel components disposed in the central region of the pixel, from approximately 9 micrometers to approximately 5 micrometers; similarly, the dimension "f" shown in FIG. 10 is reduced from approximately 7 micrometers to approximately 4 micrometers. Stated differently, some of the peripheral area of the pixel surrounding the active components is substantially reduced with respect to the dimensions given in connection with FIG. 10, without disturbing the top-view and cross-sectional layout and design of the pixel's active components as shown in FIGS. 10 and 11. A top view of such a pixel 105A is shown in FIG. 20A, in which the dimension "e" is 5.1 micrometers and the dimension "f" is 4.1 micrometers. In one aspect of this pixel design, to facilitate size reduction, fewer body connections B are included in the pixel 105A (e.g., one at each corner of the pixel) as compared to the pixel shown in FIG. 10, which includes several body connections B around the entire perimeter of the pixel.

As noted in FIG. 20, the array 100B includes 1348 columns $102_1$ through $102_{1348}$, wherein each column includes 1152 geometrically square pixels $105A_1$ through $105A_{1152}$, each having a size of approximately 5 micrometers by 5 micrometers. Thus, the array includes over 1.5 million pixels (>1.5 Mega-pixels) and, in one exemplary implementation, the complete array (ISFET pixels and associated circuitry) may be fabricated as an integrated circuit chip having dimensions of approximately 9 millimeters by 9 millimeters. Like the array 100A of FIG. 19, in one aspect the array 100B of FIG. 20 is divided into two groups of rows $400_1$ and $400_2$, as discussed above in connection with FIG. 19. In one exemplary implementation, complete data frames (all pixels from both the first and second row groups $400_1$ and $400_2$) are acquired at a frame rate of 50 frames/sec, thereby requiring 576 pairs of rows to be successively enabled for periods of approximately 35 microseconds each. For each enabled row, 674 pixels are read out by each column select register/output driver during approximately 31 microseconds (allowing 2 microseconds at the beginning and end of each row, as discussed above in connection with FIG. 18). Thus, in this example, each of the array output signals Vout1, Vout2, Vout3 and Vout4 has a data rate of approximately 22 MHz. Again, it should be appreciated that in other implementations, data may be acquired from the array 100B of FIG. 20 at frame rates other than 50 frames/sec.

Figure 21:
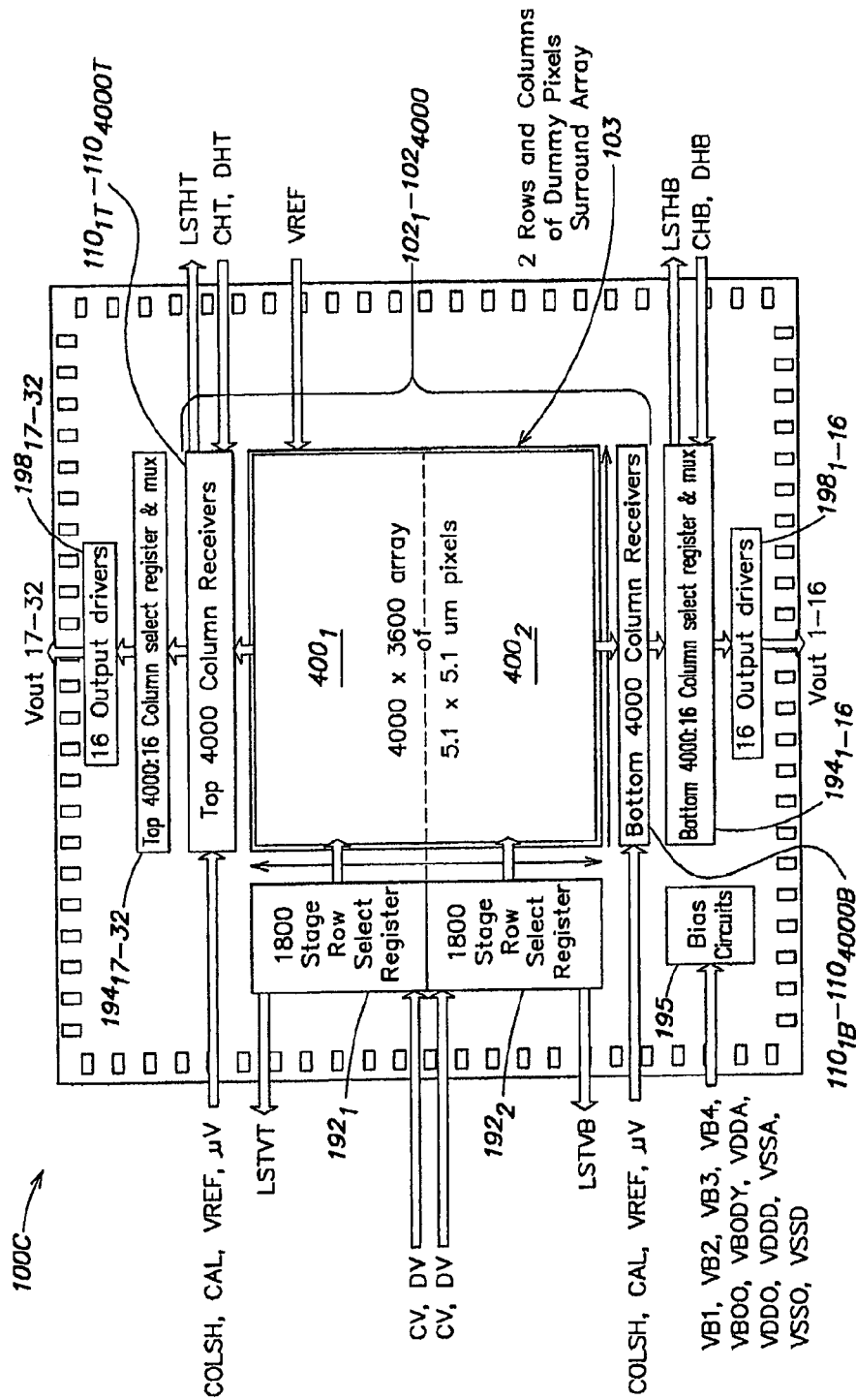
FIGS. 21-23 illustrate block diagrams of additional alternative CMOS IC chip implementations of chemFET sensor arrays, according to other inventive embodiments of the present disclosure.

FIG. 21 illustrates a block diagram of an ISFET sensor array 100C based on a 0.35 micrometer CMOS fabrication process and incorporating the smaller pixel size discussed above in connection with FIGS. 20 and 20A (5.1 micrometer square pixels), according to yet another embodiment. As noted in FIG. 21, the array 100C includes 4000 columns $102_1$ through $102_{4000}$, wherein each column includes 3600 geometrically square pixels $105A_1$ through $105A_{3600}$, each having a size of approximately 5 micrometers by 5 micrometers. Thus, the array includes over 14 million pixels (>14 Mega-pixels) and, in one exemplary implementation, the complete array (ISFET pixels and associated circuitry) may be fabricated as an integrated circuit chip having dimensions of approximately 22 millimeters by 22 millimeters. Like the arrays 100A and 100B of FIGS. 19 and 20, in one aspect the array 100C of FIG. 21 is divided into two groups of rows $400_1$ and $400_2$. However, unlike the arrays 100A and 100B, for each row group the array 100C includes sixteen column select registers and sixteen output drivers to simultaneously read sixteen pixels at a time in an enabled row, such that thirty-two output signals Vout1-Vout32 may be provided from the array 100C. In one exemplary implementation, complete data frames (all pixels from both the first and second row groups $400_1$ and $400_2$) may be acquired at a frame rate of 50 frames/sec, thereby requiring 1800 pairs of rows to be successively enabled for periods of approximately 11 microseconds each. For each enabled row, 250 pixels (4000/16) are read out by each column select register/output driver during approximately 7 microseconds (allowing 2 microseconds at the beginning and end of each row). Thus, in this example, each of the array output signals Vout1-Vout32 has a data rate of approximately 35 MHz. As with the previous embodiments, it should be appreciated that in other implementations, data may be acquired from the array 100C at frame rates other than 50 frames/sec.

Figure 22:
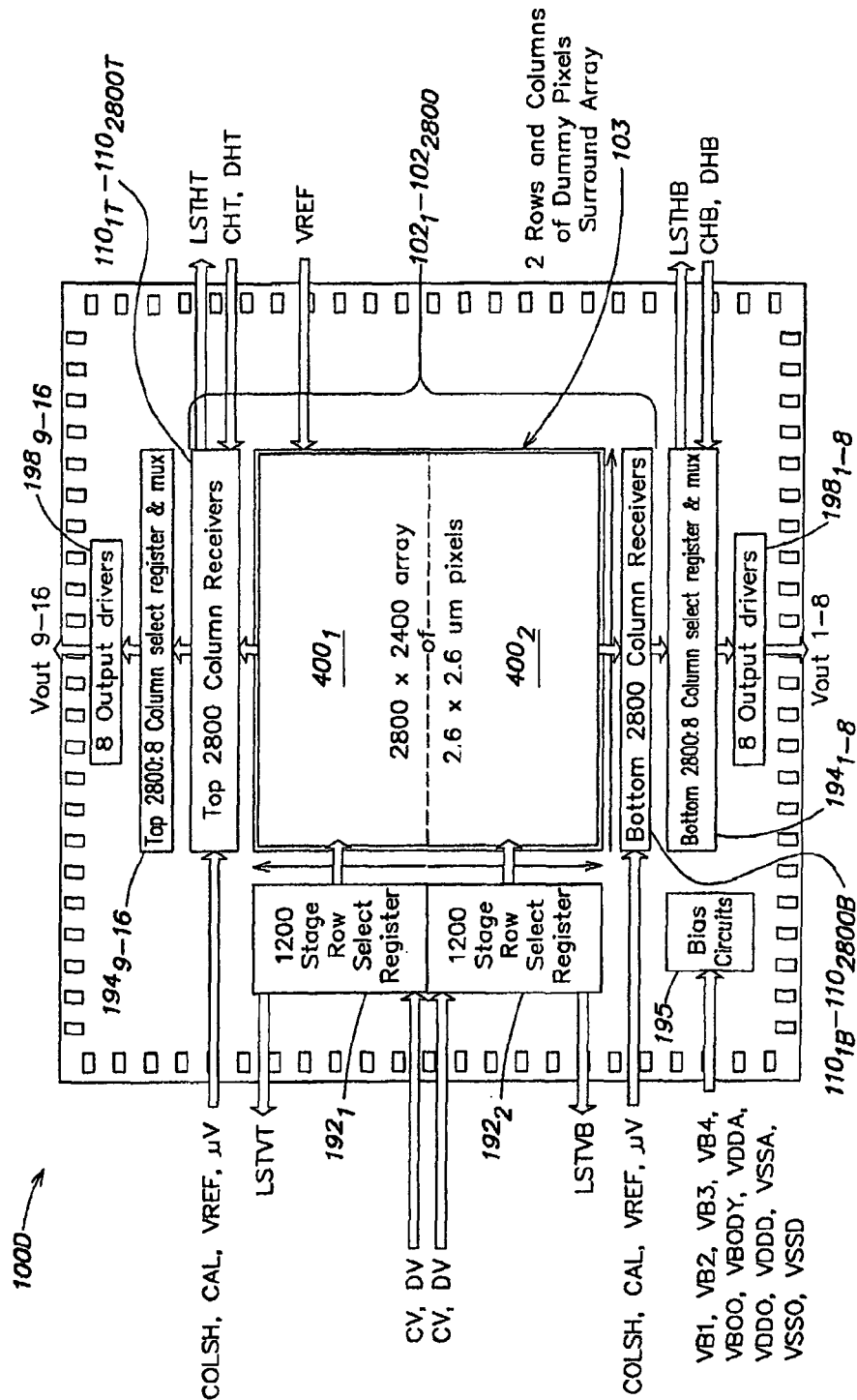
Figure 23:
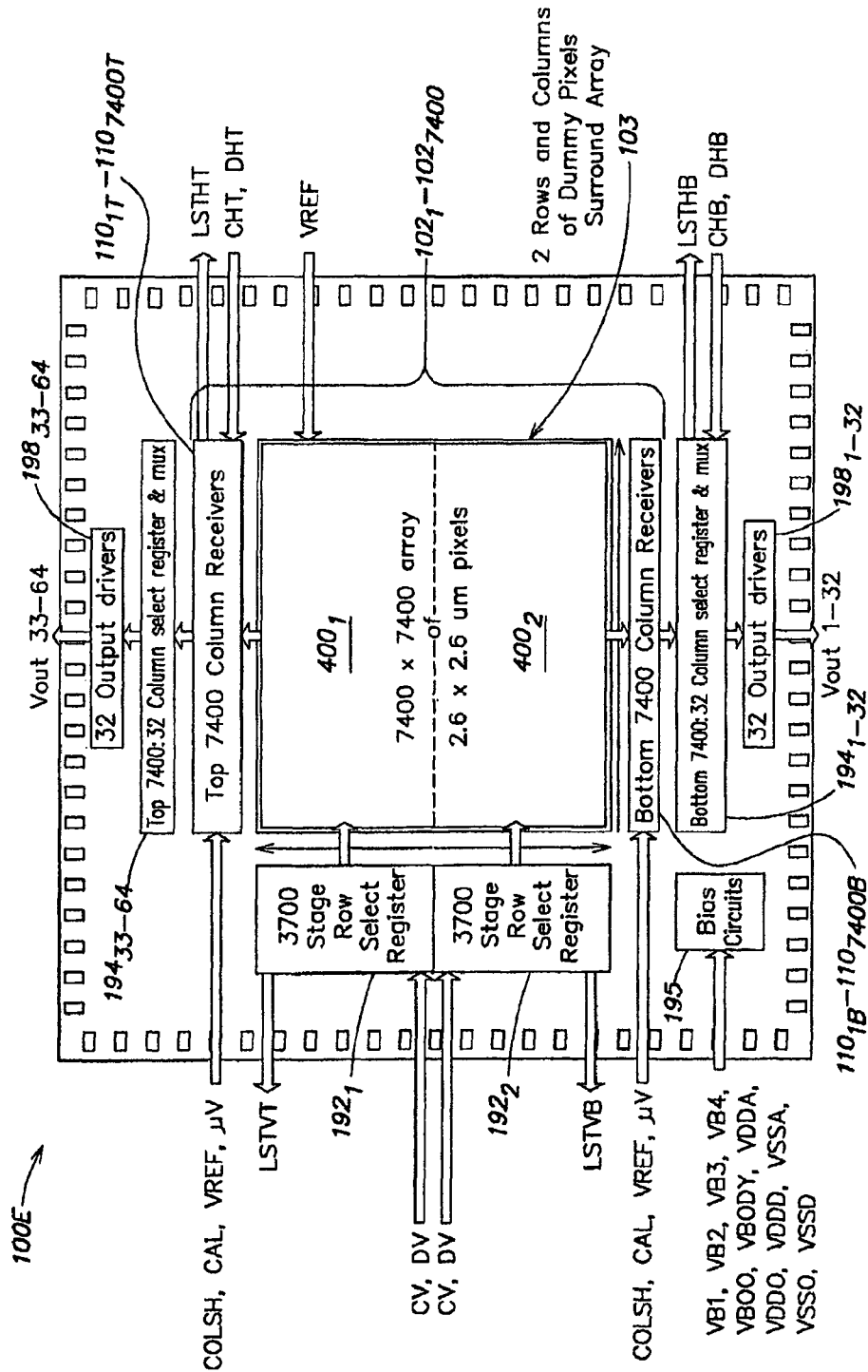

While the exemplary arrays discussed above in connection with FIGS. 13-21 are based on a 0.35 micrometer conventional CMOS fabrication process, it should be appreciated that arrays according to the present disclosure are not limited in this respect, as CMOS fabrication processes having feature sizes of less than 0.35 micrometers may be employed (e.g., 0.18 micrometer CMOS processing techniques) to fabricate such arrays. Accordingly, ISFET sensor arrays with a pixel size/pitch significantly below 5 micrometers may be fabricated, providing for significantly denser ISFET arrays. For example, FIGS. 22 and 23 illustrate respective block diagrams of ISFET sensor arrays 100D and 100E according to yet other embodiments based on a 0.18 micrometer CMOS fabrication process, in which a pixel size of 2.6 micrometers is achieved. The pixel design itself is based substantially on the pixel 105A shown in FIG. 20A, albeit on a smaller scale due to the 0.18 micrometer CMOS process.

The array 100D of FIG. 22 includes 2800 columns $102_1$ through $102_{2800}$, wherein each column includes 2400 geometrically square pixels each having a size of approximately 2.6 micrometers by 2.6 micrometers. Thus, the array includes over 6.5 million pixels (>6.5 Mega-pixels) and, in one exemplary implementation, the complete array (ISFET pixels and associated circuitry) may be fabricated as an integrated circuit chip having dimensions of approximately 9 millimeters by 9 millimeters. Like the arrays 100A, 100B and 100C of FIGS. 19-21, in one aspect the array 100D of FIG. 22 is divided into two groups of rows $400_1$ and $400_2$. However, unlike the arrays 100A, 100B, and 100C, for each row group the array 100D includes eight column select registers and eight output drivers to simultaneously read eight pixels at a time in an enabled row, such that sixteen output signals Vout1-Vout16 may be provided from the array 100D. In one exemplary implementation, complete data frames (all pixels from both the first and second row groups $400_1$ and $400_2$) may be acquired at a frame rate of 50 frames/sec, thereby requiring 1200 pairs of rows to be successively enabled for periods of approximately 16-17 microseconds each. For each enabled row, 350 pixels (2800/8) are read out by each column select register/output driver during approximately 14 microseconds (allowing 1 to 2 microseconds at the beginning and end of each row). Thus, in this example, each of the array output signals Vout1-Vout16 has a data rate of approximately 25 MHz. As with the previous embodiments, it should be appreciated that in other implementations, data may be acquired from the array 100D at frame rates other than 50 frames/sec.

The array 100E of FIG. 23 includes 7400 columns $102_1$ through $102_{7400}$, wherein each column includes 7400 geometrically square pixels each having a size of approximately 2.6 micrometers by 2.6 micrometers. Thus, the array includes over 54 million pixels (>54 Mega-pixels) and, in one exemplary implementation, the complete array (ISFET pixels and associated circuitry) may be fabricated as an integrated circuit chip having dimensions of approximately 21 millimeters by 21 millimeters. Like the arrays 100A-100D of FIGS. 19-22, in one aspect the array 100E of FIG. 23 is divided into two groups of rows $400_1$ and $400_2$. However, unlike the arrays 100A-100D, for each row group the array 100E includes thirty-two column select registers and thirty-two output drivers to simultaneously read thirty-two pixels at a time in an enabled row, such that sixty-four output signals Vout1-Vout64 may be provided from the array 100E. In one exemplary implementation, complete data frames (all pixels from both the first and second row groups $400_1$ and $400_2$) may be acquired at a frame rate of 100 frames/sec, thereby requiring 3700 pairs of rows to be successively enabled for periods of approximately 3 microseconds each. For each enabled row, 230 pixels (7400/32) are read out by each column select register/output driver during approximately 700 nanoseconds. Thus, in this example, each of the array output signals Vout1-Vout64 has a data rate of approximately 328 MHz. As with the previous embodiments, it should be appreciated that in other implementations, data may be acquired from the array 100D at frame rates other than 100 frames/sec.

Thus, in various examples of ISFET arrays based on the inventive concepts disclosed herein, an array pitch of approximately nine (9) micrometers (e.g., a sensor surface area of less than ten micrometers by ten micrometers) allows an ISFET array including over 256,000 pixels (i.e., a 512 by 512 array), together with associated row and column select and bias/readout electronics, to be fabricated on a 7 millimeter by 7 millimeter semiconductor die, and a similar sensor array including over four million pixels (i.e., a 2048 by 2048 array, over 4 Mega-pixels) to be fabricated on a 21 millimeter by 21 millimeter die. In other examples, an array pitch of approximately 5 micrometers allows an ISFET array including approximately 1.55 Mega-pixels (i.e., a 1348 by 1152 array) and associated electronics to be fabricated on a 9 millimeter by 9 millimeter die, and an ISFET sensor array including over 14 Mega-pixels and associated electronics on a 22 millimeter by 20 millimeter die. In yet other implementations, using a CMOS fabrication process in which feature sizes of less than 0.35 micrometers are possible (e.g., 0.18 micrometer CMOS processing techniques), ISFET sensor arrays with a pixel size/pitch significantly below 5 micrometers may be fabricated (e.g., array pitch of 2.6 micrometers or pixel/sensor area of less than 8 or 9 micrometers$^2$), providing for significantly dense ISFET arrays.

In the embodiments of ISFET arrays discussed above, array pixels employ a p-channel ISFET, as discussed above in connection with FIG. 9. It should be appreciated, however, that ISFET arrays according to the present disclosure are not limited in this respect, and that in other embodiments pixel designs for ISFET arrays may be based on an n-channel ISFET. In particular, any of the arrays discussed above in connection with FIGS. 13 and 19-23 may be implemented with pixels based on n-channel ISFETs.

Figure 24:
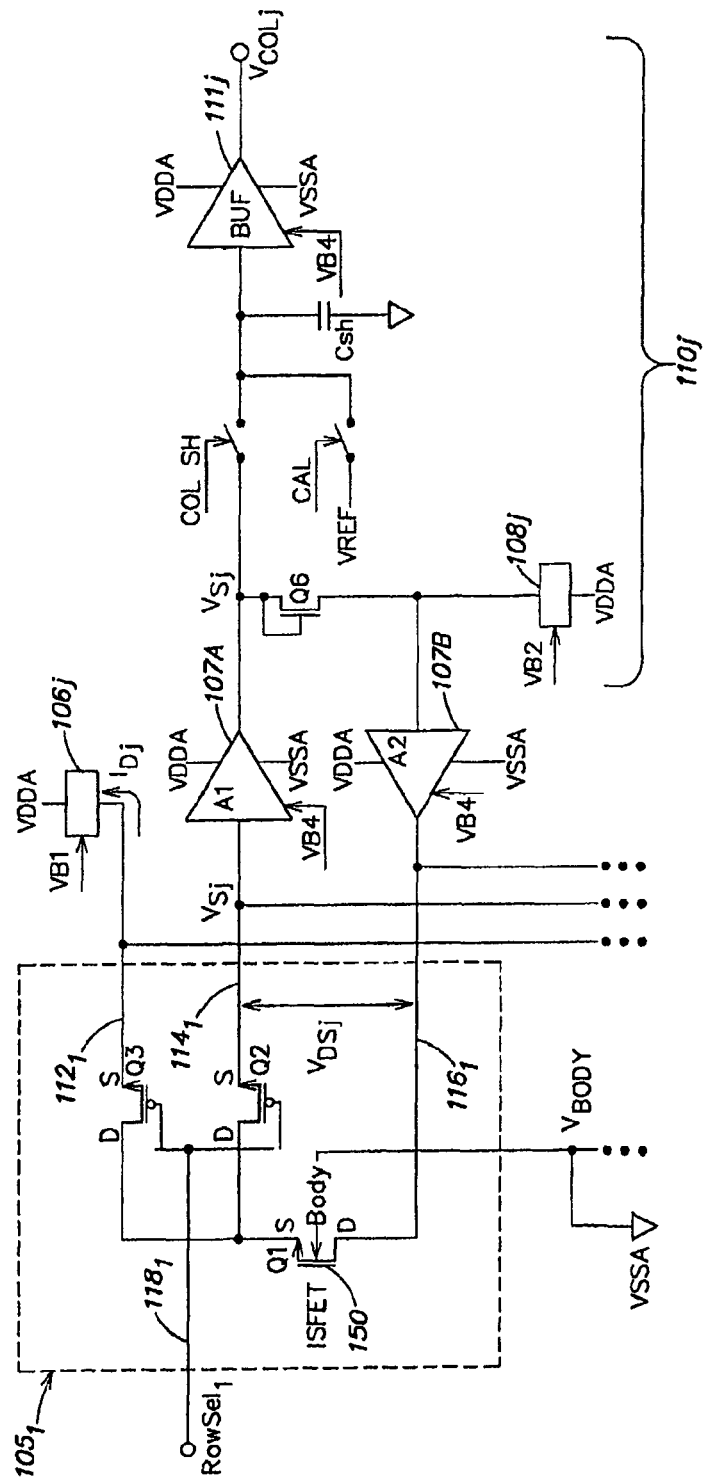
FIG. 24 illustrates the pixel design of FIG. 9 implemented with an n-channel chemFET and accompanying n-channel MOSFETs, according to another inventive embodiment of the present disclosure.

For example, FIG. 24 illustrates the pixel design of FIG. 9 implemented with an re-channel ISFET and accompanying n-channel MOSFETs, according to another inventive embodiment of the present disclosure. More specifically, FIG. 24 illustrates one exemplary pixel $105_1$ of an array column (i.e., the first pixel of the column), together with column bias/readout circuitry $110j$, in which the ISFET 150 (Q1) is an n-channel ISFET. Like the pixel design of FIG. 9, the pixel design of FIG. 24 includes only three components, namely, the ISFET 150 and two n-channel MOSFET switches Q2 and Q3, responsive to one of n row select signals (RowSel$_1$ through RowSel$_n$, logic high active). No transmission gates are required in the pixel of FIG. 24, and all devices of the pixel are of a "same type," i.e., n-channel devices. Also like the pixel design of FIG. 9, only four signal lines per pixel, namely the lines $112_1$, $114_1$, $116_1$ and $118_1$, are required to operate the three components of the pixel $105_1$ shown in FIG. 24. In other respects, the pixel designs of FIG. 9 and FIG. 24 are similar, in that they are both configured with a constant drain current $I_{Dj}$ and a constant drain-to-source voltage $V_{DSj}$ to obtain an output signal $V_{Sj}$ from an enabled pixel.

One of the primary differences between the n-channel ISFET pixel design of FIG. 24 and the p-channel ISFET design of FIG. 9 is the opposite direction of current flow through the pixel. To this end, in FIG. 24, the element 106 is a controllable current sink coupled to the analog circuitry supply voltage ground VSSA, and the element $108_j$ of the bias/readout circuitry $110j$ is a controllable current source coupled to the analog positive supply voltage VDDA. Additionally, the body connection of the ISFET 150 is not tied to its source, but rather to the body connections of other ISFETs of the array, which in turn is coupled to the analog ground VSSA, as indicated in FIG. 24.

Figure 25:
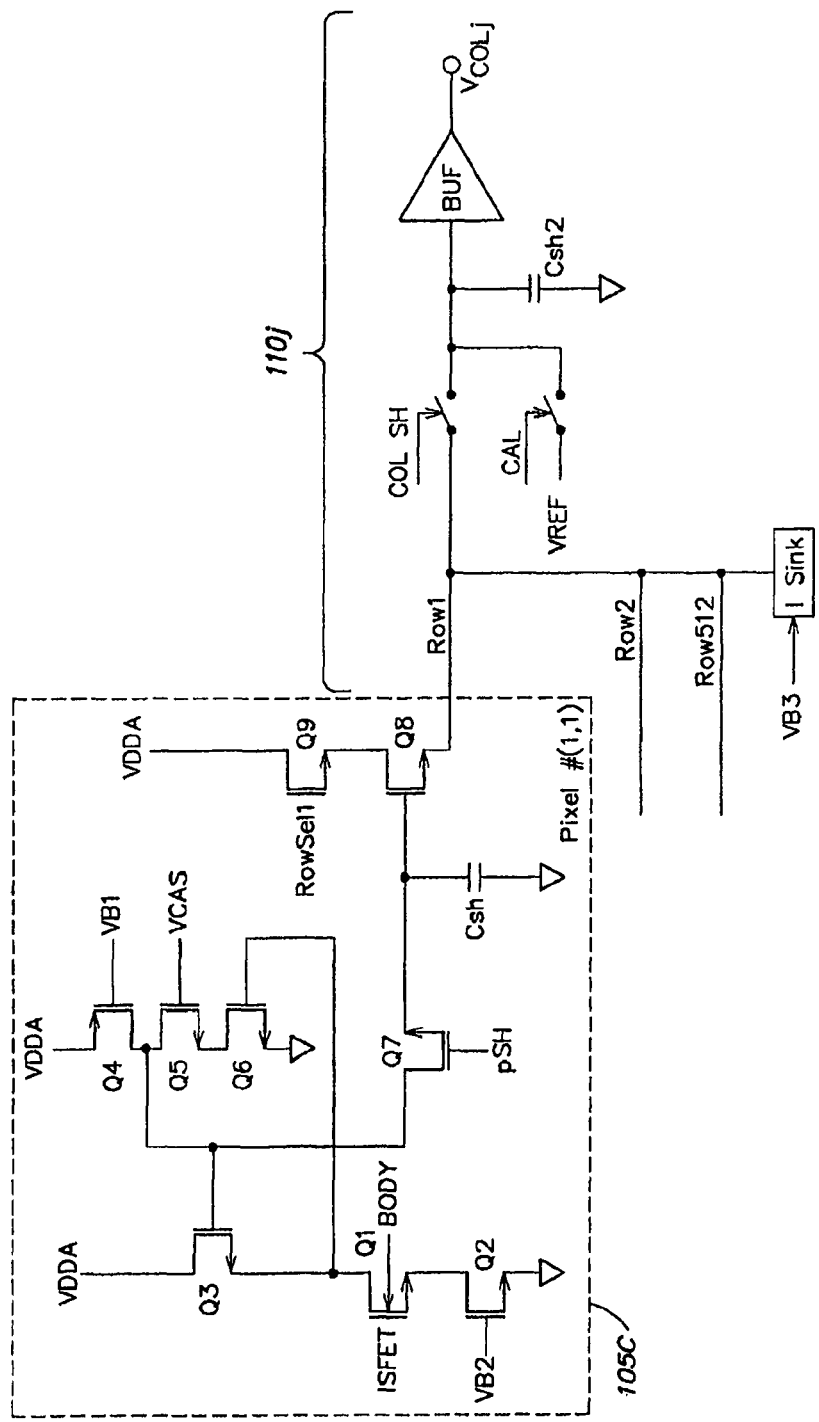
FIGS. 25-27 illustrate alternative pixel designs and associated column circuitry for chemFET arrays according to other inventive embodiments of the present disclosure.
Figure 26:
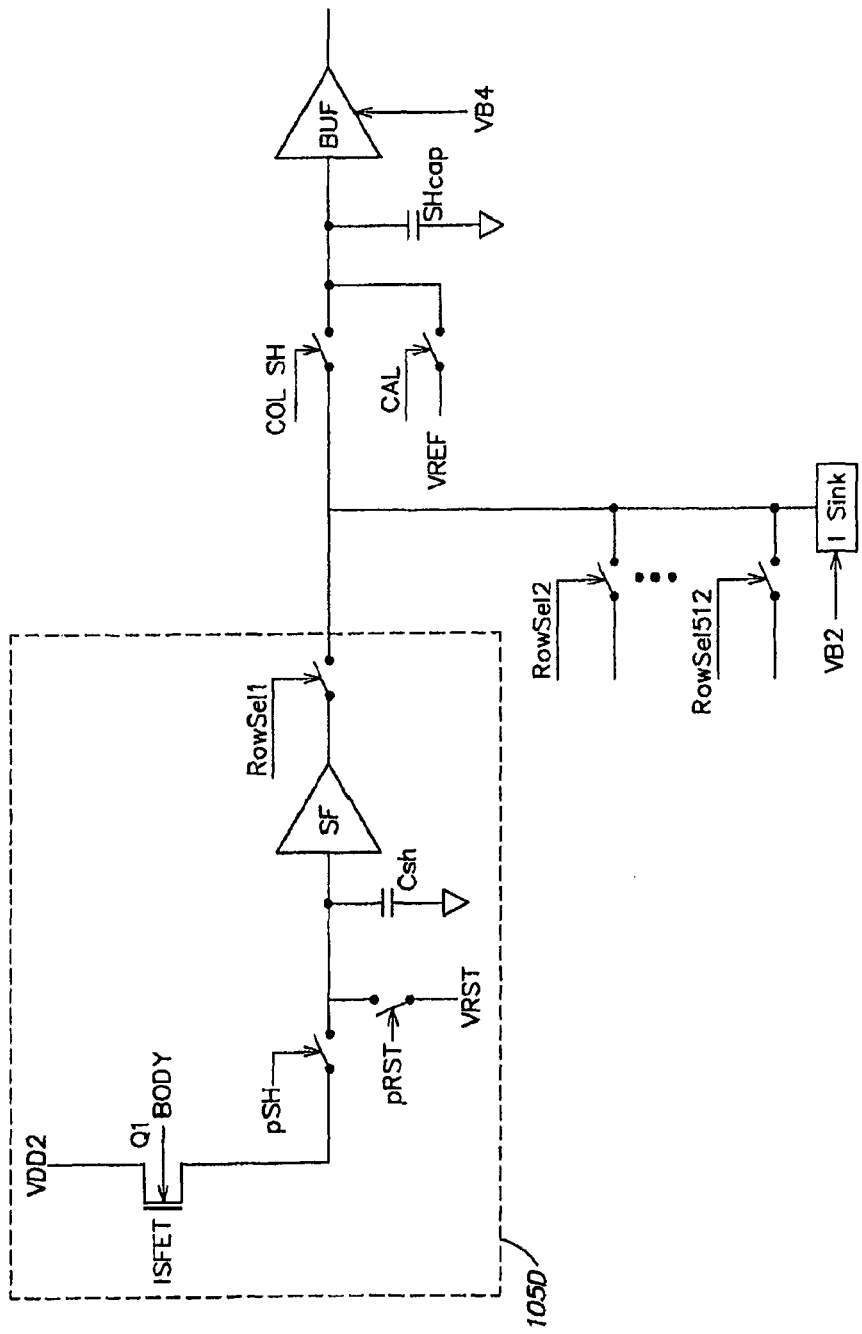
Figure 27:
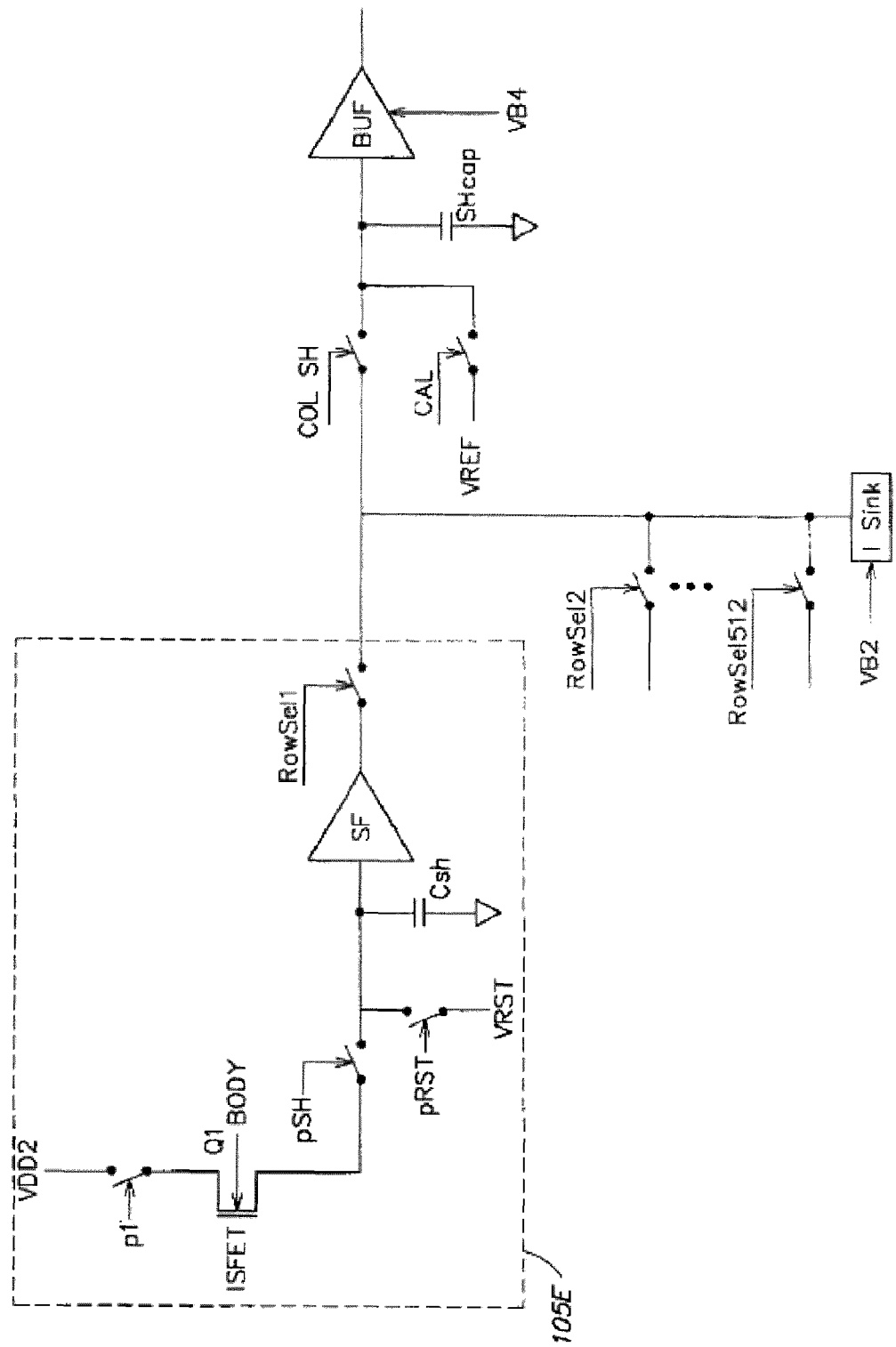

In addition to the pixel designs shown in FIGS. 9 and 24 (based on a constant ISFET drain current and constant ISFET drain-source voltage), alternative pixel designs are contemplated for ISFET arrays, based on both p-channel ISFETs and n-channel ISFETs, according to yet other inventive embodiments of the present disclosure, as illustrated in FIGS. 25-27. As discussed below, some alternative pixel designs may require additional and/or modified signals from the array controller 250 to facilitate data acquisition. In particular, a common feature of the pixel designs shown in FIGS. 25-27 includes a sample and hold capacitor within each pixel itself, in addition to a sample and hold capacitor for each column of the array. While the alternative pixel designs of FIGS. 25-27 generally include a greater number of components than the pixel designs of FIGS. 9 and 24, the feature of a pixel sample and hold capacitor enables "snapshot" types of arrays, in which all pixels of an array may be enabled simultaneously to sample a complete frame and acquire signals representing measurements of one or more analytes in proximity to respective ISFETs of the array. In some applications, this may provide for higher data acquisition speeds and/or improved signal sensitivity (e.g., higher signal-to-noise ratio).

FIG. 25 illustrates one such alternative design for a single pixel 105C and associated column circuitry $110j$. The pixel 105C employs an n-channel ISFET and is based generally on the premise of providing a constant voltage across the ISFET Q1 based on a feedback amplifier (Q4, Q5 and Q6). In particular, transistor Q4 constitutes the feedback amplifier load, and the amplifier current is set by the bias voltage VB1 (provided by the array controller). Transistor Q5 is a common gate amplifier and transistor Q6 is a common source amplifier. Again, the purpose of feedback amplifier is to hold the voltage across the ISFET Q1 constant by adjusting the current supplied by transistor Q3. Transistor Q2 limits the maximum current the ISFET Q1 can draw (e.g., so as to prevent damage from overheating a very large array of pixels). This maximum current is set by the bias voltage VB2 (also provided by the array controller). In one aspect of the pixel design shown in FIG. 25, power to the pixel 105C may be turned off by setting the bias voltage VB2 to 0 Volts and the bias voltage VB1 to 3.3 Volts. In this manner, the power supplied to large arrays of such pixels may be modulated (turned on for a short time period and then off by the array controller) to obtain ion concentration measurements while at the same time reducing overall power consumption of the array. Modulating power to the pixels also reduces heat dissipation of the array and potential heating of the analyte solution, thereby also reducing any potentially deleterious effects from sample heating.

In FIG. 25, the output of the feedback amplifier (the gate of transistor Q3) is sampled by MOS switch Q7 and stored on a pixel sample and hold capacitor Csh within the pixel itself. The switch Q7 is controlled by a pixel sample and hold signal pSH (provided to the array chip by the array controller), which is applied simultaneously to all pixels of the array so as to simultaneously store the readings of all the pixels on their respective sample and hold capacitors. In this manner, arrays based on the pixel design of FIG. 25 may be considered as "snapshot" arrays, in that a full frame of data is sampled at any given time, rather than sampling successive rows of the array. After each pixel value is stored on the corresponding pixel sample and hold capacitor Csh, each pixel 105C (ISFET and feedback amplifier) is free to acquire another pH reading or it can by turned off to conserve power.

In FIG. 25, the pixel values stored on all of the pixel sample and hold capacitors Csh are applied to the column circuitry $110j$ one row at a time through source follower Q8, which is enabled via the transistor Q9 in response to a row select signal (e.g., RowSel1). In particular, after a row is selected and has settled out, the values stored in the pixel sample and hold capacitors are then in turn stored on the column sample and hold capacitors Csh2, as enabled by the column sample and hold signal COL SH, and provided as the column output signal $V_{COLj}$.

FIG. 26 illustrates another alternative design for a single pixel 105D and associated column circuitry $110j$, according to one embodiment of the present disclosure. In this embodiment, the ISFET is shown as a p-channel device. At the start of a data acquisition cycle, CMOS switches controlled by the signals pSH (pixel sample/hold) and pRST (pixel reset) are closed (these signals are supplied by the array controller). This pulls the source of ISFET (Q1) to the voltage VRST. Subsequently, the switch controlled by the signal pRST is opened, and the source of ISFET Q1 pulls the pixel sample and hold capacitor Csh to a threshold below the level set by pH. The switch controlled by the signal pSH is then opened, and the pixel output value is coupled, via operation of a switch responsive to the row select signal RowSel1, to the column circuitry $110j$ to provide the column output signal $V_{COLj}$. Like the pixel design in the embodiment illustrated in FIG. 25, arrays based on the pixel 105D are "snapshot" type arrays in that all pixels of the array may be operated simultaneously. In one aspect, this design allows a long simultaneous integration time on all pixels followed by a high-speed read out of an entire frame of data.

FIG. 27 illustrates yet another alternative design for a single pixel 105E and associated column circuitry $110j$, according to one embodiment of the present disclosure. In this embodiment, again the ISFET is shown as a p-channel device. At the start of a data acquisition cycle, the switches operated by the control signals p1 and pRST are briefly closed. This clears the value stored on the sampling capacitor Csh and allows a charge to be stored on ISFET (Q1). Subsequently, the switch controlled by the signal pSH is closed, allowing the charge stored on the ISFET Q1 to be stored on the pixel sample and hold capacitor Csh. The switch controlled by the signal pSH is then opened, and the pixel output value is coupled, via operation of a switch responsive to the row select signal RowSel1, to the column circuitry 110*j* to provide the column output signal $V_{COLj}$. Gain may be provided in the pixel 105E via the ratio of the ISFET capacitance to the Csh cap, i.e., gain=$C_{Q1}/C_{sh}$, or by enabling the pixel multiple times (i.e., taking multiple samples of the analyte measurement) and accumulating the ISFET output on the pixel sample and hold capacitor Csh without resetting the capacitor (i.e., gain is a function of the number of accumulations). Like the embodiments of FIGS. 25 and 26, arrays based on the pixel 105D are "snapshot" type arrays in that all pixels of the array may be operated simultaneously.

Figure 28A:
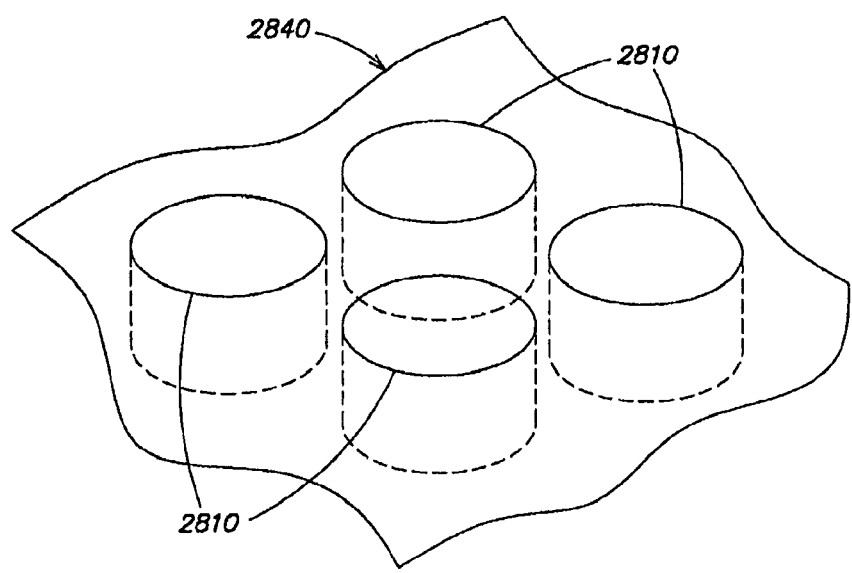
FIGS. 28A and 28B are isometric illustrations of portions of microwell arrays as employed herein, showing round wells and rectangular wells, to assist three-dimensional visualization of the array structures.
Figure 28B:
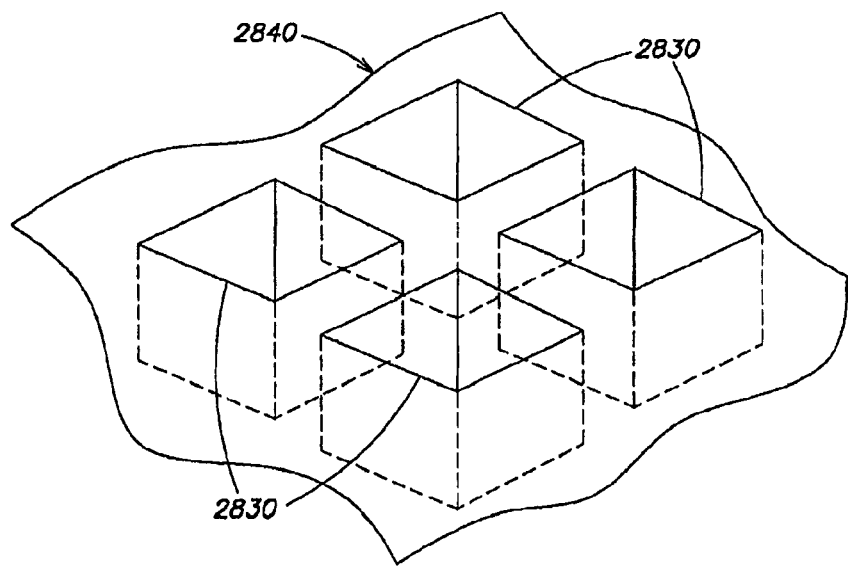

Turning from the sensor discussion, we will now be addressing the combining of the ISFET array with a microwell array and the attendant fluidics. As most of the drawings of the microwell array structure are presented only in cross-section or showing that array as only a block in a simplified diagram, FIGS. 28A and 28B are provided to assist the reader in beginning to visualize the resulting apparatus in three-dimensions. FIG. 28A shows a group of round cylindrical wells 2810 arranged in an array, while FIG. 28B shows a group of rectangular cylindrical wells 2830 arranged in an array. It will be seen that the wells are separated (isolated) from each other by the material 2840 forming the well walls. While it is certainly possible to fabricate wells of other cross sections, in some embodiments it may not be advantageous to do so. Such an array of microwells sits over the above-discussed ISFET array, with one or more ISFETs per well. In the subsequent drawings, when the microwell array is identified, one may picture one of these arrays.

For many uses, to complete a system for sensing chemical reactions or chemical agents using the above-explained high density electronic arrays, techniques and apparatus are required for delivery to the array elements (called "pixels") fluids containing chemical or biochemical components for sensing. In this section, exemplary techniques and methods will be illustrated, which are useful for such purposes, with desirable characteristics.

As high speed operation of the system may be desired, it is preferred that the fluid delivery system, insofar as possible, not limit the speed of operation of the overall system.

Accordingly, needs exist not only for high-speed, high-density arrays of ISFETs or other elements sensitive to ion concentrations or other chemical attributes, or changes in chemical attributes, but also for related mechanisms and techniques for supplying to the array elements the samples to be evaluated, in sufficiently small reaction volumes as to substantially advance the speed and quality of detection of the variable to be sensed.

There are two and sometimes three components or sub-systems, and related methods, involved in delivery of the subject chemical samples to the array elements: (1) macrofluidic system of reagent and wash fluid supplies and appropriate valving and ancillary apparatus, (2) a flow cell and (3) in many applications, a microwell array. Each of these sub-systems will be discussed, though in reverse order.

As discussed elsewhere, for many uses, such as in DNA sequencing, it is desirable to provide over the array of semiconductor sensors a corresponding array of microwells, each microwell being small enough preferably to receive only one DNA-loaded bead, in connection with which an underlying pixel in the array will provide a corresponding output signal.

The use of such a microwell array involves three stages of fabrication and preparation, each of which is discussed separately: (1) creating the array of microwells to result in a chip having a coat comprising a microwell array layer; (2) mounting of the coated chip to a fluidic interface; and in the case of DNA sequencing, (3) loading DNA-loaded bead or beads into the wells. It will be understood, of course, that in other applications, beads may be unnecessary or beads having different characteristics may be employed.

The systems described herein can include an array of microfluidic reaction chambers integrated with a semiconductor comprising an array of chemFETs. In some embodiments, the invention encompasses such an array. The reaction chambers may, for example, be formed in a glass, dielectric, photodefineable or etchable material. The glass material may be silicon dioxide.

Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns.

The above-described array can also be provided in a kit for sequencing. Thus, in some embodiments, the invention encompasses a kit comprising an array of microfluidic reaction chambers integrated with an array of chemFETs, and one or more amplification reagents.

In some embodiments, the invention encompasses a sequencing apparatus comprising a dielectric layer overlying a chemFET, the dielectric layer having a recess laterally centered atop the chemFET. Preferably, the dielectric layer is formed of silicon dioxide.

Microwell fabrication may be accomplished in a number of ways. The actual details of fabrication may require some experimentation and vary with the processing capabilities that are available.

In general, fabrication of a high density array of microwells involves photo-lithographically patterning the well array configuration on a layer or layers of material such as photoresist (organic or inorganic), a dielectric, using an etching process. The patterning may be done with the material on the sensor array or it may be done separately and then transferred onto the sensor array chip, of some combination of the two. However, techniques other than photolithography are not to be excluded if they provide acceptable results.

Figure 29:
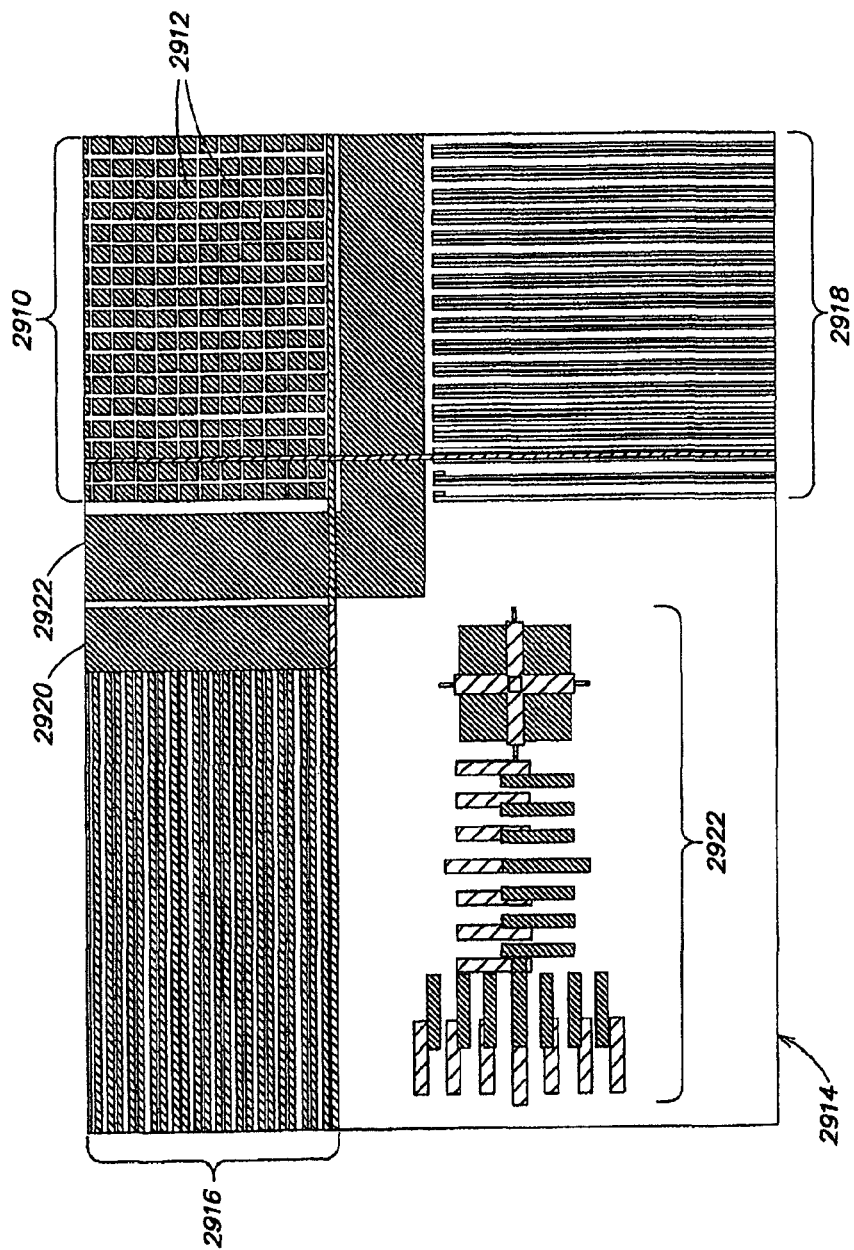
FIG. 29 is a diagrammatic depiction of a top view of one corner (i.e., the lower left corner) of the layout of a chip showing an array of individual ISFET sensors on a CMOS die.

One example of a method for forming a microwell array is now discussed, starting with reference to FIG. 29. That figure diagrammatically depicts a top view of one corner (i.e., the lower left corner) of the layout of a chip showing an array 2910 of the individual ISFET sensors 2912 on the CMOS die 2914. Signal lines 2916 and 2918 are used for addressing the array and reading its output. Block 2920 represents some of the electronics for the array, as discussed above, and layer 2922 represents a portion of a wall which becomes part of a microfluidics structure, the flow cell, as more fully explained below; the flow cell is that structure which provides a fluid flow over the microwell array or over the sensor surface directly, if there is no microwell structure. On the surface of the die, a pattern such as pattern 2922 at the bottom left of FIG. 29 may be formed during the semiconductor processing to form the ISFETs and associated circuitry, for use as alignment marks for locating the wells over the sensor pixels when the dielectric has covered the die's surface.

After the semiconductor structures, as shown, are formed, the microwell structure is applied to the die. That is, the microwell structure can be formed right on the die or it may be formed separately and then mounted onto the die, either approach being acceptable. To form the microwell structure on the die, various processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 4-12 μm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel, preferably for a nominal 1:1-1.5:1 aspect ratio, height:width or diameter. Based on signal-to-noise considerations, there is a relationship between dimensions and the required data sampling rates to achieve a desired level of performance. Thus there are a number of factors that will go into selecting optimum parameters for a given application.) Alternatively, multiple layers of different photoresists may be applied or another form of dielectric material may be deposited. Various types of chemical vapor deposition may also be used to build up a layer of materials suitable for microwell formation therein.

Once the photoresist layer (the singular form "layer" is used to encompass multiple layers in the aggregate, as well) is in place, the individual wells (typically mapped to have either one or four ISFET sensors per well) may be generated by placing a mask (e.g., of chromium) over the resist-coated die and exposing the resist to cross-linking (typically UV) radiation. All resist exposed to the radiation (i.e., where the mask does not block the radiation) becomes cross-linked and as a result will form a permanent plastic layer bonded to the surface of the chip (die). Unreacted resist (i.e., resist in areas which are not exposed, due to the mask blocking the light from reaching the resist and preventing cross-linking) is removed by washing the chip in a suitable solvent (i.e., developer) such as propyleneglycolmethylethylacetate (PGMEA) or other appropriate solvent. The resultant structure defines the walls of the microwell array.

Figure 30:
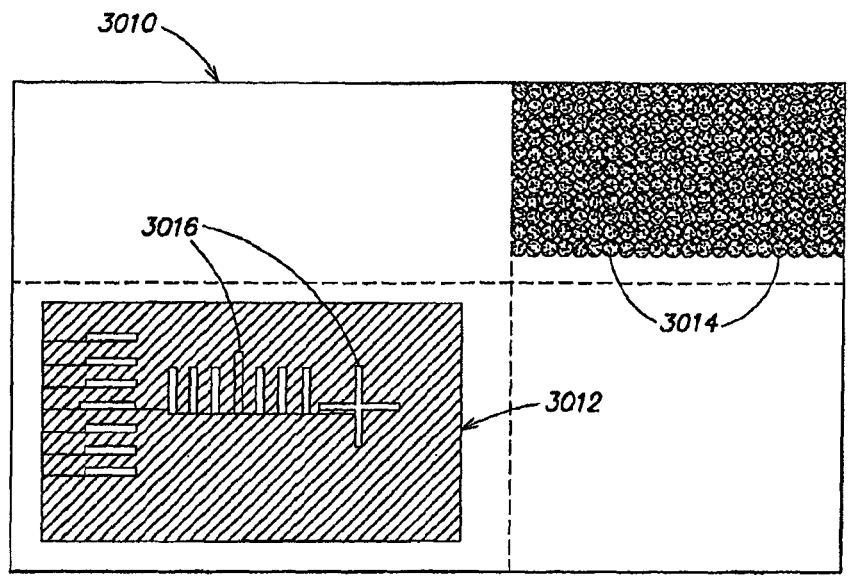
FIG. 30 is an illustration of an example of a layout for a portion of a (typically chromium) mask for a one-sensor-per-well embodiment of the above-described sensor array, corresponding to the portion of the die shown in FIG. 29.

FIG. 30 shows an example of a layout for a portion of a chromium mask 3010 for a one-sensor-per-well embodiment, corresponding to the portion of the die shown in FIG. 29. The grayed areas 3012, 3014 are those that block the UV radiation. The alignment marks in the white portions 3016 on the bottom left quadrant of FIG. 30, within gray area 3012, are used to align the layout of the wells with the ISFET sensors on the chip surface. The array of circles 3014 in the upper right quadrant of the mask block radiation from reaching the well areas, to leave unreacted resist which can be dissolved in forming the wells.

Figure 31:
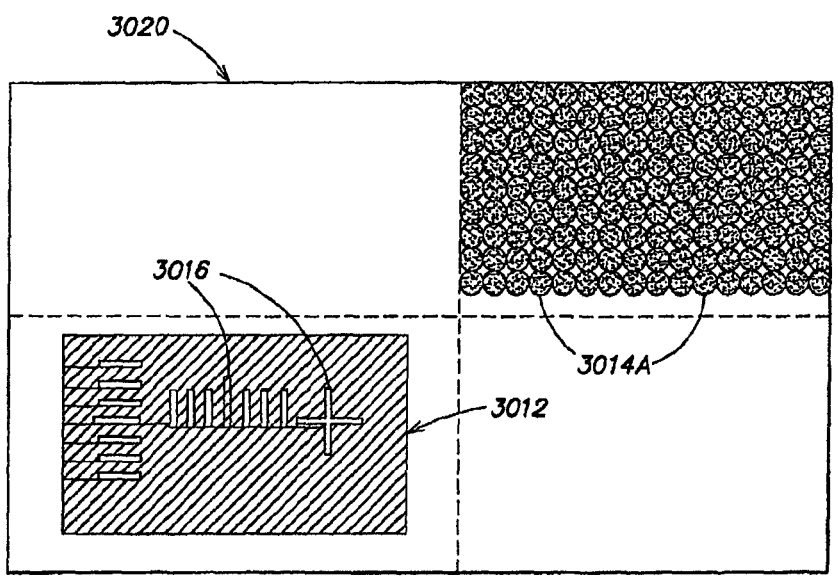
FIG. 31 is a corresponding layout for a mask for a 4-sensors-per-well embodiment.

FIG. 31 shows a corresponding layout for the mask 3020 for a 4-sensors-per-well embodiment. Note that the alignment pattern 3016 is still used and that the individual well-masking circles 3014A in the array 2910 now have twice the diameter as the wells 3014 in FIG. 30, for accommodating four sensors per well instead of one sensor-per-well.

Figure 32:
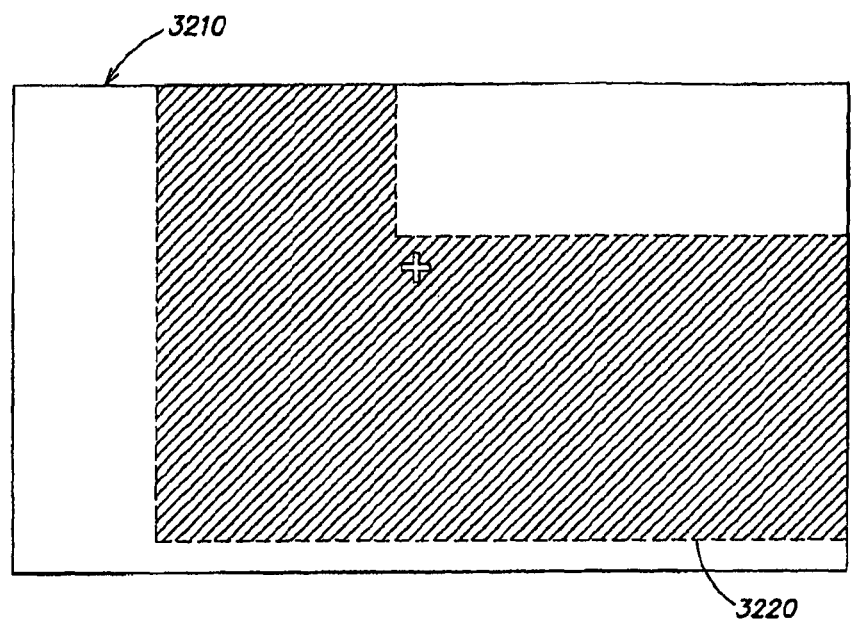
FIG. 32 is an illustration of a second mask used to mask an area which surrounds the array, to build a collar or wall (or basin, using that term in the geological sense) of resist which surrounds the active array of sensors on a substrate, as shown in FIG. 33A.
Figure 33:
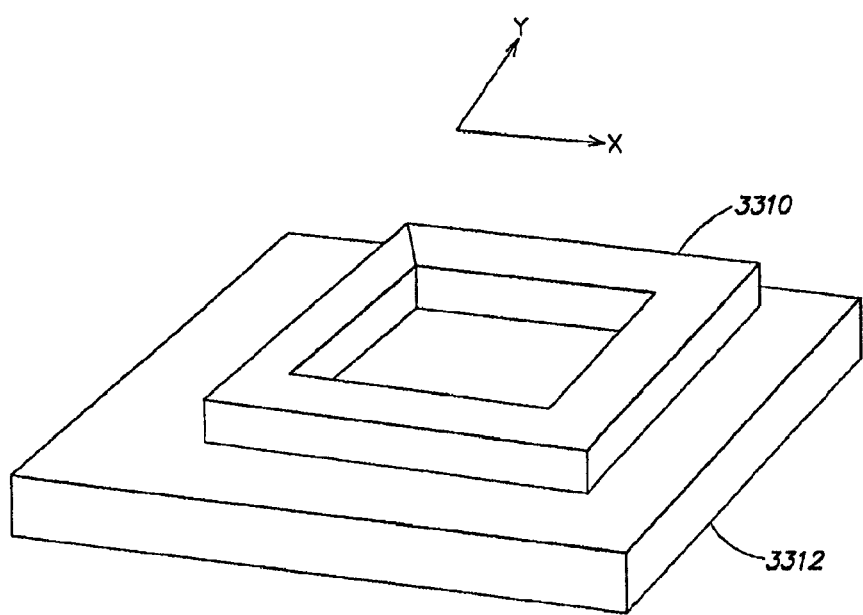
FIG. 33 is an illustration of the resulting basin.

After exposure of the die/resist to the UV radiation, a second layer of resist may be coated on the surface of the chip. This layer of resist may be relatively thick, such as about 400-450 µm thick, typically. A second mask 3210 (FIG. 32), which also may be of chromium, is used to mask an area 3220 which surrounds the array, to build a collar or wall (or basin, using that term in the geological sense) 3310 of resist which surrounds the active array of sensors on substrate 3312, as shown in FIG. 33. In the particular example being described, the collar is 150 µm wider than the sensor array, on each side of the array, in the x direction, and 9 µm wider on each side than the sensor array, in the y direction. Alignment marks on mask 3210 (most not shown) are matched up with the alignment marks on the first layer and the CMOS chip itself.

Other photolithographic approaches may be used for formation of the microwell array, of course, the foregoing being only one example.

For example, contact lithography of various resolutions and with various etchants and developers may be employed. Both organic and inorganic materials may be used for the layer(s) in which the microwells are formed. The layer(s) may be etched on a chip having a dielectric layer over the pixel structures in the sensor array, such as a passivation layer, or the layer(s) may be formed separately and then applied over the sensor array. The specific choice or processes will depend on factors such as array size, well size, the fabrication facility that is available, acceptable costs, and the like.

Among the various organic materials which may be used in some embodiments to form the microwell layer(s) are the above-mentioned SU-8 type of negative-acting photoresist, a conventional positive-acting photoresist and a positive-acting photodefineable polyimide. Each has its virtues and its drawbacks, well known to those familiar with the photolithographic art.

Naturally, in a production environment, modifications will be appropriate.

Contact lithography has its limitations and it may not be the production method of choice to produce the highest densities of wells—i.e., it may impose a higher than desired minimum pitch limit in the lateral directions. Other techniques, such as a deep UV step-and-repeat process, are capable of providing higher resolution lithography and can be used to produce small pitches and possibly smaller well diameters. Of course, for different desired specifications (e.g., numbers of sensors and wells per chip), different techniques may prove optimal. And pragmatic factors, such as the fabrication processes available to a manufacturer, may motivate the use of a specific fabrication method. While novel methods are discussed, various aspects of the invention are limited to use of these novel methods.

Preferably the CMOS wafer with the ISFET array will be planarized after the final metallization process. A chemical mechanical dielectric planarization prior to the silicon nitride passivation is suitable. This will allow subsequent lithographic steps to be done on very flat surfaces which are free of back-end CMOS topography.

By utilizing deep-UV step-and-repeat lithography systems, it is possible to resolve small features with superior resolution, registration, and repeatability. However, the high resolution and large numerical aperture (NA) of these systems precludes their having a large depth of focus. As such, it may be necessary, when using such a fabrication system, to use thinner photodefinable spin-on layers (i.e., resists on the order of 1-2 µm rather than the thicker layers used in contact lithography) to pattern transfer and then etch microwell features to underlying layer or layers. High resolution lithography can then be used to pattern the microwell features and conventional $SiO_2$ etch chemistries can be used—one each for the bondpad areas and then the microwell areas—having selective etch stops; the etch stops then can be on aluminum bondpads and silicon nitride passivation (or the like), respectively. Alternatively, other suitable substitute pattern transfer and etch processes can be employed to render microwells of inorganic materials.

Another approach is to form the microwell structure in an organic material. For example, a dual-resist "soft-mask" process may be employed, whereby a thin high-resolution deep-UV resist is used on top of a thicker organic material (e.g., cured polyimide or opposite-acting resist). The top resist layer is patterned. The pattern can be transferred using an oxygen plasma reactive ion etch process. This process sequence is sometimes referred to as the "portable conformable mask" (PCM) technique. See B. J. Lin et al., "Practicing the Novolac deep-UV portable conformable masking technique", Journal of Vacuum Science and Technology 19, No. 4, 1313-1319 (1981); and A. Cooper et al, "Optimization of a photosensitive spin-on dielectric process for copper inductor coil and interconnect protection in RF SoC devices."

Alternatively a "drill-focusing" technique may be employed, whereby several sequential step-and-repeat exposures are done at different focal depths to compensate for the limited depth of focus (DOF) of high-resolution steppers when patterning thick resist layers. This technique depends on the stepper NA and DOF as well as the contrast properties of the resist material.

Figure 33A:
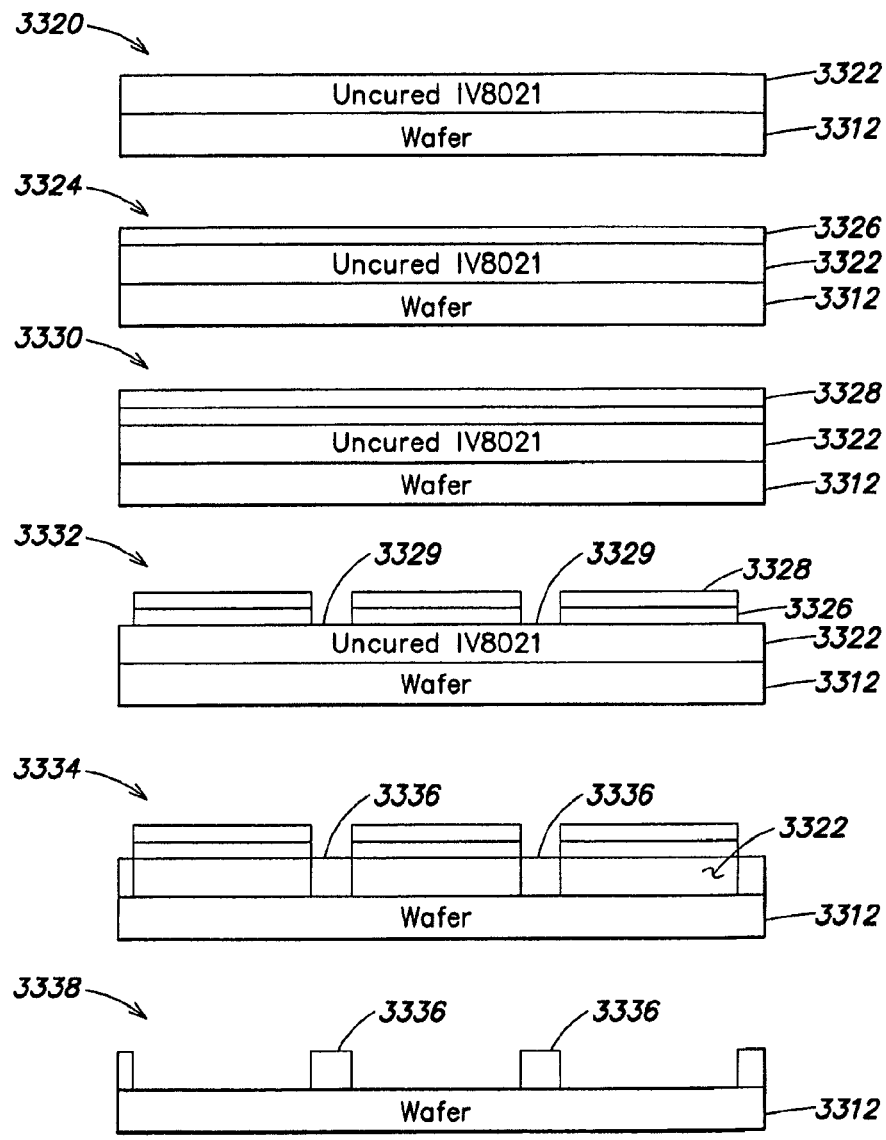
FIG. 33A is an illustration of a three-layer PCM process for making the microwell array.

Another PCM technique may be adapted to these purposes, such as that shown in U.S. patent application publication no. 2006/0073422 by Edwards et al. This is a three-layer PCM process and it is illustrated in FIG. 33A. As shown there, basically six major steps are required to produce the microwell array and the result is quite similar to what contact lithography would yield.

In a first step, 3320, a layer of high contrast negative-acting photoresist such as type Shipley InterVia Photodielectric Material 8021 (IV8021) 3322 is spun on the surface of a wafer, which we shall assume to be the wafer providing the substrate 3312 of FIG. 33 (in which the sensor array is fabricated), and a soft bake operation is performed. Next, in step 3324, a blocking anti-reflective coating (BARC) layer 3326, is applied and soft baked. On top of this structure, a thin resist layer 3328 is spun on and soft baked, step 3330, the thin layer of resist being suitable for fine feature definition. The resist layer 3328 is then patterned, exposed and developed, and the BARC in the exposed regions 3329, not protected any longer by the resist 3328, is removed, Step 3332. This opens up regions 3329 down to the uncured IV8021 layer. The BARC layer can now act like a conformal contact mask A blanket exposure with a flooding exposure tool, Step 3334, cross-links the exposed IV8021, which is now shown as distinct from the uncured IV8021 at 3322. One or more developer steps 3338 are then performed, removing everything but the cross-linked IV8021 in regions 3336. Regions 3336 now constitute the walls of the microwells.

Although as shown above, the wells bottom out (i.e. terminate) on the top passivation layer of the ISFETs, it is believed that an improvement in ISFET sensor performance (i.e. such as signal-to-noise ratio) can be obtained if the active bead(s) is(are) kept slightly elevated from the ISFET passivation layer. One way to do so is to place a spacer "bump" within the boundary of the pixel microwell. An example of how this could be rendered would be not etching away a portion of the layer-or-layers used to form the microwell structure (i.e. two lithographic steps to form the microwells—one to etch part way done, the other to pattern the bump and finish the etch to bottom out), by depositing and lithographically defining and etching a separate layer to form the "bump", by using a permanent photo-definable material for the bump once the microwells are complete, or by forming the bump prior to forming the microwell. The bump feature is shown as 3350 in FIG. 33B. An alternative (or additional) non-integrated approach is to load the wells with a layer or two of very small packing beads before loading the DNA-bearing beads.

Figure 33B:
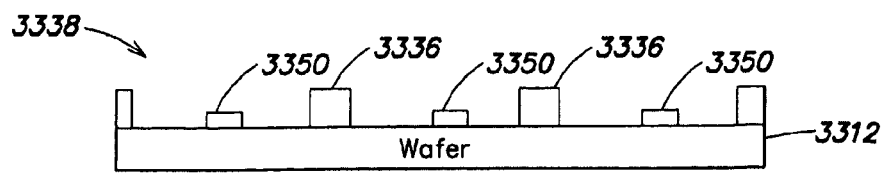
FIG. 33B is a diagrammatic cross-section of a microwell with a "bump" feature etched into the bottom.
Figures 1, 33B:
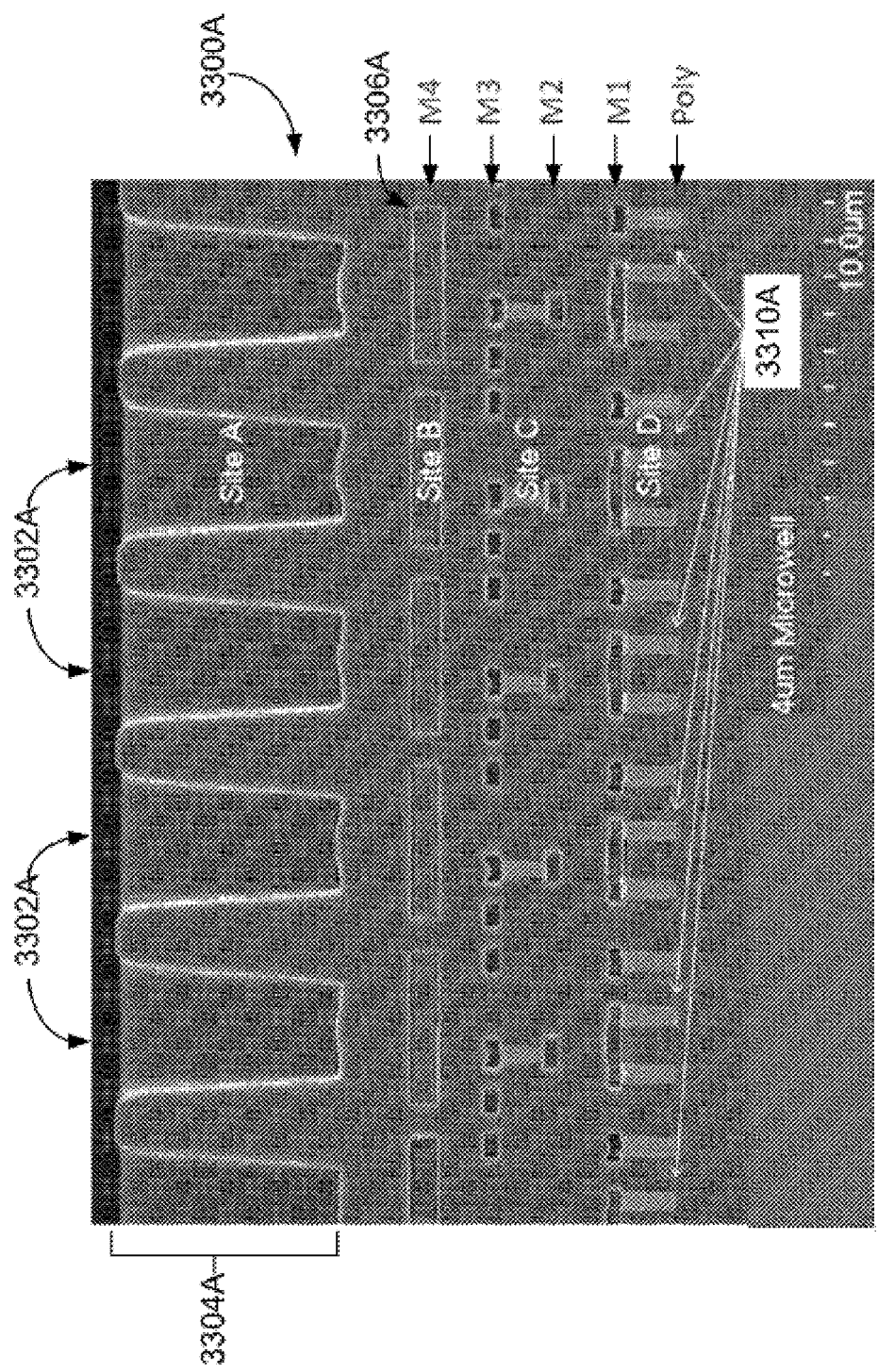
Figures 2, 33B:
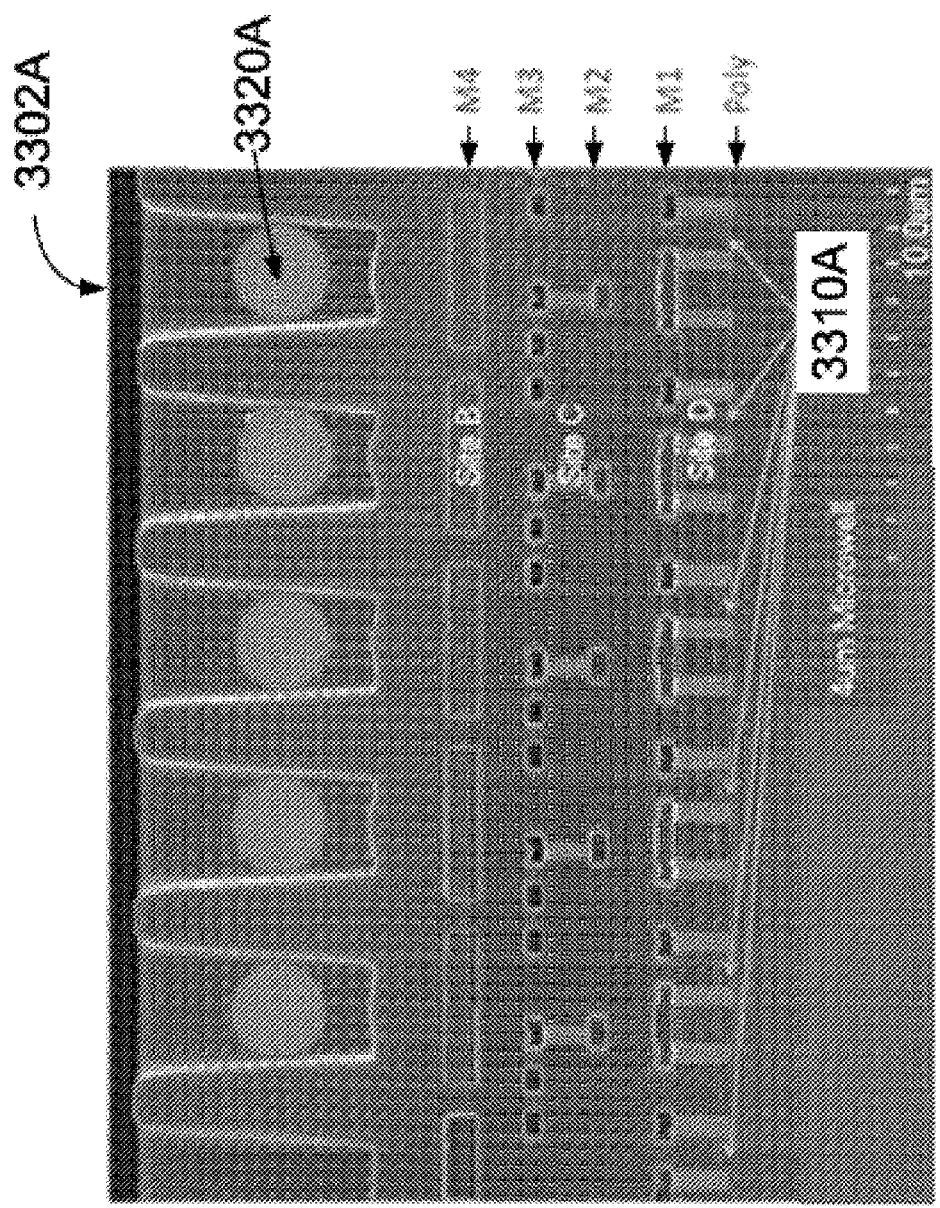
Figures 3, 33B:
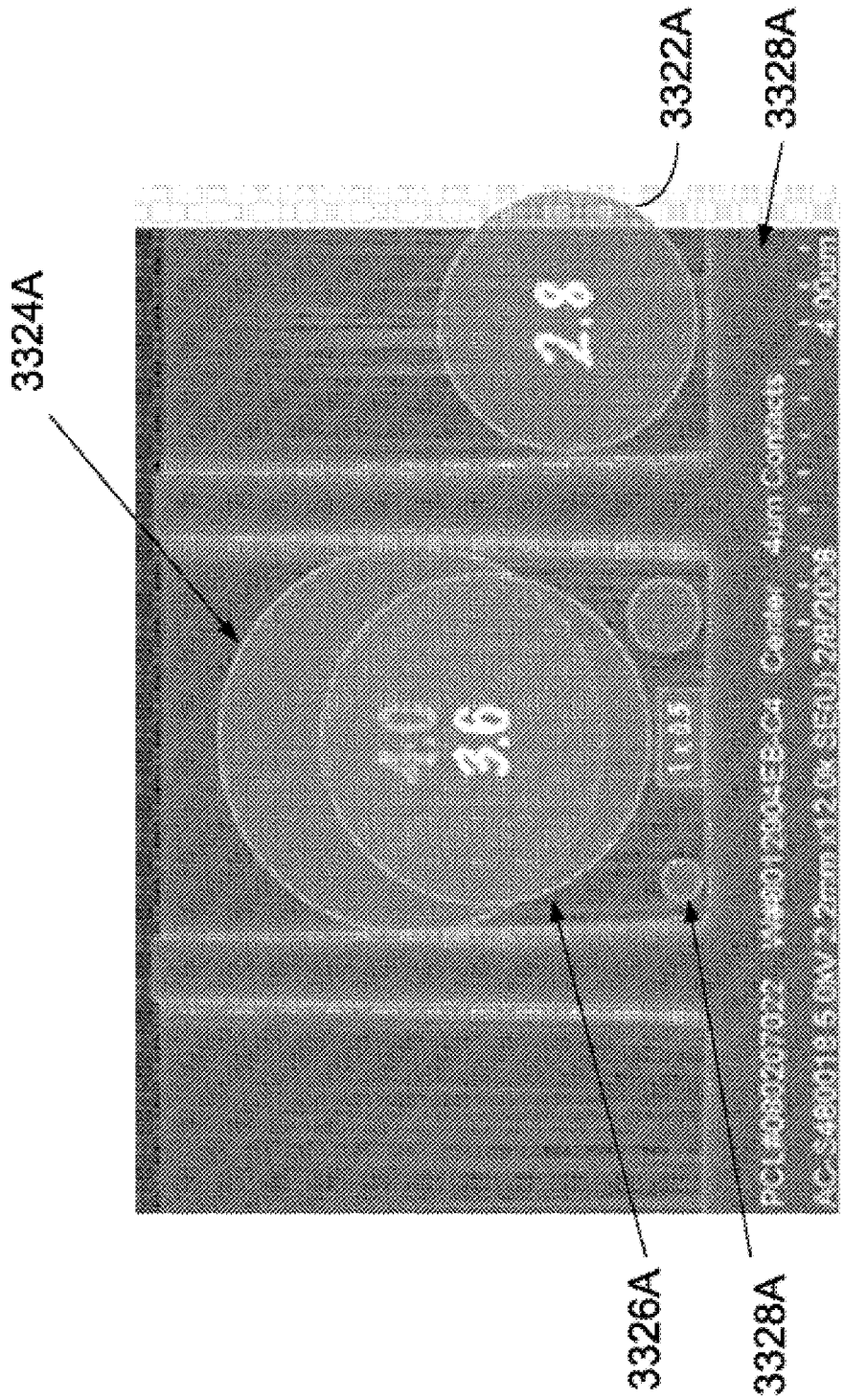

Using a 6 um (micron) thick layer of tetra-methyl-orthosilicate (TEOS) as a $SiO_2$-like layer for microwell formation, FIG. 33B-1 shows a scanning electron microscope (SEM) image of a cross-section of a portion 3300A of an array architecture as taught herein. Microwells 3302A are formed in the TEOS layer 3304A. The wells extend about 4 um into the 6 um thick layer. Typically, the etched well bottoms on an etch-stop material which may be, for example, an oxide, an organic material or other suitable material known in semiconductor processing for etch-stopping use. A thin layer of etch stop material may be formed on top of a thicker layer of polyimide or other suitable dielectric, such that there is about 2 um of etch stop+polyimide between the well bottom and the Metal4 (M4) layer of the chip in which the extended gate electrode 3308A is formed for each underlying ISFET in the array. As labeled on the side, the CMOS metallization layers M3, M2 and M1, which form lower level interconnects and structures, are shown, with the ISFET channels being formed in the areas indicated by arrows 3310A.

In the orthogonal cross-sectional view (i.e., looking down from the top), the wells may be formed in either round or square shape. Round wells may improve bead capture and may obviate the need for packing beads at the bottom or top of the wells.

Figure 2:
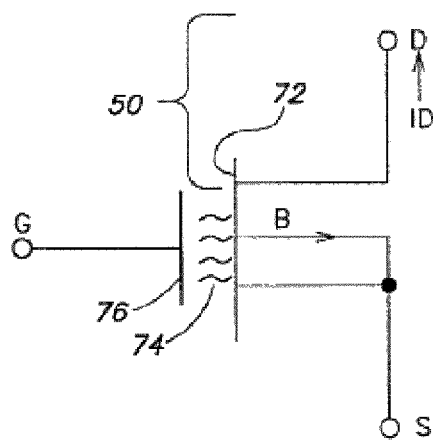
FIG. 2 illustrates an electric circuit representation of the p-channel ISFET shown in FIG. 1.
Figure 2A:
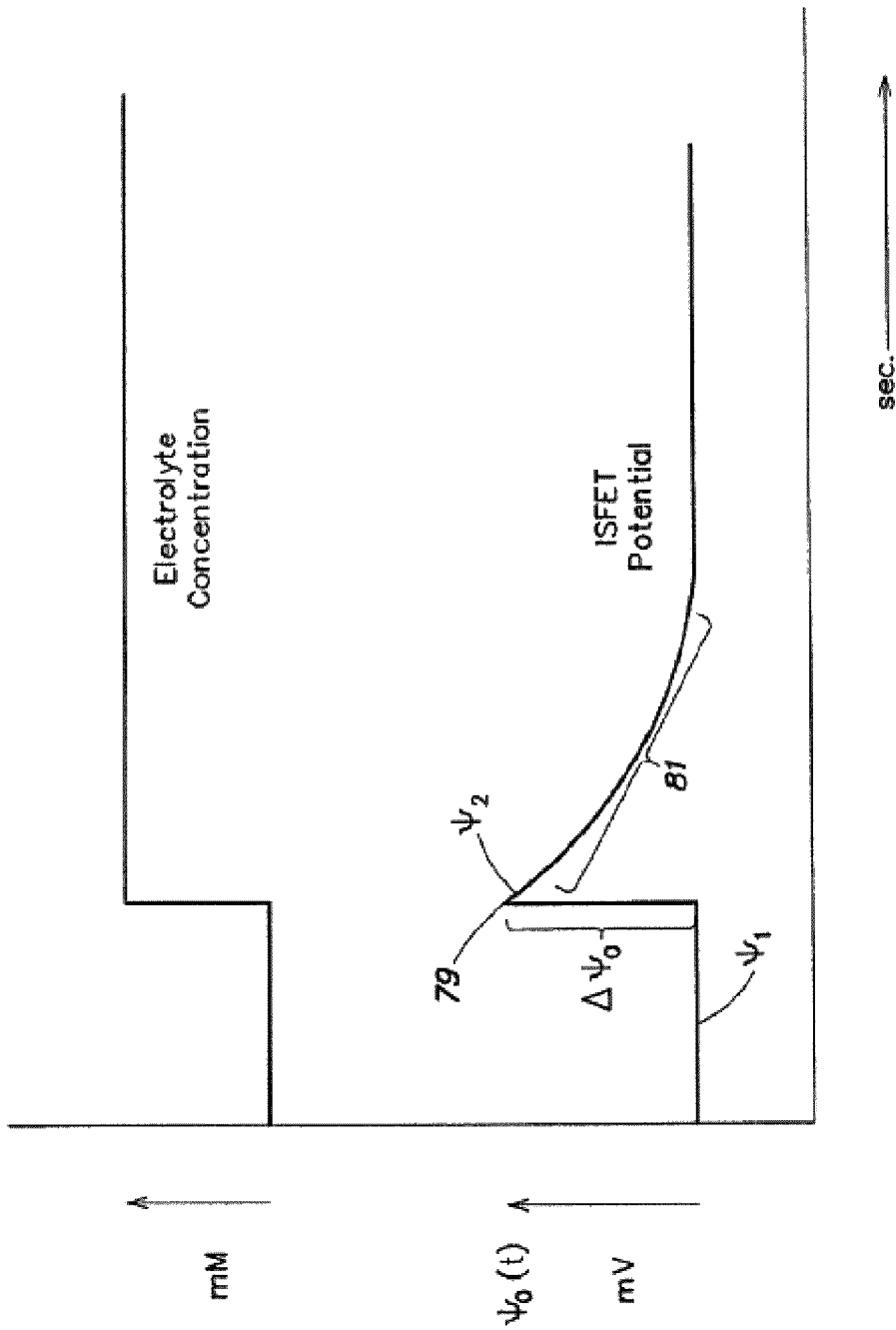
FIG. 2A illustrates an exemplary ISFET transient response to a step-change in ion concentration of an analyte.

The tapered slopes to the sides of the microwells also may be used to advantage. Referring to FIG. 33B-2, if the beads 3320A have a diameter larger than the bottom span across the wells, but small enough to fit into the mouths of the wells, the beads will be spaced off the bottom of the wells due to the geometric constraints. For example, FIG. 33B-2 illustrates the example of microwells that are square in cross-section as viewed from the top, 4 um on a side, with 3.8 um diameter beads 3320A loaded. Experimentally and with some calculation, one may determine suitable bead size and well dimension combinations. FIG. 33B-3 shows a portion of one 4 um well loaded with a 2.8 um diameter bead 3322A, which obviously is relatively small and falls all the way to the bottom of the well; a 4.0 um diameter bead 3324A which is stopped from reaching the bottom by the sidewall taper of the well; and an intermediate-sized bead 3326A of 3.6 um diameter which is spaced from the well bottom by packing beads 3328A. Clearly, bead size has to be carefully matched to the microwell etch taper.

Thus, microwells can be fabricated by any high aspect ratio photo-definable or etchable thin-film process, that can provide requisite thickness (e.g., about 4-10 um). Among the materials believed to be suitable are photosensitive polymers, deposited silicon dioxide, non-photosensitive polymer which can be etched using, for example, plasma etching processes, etc. In the silicon dioxide family, TEOS and silane nitrous oxide (SILOX) appear suitable. The final structures are similar but the various materials present differing surface compositions that may cause the target biology or chemistry to react differently.

When the microwell layer is formed, it may be necessary to provide an etch stop layer so that the etching process does not proceed further than desired. For example, there may be an underlying layer to be preserved, such as a low-K dielectric. The etch stop material should be selected according to the application. SiC and SiN materials may be suitable, but that is not meant to indicate that other materials may not be employed, instead. These etch-stop materials can also serve to enhance the surface chemistry which drives the ISFET sensor sensitivity, by choosing the etch-stop material to have an appropriate point of zero charge (PZC). Various metal oxides may be suitable addition to silicon dioxide and silicon nitride.

The PZCs for various metal oxides may be found in various texts, such as "Metal Oxides—Chemistry and Applications" by J. Fierro. We have learned that $Ta_2O_5$ may be preferred as an etch stop over $Al_2O_3$ because the PZC of $Al_2O_3$ is right at the pH being used (i.e., about 8.8) and, hence, right at the point of zero charge. In addition $Ta_2O_5$ has a higher sensitivity to pH (i.e., mV/pH), another important factor in the sensor performance. Optimizing these parameters may require judicious selection of passivation surface materials.

Using thin metal oxide materials for this purpose (i.e., as an etch stop layer) is difficult due to the fact of their being so thinly deposited (typically 200-500 Å). A post-microwell fabrication metal oxide deposition technique may allow placement of appropriate PZC metal oxide films at the bottom of the high aspect ratio microwells.

Electron-beam depositions of (a) reactively sputtered tantalum oxide, (b) non-reactive stoichiometric tantalum oxide, (c) tungsten oxide, or (d) Vanadium oxide may prove to have superior "down-in-well" coverage due to the superior directionality of the deposition process.

The array typically comprises at least 100 microfluidic wells, each of which is coupled to one or more chemFET sensors. Preferably, the wells are formed in at least one of a glass (e.g., $SiO_2$), a polymeric material, a photodefinable material or a reactively ion etchable thin film material. Preferably, the wells have a width to height ratio less than about 1:1. Preferably the sensor is a field effect transistor, and more preferably a chemFET. The chemFET may optionally be coupled to a PPi receptor. Preferably, each of the chemFETs occupies an area of the array that is $10^2$ microns or less.

In some embodiments, the invention encompasses a sequencing device comprising a semiconductor wafer device coupled to a dielectric layer such as a glass (e.g., $SiO_2$), polymeric, photodefinable or reactive ion etchable material in which reaction chambers are formed. Typically, the glass, dielectric, polymeric, photodefinable or reactive ion etchable material is integrated with the semiconductor wafer layer. In some instances, the glass, polymeric, photodefinable or reactive ion etchable layer is non-crystalline. In some instances, the glass may be $SiO_2$. The device can optionally further comprise a fluid delivery module of a suitable material such as a polymeric material, preferably an injection moldable material. More preferably, the polymeric layer is polycarbonate.

In some embodiments, the invention encompasses a method for manufacturing a sequencing device comprising: using photolithography, generating wells in a glass, dielectric, photodefinable or reactively ion etchable material on top of an array of transistors.

The process of using the assembly of an array of sensors on a chip combined with an array of microwells to sequence the DNA in a sample is referred to as an "experiment." Executing an experiment requires loading the wells with the DNA-bound beads and the flowing of several different fluid solutions (i.e., reagents and washes) across the wells. A fluid delivery system (e.g., valves, conduits, pressure source(s), etc.) coupled with a fluidic interface is needed which flows the various solutions across the wells in a controlled even flow with acceptably small dead volumes and small cross contamination between sequential solutions. Ideally, the fluidic interface to the chip (sometimes referred to as a "flow cell") would cause the fluid to reach all microwells at the same time. To maximize array speed, it is necessary that the array outputs be available at as close to the same time as possible. The ideal clearly is not possible, but it is desirable to minimize the differentials, or skews, of the arrival times of an introduced fluid, at the various wells, in order to maximize the overall speed of acquisition of all the signals from the array.

Flow cell designs of many configurations are possible; thus the system and methods presented herein are not dependent on use of a specific flow cell configuration. It is desirable, though, that a suitable flow cell substantially conform to the following set of objectives:

have connections suitable for interconnecting with a fluidics delivery system—e.g., via appropriately-sized tubing;

have appropriate head space above wells;

minimize dead volumes encountered by fluids;

minimize small spaces in contact with liquid but not quickly swept clean by flow of a wash fluid through the flow cell (to minimize cross contamination);

be configured to achieve uniform transit time of the flow over the array;

generate or propagate minimal bubbles in the flow over the wells;

be adaptable to placement of a removable reference electrode inside or as close to the flow chamber as possible;

facilitate easy loading of beads;

be manufacturable at acceptable cost; and be easily assembled and attached to the chip package.

Satisfaction of these criteria so far as possible will contribute to system performance positively. For example, minimization of bubbles is important so that signals from the array truly indicate the reaction in a well rather than being spurious noise.

Each of several example designs will be discussed, meeting these criteria in differing ways and degrees. In each instance, one typically may choose to implement the design in one of two ways: either by attaching the flow cell to a frame and gluing the frame (or otherwise attaching it) to the chip or by integrating the frame into the flow cell structure and attaching this unified assembly to the chip. Further, designs may be categorized by the way the reference electrode is integrated into the arrangement. Depending on the design, the reference electrode may be integrated into the flow cell (e.g., form part of the ceiling of the flow chamber) or be in the flow path (typically to the outlet or downstream side of the flow path, after the sensor array).

A first example of a suitable experiment apparatus 3410 incorporating such a fluidic interface is shown in FIGS. 34-37, the manufacture and construction of which will be discussed in greater detail below.

The apparatus comprises a semiconductor chip 3412 (indicated generally, though hidden) on or in which the arrays of wells and sensors are formed, and a fluidics assembly 3414 on top of the chip and delivering the sample to the chip for reading. The fluidics assembly includes a portion 3416 for introducing fluid containing the sample, a portion 3418 for allowing the fluid to be piped out, and a flow chamber portion 3420 for allowing the fluid to flow from inlet to outlet and along the way interact with the material in the wells. Those three portions are unified by an interface comprising a glass slide 3422 (e.g., Erie Microarray Cat #C22-5128-M20 from Erie Scientific Company, Portsmouth, N.H., cut in thirds, each to be of size about 25 mm×25 mm).

Mounted on the top face of the glass slide are two fittings, 3424 and 3426, such as nanoport fittings Part #N-333 from Upchurch Scientific of Oak Harbor, Wash. One port (e.g., 3424) serves as an inlet delivering liquids from the pumping/valving system described below but not shown here. The second port (e.g., 3426) is the outlet which pipes the liquids to waste. Each port connects to a conduit 3428, 3432 such as flexible tubing of appropriate inner diameter. The nanoports are mounted such that the tubing can penetrate corresponding holes in the glass slide. The tube apertures should be flush with the bottom surface of the slide.

On the bottom of the glass slide, flow chamber 3420 may comprise various structures for promoting a substantially laminar flow across the microwell array. For example, a series of microfluidic channels fanning out from the inlet pipe to the edge of the flow chamber may be patterned by contact lithography using positive photoresists such as SU-8 photoresist from MicroChem. Corp. of Newton, Mass. Other structures will be discussed below.

The chip 3412 will in turn be mounted to a carrier 3430, for packaging and connection to connector pins 3432.

Figure 36:
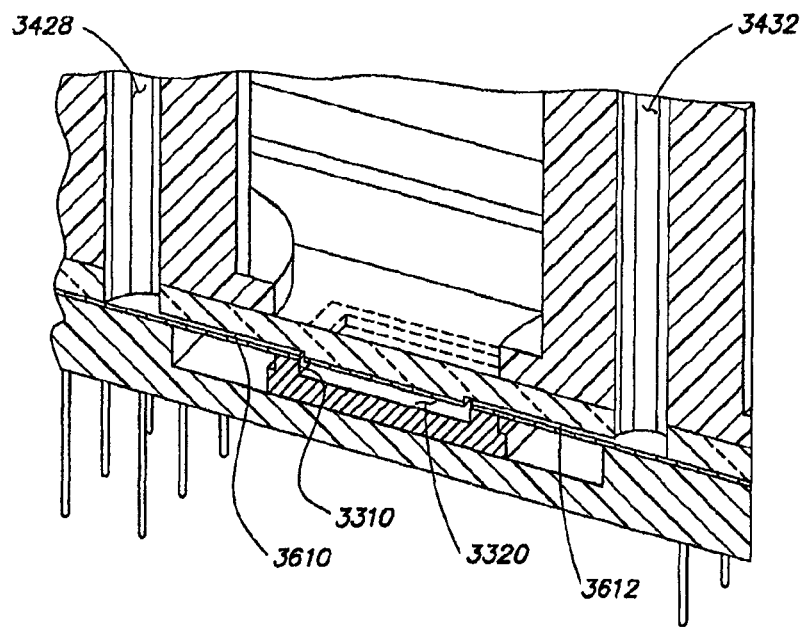
Figure 37:
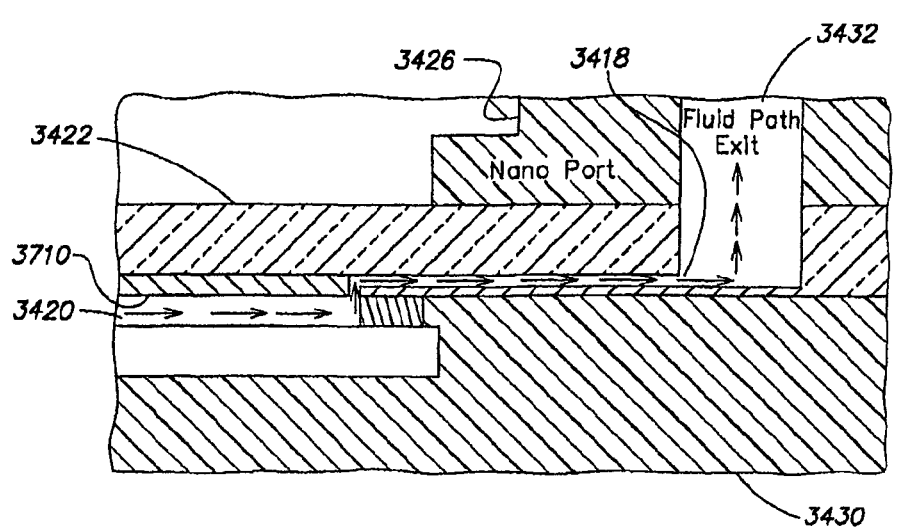
Figure 38:
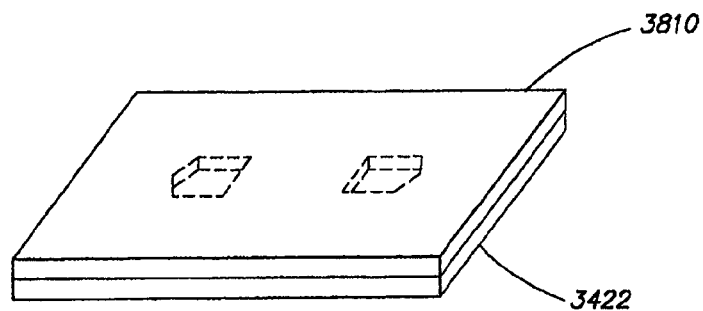
FIG. 38 is a diagrammatic illustration of a substrate with an etched photoresist layer beginning the formation of an example flow cell of a certain configuration.

For ease of description, to discuss fabrication starting with FIG. 38 we shall now consider the glass slide 3422 to be turned upside down relative to the orientation it has in FIGS. 34-37.

Figure 39:
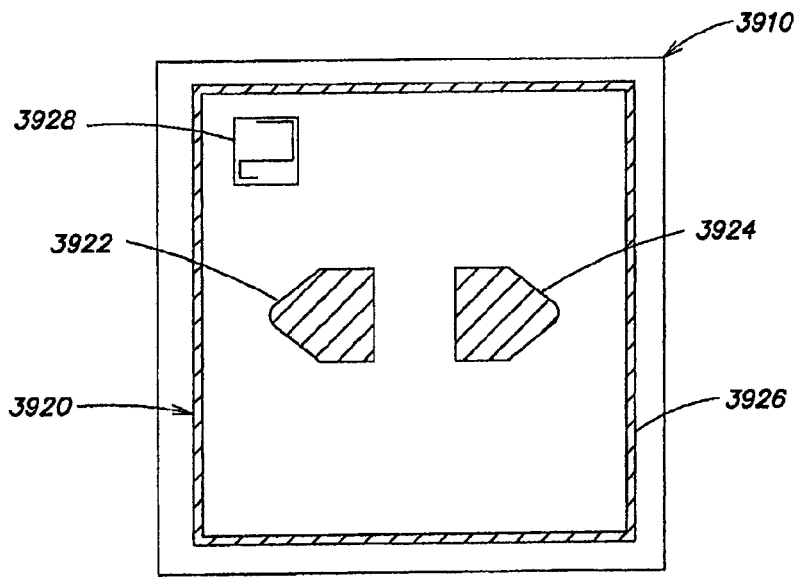
FIGS. 39-41 are diagrams of masks suitable for producing a first configuration of flow cell consistent with FIG. 38.

A layer of photoresist 3810 is applied to the "top" of the slide (which will become the "bottom" side when the slide and its additional layers is turned over and mounted to the sensor assembly of ISFET array with microwell array on it). Layer 3810 may be about 150 μm thick in this example, and it will form the primary fluid carrying layer from the end of the tubing in the nanoports to the edge of the sensor array chip. Layer 3810 is patterned using a mask such as the mask 3910 of FIG. 39 ("patterned" meaning that a radiation source is used to expose the resist through the mask and then the non-plasticized resist is removed). The mask 3910 has radiation-transparent regions which are shown as white and radiation-blocking regions 3920, which are shown in shading. The radiation-blocking regions are at 3922-3928. The region 3926 will form a channel around the sensor assembly; it is formed about 0.5 mm inside the outer boundary of the mask 3920, to avoid the edge bead that is typical. The regions 3922 and 3924 will block radiation so that corresponding portions of the resist are removed to form voids shaped as shown. Each of regions 3922, 3924 has a rounded end dimensioned to receive an end of a corresponding one of the tubes 3428, 3432 passing through a corresponding nanoport 3424, 3426. From the rounded end, the regions 3922, 3924 fan out in the direction of the sensor array to allow the liquid to spread so that the flow across the array will be substantially laminar. The region 3928 is simply an alignment pattern and may be any suitable alignment pattern or be replaced by a suitable substitute alignment mechanism. Dashed lines on FIG. 38 have been provided to illustrate the formation of the voids 3822 and 3824 under mask regions 3922 and 3924.

Figure 40:
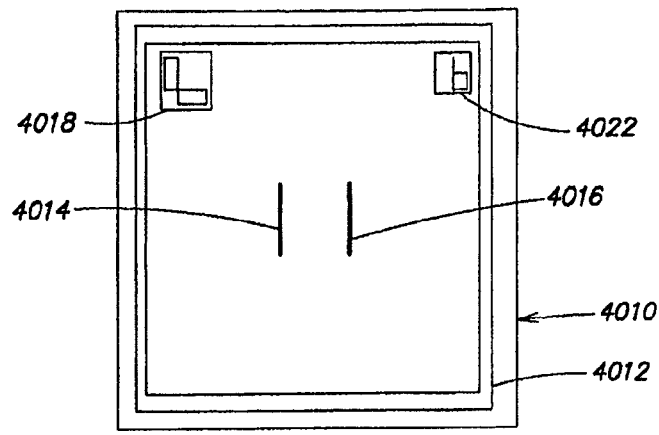

A second layer of photoresist is formed quite separately, not on the resist 3810 or slide 3422. Preferably it is formed on a flat, flexible surface (not shown), to create a peel-off, patterned plastic layer. As shown in FIG. 40, this second layer of photoresist may be formed using a mask such as mask 4010, which will leave on the flexible substrate, after patterning, the border under region 4012, two slits under regions 4014, 4016, whose use will be discussed below, and alignment marks produced by patterned regions 4018 and 4022. The second layer of photoresist is then applied to the first layer of photoresist using one alignment mark or set of alignment marks, let's say produced by pattern 4018, for alignment of these layers. Then the second layer is peeled from its flexible substrate and the latter is removed.

The other alignment mark or set of marks produced by pattern 4022 is used for alignment with a subsequent layer to be discussed.

The second layer is preferably about 150 μm deep and it will cover the fluid-carrying channel with the exception of a slit about 150 μm long at each respective edge of the sensor array chip, under slit-forming regions 4014 and 4016.

Figure 41:
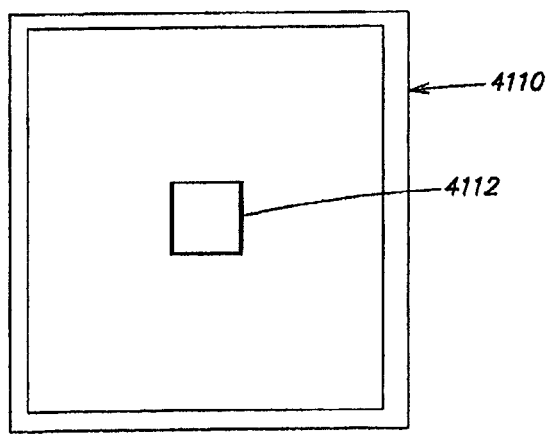

Once the second layer of photoresist is disposed on the first layer, a third patterned layer of photoresist is formed over the second layer, using a mask such as mask 4110, shown in FIG. 41. The third layer provides a baffle member under region 4112 which is as wide as the collar 3310 on the sensor chip array (see FIG. 33) but about 300 μm narrower to allow overlap with the fluid-carrying channel of the first layer. The third layer may be about 150 μm thick and will penetrate the chip collar 3310, toward the floor of the basin formed thereby, by 150 μm. This configuration will leave a headspace of about 300 μm above the wells on the sensor array chip. The liquids are flowed across the wells along the entire width of the sensor array through the 150 μm slits under 4014, 4016.

Figure 34:
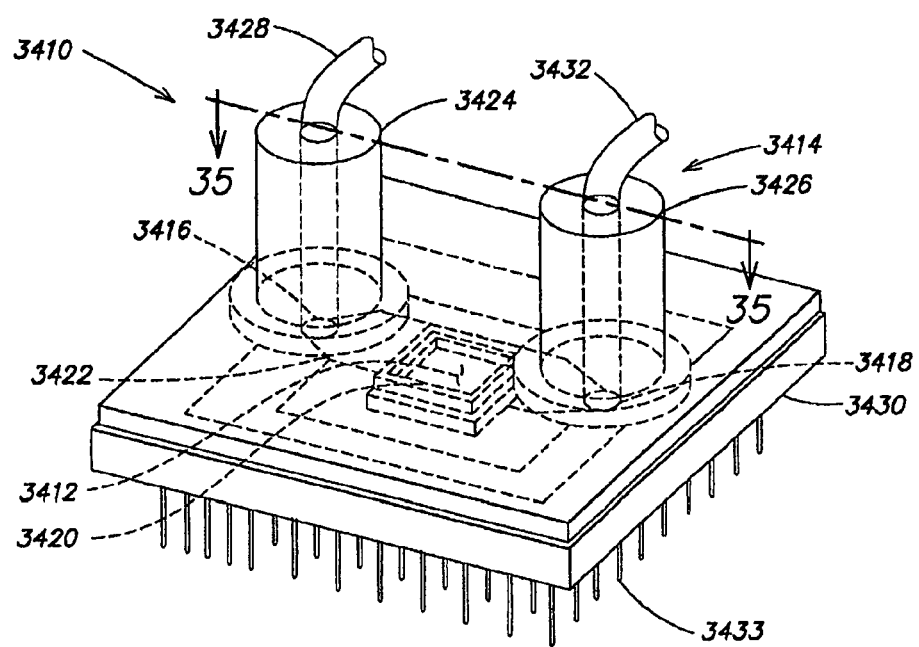
FIGS. 34-37 diagrammatically illustrate a first example of a suitable experiment apparatus incorporating a fluidic interface with the sensor array, with FIG. 35 providing a cross-section through the FIG. 34 apparatus along section line 35-35' and FIG. 36 expanding part of FIG. 35, in perspective, and FIG. 37 further expanding a portion of the structure to make the fluid flow more visible.
Figure 35:
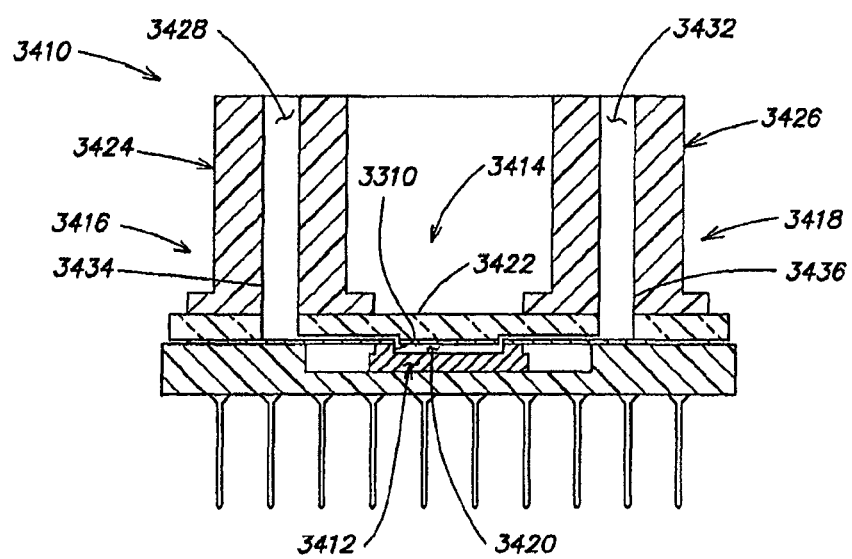

FIG. 36 shows a partial sectional view, in perspective, of the above-described example embodiment of a microfluidics and sensor assembly, also depicted in FIGS. 34 and 35, enlarged to make more visible the fluid flow path. (A further enlarged schematic of half of the flow path is shown in FIG. 37.) Here, it will be seen that fluid enters via the inlet pipe 3428 in inlet port 3424. At the bottom of pipe 3428, the fluid flows through the flow expansion chamber 3610 formed by mask area 3922, that the fluid flows over the collar 3310 and then down into the bottom 3320 of the basin, and across the die 3412 with its microwell array. After passing over the array, the fluid then takes a vertical turn at the far wall of the collar 3310 and flows over the top of the collar to and across the flow concentration chamber 3612 formed by mask area 3924, exiting via outlet pipe 3432 in outlet port 3426. Part of this flow, from the middle of the array to the outlet, may be seen also in the enlarged diagrammatic illustration of FIG. 37, wherein the arrows indicate the flow of the fluid.

The fluidics assembly may be secured to the sensor array chip assembly by applying an adhesive to parts of mating surfaces of those two assemblies, and pressing them together, in alignment.

Though not illustrated in FIGS. 34-36, the reference electrode may be understood to be a metallization 3710, as shown in FIG. 37, at the ceiling of the flow chamber.

Figure 42:
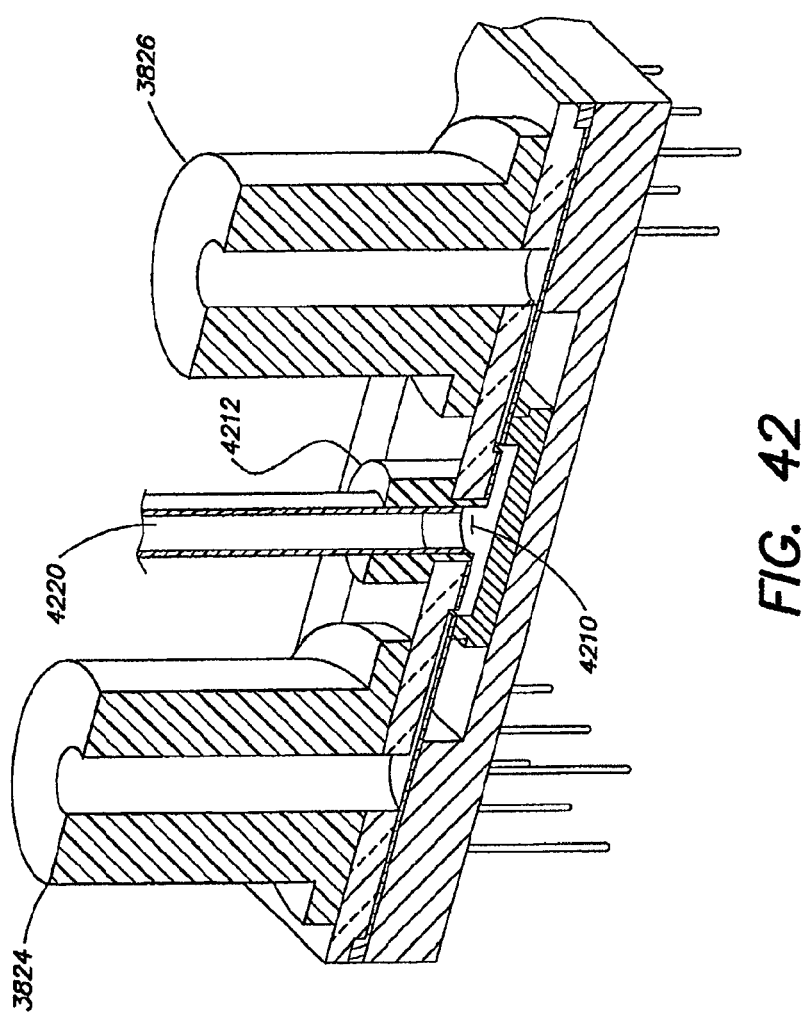
FIGS. 42-54 (but not including FIGS. 42A-42L) and 57-58 are pairs of partly isometric, sectional views of example apparatus and enlargements, showing ways of introducing a reference electrode into, and forming, a flow cell and flow chamber, using materials such as plastic and PDMS.
Figure 42A:
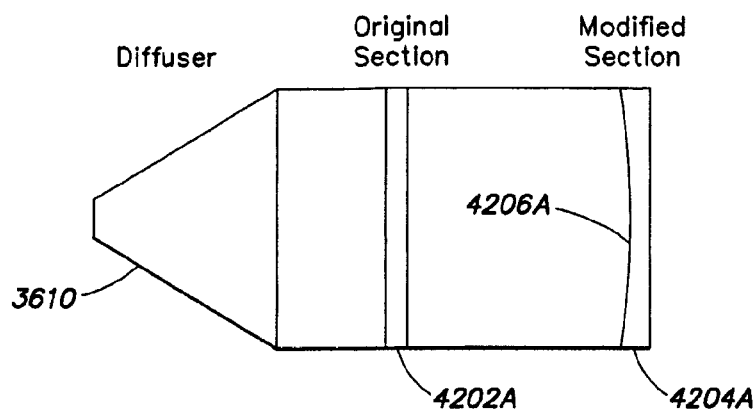
FIG. 42A is an illustration of a possible cross-sectional configuration of a non-rectangular flow chamber antechamber (diffuser section) for use to promote laminar flow into a flow cell as used in the arrangements shown herein.

Another way to introduce the reference electrode is shown in FIG. 42. There, a hole 4210 is provided in the ceiling of the flow chamber and a grommet 4212 (e.g., of silicone) is fitted into that hole, providing a central passage or bore through which a reference electrode 4220 may be inserted. Baffles or other microfeatures (not shown in FIG. 42 but discussed below in connection with FIG. 42A) may be patterned into the flow channel to promote laminar flow over the microwell array.

Achieving a uniform flow front and eliminating problematic flow path areas is desirable for a number of reasons. One reason is that very fast transition of fluid interfaces within the system's flow cell is desired for many applications, particularly gene sequencing. In other words, an incoming fluid must completely displace the previous fluid in a short period of time. Uneven fluid velocities and diffusion within the flow cell, as well as problematic flow paths, can compete with this requirement. Simple flow through a conduit of rectangular cross section can exhibit considerable disparity of fluid velocity from regions near the center of the flow volume to those adjacent the sidewalls, one sidewall being the top surface of the microwell layer and the fluid in the wells. Such disparity leads to spatially and temporally large concentration gradients between the two traveling fluids. Further, bubbles are likely to be trapped or created in stagnant areas like sharp corners interior the flow cell. (The surface energy (hydrophilic vs. hydrophobic) can significantly affect bubble retention. Avoidance of surface contamination during processing and use of a surface treatment to create a more hydrophilic surface should be considered if the as-molded surface is too hydrophobic.) Of course, the physical arrangement of the flow chamber is probably the factor which most influences the degree of uniformity achievable for the flow front.

Figure 42E:
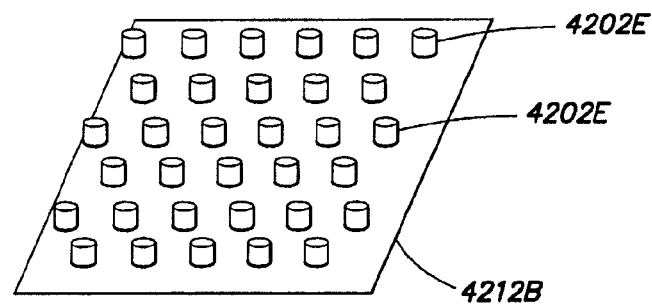
FIGS. 42B-42F are diagrammatic illustrations of examples of flow cell structures for unifying fluid flow.

One approach is to configure the flow cross section of the flow chamber to achieve flow rates that vary across the array width so that the transit times are uniform across the array. For example, the cross section of the diffuser (i.e., flow expansion chamber) section 3416, 3610 may be made as shown at 4204A in FIG. 42A, instead of simply being rectangular, as at 4204A. That is, it may have a curved (e.g., concave) wall. The non-flat wall 4206A of the diffuser can be the top or the bottom. Another approach is to configure the effective path lengths into the array so that the total path lengths from entrance to exit over the array are essentially the same. This may be achieved, for example, by placing flow-disrupting features such as cylinders or other structures oriented normal to the flow direction, in the path of the flow. If the flow chamber has as a floor the top of the microwell array and as a ceiling an opposing wall, these flow-disrupting structures may be provided either on the top of the microwell layer or on (or in) the ceiling wall. The structures must project sufficiently into the flow to have the desired effect, but even small flow disturbances can have significant impact. Turning to FIGS. 42B-42F, there are shown diagrammatically some examples of such structures. In FIG. 42B, on the surface of microwell layer 4210B there are formed a series of cylindrical flow disruptors 4214B extending vertically toward the flow chamber ceiling wall 4212B, and serving to disturb laminar flow for the fluid moving in the direction of arrow A. FIG. 42C depicts a similar arrangement except that the flow disruptors 4216C have rounded tops and appear more like bumps, perhaps hemispheres or cylinders with spherical tops. By contrast, in FIG. 42D, the flow disruptors 4218D protrude, or depend, from the ceiling wall 4212B of the flow chamber. Only one column of flow disruptors is shown but it will be appreciated that a plurality of more or less parallel columns typically would be required. For example, FIG. 42E shows several columns 4202E of such flow disruptors (projecting outwardly from ceiling wall 4212B (though the orientation is upside down relative to FIGS. 42B-42D). The spacing between the disruptors and their heights may be selected to influence the distance over which the flow profile becomes parabolic, so that transit time equilibrates.

Figure 42F:
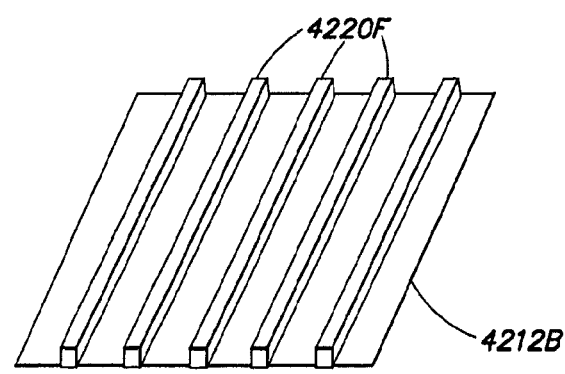
Figure 42B:
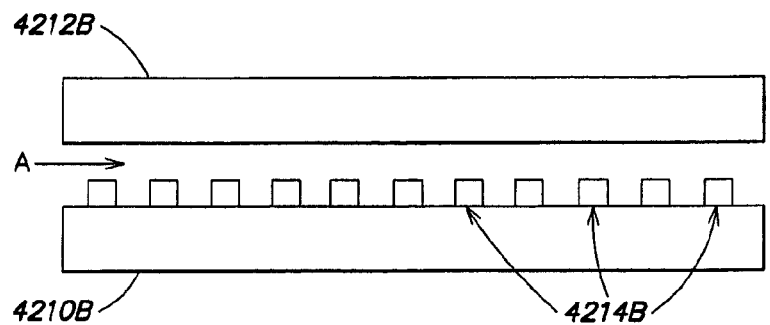
Figure 42C:
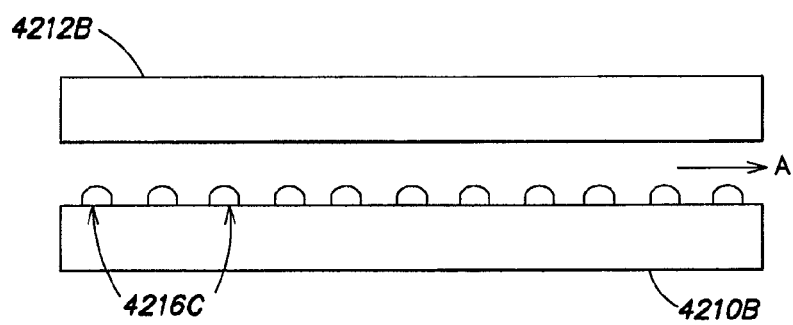
Figure 42D:
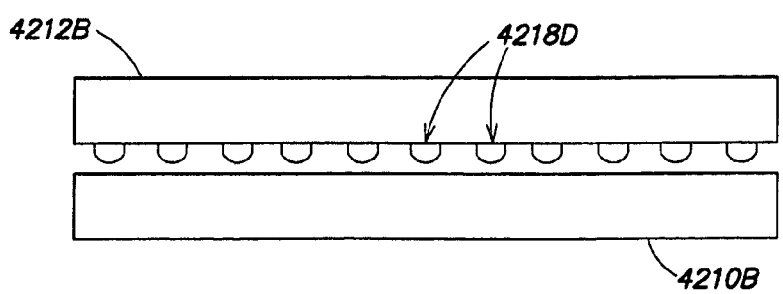

Another configuration, shown in FIGS. 42F and 42F1, involves the use of solid, beam-like projections or baffles 4220F as disruptors. This concept may be used to form a ceiling member for the flow chamber. Such an arrangement encourages more even fluid flow and significantly reduces fluid displacement times as compared with a simple rectangular cross-section without disruptor structure. Further, instead of fluid entry to the array occurring along one edge, fluid may be introduced at one corner 4242F, through a small port, and may exit from the opposite corner, 4244F, via a port in fluid communication with that corner area. The series of parallel baffles 4220F separates the flow volume between input and outlet corners into a series of channels. The lowest fluid resistant path is along the edge of the chip, perpendicular to the baffles. As incoming liquid fills this channel, the fluid is then directed between the baffles to the opposite side of the chip. The channel depth between each baffle pair preferably is graded across the chip, such that the flow is encouraged to travel toward the exit port through the farthest channel, thereby evening the flow front between the baffles. The baffles extend downwardly nearly to the chip (i.e., microwell layer) surface, but because they are quite thin, fluid can diffuse under them quickly and expose the associated area of the array assembly.

Figure 7:
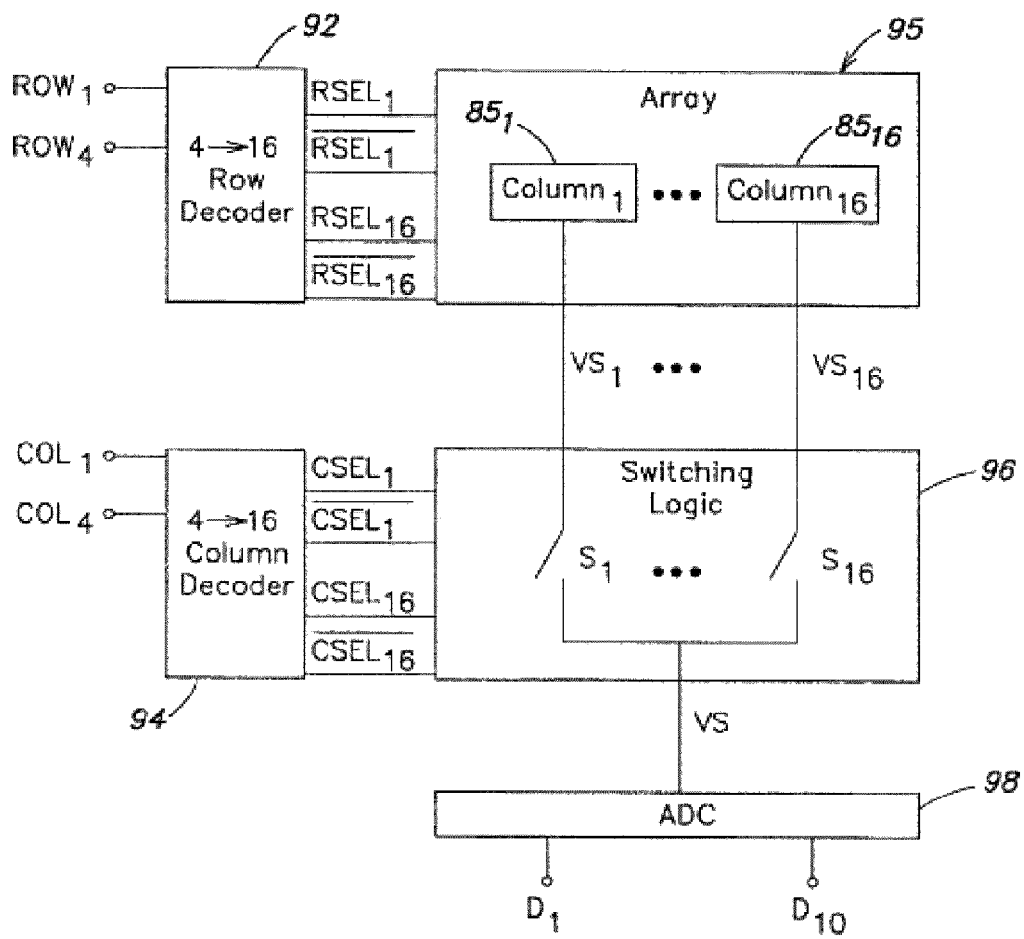
FIG. 7 illustrates an example of a complete two-dimensional ISFET pixel array based on the column design of FIG. 3, together with accompanying row and column decoder circuitry and measurement readout circuitry.

FIGS. 42F2-42F8 illustrate an example of a single-piece, injection-molded (preferably of polycarbonate) flow cell member 42F200 which may be used to provide baffles 4220F, a ceiling to the flow chamber, fluid inlet and outlet ports and even the reference electrode. FIG. 42F7 shows an enlarged view of the baffles on the bottom of member 42F200 and the baffles are shown as part of the underside of member 42F200 in FIG. 42F6. As it is difficult to form rectangular features in small dimensions by injection molding, the particular instance of these baffles, shown as 4220F', are triangular in cross section.

Figure 4:
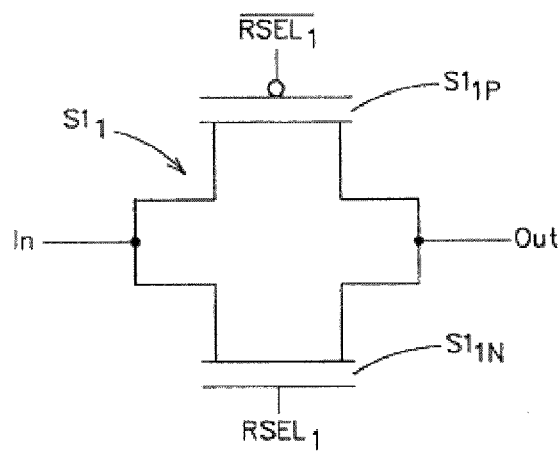
FIG. 4 illustrates a transmission gate including a p-channel MOSFET and an re-channel MOSFET that is employed in each pixel of the array column shown in FIG. 3.
Figure 5:
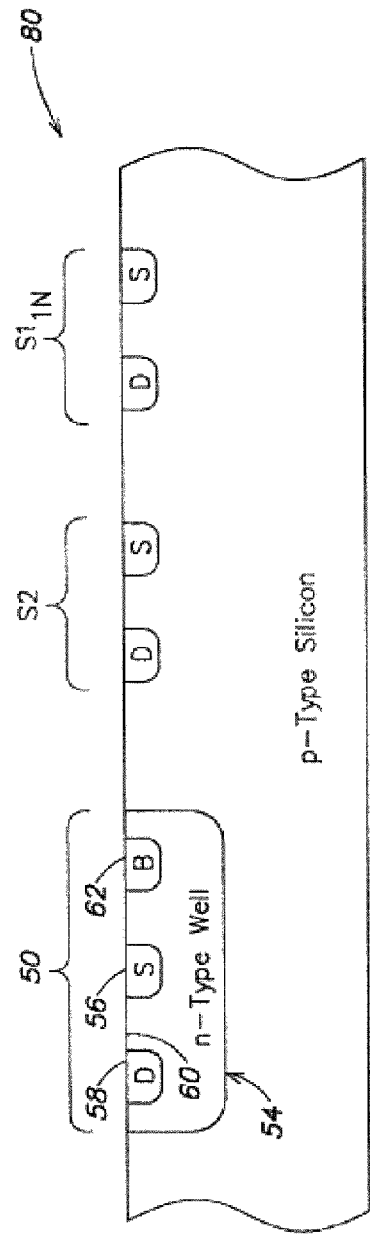
FIG. 5 is a diagram similar to FIG. 1, illustrating a wider cross-section of a portion of a substrate corresponding to one pixel of the array column shown in FIG. 3, in which the ISFET is shown alongside two n-channel MOSFETs also included in the pixel.
Figure 6:
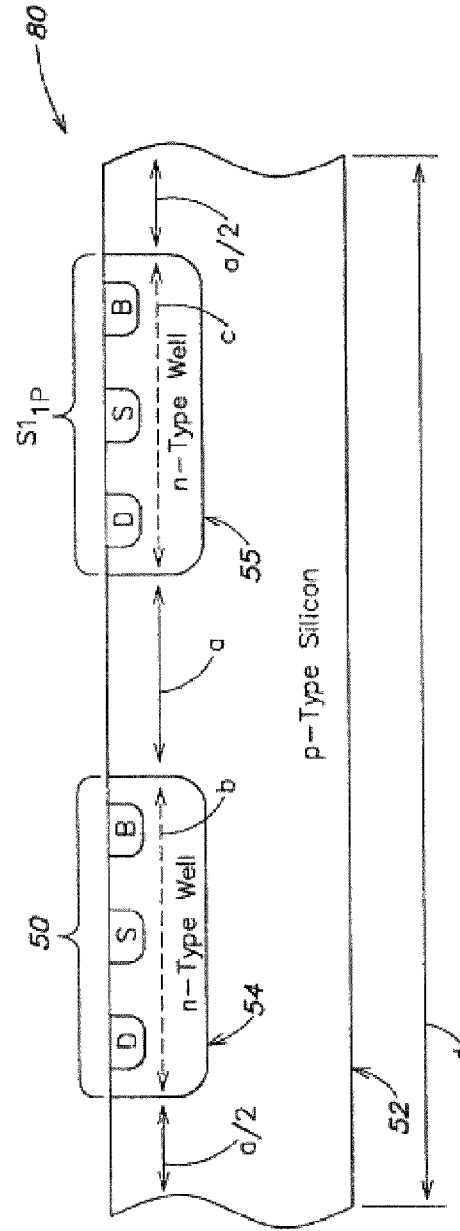
FIG. 6 is a diagram similar to FIG. 5, illustrating a cross-section of another portion of the substrate corresponding to one pixel of the array column shown in FIG. 3, in which the ISFET is shown alongside the p-channel MOSFET of the transmission gate shown in FIG. 4.

In FIG. 42F2, there is a top, isometric view of member 42F200 mounted onto a sensor array package 42F300, with a seal 42F202 formed between them and contact pins 42F204 depending from the sensor array chip package. FIGS. 42F3 and 42F4 show sections, respectively, through section lines H-H and I-I of FIG. 42F5, permitting one to see in relationship the sensor array chip 42F250, the baffles 4220F' and fluid flow paths via inlet 42F260 and outlet 42F270 ports.

By applying a metallization to bottom 42F280 of member 42F200, the reference electrode may be formed.

Various other locations and approaches may be used for introducing fluid flow into the flow chamber, as well. In addition to embodiments in which fluid may be introduced across the width of an edge of the chip assembly 42F1, as in FIGS. 57-58, for example, or fluid may be introduced at one corner of the chip assembly, as in FIG. 42F1. Fluid also may be introduced, for example, as in FIGS. 42G and 42H, where fluid is flowed through an inlet conduit 4252G to be discharged adjacent and toward the center of the chip, as at 4254G, and flowed radially outwardly from the introduction point.

Figure 42G:
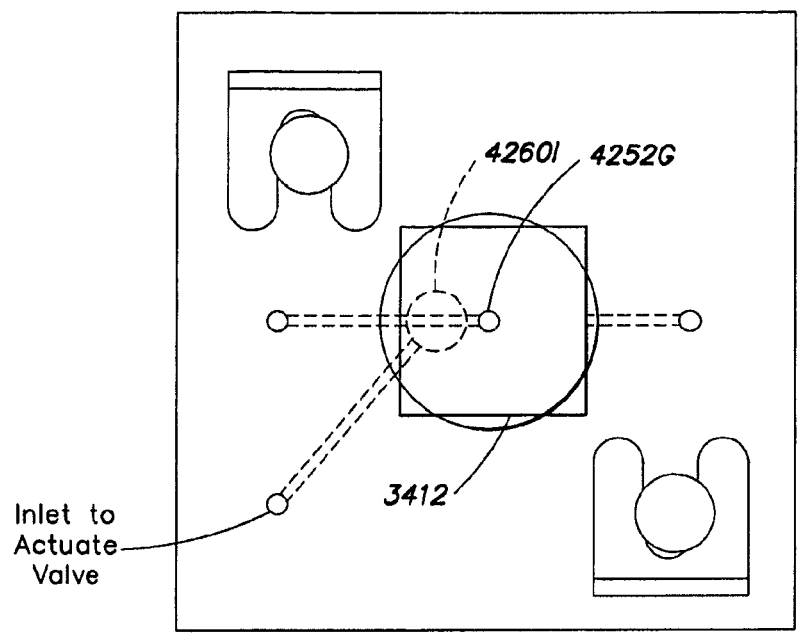
FIGS. 42G and 42H are diagrammatic illustrations of alternative embodiments of flow cells in which fluid flow is introduced to the middle of the chip assembly.
Figure 42H:
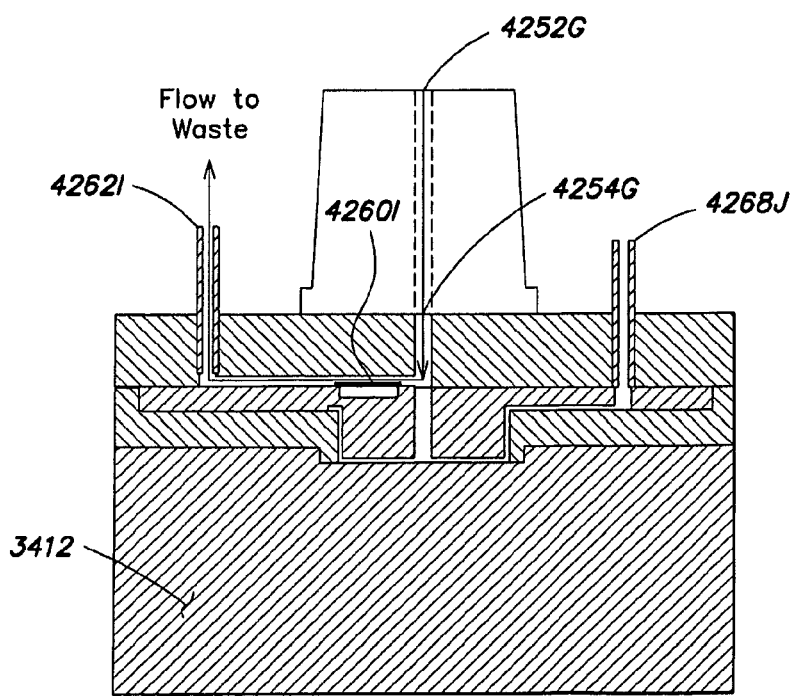
Figure 42I:
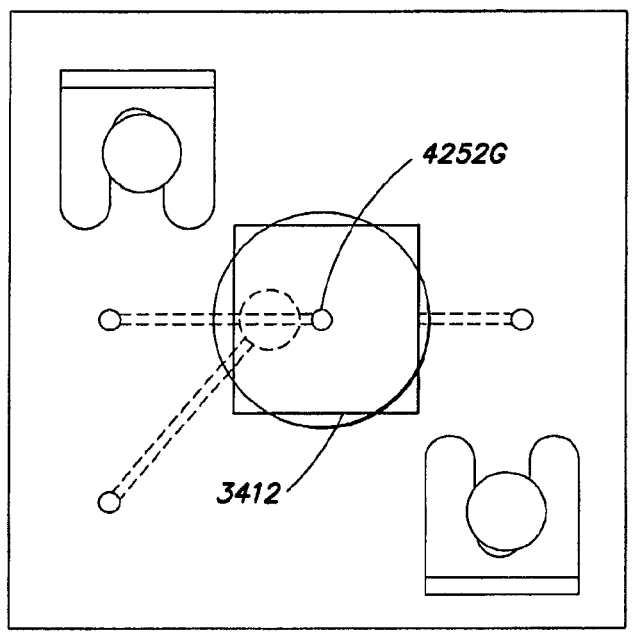
FIGS. 42I and 42J are cross-sectional illustrations of the type of flow cell embodiments shown in FIGS. 42G and 42H, mounted on a chip assembly.
Figure 42J:
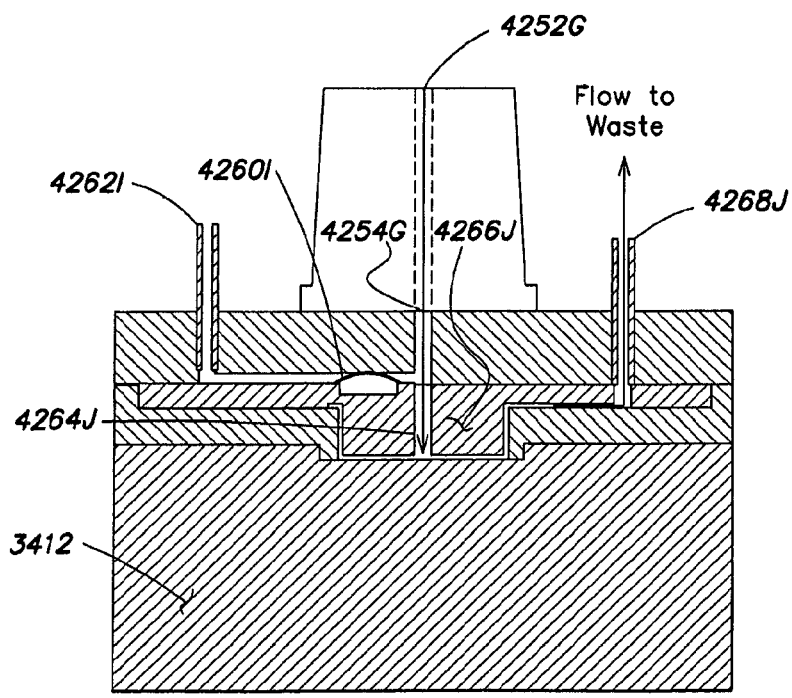

FIGS. 42I and 42J in conjunction with FIGS. 42G and 42H depict in cross-section an example of such a structure and its operation. In contrast with earlier examples, this embodiment contains an additional element, a diaphragm valve, 4260I. Initially, as shown in FIG. 42H, the valve 4260I is open, providing a path via conduit 4262I to a waste reservoir (not shown). The open valve provides a low impedance flow to the waste reservoir or outlet. Air pressure is then applied to the diaphragm valve, as in FIG. 42J, closing the low impedance path and causing the fluid flow to continue downwardly through central bore 4264J in member 4266J which forms the ceiling of the flow chamber, and across the chip (sensor) assembly. The flow is collected by the channels at the edges of the sensor, as described above, and exits to the waste output via conduit 4268J.

Figure 42K:
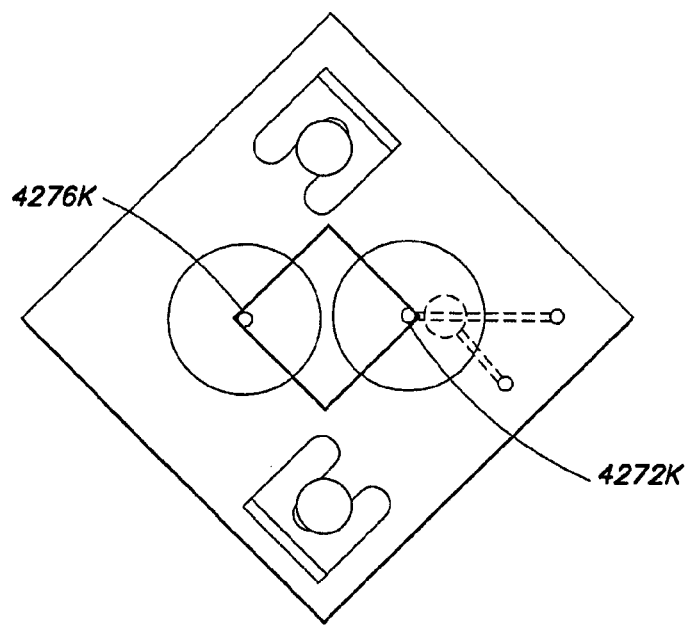
FIGS. 42K and 42L are diagrammatic illustrations of flow cells in which the fluid is introduced at a corner of the chip assembly.
Figure 42L:
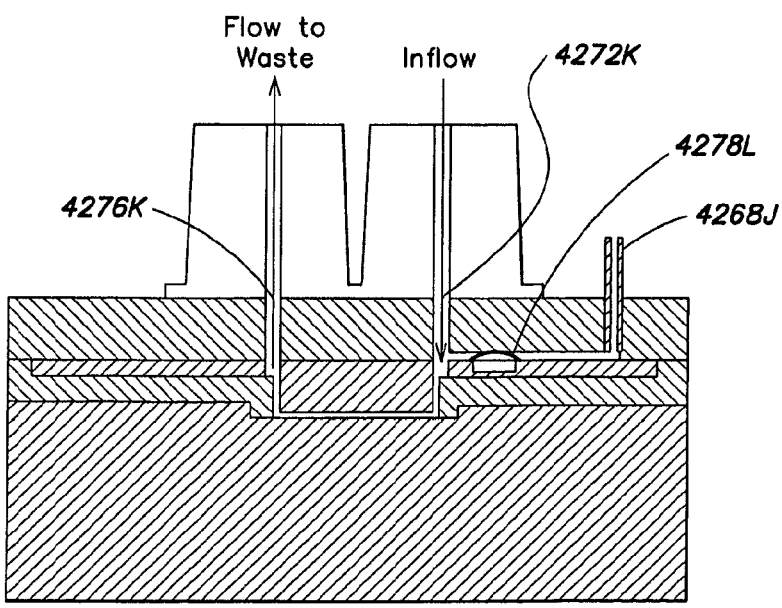
Figure 42M:
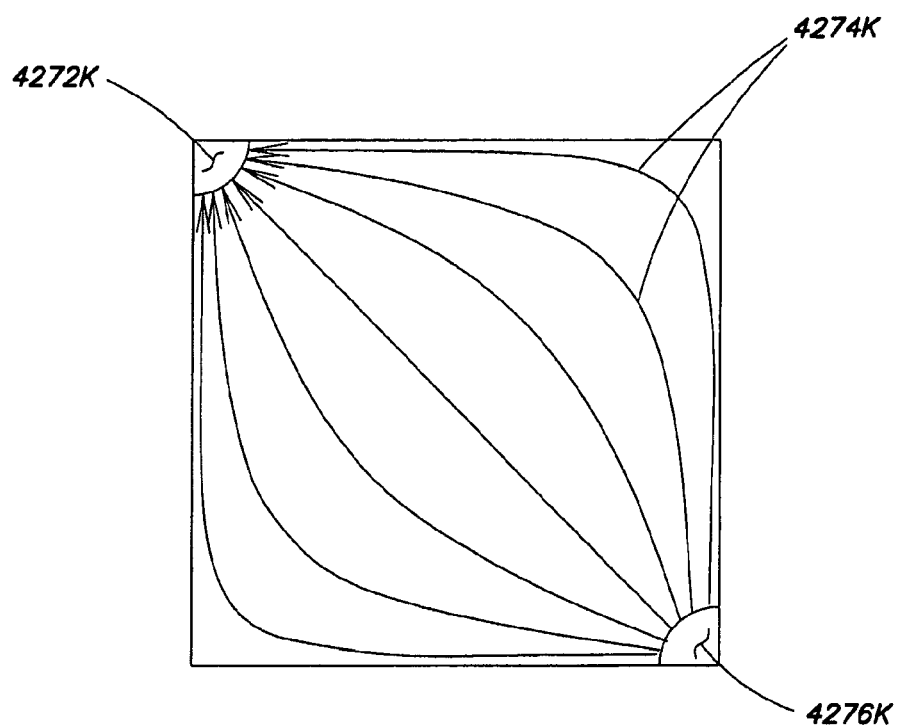
FIG. 42M is a diagrammatic illustration of fluid flow from one corner of an array on a chip assembly to an opposite corner, in apparatus such as that depicted in FIGS. 42K and 42L.

A variation on this idea is depicted in FIGS. 42K-42M, which show fluid being introduced not at the center of the chip assembly, but at one corner, 4272K, instead. It flows across the chip 3412 as symbolically indicated by lines 4274K and is removed at the diagonally opposing corner, 4276K. The advantage of this concept is that it all but eliminates any stagnation points. It also has the advantage that the sensor array can be positioned vertically so that the flow is introduced at the bottom and removed at the top to aid in the clearance of bubbles. This type of embodiment, by the way, may be considered as one quadrant of the embodiments with the flow introduced in the center of the array. An example of an implementation with a valve 4278L closed and shunting flow to the waste outlet or reservoir is shown in FIG. 42L. The main difference with respect to the embodiment of FIGS. 42I and 42J is that the fluid flow is introduced at a corner of the array rather than at its center.

In all cases, attention should be given to assuring a thorough washing of the entire flow chamber, along with the microwells, between reagent cycles. Flow disturbances may exacerbate the challenge of fully cleaning out the flow chamber.

Flow disturbances may also induce or multiply bubbles in the fluid. A bubble may prevent the fluid from reaching a microwell, or delay its introduction to the microwell, introducing error into the microwell reading or making the output from that microwell useless in the processing of outputs from the array. Thus, care should be taken in selecting configurations and dimensions for the flow disruptor elements to manage these potential adverse factors. For example, a tradeoff may be made between the heights of the disruptor elements and the velocity profile change that is desired.

Figure 43:
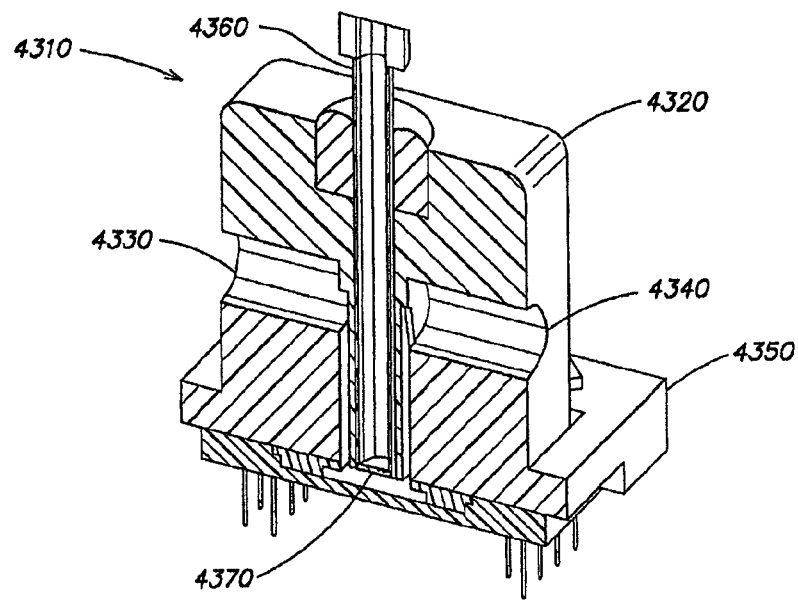
Figure 44:
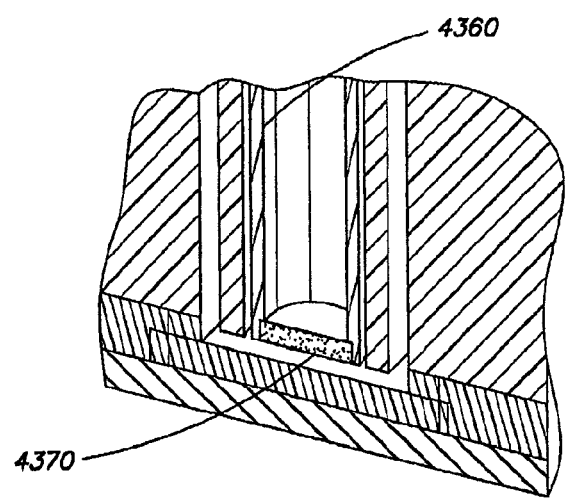

FIGS. 43-44 show another alternative flow cell design, 4310. This design relies on the molding of a single plastic piece or member 4320 to be attached to the chip to complete the flow cell. The connection to the fluidic system is made via threaded connections tapped into appropriate holes in the plastic piece at 4330 and 4340. Or, if the member 4320 is made of a material such as polydimethylsiloxane (PDMS), the connections may be made by simply inserting the tubing into an appropriately sized hole in the member 4320. A vertical cross section of this design is shown in FIGS. 43-44. This design may use an overhanging plastic collar 4350 (which may be a solid wall as shown or a series of depending, spaced apart legs forming a downwardly extending fence-like wall) to enclose the chip package and align the plastic piece with the chip package, or other suitable structure, and thereby to alignment the chip frame with the flow cell forming member 4320. Liquid is directed into the flow cell via one of apertures 4330, 4340, thence downwardly towards the flow chamber.

In the illustrated embodiment, the reference electrode is introduced to the top of the flow chamber via a bore 4325 in the member 4320. The placement of the removable reference electrode is facilitated by a silicone sleeve 4360 and an epoxy stop ring 4370 (see the blow-up of FIG. 44). The silicone sleeve provides a tight seal and the epoxy stop ring prevent the electrode from being inserted too far into the flow cell. Of course, other mechanisms may be employed for the same purposes, and it may not be necessary to employ structure to stop the electrode. And if a material such as PDMS is used for member 4320, the material itself may form a watertight seal when the electrode is inserted, obviating need for the silicone sleeve.

Figure 45:
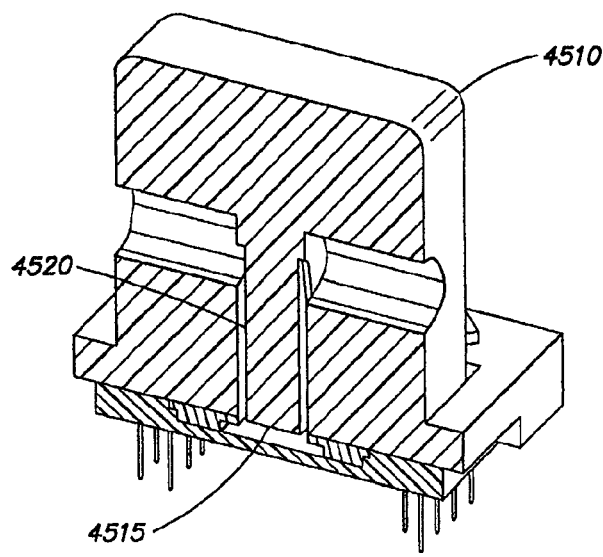
Figure 46:
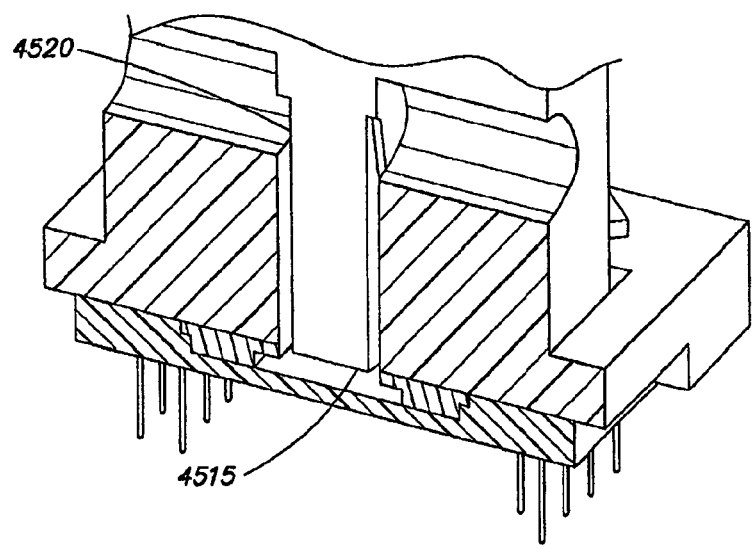

FIGS. 45 and 46 show a similar arrangement except that member 4510 lacks a bore for receiving a reference electrode. Instead, the reference electrode 4515 is formed on or affixed to the bottom of central portion 4520 and forms at least part of the flow chamber ceiling. For example, a metallization layer may be applied onto the bottom of central portion 4520 before member 4510 is mounted onto the chip package.

Figure 47:
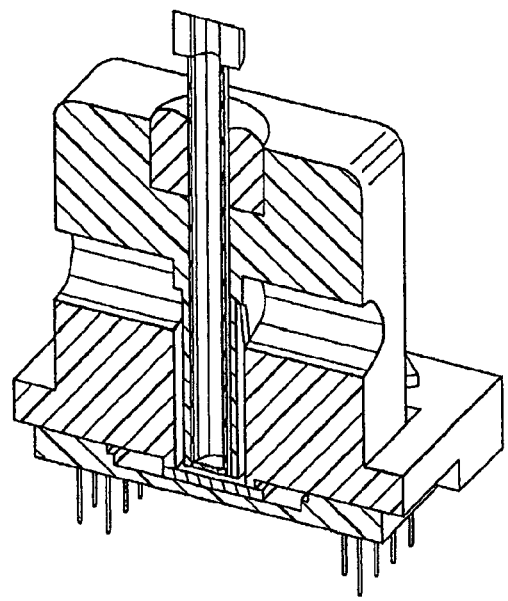
Figure 48:
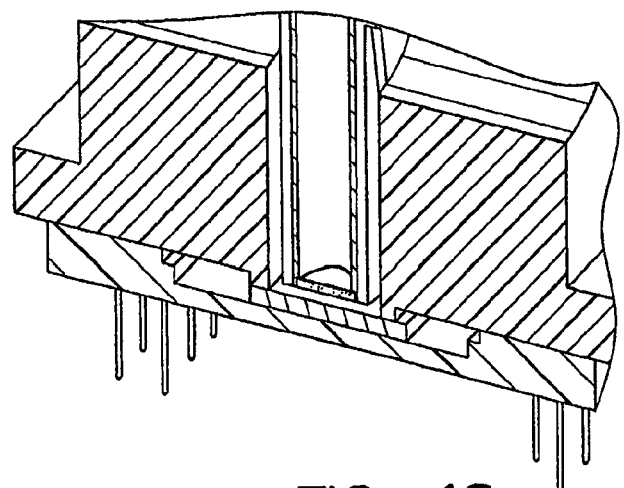
Figure 49:
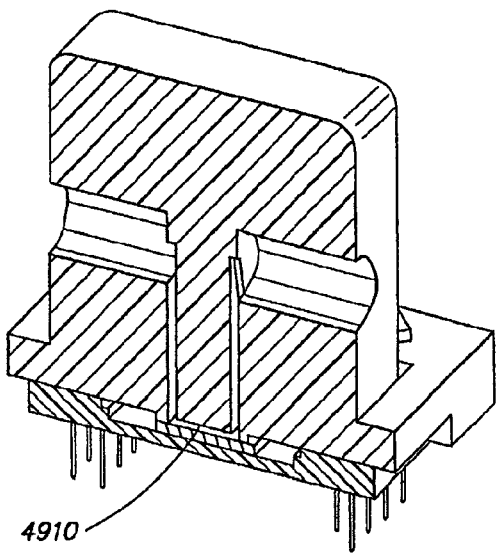
Figure 50:
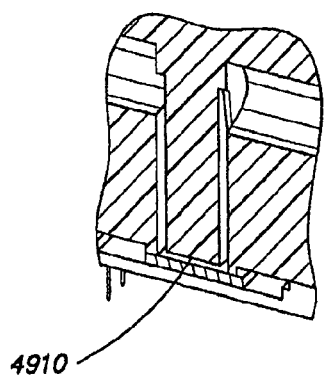

FIGS. 47-48 show another example, which is a variant of the embodiment shown in FIGS. 43-44, but wherein the frame is manufactured as part of the flow cell rather attaching a flow port structure to a frame previously attached to the chip surface. In designs of this type, assembly is somewhat more delicate since the wirebonds to the chip are not protected by the epoxy encapsulating the chip. The success of this design is dependent on the accurate placement and secure gluing of the integrated "frame" to the surface of the chip. A counterpart embodiment to that of FIGS. 45-46, with the reference electrode 4910 on the ceiling of the flow chamber, and with the frame manufactured as part of the flow cell, is shown in FIGS. 49-50.

Figure 51:
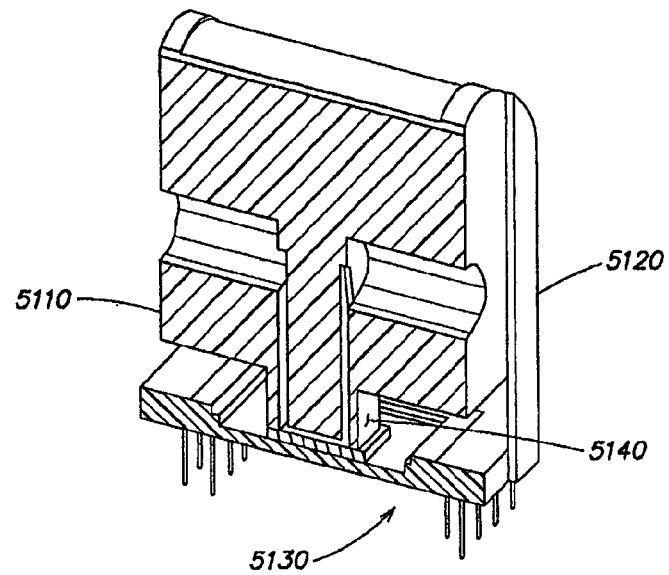
Figure 52:
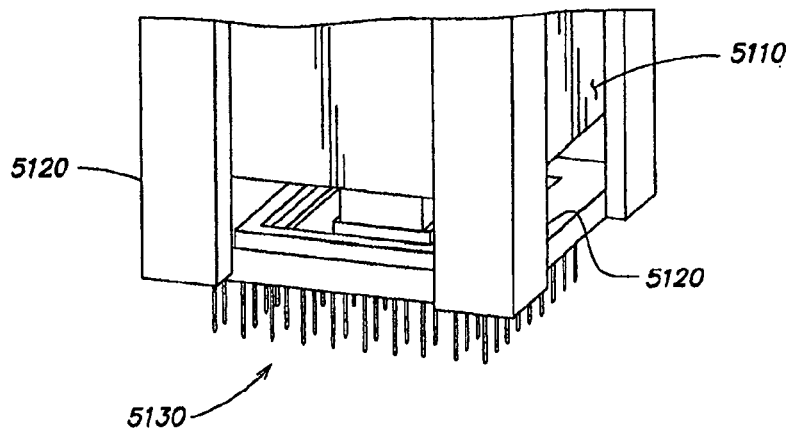

Yet another alternative for a fluidics assembly, as shown in FIGS. 51-52, has a fluidics member 5110 raised by about 5.5 mm on stand-offs 5120 from the top of the chip package 5130. This allows for an operator to visually inspect the quality of the bonding between plastic piece 5140 and chip surface and reinforce the bonding externally if necessary.

Figure 53:
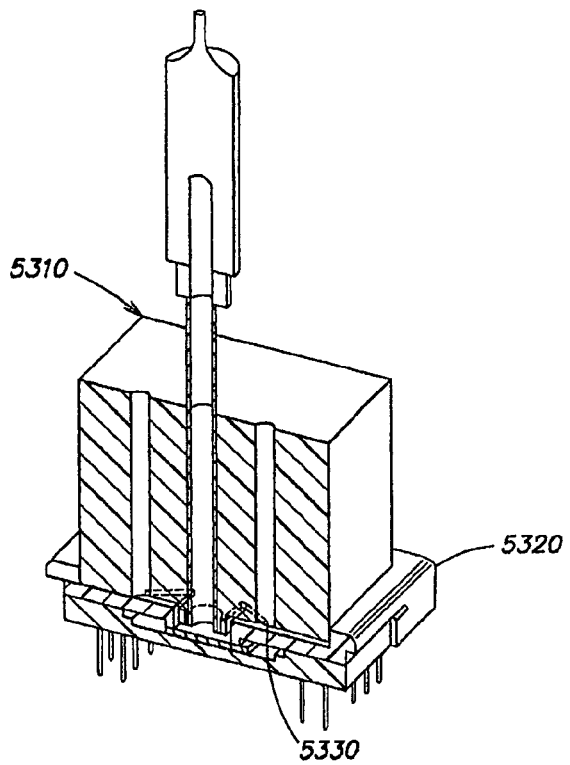
Figure 54:
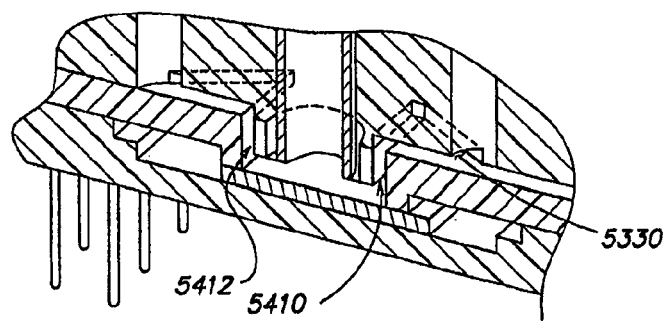

Some of the foregoing alternative embodiments also may be implemented in a hybrid plastic/PDMS configuration. For example, as shown in FIGS. 53-54, a plastic part 5310 may make up the frame and flow chamber, resting on a PDMS "base" portion 5320. The plastic part 5310 may also provides a region 5330 to the array, for expansion of the fluid flow from the inlet port; and the PDMS part may then include communicating slits 5410, 5412 through which liquids are passed from the PDMS part to and from the flow chamber below.

The fluidic structure may also be made from glass as discussed above, such as photo-definable (PD) glass. Such a glass may have an enhanced etch rate in hydrofluoric acid once selectively exposed to UV light and features may thereby be micromachined on the top-side and back-side, which when glued together can form a three-dimensional low aspect ratio fluidic cell.

Figure 55:
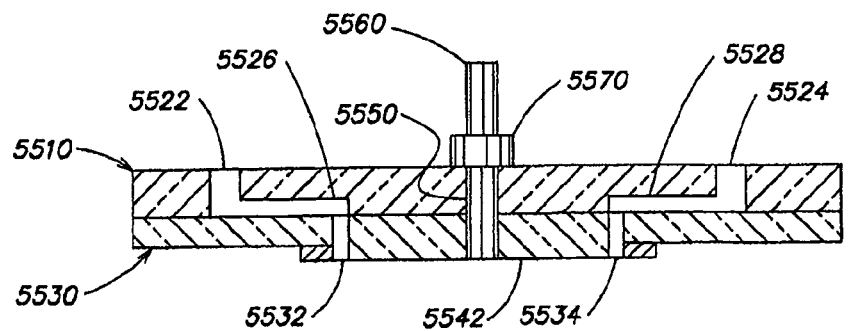
FIGS. 55 and 56 are schematic, cross-sectional views of two-layer glass (or plastic) arrangements for manufacturing fluidic apparatus for mounting onto a chip for use as taught herein.

An example is shown in FIG. 55. A first glass layer or sheet 5510 has been patterned and etched to create nanoport fluidic holes 5522 and 5524 on the top-side and fluid expansion channels 5526 and 5528 on the back-side. A second glass layer or sheet 5530 has been patterned and etched to provide downward fluid input/output channels 5532 and 5534, of about 300 μm height (the thickness of the layer). The bottom surface of layer 5530 is thinned to the outside of channels 5532 and 5534, to allow the layer 5530 to rest on the chip frame and protrusion area 5542 to be at an appropriate height to form the top of the flow channel. Two glass layers, or wafers, and four lithography steps required. Both wafers should be aligned and bonded (e.g., with an appropriate glue, not shown) such that the downward fluid input/output ports are aligned properly with the fluid expansion channels. Alignment targets may be etched into the glass to facilitate the alignment process.

Nanoports may be secured over the nanoport fluidic holes to facilitate connection of input and output tubing.

A central bore 5550 may be etched through the glass layers for receiving a reference electrode, 5560. The electrode may be secured and sealed in place with a silicone collar 5570 or like structure; or the electrode may be equipped integrally with a suitable washer for effecting the same purpose.

Figure 56:
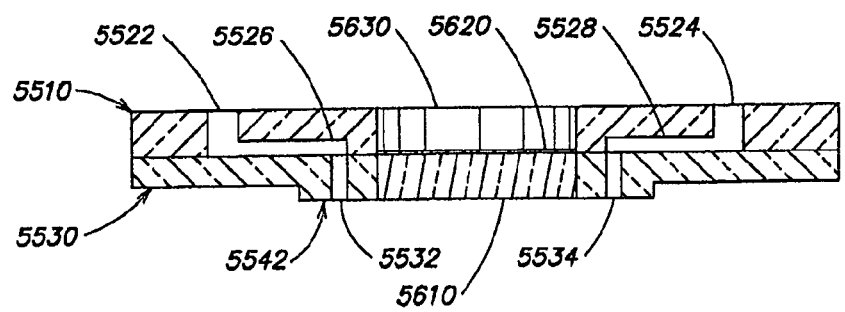

By using glass materials for the two-layer fluidic cell, the reference electrode may also be a conductive layer or pattern deposited on the bottom surface of the second glass layer (not shown). Or, as shown in FIG. 56, the protrusion region may be etched to form a permeable glass membrane 5610 on the top of which is coated a silver (or other material) thin-film 5620 to form an integrated reference electrode. A hole 5630 may be etched into the upper layer for accessing the electrode and if that hole is large enough, it can also serve as a reservoir for a silver chloride solution. Electrical connection to the thin-film silver electrode may be made in any suitable way, such as by using a clip-on pushpin connector or alternatively wirebonded to the ceramic ISFET package.

Another alternative is to integrate the reference electrode to the sequencing chip/flow cell by using a metalized surface on the ceiling of the flow chamber—i.e., on the underside of the member forming the ceiling of the fluidic cell. An electrical connection to the metalized surface may be made in any of a variety of ways, including, but not limited to, by means of applying a conductive epoxy to the ceramic package seal ring that, in turn, may be electrically connected through a via in the ceramic substrate to a spare pin at the bottom of the chip package. Doing this would allow system-level control of the reference potential in the fluid cell by means of inputs through the chip socket mount to the chip's control electronics.

By contrast, an externally inserted electrode requires extra fluid tubing to the inlet port, which requires additional fluid flow between cycles.

Ceramic pin grid array (PGA) packaging may be used for the ISFET array, allowing customized electrical connections between various surfaces on the front face with pins on the back.

The flow cell can be thought of as a "lid" to the ISFET chip and its PGA. The flow cell, as stated elsewhere, may be fabricated of many different materials. Injection molded polycarbonate appears to be quite suitable. A conductive metal (e.g., gold) may be deposited using an adhesion layer (e.g., chrome) to the underside of the glow cell roof (the ceiling of the flow chamber). Appropriate low-temperature thin-film deposition techniques preferably are employed in the deposition of the metal reference electrode due to the materials (e.g., polycarbonate) and large step coverage topography at the bottom-side of the fluidic cell (i.e., the frame surround of ISFET array). One possible approach would be to use electron-beam evaporation in a planetary system.

The active electrode area is confined to the central flow chamber inside the frame surround of the ISFET array, as that is the only metalized surface that would be in contact with the ionic fluid during sequencing.

Once assembly is complete—conductive epoxy (e.g., Epo-Tek H20E or similar) may be dispensed on the seal ring with the flow cell aligned, placed, pressed and cured—the ISFET flow cell is ready for operation with the reference potential being applied to the assigned pin of the package.

The resulting fluidic system connections to the ISFET device thus incorporate shortened input and output fluidic lines, which is desirable.

Figure 57:
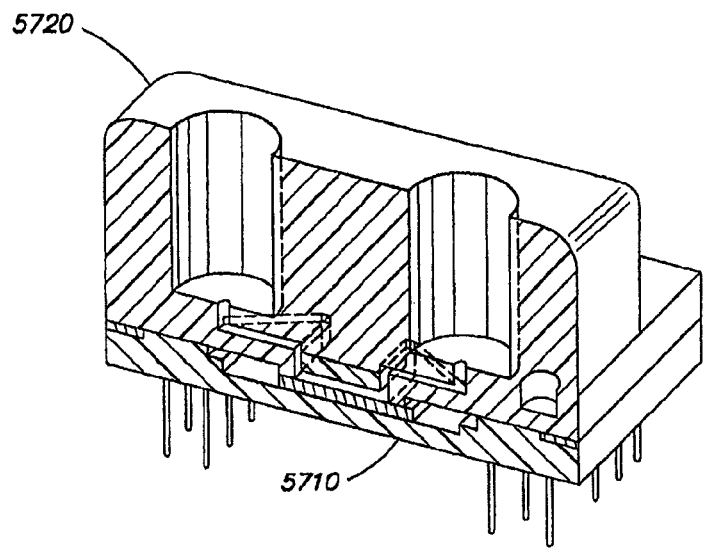
FIGS. 57 and 58 are schematic embodiments of a fluidic assembly.
Figure 58:
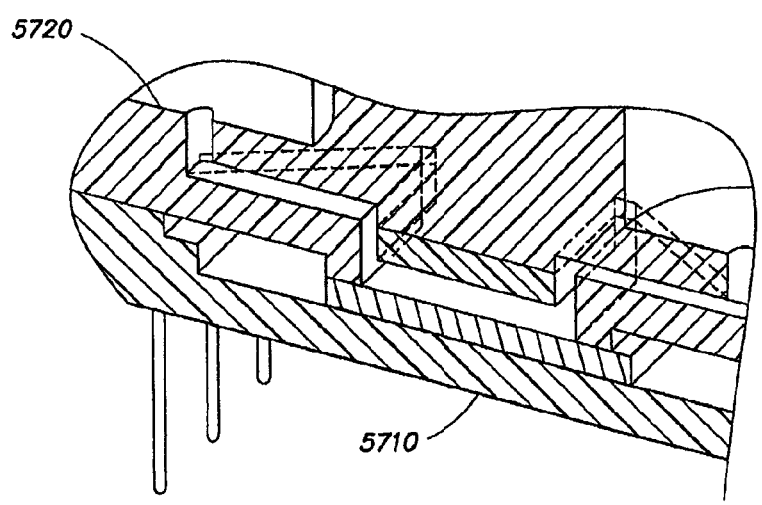

Still another example embodiment for a fluidic assembly is shown in FIGS. 57-58. This design is limited to a plastic piece 5710 which incorporates the frame and is attached directly to the chip surface, and to a second piece 5720 which is used to connect tubing from the fluidic system and similarly to the PDMS piece discussed above, distributes the liquids from the small bore tube to a wide flat slit. The two pieces are glued together and multiple (e.g., three) alignment markers (not shown) may be used to precisely align the two pieces during the gluing process. A hole may be provided in the bottom plate and the hole used to fill the cavity with an epoxy (for example) to protect the wirebonds to the chip and to fill in any potential gaps in the frame/chip contact. In the illustrated example, the reference electrode is external to the flow cell (downstream in the exhaust stream, through the outlet port—see below), though other configurations of reference electrode may, of course, be used.

Figure 59A:
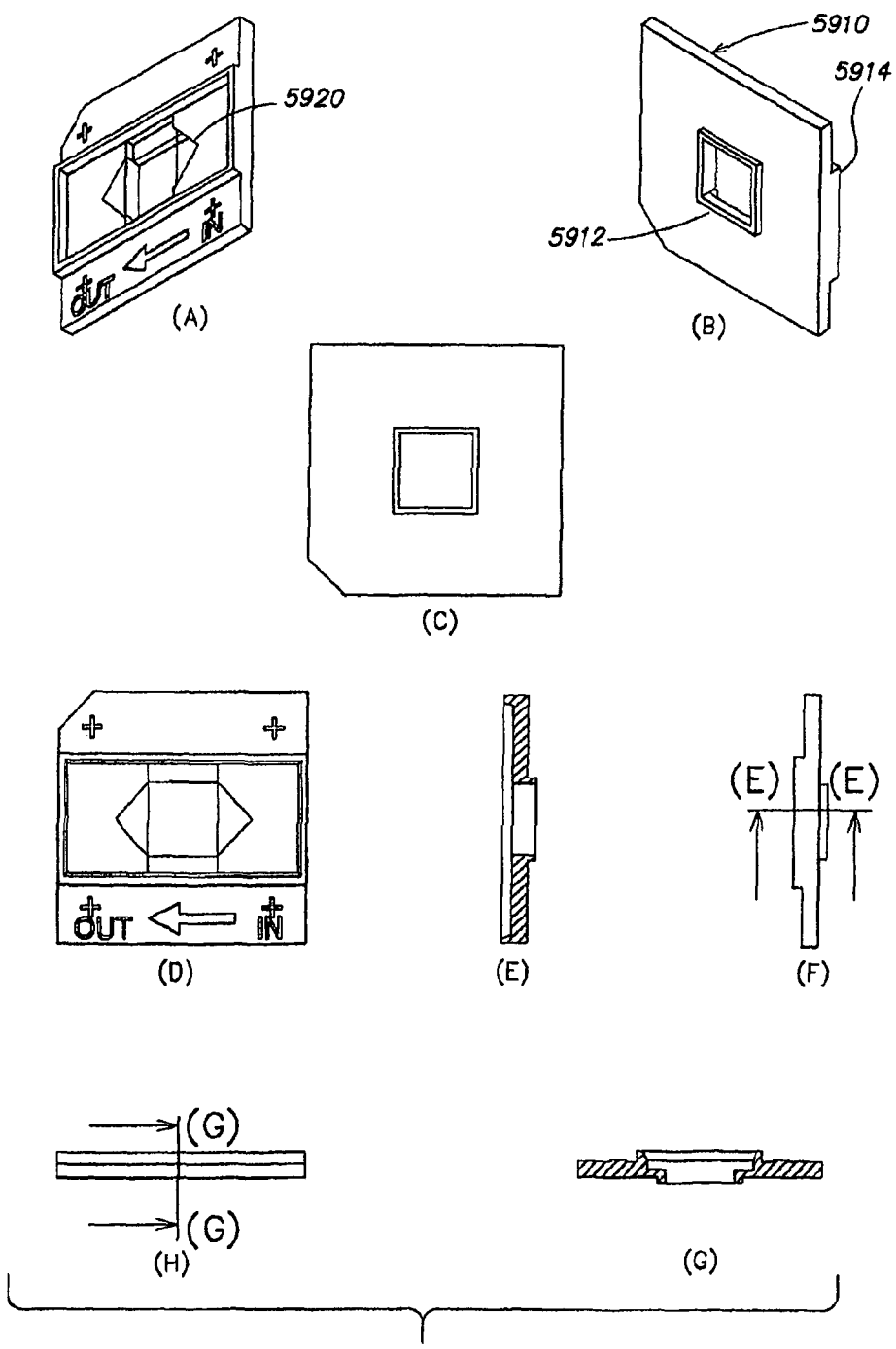
Figure 59B:
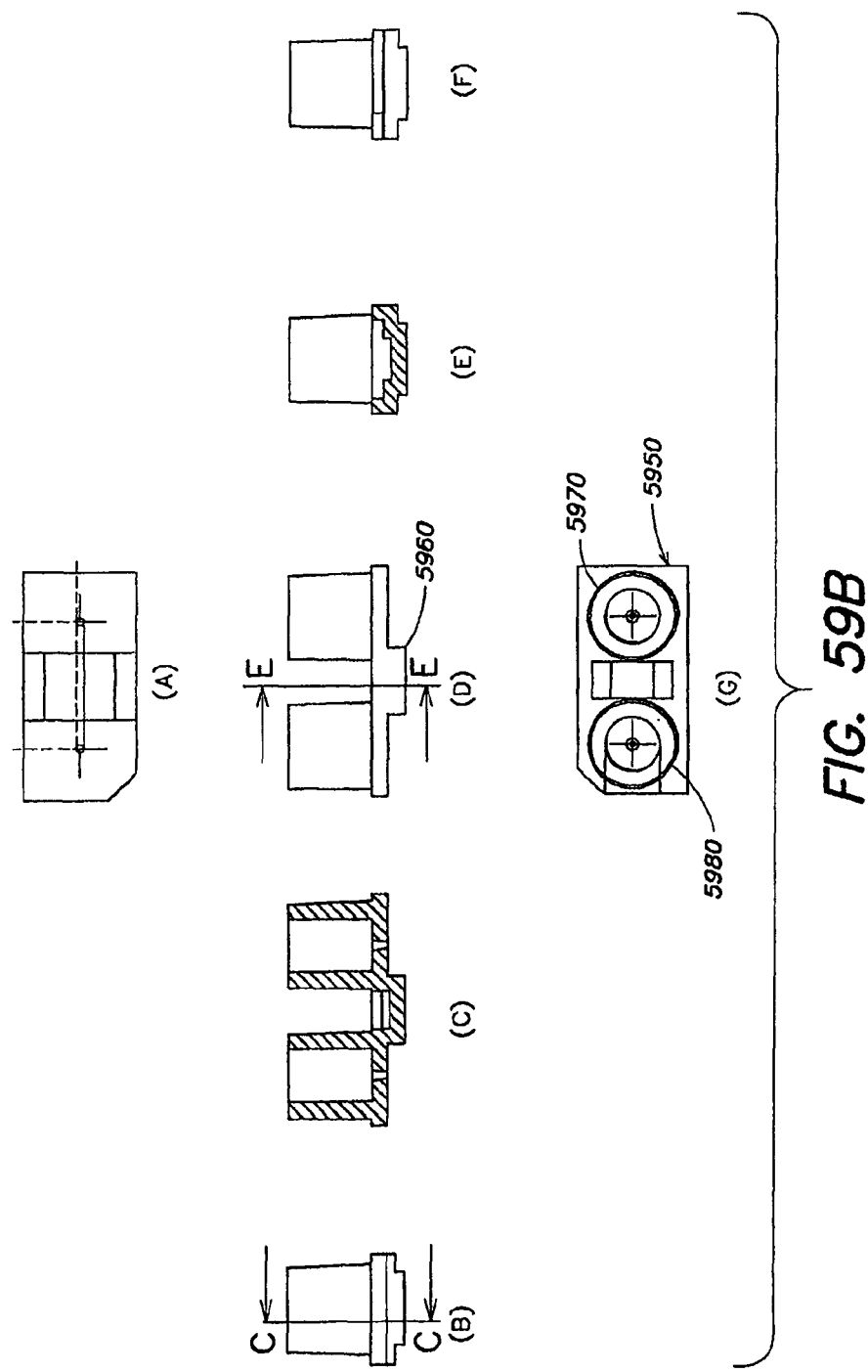
Figure 60:
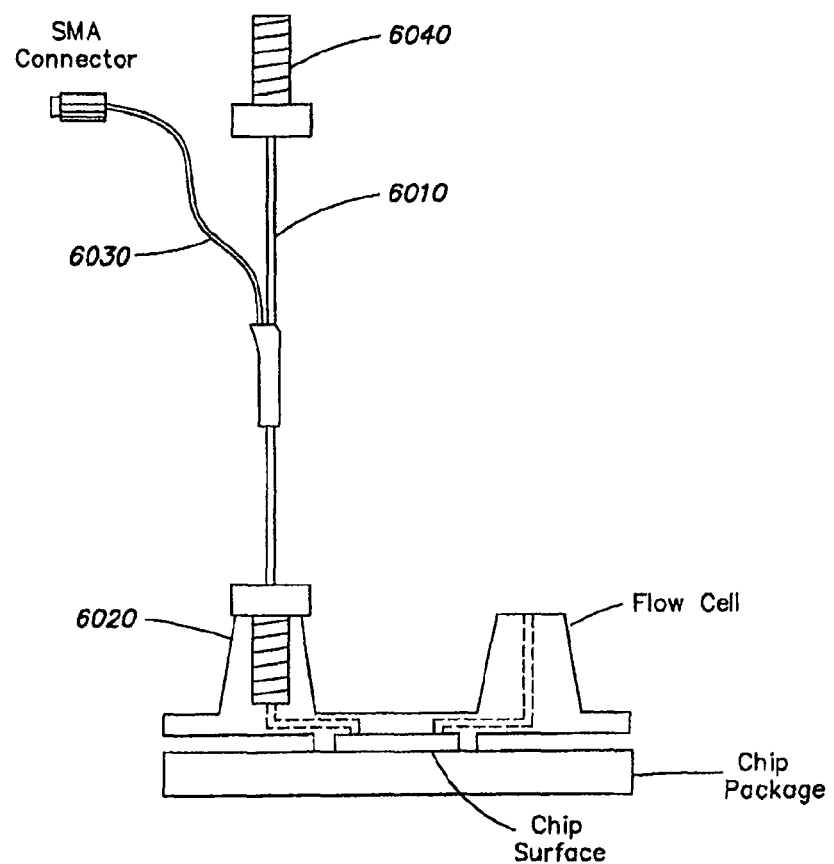
FIG. 60 is a schematic illustration, in cross-section, for introducing a stainless steel capillary tube as an electrode, into a downstream port of a flow cell such as the flow cells of FIGS. 59A-59C, or other flow cells.

Still further examples of flow cell structures are shown in FIGS. 59-60. FIG. 59A comprises eight views (A-H) of an injection molded bottom layer, or plate, 5910, for a flow cell fluidics interface, while FIG. 59B comprises seven views (A-G) of a mating, injection molded top plate, or layer, 5950. The bottom of plate 5910 has a downwardly depending rim 5912 configured and arranged to enclose the sensor chip and an upwardly extending rim 5914 for mating with the top plate 5610 along its outer edge. To form two fluid chambers (an inlet chamber and an outlet chamber) between them. A stepped, downwardly depending portion 5960 of top plate 5950, separates the input chamber from the output chamber. An inlet tube 5970 and an outlet tube 5980 are integrally molded with the rest of top plate 5950. From inlet tube 5970, which empties at the small end of the inlet chamber formed by a depression 5920 in the top of plate 5910, to the outlet edge of inlet chamber fans out to direct fluid across the whole array.

Whether glass or plastic or other material is used to form the flow cell, it may be desirable, especially with larger arrays, to include in the inlet chamber of the flow cell, between the inlet conduit and the front edge of the array, not just a gradually expanding (fanning out) space, but also some structure to facilitate the flow across the array being suitably laminar. Using the bottom layer 5990 of an injection molded flow cell as an example, one example type of structure for this purpose, shown in FIG. 59C, is a tree structure 5992 of channels from the inlet location of the flow cell to the front edge of the microwell array or sensor array, which should be understood to be under the outlet side of the structure, at 5994.

The above-described systems for sequencing typically utilize a laminar fluid flow system to sequence a biological polymer. In part, the fluid flow system preferably includes a flow chamber formed by the sensor chip and a single piece, injection molded member comprising inlet and outlet ports and mountable over the chip to establish the flow chamber. The surface of such member interior to the chamber is preferably formed to facilitate a desired expedient fluid flow, as described herein.

In some embodiments, the invention encompasses an apparatus for detection of ion pulses comprising a laminar fluid flow system. Preferably, the apparatus is used for sequencing a plurality of nucleic acid templates, wherein the nucleic acid templates are optionally deposited on an array.

The apparatus typically includes a fluidics assembly comprising a member comprising one or more apertures for non-mechanically directing a fluid to flow to an array of at least 100K, 500K, or 1M microfluidic reaction chambers such that the fluid reaches all of the microfluidic reaction chambers at the same time or substantially the same time. Typically, the fluid flow is parallel to the sensor surface. Typically, the assembly has a Reynolds number of less than 1000, 500, 200, 100, 50, 20, or 10. Preferably, the member further comprises a first aperture for directing fluid towards the sensor array and a second aperture for directing fluid away from the sensor array.

In some embodiments, the invention encompasses a method for directing a fluid to a sensor array comprising: providing a fluidics assembly comprising an aperture fluidly coupling a fluid source to the sensor array; and non-mechanically directing a fluid to the sensor array. By "non-mechanically" it is meant that the fluid is moved under pressure from a gaseous pressure source, as opposed to a mechanical pump.

In some embodiments, the invention encompasses an array of wells, each of which is coupled to a lid having an inlet port and an outlet port and a fluid delivery system for delivering and removing fluid from said inlet and outlet ports non-mechanically.

In some embodiments, the invention encompasses a method for sequencing a biological polymer utilizing the above-described apparatus, comprising: directing a fluid comprising a monomer to an array of reaction chambers wherein the fluid has a fluid flow Reynolds number of at most 2000, 1000, 200, 100, 50, or 20. The method may optionally further comprise detecting an ion pulse from each said reaction chamber. The ion pulse is typically detected by ion diffusion to the sensor surface. There are various other ways of providing a fluidics assembly for delivering an appropriate fluid flow across the microwell and sensor array assembly, and the forgoing examples are thus not intended to be exhaustive.

Commercial flow-type fluidic electrodes, such as silver chloride proton-permeable electrodes, may be inserted in series in a fluidic line and are generally designed to provide a stable electrical potential along the fluidic line for various electrochemical purposes. In the above-discussed system, however, such a potential must be maintained at the fluidic volume in contact with the microwell ISFET chip. With conventional silver chloride electrodes, it has been found difficult, due to an electrically long fluidic path between the chip surface and the electrode (through small channels in the flow cell), to achieve a stable potential. This led to reception of noise in the chip's electronics. Additionally, the large volume within the flow cavity of the electrode tended to trap and accumulate gas bubbles that degraded the electrical connection to the fluid. With reference to FIG. 60, a solution to this problem has been found in the use of a stainless steel capillary tube electrode 6010, directly connected to the chip's flow cell outlet port 6020 and connected to a voltage source (not shown) through a shielded cable 6030. The metal capillary tube 6010 has a small inner diameter (e.g., on the order of 0.01") that does not trap gas to any appreciable degree and effectively transports fluid and gas like other microfluidic tubing. Also, because the capillary tube can be directly inserted into the flow cell port 6020, it close to the chip surface, reducing possible electrical losses through the fluid. The large inner surface area of the capillary tube (typically about 2" long) may also contribute to its high performance. The stainless steel construction is highly chemically resistant, and should not be subject to electrochemical effects due to the very low electrical current use in the system (<1 µA). A fluidic fitting 6040 is attached to the end of the capillary that is not in the flow cell port, for connection to tubing to the fluid delivery and removal subsystem.

A complete system for using the sensor array will include suitable fluid sources, valving and a controller for operating the valving to low reagents and washes over the microarray or sensor array, depending on the application. These elements are readily assembled from off-the-shelf components, with and the controller may readily be programmed to perform a desired experiment.

It should be understood that the readout at the chemFET may be current or voltage (and change thereof) and that any particular reference to either readout is intended for simplicity and not to the exclusion of the other readout. Therefore any reference in the following text to either current or voltage detection at the chemFET should be understood to contemplate and apply equally to the other readout as well. In important embodiments, the readout reflects a rapid, transient change in concentration of an analyte. The concentration of more than one analyte may be detected at different times. Such measurements are to be contrasted with prior art methods which focused on steady state concentration measurements.

As already discussed, the apparatus and systems of the invention can be used to detect and/or monitor interactions between various entities. These interactions include biological and chemical reactions and may involve enzymatic reactions and/or non-enzymatic interactions such as but not limited to binding events. As an example, the invention contemplates monitoring enzymatic reactions in which substrates and/or reagents are consumed and/or reaction intermediates, byproducts and/or products are generated. An example of a reaction that can be monitored according to the invention is a nucleic acid synthesis method such as one that provides information regarding nucleic acid sequence. This reaction will be discussed in greater detail herein.

In the context of a sequencing reaction, the apparatus and system provided herein is able to detect nucleotide incorporation based on changes in the chemFET current and/or voltage, as those latter parameters are interrelated. Current changes may be the result of one or more of the following events either singly or some combination thereof: generation of PPi, generation of Pi (e.g., in the presence of pyrophosphatase), generation of hydrogen (and concomitant changes in pH for example in the presence of low strength buffer), reduced concentration of unincorporated dNTP at the chemFET surface, delayed arrival of unincorporated dNTP at the chemFET surface, and the like. The methods described herein are able to detect changes in analyte concentration at the chemFET surface, and such changes may result from one or more of the afore-mentioned events. The invention contemplates the use of a chemFET such as an ISFET in the sequencing methods described herein, even if the readout is independent of (or insensitive to) pH. In other words, the invention contemplates the use of an ISFET for the detection of analytes such as PPi and unincorporated nucleotides. The methods provided herein in regards to sequencing can be contrasted to those in the literature including Pourmand et al. PNAS 2006 103(17):6466-6470. As discussed herein, the invention contemplates methods for determining the nucleotide sequence (i.e., the "sequence") of a nucleic acid. Such methods involve the synthesis of a new nucleic acid (primed by a pre-existing nucleic acid, as will be appreciated by those of ordinary skill), based on the sequence of a template nucleic acid. That is, the sequence of the newly synthesized nucleic acid is complimentary to the sequence of the template nucleic acid and therefore knowledge of sequence of the newly synthesized nucleic acid yields information about the sequence of the template nucleic acid. Knowledge of the sequence of the newly synthesized nucleic acid is derived by determining whether a known nucleotide has been incorporated into the newly synthesized nucleic acid and, if so, how many of such known nucleotides have been incorporated. Nucleotide incorporation can be monitored in a number of ways, including the production of products such as PPi, Pi and/or H.

Figure 61:
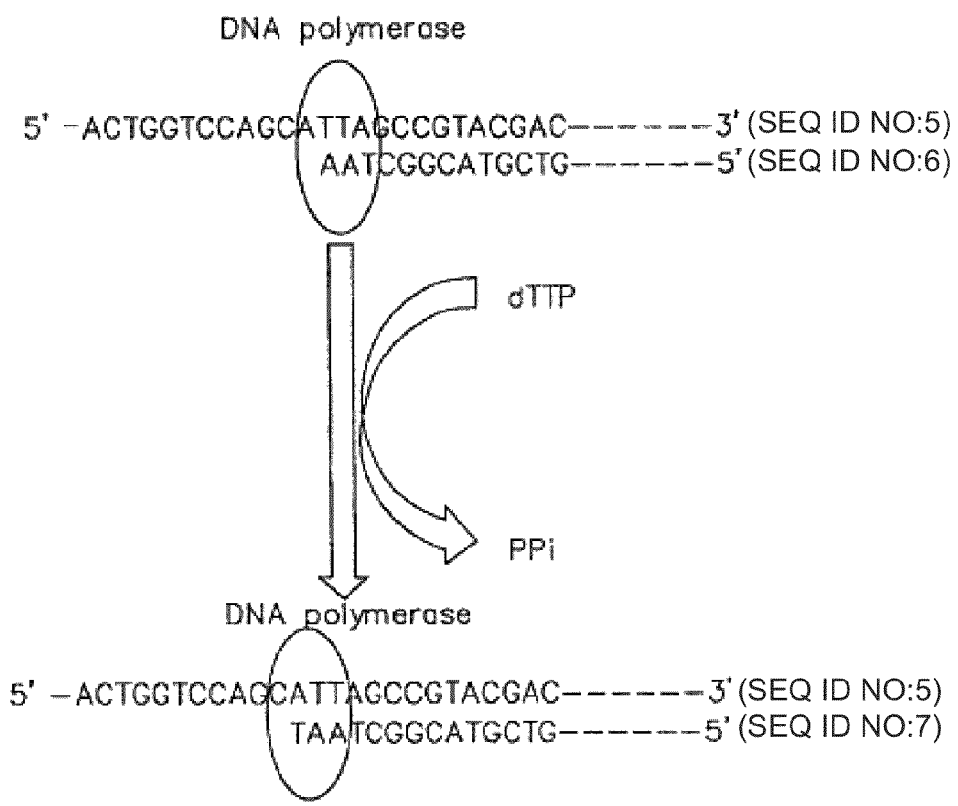
FIG. 61 is a schematic illustrating the incorporation of a dNTP into a synthesized nucleic acid strand with concomitant release of inorganic pyrophosphate (PPi).

FIG. 61 illustrates the production/generation of PPi resulting from the incorporation of a nucleotide in a newly synthesized nucleic acid strand. PPi generated as a reaction byproduct of nucleotide incorporation in a nucleic acid strand can be detected directly even in the absence of a PPi receptor (such as those provided in FIG. 11B1-3) and in the absence of a detectable pH change (e.g., as may occur in the presence of a strong buffer, as defined herein). The simple presence of PPi is sufficient, in some instances, to cause an electrical change in the chemFET surface, thereby resulting in a current change. The current change may result from PPi generation alone or in combination with other events such as those described above.

FIG. 8A shows the calculated concentrations of substrates and products of a nucleotide incorporation reaction. These calculations are based on a model in which a plurality of nucleic acids are synchronously synthesized from a plurality of identical template nucleic acids bound to a bead situated in a well, as described herein. The model assumes that the wells contain template nucleic acids hybridized to primer nucleic acids, polymerases, and co-factors needed for nucleotide incorporation, except for nucleotides. The incorporation reaction is initiated by introducing (through flow) a population of known, identical nucleotide triphosphates into the well. The model indicates that the first analyte detected by the chemFET surface is the newly generated PPi, and that at some time point thereafter unincorporated nucleotide triphosphates are generated. Each of these analyte populations will give rise to a current readout at the chemFET. FIG. 8B shows the voltage pulses and/or peaks (referred to herein interchangeably) that correspond to changes in the concentration of PPi and unincorporated nucleotides. The time of the first observable pulse is referred to herein as $t_0$ and the time of the second observable pulse is referred to herein as $t_1$. The various overlayed traces reflect the incorporation of none, one or more identical nucleotides in a given reaction. As can be seen in FIG. 8B, the difference in time between $t_1$ and $t_0$ (i.e., $t_1-t_0$) increases with increasing nucleotide incorporation. As a result, the time difference between the PPi pulse and the unincorporated nucleotide triphosphate pulse may be used as a measure of how many nucleotide triphosphates have been incorporated in any given step. This will typically be used to determine how many of a known single type of dNTP is incorporated. However it may also be used to determine the number of dNTP incorporated regardless of the identity of the dNTP according to other aspects of the invention.

Thus, some embodiments the invention contemplate that upon introduction of nucleotides that are complementary to the next position to be sequenced on the template nucleic acid, such nucleotides will be effectively consumed yielding PPi which is then detected at the chemFET. Only once the synthesis reactions have gone to completion (i.e., the appropriate number of nucleotides have been incorporated into all newly synthesized nucleic acids) is the population of unincorporated nucleotides able to diffuse to and be detected by the chemFET surface. The delay in the detection of the unincorporated nucleotides is indicative of how many such nucleotides have been incorporated. These delays are modeled in FIG. 8B. If the nucleotides introduced into the wells are not complimentary to the next position to be sequenced on the template nucleic acid, then no incorporation should occur. Accordingly, the first analyte detected at the surface of the chemFET will be the population of unincorporated nucleotides since no PPi would be generated. Thus, detection of a single ionic pulse by the chemFET (which is translated into a single voltage pulse) indicates that no nucleotide incorporation has occurred, detection of two, temporally separated, ionic pulses (which are translated into two voltage pulses) indicates that nucleotide incorporation has occurred, and the time difference between the latter two pulses indicates the number of nucleotides that have been incorporated.

The incorporation of a dNTP into the nucleic acid strand releases PPi which can then be hydrolyzed to two orthophosphates (Pi) and one hydrogen ion. The generation of the hydrogen ion therefore can be detected as an indicator of nucleotide incorporation. Alternatively, Pi may be detected directly or indirectly. Any and all of these events (and more as described herein) may be detected at the chemFET thereby causing a current change that correlates with nucleotide incorporation.

The limit of this dual pulse detection occurs when the two pulses cannot be resolved in time (i.e., the two peaks may merge into one, where $t_0$ and $t_1$ peaks are not distinguishable). This limit, for the case $N_{poly}=0$ vs $N_{poly}=1$ is given by the following: Consider a first peak $N_{poly}=0$ which has a width=$W_0$ and standard deviation $\sigma_{W_0}$ and a second peak $N_{poly}=1$ which has a width=$W_1$ and standard deviation $\sigma_{W_1}$. For a $P_e$ of 1% [where $P_e$=erfc(SNR/2*(sqr(2)))], the signal-to-noise ratio (SNR)=5.15. Therefore the limit of detection is the difference in peak widths, $\Delta W$, is given by $\Delta W=(W_1-W_0)>5.15*\sigma_{W_0}$. Similar calculations may be done for other SNRs.

In certain embodiments the chemFET (or ISFET) readouts are independent of (or insensitive to) changes in the concentration of Pi and/or $H^+$. In these embodiments, the rate of PPi hydrolysis to Pi with the concomitant release of $H^+$ is reduced, sometimes significantly. The PPi to Pi conversion may be catalyzed by an enzyme such as a pyrophosphatase and/or by certain ions. In the absence of the both (and in some cases, either) the enzyme and the particular ion, the rate of conversion is sufficiently slow to be negligible. (See for example J. Chem, Soc. Farady Trans. 2007, 93:4295 which reports the rate constant for the conversion in the absence of enzyme or ion to be on the order of about $3^{-1}$ years$^{-1}$, as compared to Biochemistry, 2002, 41:12025 which reports the rate in the presence of enzyme and $Mg^{2+}$ to be on the order of about $10^3$ s$^{-1}$.) A pH insensitive environment may be one that is buffered sufficiently to obscure any changes in pH resulting from release of hydrogen. The reaction may be pH insensitive or independent as a result of there being few if any hydrogen ions released as a result of the reaction.

The nucleic acid being sequenced is referred to herein as the target nucleic acid. Target nucleic acids include but are not limited to DNA such as but not limited to genomic DNA, mitochondrial DNA, cDNA and the like, and RNA such as but not limited to mRNA, miRNA, and the like. The nucleic acid may be from any source including naturally occurring sources or synthetic sources. The nucleic acids may be PCR products, cosmids, plasmids, naturally occurring or synthetic libraries, and the like. The invention is not intended to be limited in this regard. The methods provided herein can be used to sequence nucleic acids of any length. To be clear, the Examples provide a proof of principle demonstration of the sequencing of four templates of known sequence. This artificial model is intended to show that embodiments of the apparatuses and systems described herein are able to readout nucleotide incorporation that correlates to the known sequence of the templates. This is not intended to represent typical use of the method or system in the field. The following is a brief description of these methods.

Target nucleic acids are prepared using any manner known in the art. As an example, genomic DNA may be harvested from a sample according to techniques known in the art (see for example Sambrook et al. "Maniatis"). Following harvest, the DNA may be fragmented to yield nucleic acids of smaller length. The resulting fragments may be on the order of hundreds, thousands, or tens of thousands nucleotides in length. In some embodiments, the fragments are 200-1000 base pairs in size, or 300-800 base pairs in size, about 200, about 300, about 400, about 500, about 600, about 700, about 800, about 900, or about 1000 base pairs in length, although they are not so limited. Nucleic acids may be fragmented by any means including but not limited to mechanical, enzymatic or chemical means. Examples include shearing, sonication, nebulization, endonuclease (e.g., DNase I) digestion, amplification such as PCR amplification, or any other technique known in the art to produce nucleic acid fragments, preferably of a desired length. As used herein, fragmentation also embraces the use of amplification to generate a population of smaller sized fragments of the target nucleic acid. That is, the target nucleic acids may be melted and then annealed to two (and preferably more) amplification primers and then amplified using for example a thermostable polymerase (such as Taq). An example is a massively parallel PCR-based amplification. Fragmentation can be followed by size selection techniques to enrich or isolate fragments of a particular length or size. Such techniques are also known in the art and include but are not limited to gel electrophoresis or SPRI.

Alternatively, target nucleic acids that are already of sufficient small size (or length) may be used. Such target nucleic acids include those derived from an exon enrichment process. Thus, rather than fragmenting (randomly or non-randomly) longer target nucleic acids, the targets may be nucleic acids that naturally exist or can be isolated in shorter, useable lengths such as mRNAs, cDNAs, exons, PCR products (as described above), and the like. See Albert et al. Nature Methods 2007 4(11):903-905 (microarray hybridization of exons and locus-specific regions), Porreca et al. Nature Methods 2007 4(11):931-936, and Okou et al. Nature Methods 2007 4(11):907-909 for methods of isolating and/or enriching sequences such as exons prior to sequencing.

In some embodiments, the size selected target nucleic acids are ligated to adaptor sequences on both the 5' and 3' ends. These adaptor sequences comprise sequences complementary to amplification primer sequences, to be used in amplifying the target nucleic acids. One adaptor sequence may also comprise a sequence complementary to the sequencing primer. The opposite adaptor sequence may comprise a moiety that facilitates binding of the nucleic acid to a solid support such as but not limited to a bead. An example of such a moiety is a biotin molecule (or a double biotin moiety, as described by Diehl et al. Nature Methods, 2006, 3(7):551-559) and such a labeled nucleic acid can therefore be bound to a solid support having avidin or streptavidin groups. Another moiety that can be used is the NHS-ester and amine affinity pair. It is to be understood that the invention is not limited in this regard and one of ordinary skill is able to substitute these affinity pairs with other binding pairs. The resulting nucleic acid is referred to herein as a template nucleic acid. The template nucleic acid comprises at least the target nucleic acid and usually comprises nucleotide sequences in addition to the target at both the 5' and 3' ends.

In some embodiments, the template nucleic acid is able to self-anneal thereby creating a 3' end from which to incorporate nucleotide triphosphates. In such instances, there is no need for a separate sequencing primer since the template acts as both template and primer. See Eriksson et al. Electrophoresis 2004 25:20-27 for a discussion of the use of self-annealing template in a pyrosequencing reaction.

In still other embodiments, the template is used in a double stranded (or partially double stranded) from which is nicked preferably within an adaptor sequence (at the free end of the bead bound template). The opening in the double stranded template allows a polymerase such as DNA polymerase to enter at the nicked site and begin nucleotide incorporation. These openings can be introduced into the template in a controlled manner particularly since the sequence acted upon by DNA nickase (i.e., the nicking enzyme in this instance) is know (i.e., 5'GAGTC3'). See Zyrina et al. for a discussion of these consensus nicking target sequences.

In some instances a spacer is used to distance the template nucleic acid (and in particular the target nucleic acid sequence comprised therein) from a solid support such as a bead. This facilitates sequencing of the end of the target closest to the bead, for instance. Examples of suitable linkers are known in the art (see Diehl et al. Nature Methods, 2006, 3(7):551-559) and include but are not limited to carbon-carbon linkers such as but not limited to iSp18.

The solid support to which the template nucleic acids are bound is referred to herein as the "capture solid support". If the solid support is a bead, then such bead is referred to herein as a "capture bead". The beads can be made of any material including but not limited to cellulose, cellulose derivatives, gelatin, acrylic resins, glass, silica gels, polyvinyl pyrrolidine (PVP), co-polymers of vinyl and acrylamide, polystyrene, polystyrene cross-linked with divinylbenzene or the like (see, Merrifield Biochemistry 1964, 3, 1385-1390), polyacrylamides, latex gels, dextran, crosslinked dextrans (e.g., Sephadex™), rubber, silicon, plastics, nitrocellulose, natural sponges, metal, and agarose gel (Sepharose™). In one embodiment, the beads are streptavidin-coated beads. The bead diameter will depend on the density of the chemFET and microwell array used with larger arrays (and thus smaller sized wells) requiring smaller beads. Generally the bead size may be about 1-10 µM, and more preferably 2-6 µM. In some embodiments, the beads are about 5.91 µM while in other embodiments the beads are about 2.8 µM. In still other embodiments, the beads are about 1.5 µm, or about 1 µm in diameter. It is to be understood that the beads may or may not be perfectly spherical in shape. It is also to be understood that other beads may be used and other mechanisms for attaching the nucleic acid to the beads may be used. In some instances the capture beads (i.e., the beads on which the sequencing reaction occurs) are the same as the template preparation beads including the amplification beads.

Important aspects of the invention contemplate sequencing a plurality of different template nucleic acids simultaneously. This may be accomplished using the sensor arrays described herein. In one embodiment, the sensor arrays are overlayed (and/or integral with) an array of microwells (or reaction chambers or wells, as those terms are used interchangeably herein), with the proviso that there be at least one sensor per microwell. Present in a plurality of microwells is a population of identical copies of a template nucleic acid. There is no requirement that any two microwells carry identical template nucleic acids, although in some instances such templates may share overlapping sequence. Thus, each microwell comprises a plurality of identical copies of a template nucleic acid, and the templates between microwells may be different.

The microwells may vary in size between arrays. The microwell size may be described in terms of cross section. The cross section may refer to a "slice" parallel to the depth (or height) of the well, or it may be a slice perpendicular to the depth (or height) of the well.

The size of these microwells may be described in terms of a width (or diameter) to height ratio. In some embodiments, this ratio is 1:1 to 1:1.5. The bead to well size (e.g., the bead diameter to well width, diameter, or height) is preferably in the range of 0.6-0.8.

The microwells may be square in cross-section, but they are not so limited. The dimensions at the bottom of a microwell (i.e., in a cross section that is perpendicular to the depth of the well) may be 1.5 µm by 1.5 µm, or it may be 1.5 µm by 2 µm. Various diameters are shown in the Examples and include but are not limited to diameters at or about 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 10 µm, 9 µm, 8 µm, 7 µm, 6 µm, 5 µm, 4 µm, 3 µm, 2 µm, 1 µm or less. In some particular embodiments, the diameters may be at or about 44 µm, 32 µm, 8 µm, 4 µm, or 1.5 µm. Various heights are shown in the Examples and include but are not limited to heights at or about 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 10 µm, 9 µm, 8 µm, 7 µm, 6 µm, 5 µm, 4 µm, 3 µm, 2 µm, 1 µm or less. In some particular embodiments, the heights may be at or about 55 µm, 48 µm, 32 µm, 12 µm, 8 µM, 6 µm, 4 µm, 2.25 µm, 1.5 µm, or less. Various embodiments of the invention contemplate the combination of any of these diameters with any of these heights. In still other embodiments, the reaction well dimensions may be (diameter in µm by height in µm) 44 by 55, 32 by 32, 32 by 48, 8 by 8, 8 by 12, 4 by 4, 4 by 6, 1.5 by 1.5, or 1.5 by 2.25.

The reaction well volume may range (between arrays, and preferably not within a single array) based on the well dimensions. This volume may be at or about 100 picoliter (pL), 90, 80, 70, 60, 50, 40, 30, 20, 10, or fewer pL. In important embodiments, the well volume is less than 1 pL, including equal to or less than 0.5 pL, equal to or less than 0.1 pL, equal to or less than 0.05 pL, equal to or less than 0.01 pL, equal to or less than 0.005 pL, or equal to or less than 0.001 pL. The volume may be 0.001 to 0.9 pL, 0.001 to 0.5 pL, 0.001 to 0.1 pL, 0.001 to 0.05 pL, or 0.005 to 0.05 pL. In particular embodiments, the well volume is 75 pL, 34 pL, 23 pL, 0.54 pL, 0.36 pL, 0.07 pL, 0.045 pL, 0.0024 pL, or 0.004 pL. The plurality of templates in each microwell may be introduced into the microwells (e.g., via a nucleic acid loaded bead), or it may be generated in the microwell itself. A plurality is defined herein as at least two, and in the context of template nucleic acids in a microwell or on a nucleic acid loaded bead includes tens, hundreds, thousands, ten thousands, hundred thousands, millions, or more copies of the template nucleic acid. The limit on the number of copies will depend on a number of variables including the number of binding sites for template nucleic acids (e.g., on the beads or on the walls of the microwells), the size of the beads, the length of the template nucleic acid, the extent of the amplification reaction used to generate the plurality, and the like. It is generally preferred to have as many copies of a given template per well in order to increase signal to noise ratio as much as possible. Amplification and conjugation of nucleic acids to solid supports such as beads may be accomplished in a number of ways, including but not limited to emulsion PCR (i.e., water in oil emulsion amplification) as described by Margulies et al. Nature 2005 437(15): 376-380 and accompanying supplemental materials. In some embodiments, the amplification is a representative amplification. A representative amplification is an amplification that does not alter the relative representation of any nucleic acid species. The wells generally also include sequencing primers, polymerases and other substrates or catalysts necessary for the synthesis reaction.

The degree of saturation of any capture (i.e., sequencing) bead with template nucleic acid to be sequenced may not be 100%. In some embodiments, a saturation level of 10%-100% exists. As used herein, the degree of saturation of a capture bead with a template refers to the proportion of sites on the bead that are conjugated to template. In some instances this may be at least 5%, 10%, 15%, 20%, 25%, 30%, 35%, 40%, 45%, 50%, 55%, 60%, 65%, 70%, 75%, 80%, 85%, 90%, 95%, or it may be 100%.

It will be understood that the amount of sequencing primers and polymerases may be saturating, above saturating level, or in some instances below saturating levels. As used herein, a saturating level of a sequencing primer or a polymerase is a level at which every template nucleic acid is hybridized to a sequencing primer or bound by a polymerase, respectively. Thus the saturating amount is the number of polymerases or primers that is equal to the number of templates on a single bead. In some embodiments, the level is at greater than this, including at least 2 fold, 3 fold, 4 fold, 5 fold, 10 fold, or more over the level of the template nucleic acid. In other embodiments, the number of polymerases and/or primers may be 10%, 20%, 30%, 40%, 50%, 60%, 70%, 80%, 90%, or up to 100% of the number of templates on a single bead in a single well.

Thus, for example, before and/or while in the wells, the template nucleic acids are incubated with a sequencing primer that binds to its complementary sequence located on the 3' end of the template nucleic acid (i.e., either in the amplification primer sequence or in another adaptor sequence ligated to the 3' end of the target nucleic acid) and with a polymerase for a time and under conditions that promote hybridization of the primer to its complementary sequence and that promote binding of the polymerase to the template nucleic acid. The primer can be of virtually any sequence provided it is long enough to be unique. The hybridization conditions are such that the primer will hybridize to only its true complement on the 3' end of the template. Suitable conditions are disclosed in Margulies et al. Nature 2005 437(15): 376-380 and accompanying supplemental materials.

As described herein, the template nucleic acids may be engineered such that different templates have identical 5' ends and identical 3' ends. In some embodiments, however, the invention contemplates the use of a plurality of template populations, wherein each member of a given plurality shares the same 3' end but different template populations differ from each other based on their 3' end sequences. As an example, the invention contemplates in some instances sequencing nucleic acids from more than one subject or source. Nucleic acids from first source may have a first 3' sequence, nucleic acids from a second source may have a second 3' sequence, and so on, provided that the first and second 3' sequences are different. In this respect, the 3' end, which is typically a unique sequence, can be used as a barcode or identifier to label (or identify) the source of the particular nucleic acid in a given well. Reference can be made to Meyer et al. Nucleic Acids Research 2007 35(15):e97 for a discussion of labeling nucleic acid with barcodes followed by sequencing. In some instances, the sequencing primers (if used) may be hybridized (or annealed, as the terms are used interchangeably herein) to the templates prior to loading (or introducing) the beads to the wells or after such loading.

The 5' and 3' ends on every individual template however are preferably different in sequence. In particular, the templates share identical primer binding sequences. This facilitates the use of an identical primer across microwells and also ensures that a similar (or identical) degree of primer hybridization occurs across microwells. Once annealed to complementary primers such as sequencing primers, the templates are in a complex referred to herein as a template/primer hybrid. In this hybrid, one region of the template is double stranded (i.e., where it is bound to its complementary primer) and one region is single stranded. It is this single stranded region that acts as the template for the incorporation of nucleotides to the end of the primer and thus it is also this single stranded region which is ultimately sequenced according to the invention.

Suitable polymerases include but are not limited to DNA polymerase, RNA polymerase, or a subunit thereof, provided it is capable of synthesizing a new nucleic acid strand based on the template and starting from the hybridized primer. An example of a suitable polymerase subunit is the exo– version of the Klenow fragment of E. coli DNA polymerase I which lacks 3' to 5' exonuclease activity. Other polymerases include T4 exo–, Therminator, and Bst polymerases. The polymerase may be free in solution (and may be present in wash and dNTP solutions) or it may be bound for example to the beads (or corresponding solid support) or to the walls of the chemFET but preferably not to the ISFET surface itself. In another aspect, the invention provides a method for sequencing a nucleic acid comprising disposing a plurality of template nucleic acids into a plurality of reaction chambers and each reaction chamber is in contact with a chemFET. Sequencing includes synthesizing a new nucleic acid strand by incorporating one or more known nucleotide triphosphates sequentially at the 3' end of the sequencing primer, and detecting incorporation of the one or more known nucleotide triphosphates. The incorporation is carried out by a DNA polymerase. In some embodiments, the polymerase has high affinity for the template, and has a processivity of 100 bp, 250 bp, 500 bp, 750 bp or even 1000 bp. In some embodiments, the polymerase has high activity and a high catalytic rate in high pH conditions. In some embodiments, the pH of the reaction mixture is about 7 to 10, and preferably about 9. In some embodiments, the enzyme has high activity and a high catalytic rate in low concentrations of dNTPs. In some embodiments the dNTP concentration is 50 µM, 40 µM, 30 µM, 20 µM, 10 µM, 5 µM, and preferably 20 µM or less. In some embodiments the enzyme has high activity a catalytic rate where the reaction mixture is of low ionic strength. In some embodiments the concentration of $MgCl_2$ or $MnCl^2$ is 100 µM or less. In some embodiments the concentration of Tris is 0.5 mM or less.

Various aspects of the invention relate to nucleotide incorporation into a pre-existing nucleic acid (such as for example a sequencing primer) in the presence of low ionic strength solutions or environments. As used herein, a low ionic strength solution is a solution that has an ion concentration equal to or less than 3 mM total ion concentration. An example of a low ionic strength solution is a 0.5 mM Tris-HCl solution having less than 100 μM $MgCl_2$. The $MgCl_2$ concentration may be equal to or less than 90 μM, equal to or less than 80 μM, equal to or less than 70 μM, equal to or less than 60 μM, equal to or less than 50 μM, equal to or less than 40 μM, equal to or less than 30 μM, equal to or less than 20 μM, equal to or less than 10 μM, or less. The polymerase in some embodiments therefore must be capable of functioning at low ionic strength. As described in the Examples, polymerases preferably will be able to recognize and bind to the primer/template hybrid, have sufficient affinity for the hybrid resulting for example in increased processivity of the polymerase, and extend the primer, in low ionic strength conditions. Example 2 demonstrates these various properties for T4 exo−, Therminator, Bst, and Klenow exo− polymerases. The Example further demonstrates that these polymerases are able to incorporate nucleotides into and thereby extend a primer in the context of a silicon well in contact with a chemFET.

In some embodiments, the polymerase must also be capable of incorporating nucleotides in low concentrations of dNTPs. In some embodiments, a low concentration of dNTPs is a concentration that is less 20 μM total dNTP. It will be understood by those of ordinary skill in the art that this concentration relates to the concentration of each dNTP added to the reaction wells, in those embodiments contemplating sequential rather than concurrent introduction of dNTP to a reaction well. In other embodiments, the dNTP concentration (either per dNTP or in some instances total dNTP present in a reaction well at any time during a reaction) is equal to or less than 19 μM, equal to or less than 18 μM, equal to or less than 17 μM, equal to or less than 16 μM, equal to or less than 15 μM, equal to or less than 14 μM, equal to or less than 13 μM, equal to or less than 12 μM, equal to or less than 11 μM, equal to or less than 10 μM, equal to or less than 9 μM, equal to or less than 8 μM, equal to or less than 7 μM, equal to or less than 6 μM, equal to or less than 5 μM, equal to or less than 4 μM, equal to or less than 3 μM, equal to or less than 2 μM, equal to or less than 1 μM, or less. In some embodiments, the dNTP concentration is between 0-20 μM, between 1-19 μM, or between 5-15 μM.

Some embodiments of the invention require that the polymerase have sufficient processivity. As used herein, processivity is the ability of a polymerase to remain bound to a single primer/template hybrid. As used herein, it is measured by the number of nucleotides that a polymerase incorporates into a nucleic acid (such as a sequencing primer) prior to disassociation of the polymerase from the primer/template hybrid. In some embodiments, the polymerase has a processivity of at least 100 nucleotides, although in other embodiments it has a processivity of at least 200 nucleotides, at least 300 nucleotides, at least 400 nucleotides, or at least 500 nucleotides. It will be understood those of ordinary skill in the art that the higher the processivity of the polymerase, the more nucleotides that can be incorporated prior to disassociation, and therefore the longer the nucleic acid that can be sequenced. In other words, polymerases having low processivity (e.g., a polymerase that dissociates from the hybrid after five incorporations will only provide sequence of 5 nucleotides in length, according to some aspects of the invention.

Still other aspects and embodiments of the invention contemplate performing nucleotide incorporation at a high pH (i.e., a pH that is greater than 7). Thus, some reactions are carried out at a pH equal to or greater than 7.5, equal to or greater than 8, equal to or greater than 8.5, equal to or greater than 9, equal to or greater than 9.5, equal to or greater than 10, or equal to or greater than 11. The polymerase may be one that incorporates nucleotides into a nucleic acid (such as a sequencing primer) at a pH of 7-11, 7.5-10.5, 8-10, 8.5-9.5, or at about 9.

It will be understood based on the teachings herein that some aspects and embodiments of the invention will employ polymerases demonstrating high activity in low ionic strength solutions, and/or low dNTP concentrations, and/or high pH. Suitable rates of incorporation will vary depending on the embodiment. In some embodiments, nucleotide incorporation occurs at a rate faster than the diffusion of reagents within a reaction chamber. For example, in one embodiment, nucleotide incorporation occurs at a rate that exceeds the rate of diffusion of dNTP in the reaction well and preferably of dNTP towards the bottom or the reaction well (i.e., to the sensor). In these instances, the newly introduced dNTP do not diffuse towards the sensor until the incorporation reactions are complete. At that time, the remaining dNTP (i.e., the unincorporated dNTP) diffuse past the hybrids (or the beads, as the case may be) and towards the sensor bottom. In these instances, until the incorporation reactions are complete, the dNTP diffusing in the direction of the bead and the well bottom are used up before even reaching the well bottom.

The rate at which a polymerase incorporates nucleotides will vary depending on the particular application, although generally faster rates of incorporation are preferable. The rate of incorporation of a single polymerase to a single nucleic acid (such as a sequencing primer) in some instances is faster than the rate of diffusion of the unincorporated nucleotide triphosphates in the well, and particularly their diffusion towards the bottom of the well. The rate of "sequencing" will depend on the number of arrays on chip, the size of the wells, the temperature and conditions at which the reactions are run, etc. As discussed elsewhere herein, the diffusion rate can also be manipulated by effectively impeding the movement of unincorporated nucleotide triphosphates. This can be done for example by increasing the viscosity in the reaction chamber. This can be accomplished by adding to the reaction chamber a viscosity increasing agent such as but not limited to polyethylene glycol (PEG) or PEA. Diffusion can also be delayed by the use of packing beads in the reaction wells. In some embodiments of the invention, the time for a 4 nucleotide cycle may be 50-100 seconds, 60-90 seconds, or about 70 seconds. In other embodiments, this cycle time can be equal to or less than 70 seconds, including equal to or less than 60 seconds, equal to or less than 50 seconds, equal to or less than 40 seconds, or equal to or less than 30 seconds. A read length of about 400 bases may take on the order of 30 minutes, 60 minutes, 1.5 hours, 2 hours, 2.5 hours, 3 hours, 3.5 hours, 4 hours, 4.5 hours, or in some instance 5 or more hours. These times are sufficient for the sequencing of megabases, and more preferably gigabases of sequence, with greater amounts of sequence being attainable through the use of denser arrays (i.e., arrays with greater numbers of reaction wells and FETs) and/or the simultaneous use of multiple arrays.

Table 2 provides estimates for the rates sequencing based on various array, chip and system configurations contemplated herein. It is to be understood that the invention contemplates even denser arrays than those shown in Table 2. These denser arrays can be characterized as 90 nm CMOS with a pitch of 1.4 μm and a well size of 1 μm which may be used with 0.7 μm beads, or 65 nm CMOS with a pitch of 1 μm and a well size of 0.5 μm which may be used with 0.3 μm beads, or 45 μm CMOS with a pitch of 0.7 μm and a well size of 0.3 μm which can be used with 0.2 μm beads.

TABLE 2

Reaction Parameters and Read Rates.

| chip type | A | B | C | D | E |
|---|---|---|---|---|---|
| pixel/CMOS | 2.8 um/0.18 um | 5.1 um/0.35 um | 5.1 um/0.35 um | 9 um/3.5 um | 9 um/0.35 um |
| chip size | 17.5 × 17.5 | 17.5 × 17.5 | 12 × 12 | 17.5 × 17.5 | 12 × 12 |
| # possible reads | 27,800,000 | 7,220,000 | 2,950,000 | 2,320,000 | 1,060,000 |
| read length (assumption) | 400 | 400 | 400 | 400 | 400 |
| # chips/board | 4 | 4 | 4 | 4 | 4 |
| bead load efficiency | 0.80 | 0.80 | 0.80 | 0.80 | 0.80 |
| # yielded Gbp* per run | 35.6 | 9.2 | 3.8 | 3.0 | 1.4 |
| # times HG** (3 Gbp/HG) | 11.86 | 3.08 | 1.26 | 0.99 | 0.45 |

*Gbp is gigabases
**HG is human genome

The template nucleic acid is also contacted with other reagents and/or cofactors including but not limited to buffer, detergent, reducing agents such as dithiothrietol (DTT, Cleland's reagent), single stranded binding proteins, and the like before and/or while in the well. In one embodiment, the polymerase comprises one or more single stranded binding proteins (e.g., the polymerase may be one that is engineered to include one or more single stranded binding proteins). In one embodiment, the template nucleic acid is contacted with the primer and the polymerase prior to its introduction into the flow chamber and wells thereof.

Figure 61A:
FIGS. 61A and B are data capture images of microwell arrays following bead deposition. The white spots are beads.
Figure 61B:
Figure 62:
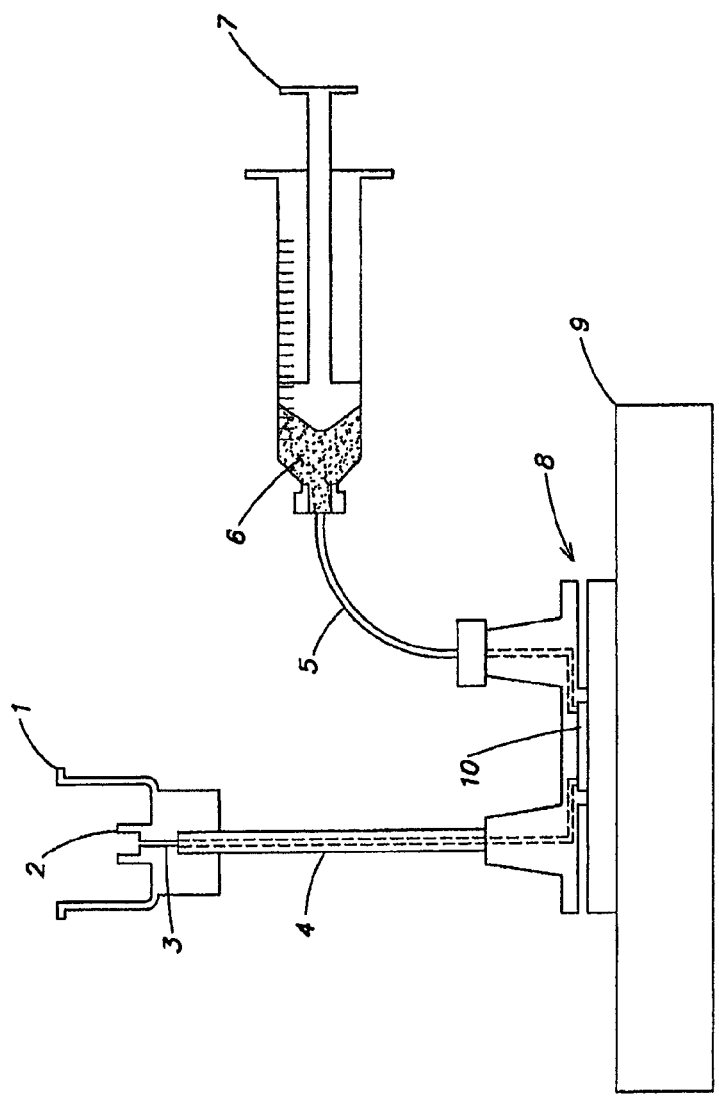
FIGS. 62-70 illustrate bead loading into the microfluidic arrays of the invention.
Figure 63:
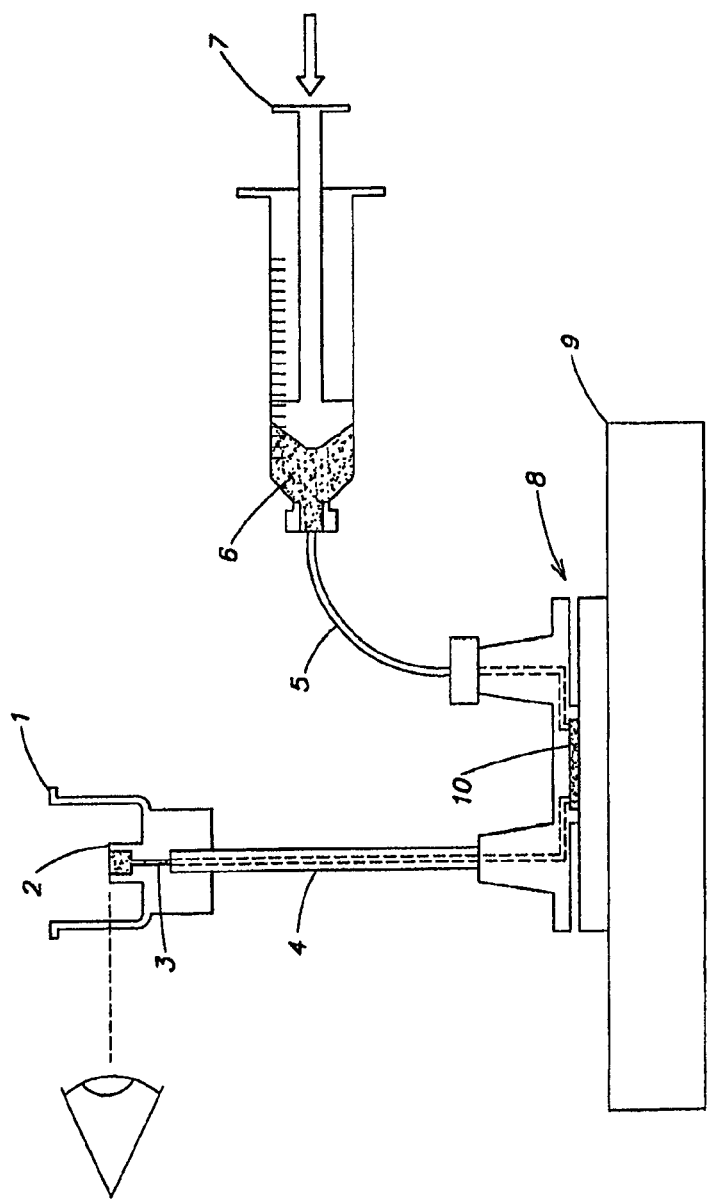
Figure 64:
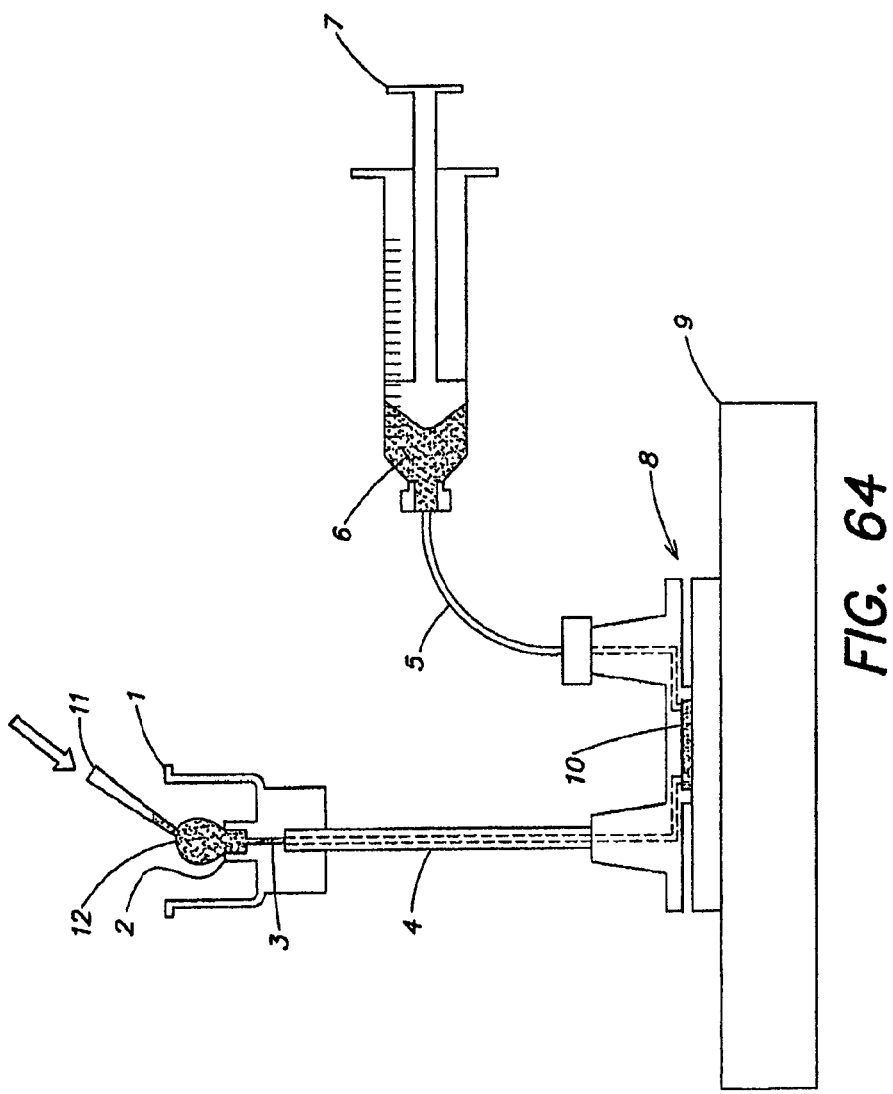
Figure 65:
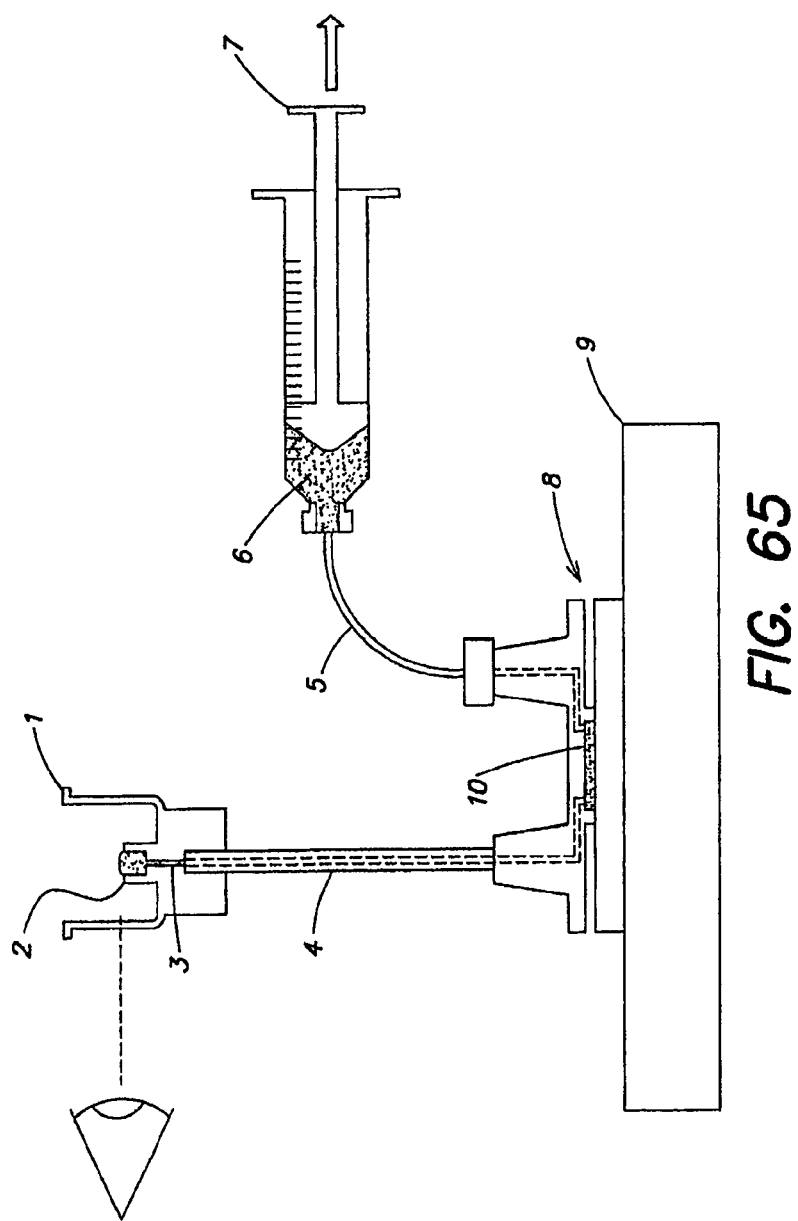
Figure 66:
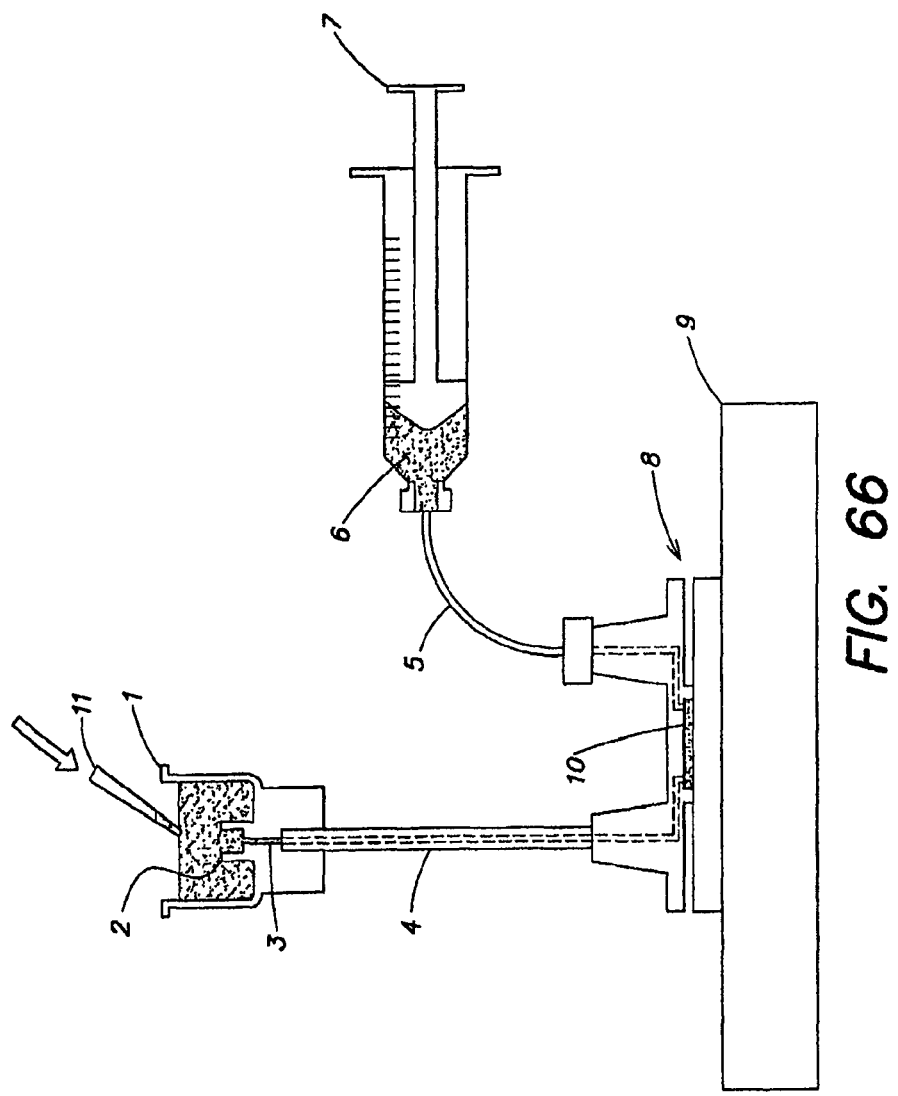
Figure 67:
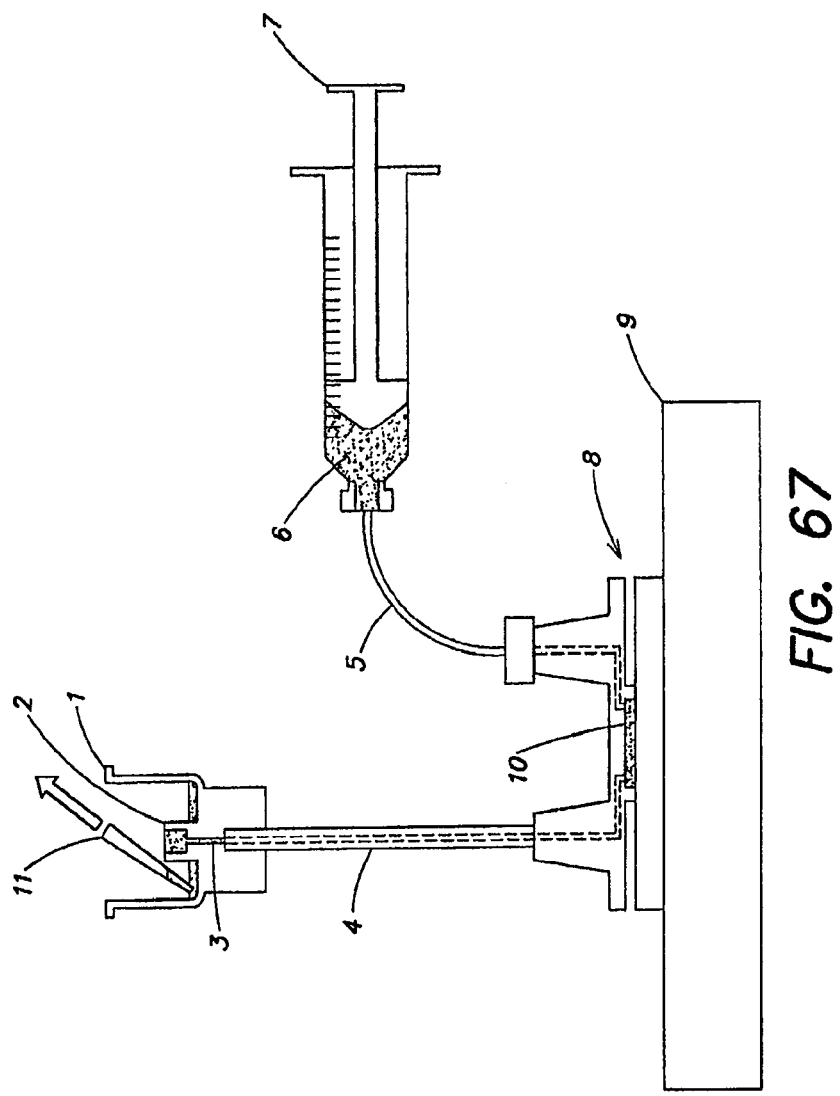
Figure 68:
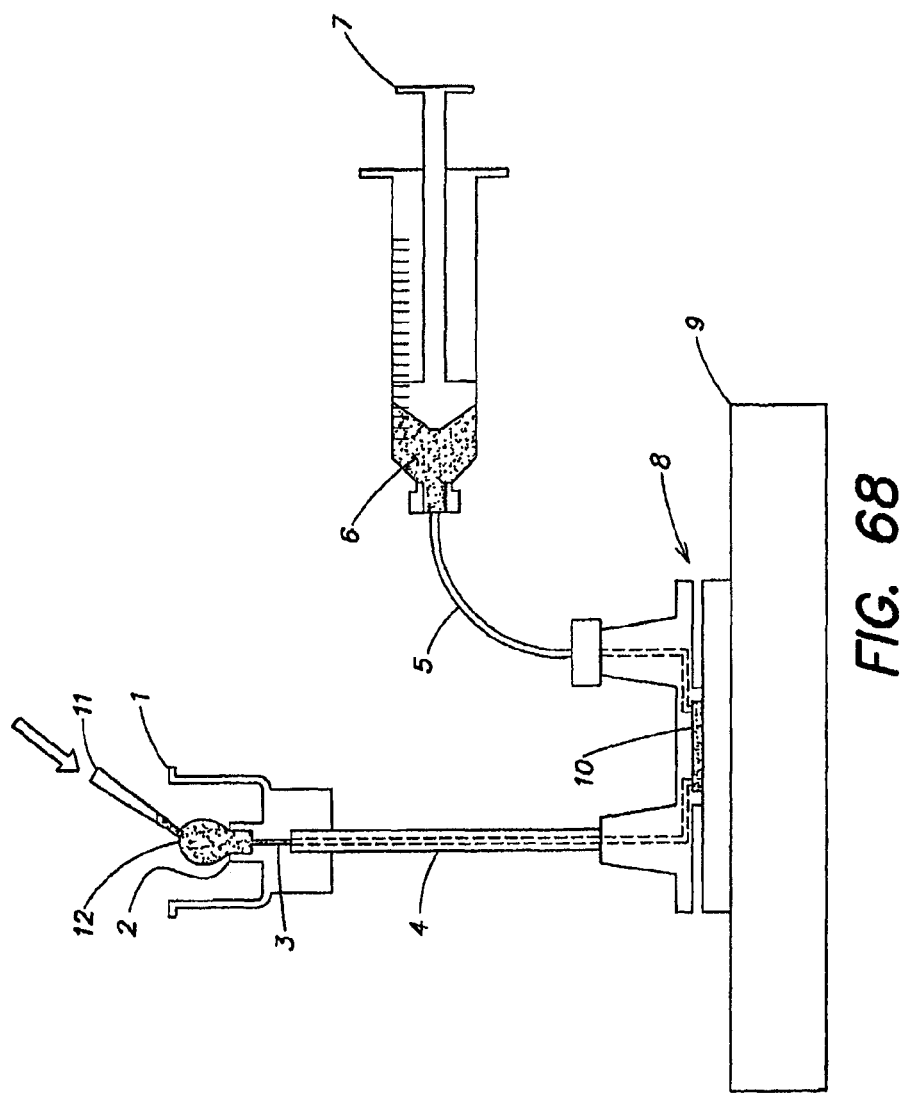
Figure 69:
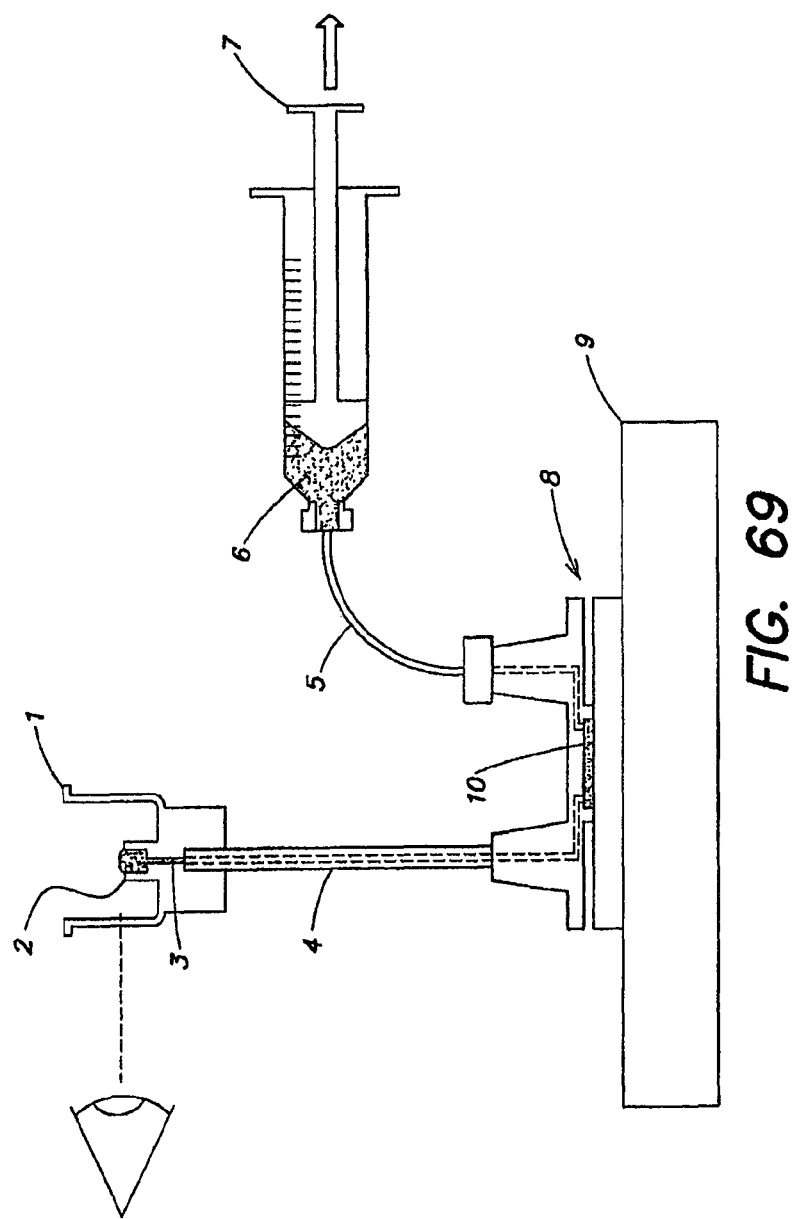
Figure 70:
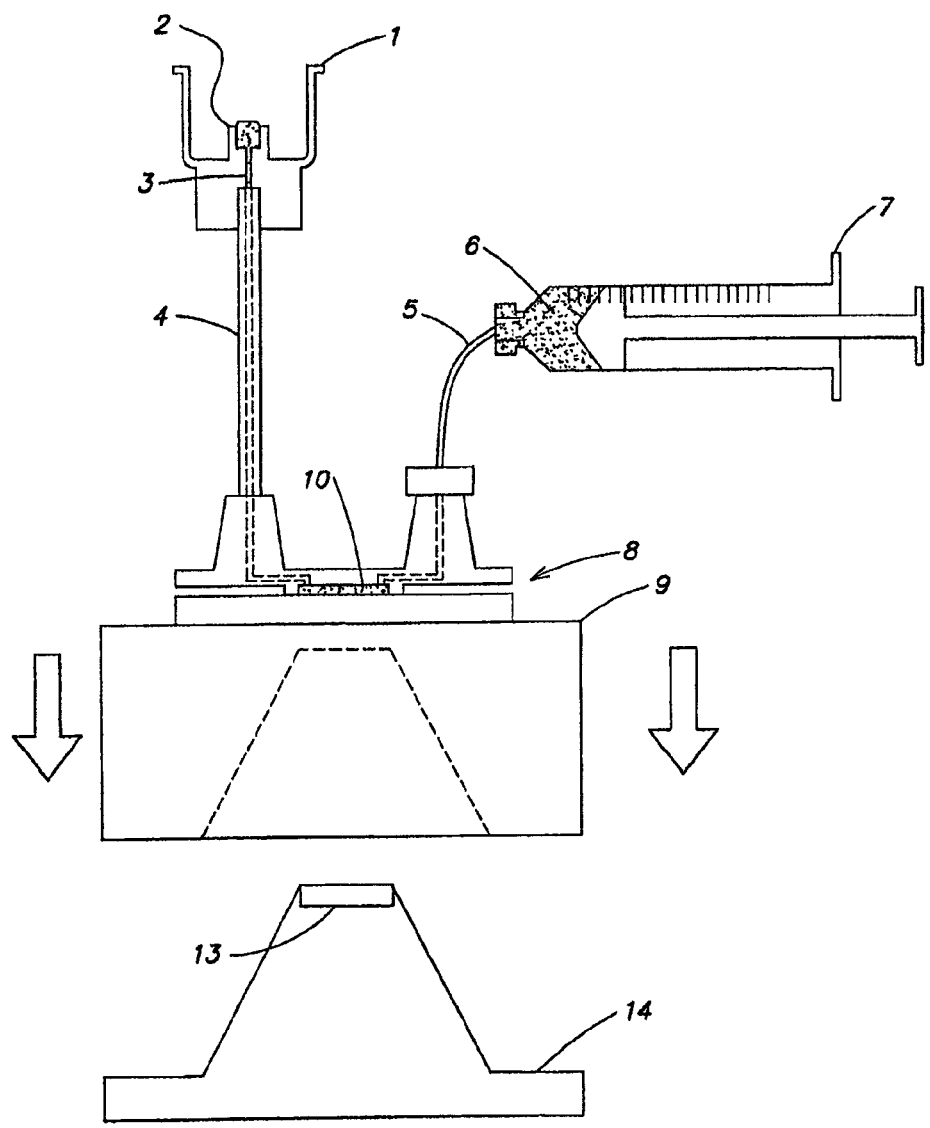

In one embodiment, the nucleic acid loaded beads are introduced into the flow chamber and ultimately the wells situated above the chemFET array. The method requires that each well in the flow chamber contain only one nucleic acid loaded bead since the presence of two beads per well will yield unusable sequencing information derived from two different template nucleic acids. The Examples provides a brief description of an exemplary bead loading protocol in the context of magnetic beads. It is to be understood that a similar approach could be used to load other bead types. The protocol has been demonstrated to reduce the likelihood and incidence of trapped air in the wells of the flow chamber, uniformly distribute nucleic acid loaded beads in the totality of wells of the flow chamber, and avoid the presence and/or accumulation of excess beads in the flow chamber. In some embodiments, the microwell array may be analyzed to determine the degree of loading of beads into the microwells, and in some instances to identify those microwells having beads and those lacking beads. The ability to know which microwells lack beads provides another internal control for the sequencing reaction. The presence or absence of a bead in a well can be determined by standard microscopy or by the sensor itself. FIGS. 61A and B are images captured from an optical microscope inspection of a microwell array (A) and from the sensor array underlying the microwell array (B). The white spots in both images each represent a bead in a well. Such microwell observation usually is only made once per run particularly since the beads once disposed in a microwell are unlikely to move to another well.

The percentage of occupied wells in the well array may vary depending on the methods being performed. If the method is aimed at extracting maximum sequence data in the shortest time possible, then higher occupancy is desirable. If speed and throughout is not as critical, then lower occupancy may be tolerated. Therefore depending on the embodiment, suitable occupancy percentages may be at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, or 100% of the wells. As used herein, occupancy refers to the presence of one nucleic acid loaded bead in a well and the percentage occupancy refers to the proportion of total wells in an array that are occupied by a single bead. Wells that are occupied by more than one bead cannot be used in the analyses contemplated by the invention.

Ultimately a homogeneous population of template nucleic acids is placed into each of a plurality of wells, each well situated over and thus corresponding to at least one sensor. As discussed above, preferably the well contains at least 10, at least 100, at least 1000, at least $10^4$, at least $10^5$, at least $10^6$, or more copies of an identical template nucleic acid. Identical template nucleic acids means that the templates are identical in sequence. Most and preferably all the template nucleic acids within a well are uniformly hybridized to a primer. Uniform hybridization of the template nucleic acids to the primers means that the primer hybridizes to the template at the same location (i.e., the sequence along the template that is complementary to the primer) as every other template/primer hybrid in the well. The uniform positioning of the primer on every template allows the coordinated synthesis of all new nucleic acid strands within a well, thereby resulting in a greater signal-to-noise ratio.

In some embodiments, nucleotides are then added in flow, or by any other suitable method, in sequential order to the flow chamber and thus the wells. The nucleotides can be added in any order provided it is known and for the sake of simplicity kept constant throughout a run.

As mentioned herein, in some embodiments, the method relies on detection of PPi and unincorporated nucleotides. In other embodiments, unincorporated nucleotides are not detected. This can be accomplished for example by adding ATP to the wash buffer so that dNTPs flowing into a well displace ATP from the well. The ATP matches the ionic strength of the dNTPs entering the wells and it also has a similar diffusion profile as those dNTPs. In this way, influx and efflux of dNTPs during the sequencing reaction do not interfere with measurements at the chemFET. The concentration of ATP used is on the order of the concentration of dNTP used.

In some embodiments, particularly those in which a low ionic strength environment is used, the dNTP and/or the polymerase will be pre-incubated with divalent cation such as but not limited to $Mg^{2+}$ (for example in the form of $MgCl_2$) or $Mn^{2+}$ (for example in the form of $MnCl_2$). Other divalent cations can also be used including but not limited to $Ca^{2+}$, $Co^{2+}$. This pre-incubation (and thus "pre-loading" of the dNTP and/or the polymerase can ensure that the polymerase is exposed to a sufficient amount of divalent cation for proper and necessary functioning even if it is present in a low ionic strength environment. Pre-incubation may occur for 1-60 minutes, 5-45 minutes, or 10-30 minutes, depending on the embodiment, although the invention is not limited to these time ranges.

A sequencing cycle may therefore proceed as follows washing of the flow chamber (and wells) with wash buffer (optionally containing ATP), introduction of a first dNTP species (e.g., dATP) into the flow chamber (and wells), release and detection of PPi and then unincorporated nucleotides (if incorporation occurred) or detection of solely unincorporated nucleotides (if incorporation did not occur) (by any of the mechanisms described herein), washing of the flow chamber (and wells) with wash buffer, washing of the flow chamber (and wells) with wash buffer containing apyrase (to remove as many of the unincorporated nucleotides as possible prior to the flow through of the next dNTP, washing of the flow chamber (and wells) with wash buffer, and introduction of a second dNTP species. This process is continued until all 4 dNTP (i.e., dATP, dCTP, dGTP and dTTP) have been flowed through the chamber and allowed to incorporate into the newly synthesized strands. This 4-nucleotide cycle may be repeated any number of times including but not limited to 10, 25, 50, 100, 200 or more times. The number of cycles will be governed by the length of the template being sequenced and the need to replenish reaction reagents, in particular the dNTP stocks and wash buffers.

As part of the sequencing reaction, a dNTP will be ligated to (or "incorporated into" as used herein) the 3' of the newly synthesized strand (or the 3' end of the sequencing primer in the case of the first incorporated dNTP) if its complementary nucleotide is present at that same location on the template nucleic acid. Incorporation of the introduced dNTP (and concomitant release of PPi) therefore indicates the identity of the corresponding nucleotide in the template nucleic acid. If no dNTP has been incorporated, then only a single ion pulse is detected corresponding to unincorporated nucleotides at the surface of the chemFET. One can therefore conclude that the complementary nucleotide was not present in the template at that location. If the introduced dNTP has been incorporated into the newly synthesized strand, then the chemFET will detect a first ion pulse corresponding to the PPi and a second pulse corresponding to the unincorporated nucleotides. It is further possible to quantitate the number of dNTP incorporated by for example measuring the time difference between the time for of the first (PPi) ion pulse (i.e., $t_0$) and the second (unincorporated nucleotides) ion pulse (i.e., $t_1$). The greater the time difference, the greater the number of nucleotides incorporated. The result is that no sequence information is lost through the sequencing of a homopolymer stretch (e.g., poly A, poly T, poly C, or poly G) in the template.

Apyrase is an enzyme that degrades residual unincorporated nucleotides converting them into monophosphate and releasing inorganic phosphate in the process. It is useful for degrading dNTPs that are not incorporated and/or that are in excess. It is important that excess and/or unincorporated dNTP be washed away from all wells after measurements are complete and before introduction of the subsequent dNTP. Accordingly, addition of apyrase between the introduction of different dNTPs is useful to remove unincorporated dNTPs that would otherwise obscure the sequencing data.

Additional sequencing reaction reagents such as those described above may be introduced throughout the reaction, although in some cases this may not be necessary. For example additional polymerase, DTT, SBB and the like may be added if necessary.

The invention therefore contemplates performing a plurality of different sequencing reactions simultaneously. A plurality of identical sequencing reactions is occurring in each occupied well simultaneously. It is this simultaneous and identical incorporation of dNTP within each well that increases the signal to noise ratio. By performing sequencing reactions in a plurality of wells simultaneously, a plurality of different nucleic acids are simultaneously sequenced.

The methods aim to maximize complete incorporation across all microwells for any given dNTP, reduce or decrease the number of unincorporated dNTPs that remain in the wells after signal detection is complete, and achieve as a high a signal to noise ratio as possible.

The sequencing reaction can be run at a range of temperatures. Typically, the reaction is run in the range of 30-60° C., 35-55° C., or 40-45° C. It is preferable to run the reaction at temperatures that prevent formation of secondary structure in the nucleic acid. However this must be balanced with the binding of the primer (and the newly synthesized strand) to the template nucleic acid and the reduced half-life of apyrase at higher temperatures. A suitable temperature is about 41° C. The solutions including the wash buffers and the dNTP solutions are generally warmed to these temperatures in order not to alter the temperature in the wells. The wash buffer containing apyrase however is preferably maintained at a lower temperature in order to extend the half-life of the enzyme. Typically, this solution is maintained at about 4-15° C., and more preferably 4-10° C. It will be appreciated that sequencing in a low ionic concentration can lower the Tm of the sequencing primer, possibly below that optimal for the polymerase. The invention therefore contemplates that sequencing primers may comprise nucleotide modifications such as modified bases, linked nucleic acid (LNA) monomers, peptide nucleic acid (PNA) monomers, or alternatively minor groove binders could be used to elevate the primer Tm into a suitable range. The nucleotide incorporation reaction can occur very rapidly. As a result, it may be desirable in some instances to slow the reaction down or to slow the diffusion of analytes in the well in order to ensure maximal data capture during the reaction. The diffusion of reagents and/or byproducts can be slowed down in a number of ways including but not limited to addition of packing beads in the wells, and/or the use of polymers such as polyethylene glycol in the wells (e.g., PEG attached to the capture beads and/or to packing beads). The packing beads also tend to increase the concentration of reagents and/or byproducts at the chemFET surface, thereby increasing the potential for signal. The presence of packing beads generally allows a greater time to sample (e.g., by 2- or 4-fold).

Data capture rates can vary and be for example anywhere from 10-100 frames per second and the choice of which rate to use will be dictated at least in part by the well size and the presence of packing beads or other diffusion limiting techniques. Smaller well sizes generally require faster data capture rates.

In some aspects of the invention that are flow-based and where the top face of the well is open and in communication with fluid over the entirety of the chip, it is important to detect the released PPi or other byproduct (e.g., $H^+$) prior to its diffusion out of the well. Diffusion of reaction byproducts out of the well will lead to false negatives (because the byproduct is not detected in that well) and potential false positives in adjacent or downstream wells (where the byproduct may be detected), and thus should be avoided. Packing beads and/or polymers such as PEG may also help reduce the degree of diffusion and/or cross-talk between wells.

Thus in some embodiments packing beads are used in addition to the nucleic acid-loaded beads. The packing beads may be magnetic (including superparamagnetic) but they are not so limited. In some embodiments the packing beads and the capture beads are made of the same material (e.g., both are magnetic, both are polystyrene, etc.), while in other embodiment they are made of different materials (e.g., the packing beads are polystyrene and the capture beads are magnetic). The packing beads are generally smaller than the capture beads. The difference in size may be vary and may be 5-fold, 10-fold, 15-fold, 20-fold or more. As an example, 0.35 μm diameter packing beads can be used with 5.91 μm capture beads. Such packing beads are commercially available from sources such as Bang Labs. The placement of the packing beads relative to the capture bead may vary. For example, the packing beads may surround the capture bead and thereby prevent the capture bead from contacting the chemFET surface. As another example, the packing beads may be loaded into the wells following the capture beads in which case the capture bead is in contact with the chemFET surface. The presence of packing beads between the capture bead and the chemFET surface slows the diffusion of the sequencing byproducts such as PPi, thereby facilitating data capture.

The invention further contemplates the use of packing beads or modifications to the chemFET surface (as described herein) to prevent contact and thus interference of the chemFET surface with the template nucleic acids bound to the capture beads. A layer of packing beads that is 0.1-0.5 μm in depth or height would preclude this interaction.

The sequencing reaction may be preceded by an analysis of the arrays to determine the location of beads. It has been found that in the absence of flow the background signal (i.e., noise) is less than or equal to about 0.25 mV, but that in the presence of DNA-loaded capture beads that signal increases to about 1.0 mV=/−0.5 mV. This increase is sufficient to allow one to determine wells with beads.

The invention further contemplates kits comprising the various reagents necessary to perform a sequencing reaction and instructions of use according to the methods set forth herein.

One preferred kit comprises one or more containers housing wash buffer, one or more containers each containing one of the following reagents: dATP buffer, dCTP buffer, dGTP buffer or dTTP buffer, dATP, dCTP, dGTP and dTTP stocks, apyrase, SSB, polymerase, packing beads, and optionally pyrophosphatase. Importantly the kits may comprise only naturally occurring dNTPs. The kits may also comprise one or more wash buffers comprising components as described in the Examples, but are not so limited. The kits may also comprise instructions for use including diagrams that demonstrate the methods of the invention.

It is to be understood that interactions between receptors and ligands or between two members of a binding pair or between components of a molecular complex can also be detected using the chemFET arrays. Examples of such interactions include hybridization of nucleic acids to each other, protein-nucleic acid binding, protein-protein binding, enzyme-substrate binding, enzyme-inhibitor binding, antigen-antibody binding, and the like. Any binding or hybridization event that causes a change of the semiconductor charge density at the FET interface and thus changes the current that flows from the source to the drain of the sensors described herein can be detected according to the invention.

In these embodiments, the passivation layer (or possibly an intermediate layer coated onto the passivation layer) is functionalized with nucleic acids (e.g., DNA, RNA, miRNA, cDNA, and the like), antigens (which can be of any nature), proteins (e.g., enzymes, cofactors, antibodies, antibody fragments, and the like), and the like. Conjugation of these entities to the passivation layer can be direct or indirect (e.g., using bifunctional linkers that bind to both the passivation layer reactive group and the entity to be bound).

As an example, reaction groups such as amine or thiol groups may be added to a nucleic acid at any nucleotide during synthesis to provide a point of attachment for a bifunctional linker. As another example, the nucleic acid may be synthesized by incorporating conjugation-competent reagents such as Uni-Link AminoModifier, 3'-DMT-C6-Amine-ON CPG, AminoModifier II, N-TFA-C6-Amino-Modifier, C6-ThiolModifier, C6-Disulfide Phosphoramidite and C6-Disulfide CPG (Clontech, Palo Alto, Calif.). Other methods for attaching nucleic acids are discussed below.

In one aspect of the invention, the chemFET arrays are provided in combination with nucleic acid arrays. Nucleic acids in the form of short nucleic acids (e.g., oligonucleotides) or longer nucleic acids (e.g., full length cDNAs) can be provided on chemFET surfaces of the arrays described herein. Nucleic acid arrays generally comprise a plurality of physically defined regions on a planar surface (e.g., "spots") each of which has conjugated to it one and more preferably more nucleic acids. The nucleic acids are usually single stranded. The nucleic acids conjugated to a given spot are usually identical. In the context of an oligonucleotide array, these nucleic acids may be on the order of less 100 nucleotides in length (including about 10, 20, 25, 30, 40, 50, 60, 70, 80, 90 or 100 nucleotides in length). If the arrays are used to detect certain genes (including mutations in such genes or expression levels of such genes), then the array may include a number of spots each of which contains oligonucleotides that span a defined and potentially different sequence of the gene. These spots are then located across the planar surface in order to exclude position related effects in the hybridization and readout means of the array.

The arrays are contacted with a sample being tested. The sample may be a genomic DNA sample, a cDNA sample from a cell, a tissue or a mass (e.g., a tumor), a population of cells that are grown on the array, potentially in a two dimensional array that corresponds to the underlying sensor array, and the like. Such arrays are therefore useful for determining presence and/or level of a particular gene or of its expression, detecting mutations within particular genes (such as but not limited to deletions, additions, substitutions, including single nucleotide polymorphisms), and the like.

The binding or hybridization of the sample nucleic acids and the immobilized nucleic acids is generally performed under stringent hybridization conditions as that term is understood in the art. (See for example Sambrook et al. "Maniatis".) Examples of relevant conditions include (in order of increasing stringency): incubation temperatures of 25° C., 37° C., 50° C. and 68° C.; buffer concentrations of 10×SSC, 6×SSC, 4×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. By way of example hybridization may be performed at 50% formamide and 4×SSC followed by washes of 2×SSC/formamide at 50° C. and with 1×SSC.

Nucleic acid arrays include those in which already formed nucleic acids such as cDNAs are deposited (or "spotted") on the array in a specific location. Nucleic acids can be spotted onto a surface by piezoelectrically deposition, UV crosslinking of nucleic acids to polymer layers such as but not limited to poly-L-lysine or polypyrrole, direct conjugation to silicon coated $SiO_2$ as described in published US patent application 2003/0186262, direct conjugation to a silanised chemFET surface (e.g., a surface treated with 3-aminopropyltriethoxysilane (APTES) as described by Uslu et al. Biosensors and Bioelectronics 2004, 19:1723-1731, for example.

Nucleic acid arrays also include those in which nucleic acids (such as oligonucleotides of known sequence) are synthesized directly on the array. Nucleic acids can be synthesized on arrays using art-recognized techniques such as but not limited to printing with fine-pointed pins onto glass slides, photolithography using pre-made masks, photolithography using dynamic micromirror devices (such as DLP mirrors), ink-jet printing, or electrochemistry on microelectrode arrays. Reference can also be made to Nuwaysir et al. 2002 "Gene expression analysis using oligonucleotide arrays produced by maskless photolithography.". Genome Res 12: 1749-1755. Commercial sources of this latter type of array include Agilent, Affymetrix, and NimbleGen. Thus the chemFET passivation layer may be coated with an intermediate layer of reactive molecules (and therefore reactive groups) to which the nucleic acids are bound and/or from which they are synthesized.

The invention contemplates combining such nucleic acid arrays with the chemFET arrays and particularly the "large scale" chemFET arrays described herein. The chemFET/nucleic acid array can be used in a variety of applications, some of which will not require the wells (or microwells or reaction chambers, as they are interchangeably referred to herein). Since analyses may still be carried out in flow, including in a "closed" system (i.e., where the flow of reagents and wash solutions and the like is automated), there will be one or more flow chambers situated above and in contact with the array. The use of multiple flow chambers allows multiple samples (or nucleic acid libraries) to be analyzed simultaneously. There may be 2, 3, 4, 5, 6, 7, 8, 9, 10 or more flow chambers. This configuration applies equally to other biological arrays including those discussed herein such as protein arrays, antibody arrays, enzyme arrays, chemical arrays, and the like.

Since the binding event between binding partners or between components of a complex is detected electronically via the underlying FET, such assays may be carried out without the need to manipulate (e.g., extrinsically label) the sample being assayed. This is advantageous since such manipulation invariably results in loss of sample and generally requires increased time and work up. In addition, the present method allows binding interactions to be studied in real time.

Protein arrays used in combination with the chemFET arrays of the invention are also contemplated. Protein arrays comprise proteins or peptides or other amino acid comprising biological moiety bound to a planar surface in an organized and predetermined manner. Such proteins include but are not limited to enzymes, antibodies and antibody fragments or antibody mimics (e.g., single chain antibodies).

In one embodiment, a protein array may comprise a plurality of different proteins (or other amino acid containing biological moieties). Each protein, and preferably a plurality of proteins, is present in a predetermined region or "cell" of the array. The regions (or cells) are aligned with the sensors in the sensor array such that there is one sensor for each region (or cell). The plurality of proteins in a single region (or cell) may vary depending on the size of the protein and the size of the region (or cell) and may be but is not limited to at least 10, 50, 100, 500, $10^3$, $10^4$ or more. The array itself may have any number of cells, including but not limited to at least 10, $10^2$, $10^3$, $10^4$, $10^5$, $10^6$, $10^7$, or more. In one application, the array is exposed to a sample that is known to contain or is suspected of containing an analyte that binds to the protein. The analyte may be a substrate or an inhibitor if the protein is an enzyme. The analyte may be any molecule that binds to the protein including another protein, a nucleic acid, a chemical species (whether synthetic or naturally occurring), and the like.

It is to be understood that, like the nucleic acid arrays contemplated herein, the readout from the protein arrays will be a change in current through the chemFET and thus no additional step of labeling and/or label detection is required in these array methods.

In another embodiment, the protein array may comprise a plurality of identical proteins (or other amino acid containing biological moieties). The identical proteins may be uniformly distributed on a planar surface or they may be organized into discrete regions (or cells) on that surface. In these latter embodiments, the regions (or cells) are aligned with the sensors in the sensor array such that there is one sensor for each region (or cell).

The proteins may be synthesised off-chip, then purified and attached to the array. Alternatively they can be synthesised on-chip, similarly to the nucleic acids discussed above. Synthesis of proteins using cell-free DNA expression or chemical synthesis is amenable to on-chip synthesis. Using cell-free DNA expression, proteins are attached to the solid support once synthesized. Alternatively, proteins may be chemically synthesized on the solid support using solid phase peptide synthesis. Selective deprotection is carried out through lithographic methods or by SPOT-synthesis. Reference can be made to at least MacBeath and Schreiber, Science, 2000, 289:1760-1763, or Jones et al. Nature, 2006, 439:168-174. Reference can also be made to U.S. Pat. No. 6,919,211 to Fodor et al.

Chemical compound microarrays in combination with chemFET arrays are also envisioned. Chemical compound microarrays can be made by covalently immobilizing the compounds (e.g., organic compounds) on the solid surface with diverse linking techniques (may be referred to in the literature as "small molecule microarray"), by spotting and drying compounds (e.g., organic compounds) on the solid surface without immobilization (may be referred to in the literature as "micro arrayed compound screening (µARCS)"), or by spotting organic compounds in a homogenous solution without immobilization and drying effect (commercialized as DiscoveryDot™ technology by Reaction Biology Corporation).

Tissue microarrays in combination with chemFET arrays are further contemplated by the invention. Tissue microarrays are discussed in greater detail in Battifora Lab Invest 1986, 55:244-248; Battifora and Mehta Lab Invest 1990, 63:722-724; and Kononen et al. Nat Med 1998, 4:844-847.

The configurations of the chemFET arrays and the biological or chemical arrays are similar in each instance and the discussion of one combination array will apply to others described herein or otherwise known in the art.

In yet another aspect, the invention contemplates analysis of cell cultures (e.g., two-dimensional cells cultures) (see for example Baumann et al. Sensors and Actuators B 55 1999 77:89), and tissue sections placed in contact with the chemFET array. As an example, a brain section may be placed in contact with the chemFET array of the invention and changes in the section may be detected either in the presence or absence of stimulation such as but not limited to neurotoxins and the like. Transduction of neural processes and/or stimulation can thereby be analyzed. In these embodiments, the chemFETs may operate by detecting calcium and/or potassium fluxes via the passivation layer itself or via receptors for these ions that are coated onto the passivation layer.

In yet another aspect, the invention contemplates the use of chemFET arrays, functionalized as described herein or in another manner, for use in vivo. Such an array may be introduced into a subject (e.g., in the brain or other region that is subject to ion flux) and then analyzed for changes based on the status of the subject.

Methods for attaching nucleic acids, proteins, molecules, and the like to solid supports, particularly in the context of an array, have been described in the art. See for example Lipshutz et al. Nat. Genet. (supplement) 1999 21:20-24; Li et al. *Proc. Natl. Acad. Sci.,* 2001, 98:31-36; Lockhart et al. Nat. Biotechnol. 1996 14:1675-1680; Wodicka et al. *Nat. Biotechnol.* 1997 15: 1359-1367; Chen et al. Journal of Biomedical Optics 1997 2:364; Duggan et al. Nat Genet. 1991 21(1 Suppl):10-4; Marton et al. Nat. Med. 1998 4(11):1293-301; Kononen et al. Nat Med 1998 4(7):844-847; MacBeath et al., Science 2000 289(5485):1760-1763; Haab et al. Genome Biology 2001 2(2); Pollack et al. Nat Genet. 1999 23(1):41-6; Wang D G et al. Science 1998 280(5366):1077-82; Fodor et al. Science 1991 251:767-773; Fodor et al. Nature 1993 364: 555-556; Pease et al. Proc. Natl. Acad. Sci. USA 1994 91:5022-5026; Fodor Science 1997 277:393-395; Southern et al. Genomics 1992 13: 1008-1017; Schena et al. Science 1995 270(5235):467-70; Shalon et al. Genome Res 1996 6(7):639-45; Jongsma Proteomics 2006, 6:2650-2655; Sakata, Biosensors and Bioelectronics 2007, 22: 1311-1316.

The systems described herein can be used for sequencing unlabeled biological polymers without optical detection.

In some embodiments, the invention encompasses a sequencing apparatus adapted for sequencing unlabeled biological polymers without optical detection and comprising an array of at least 100 reaction chambers.

Typically, each reaction chamber is capacitively coupled to a chemFET.

Preferably, each reaction chamber is no greater than about 0.39 pL in volume and about 49 μm² surface aperture, and more preferably has an aperture no greater than about 16 μm² and volume no greater than about 0.064 pL. Preferably, the array has at least 1,000, 10,000, 100,000, or 1,000,000 reaction chambers.

Typically, the reaction chambers comprise microfluidic wells.

Preferably, the apparatus is adapted to sequence at least $10^6$ base pairs per hour, more preferably at least $10^7$ base pairs per hour, and most preferably at least $10^8$ base pairs per hour.

In another embodiment, the invention encompasses a method for sequencing a biological polymer with the above-described apparatus comprising measuring time of incorporation of individual monomers into an elongating polymer.

Typically, the biological polymer is a nucleic acid template and the monomer is a nucleotide. Preferably, the nucleic acid template has 200-700 base pairs. Preferably, the nucleic acid template is amplified prior to determining the sequence.

Typically, the measuring is performed under diffusion limited conditions. The measuring may comprise detecting an electrical change, detecting an ion pulse, or detecting the release of inorganic pyrophosphate ("PPi"). Preferably, the incorporation takes place at an ionic strength no greater than 400 μM, wherein the concentration of $Mg^{2+}$ or $Mn^{2+}$ or other divalent cation is no greater than 100 μM. Preferably, at least $10^6$ base pairs are sequenced per hour, more preferably at least $10^7$ base pairs are sequenced per hour, and most preferably at least $10^8$ base pairs are sequenced per hour using the above-described method. Preferably the detecting is accomplished by an array of chemFETs as above described.

In some embodiments, the invention encompasses a method for determining a nucleic acid sequence comprising: performing at least 100 sequencing reactions simultaneously; and determining the sequence without the use of labels and without the use of optical detection.

The nucleic acid template used in this and other methods of the invention may be derived from a variety of sources by a variety of methods, all known to those of ordinary skill in the art. Templates may be derived from, but are not limited to, entire genomes of varying complexity, cDNA, mRNA or siRNA samples, or may represent entire populations, as in the various environmental and metabiome sequencing projects. Template nucleic acids may also be generated from specific subsets of nucleic acid populations including but not limited to PCR products, specific exons or regions of interest, or 16S or other diagnostic or identifying genomic regions.

Typically, the required starting material for sequencing is less than 3 μg of nucleic acids. Preferably, the template nucleic acid is amplified prior to sequencing. The template nucleic acid may be optionally bound to one or more beads prior to sequencing.

Typically, the determining step comprises measuring the amount of time it takes for one or more of a first monomer to incorporate into an elongating sequence. Typically, the incorporation of the monomer is measured under diffusion limited conditions. The measuring may comprise detecting an electrical change, detecting an ion pulse, or detecting the release of inorganic pyrophosphate ("PPi").

Preferably, at least $10^6$ base pairs are sequenced per hour, more preferably at least $10^7$ base pairs are sequenced per hour, and most preferably at least $10^8$ base pairs are sequenced per hour using the above-described method. Thus, the method may be used to sequence an entire human genome within about 24 hours, more preferably within about 20 hours, even more preferably within about 15 hours, even more preferably within about 10 hours, even more preferably within about 5 hours, and most preferably within about 1 hour. These rates may be achieved using multiple ISFET arrays as shown herein, and processing their outputs in parallel.

The following examples are included for purposes of illustration and are not intended to limit the scope of the invention.

EXAMPLES

Example 1

Bead Preparation

Binding of Single-Stranded Oligonucleotides to Streptavidin-Coated Magnetic Beads. Single-stranded DNA oligonucleotide templates with a 5' Dual Biotin tag (HPLC purified), and a 20-base universal primer were ordered from IDT (Integrated DNA Technologies, Coralville, Ind.). Templates were 60 bases in length, and were designed to include 20 bases at the 3' end that were complementary to the 20-base primer (Table 3, italics). The lyophilized and biotinylated templates and primer were re-suspended in TE buffer (10 mM Tris-HCl, 1 mM EDTA, pH 8) as 40 μM stock solutions and as a 400 μM stock solution, respectively, and stored at −20° C. until use.

For each template, 60 μl of magnetic 5.91 μm (Bangs Laboratories, Inc. Fishers, Ind.) streptavidin-coated beads, stored as an aqueous, buffered suspension ($8.57 \times 10^4$ beads/ μL), at 4° C., were prepared by washing with 120 μl bead wash buffer three times and then incubating with templates 1, 2, 3 and 4 (T1, T2, T3, T4: Table 3) with biotin on the 5' end, respectively.

Due to the strong covalent binding affinity of streptavidin for biotin (Kd~10-15), these magnetic beads are used to immobilize the templates on a solid support, as described below. The reported binding capacity of these beads for free biotin is 0.650 pmol/μL of bead stock solution. For a small (<100 bases) biotinylated ssDNA template, it was conservatively calculated that $9.1 \times 10^5$ templates could be bound per bead. The beads are easily concentrated using simple magnets, as with the Dynal Magnetic Particle Concentrator or MPC-s (Invitrogen, Carlsbad, Calif.). The MPC-s was used in the described experiments.

An MPC-s was used to concentrate the beads for 1 minute between each wash, buffer was then added and the beads were resuspended. Following the third wash the beads were resuspended in 120 μL bead wash buffer plus 1 μl of each template (40 μM). Beads were incubated for 30 minutes with rotation (Labquake Tube Rotator, Barnstead, Dubuque, Iowa). Following the incubation, beads were then washed three times in 120 μL Annealing Buffer (20 mM Tris-HCl, 5 mM magnesium acetate, pH 7.5), and re-suspended in 60 μL of the same buffer.

TABLE 3

Sequences for Templates 1, 2, 3, and 4

T1: 5'/52Bio/GCA AGT GCC CTT AGG CTT CAG TTC AAA AGT CCT AAC TGG GCA AGG CAC ACA GGG GAT AGG-3' (SEQ ID NO: 1)

T2: 5'/52Bio/CCA TGT CCC CTT AAG CCC CCC CCA TTC CCC CCT GAA CCC CCA AGG CAC ACA GGG GAT AGG-3' (SEQ ID NO: 2)

T3: 5'/52Bio/AAG CTC AAA AAC GGT AAA AAA AAG CCA AAA AAC TGG AAA ACA AGG CAC ACA GGG GAT AGG-3' (SEQ ID NO: 3)

T4: 5'/52Bio/TTC GAG TTT TTG CCA TTT TTT TTC GGT TTT TTG ACC TTT TCA AGG CAC ACA GGG GAT AGG-3' (SEQ ID NO: 4)

Annealing of Sequencing Primer. The immobilized templates, bound at the 5' end to 5.91 μm magnetic beads, are then annealed to a 20-base primer complementary to the 3' end of the templates (Table 3). A 1.0 μL aliquot of the 400 μM primer stock solution, representing a 20-fold excess of primer to immobilized template, is then added and then the beads plus template are incubated with primer for 15 minutes at 95° C. and the temperature was then slowly lowered to room temperature. The beads were then washed 3 times in 120 of 25 mM Tricine buffer (25 mM Tricine, 0.4 mg/ml PVP, 0.1% Tween 20, 8.8 mM Magnesium Acetate; ph 7.8) as described above using the MPC-s. Beads were resuspended in 25 mM Tricine buffer.

Incubation of Hybridized Templates/Primer with DNA Polymerase. Template and primer hybrids are incubated with polymerase essentially as described by Margulies et al. Nature 2005 437(15):376-380 and accompanying supplemental materials.

Loading of Prepared Test Samples onto the ISFET Sensor Array. The dimensions and density of the ISFET array and the microfluidics positioned thereon may vary depending on the application. A non-limiting example is a 512×512 array. Each grid of such an array (of which there would be 262144) has a single ISFET. Each grid also has a well (or as they may be interchangeably referred to herein as a "microwell") positioned above it. The well (or microwell) may have any shape including columnar, conical, square, rectangular, and the like. In one exemplary conformation, the wells are square wells having dimensions of 7×7×10 μm. The center-to-center distance between wells is referred to herein as the "pitch". The pitch may be any distance although it is preferably to have shorter pitches in order to accommodate as large of an array as possible. The pitch may be less than 50 μm, less than 40 μm, less than 30 μm, less than 20 μm, or less than 10 μm. In one embodiment, the pitch is about 9 μm. The entire chamber above the array (within which the wells are situated) may have a volume of equal to or less than about 30 μL, equal to or less than about 20 μL, equal to or less than about 15 μL, or equal to or less than 10 μL. These volumes therefore correspond to the volume of solution within the chamber as well.

Loading of Beads in an 'Open' System. Beads with templates 1-4 were loaded on the chip (10 μL of each template). Briefly, an aliquot of each template was added onto the chip using an Eppendorf pipette. A magnet was then used to pull the beads into the wells.

Loading of Beads in a 'Closed' System. Both the capture beads the packing beads are loaded using flow. Microliter precision of bead solution volume, as well as positioning of the bead solution through the fluidics connections, is achieved as shown in FIGS. 62-70 using the bead loading fitting, which includes a major reservoir (approx. 1 mL in volume), minor reservoir (approx. 10 μL in volume), and a microfluidic channel for handling small volumes of bead solution. This method also leverages the microliter precision of fluid application allowed by precision pipettes.

The chip comprising the ISFET array and flow cell is seated in the ZIF (zero insertion force) socket of the loading fixture, then attaching a stainless steel capillary to one port of the flow cell and flexible nylon tubing on the other port. Both materials are microfluidic-type fluid paths (e.g., on the order of <0.01" inner diameter). The bead loading fitting, consisting of the major and minor reservoirs, it attached to the end of the capillary. A common plastic syringe is filled with buffer solution, then connected to the free end of the nylon tubing. The electrical leads protruding from the bottom of the chip are inserted into a socket on the top of a fixture unit (not shown).

The chip comprising the ISFET array and flow cell is seated in a socket such as a ZIF (zero insertion force) socket of the loading fixture, then a stainless steel capillary may be attached to one port of the flow cell and flexible nylon tubing on the other port. Both materials are microfluidic-type fluid paths (e.g., on the order of <0.01" inner diameter). The bead loading fitting, consisting of the major and minor reservoirs, it attached to the end of the capillary. A common plastic syringe is filled with buffer solution, then connected to the free end of the nylon tubing. The electrical leads protruding from the bottom of the chip are inserted into a socket on the top of a fixture unit (not shown).

It will be appreciated that there will be other ways of drawing the beads into the wells of the flow chamber, including centrifugation or gravity. The invention is not limited in this respect.

DNA Sequencing using the ISFET Sensor Array in an Open System. A illustrative sequencing reaction can be performed in an 'open' system (i.e., the ISFET chip is placed on the platform of the ISFET apparatus and then each nucleotide (5 μL resulting in 6.5 μM each) is manually added in the following order: dATP, dCTP, dGTP and dTT (100 mM stock solutions, Pierce, Milwaukee, Wis.), by pipetting the given nucleotide into the liquid already on the surface of the chip and collecting data from the chip at a rate of 2.5 mHz. This can result in data collection over 7.5 seconds at approximately 18 frames/second. Data may then analyzed using LabView.

Given the sequences of the templates, it is expected that addition of dATP will result in a 4 base extension for template 4. Addition of dCTP will result in a 4 base extension in template 1. Addition of dGTP will cause template 1, 2 and 4 to extend as indicated in Table 4 and addition of dTTP will result in a run-off (extension of all templates as indicated).

Preferably when the method is performed in a non-automated manner (i.e., in the absence of automated flow and reagent introduction), each well contains apyrase in order to degrade the unincorporated dNTPs, or alternatively apyrase is added into each well following the addition and incorporation of each dNTP (e.g., dATP) and prior to the addition of another dNTP (e.g., dTTP). It is to be understood that apyrase can be substituted, in this embodiment or in any other embodiment discussed herein, with another compound (or enzyme) capable of degrading dNTPs.

TABLE 4

Set-up of experiment and order of nucleotide addition.

| | dATP | dCTP | dGTP | dTTP |
|---|---|---|---|---|
| T1 | 0 | (3:C; 1:A)4 | 1 | Run-off (25) |
| T2 | 0 | 0 | 4 | Run-off (26) |
| T3 | 0 | 0 | 0 | Run-off (30) |
| T4 | 4 | 0 | 2 | Run-off (24) |

DNA Sequencing Using Microfluidics on Sensor Chip. Sequencing in the flow regime is an extension of open application of nucleotide reagents for incorporation into DNA. Rather than add the reagents into a bulk solution on the ISFET chip, the reagents are flowed in a sequential manner across the chip surface, extending a single DNA base(s) at a time. The dNTPs are flowed sequentially, beginning with dTTP, then dATP, dCTP, and dGTP. Due to the laminar flow nature of the fluid movement over the chip, diffusion of the nucleotide into the microwells and finally around the nucleic acid loaded bead is the main mechanism for delivery. The flow regime also ensures that the vast majority of nucleotide solution is washed away between applications. This involves rinsing the chip with buffer solution and apyrase solution following every nucleotide flow. The nucleotides and wash solutions are stored in chemical bottles in the system, and are flowed over the chip using a system of fluidic tubing and automated valves. The ISFET chip is activated for sensing chemical products of the DNA extension during nucleotide flow.

Example 2

Low Ionic Strength Effects on Polymerase Activity

Experiments were conducted to test various polymerases for certain functionalities associated with the sequencing aspects and embodiments discussed herein, including in particular low ionic strength nucleotide incorporation reactions. These functionalities include the ability of a polymerase to extend a sequencing primer in low ionic strength, affinity of a polymerase for primer/template nucleic acid hybrids in low ionic strength, rate of primer extension, and ability of polymerase to extend primers in the context of a well situated above a chemFET sensor. Each of these functionalities will be discussed below.

Figure 72A:
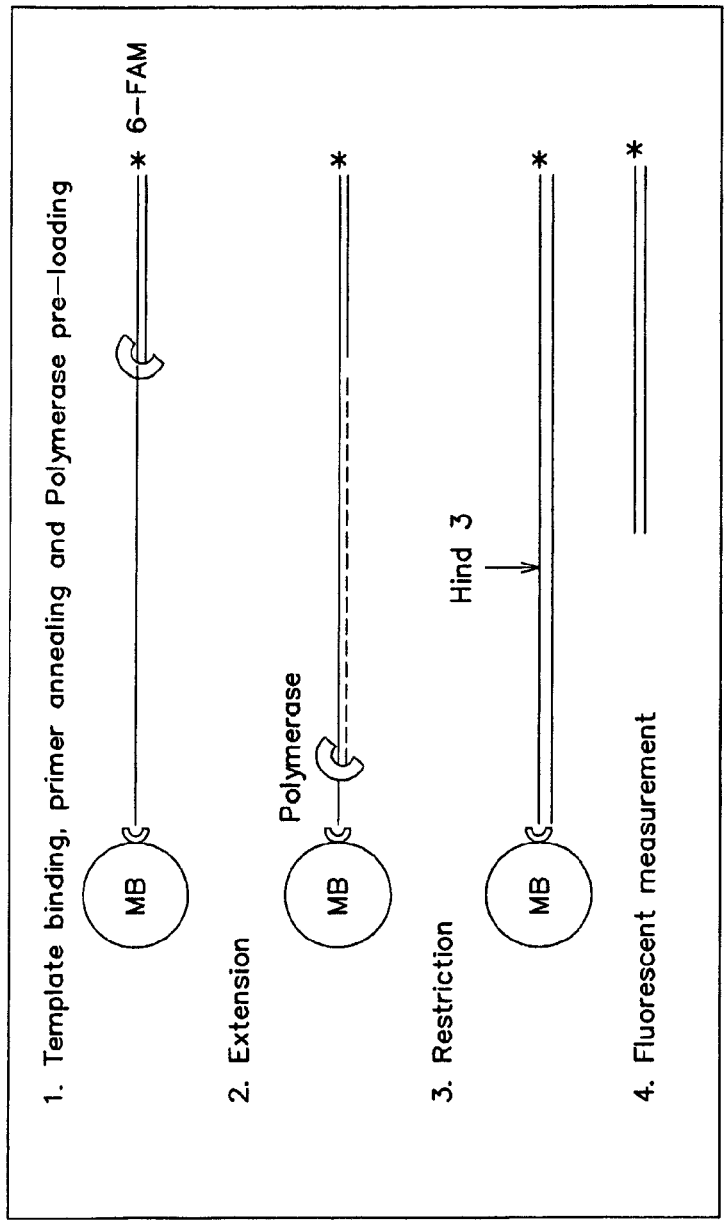

Polymerase Activity in Low Ionic Strength. Polymerase activity can be measured by determining the extent to which a primer is extended along a template. A fluorescent reporter assay was devised to measure polymerase activity (FIG. 72A). Briefly, a fluorescently-labeled DNA oligonucleotide (referred to in the context of this Example as the template) is attached to superparamagnetic beads via a streptavidin-biotin interaction. The 5' end of the template is labeled with biotin and the 3' end is labeled with for example 6-FAM. The beads are labeled with streptavidin. A DNA oligonucleotide primer complementary to the 3' end of the template is annealed to the template, and the beads are incubated with polymerases in an extension solution containing buffer, salt and dNTP for sufficient time for extension of the primer based on the template sequence. After the incubation the polymerase and other reaction components are removed by serial washing of the beads. If the primer is extended through a predetermined restriction enzyme recognition site, the fluorescently-labeled double stranded DNA will be released when incubated with the proper endonuclease (e.g., HindIII). The supernatant from the restriction digestion is then subjected to fluorescence quantification. The magnitude of the released fluorescence is proportional to the amount of DNA released by restriction endonuclease activity, which is proportional to the amount of double-stranded DNA present on the bead, which in turn is proportional to the polymerase activity.

Figure 72C:
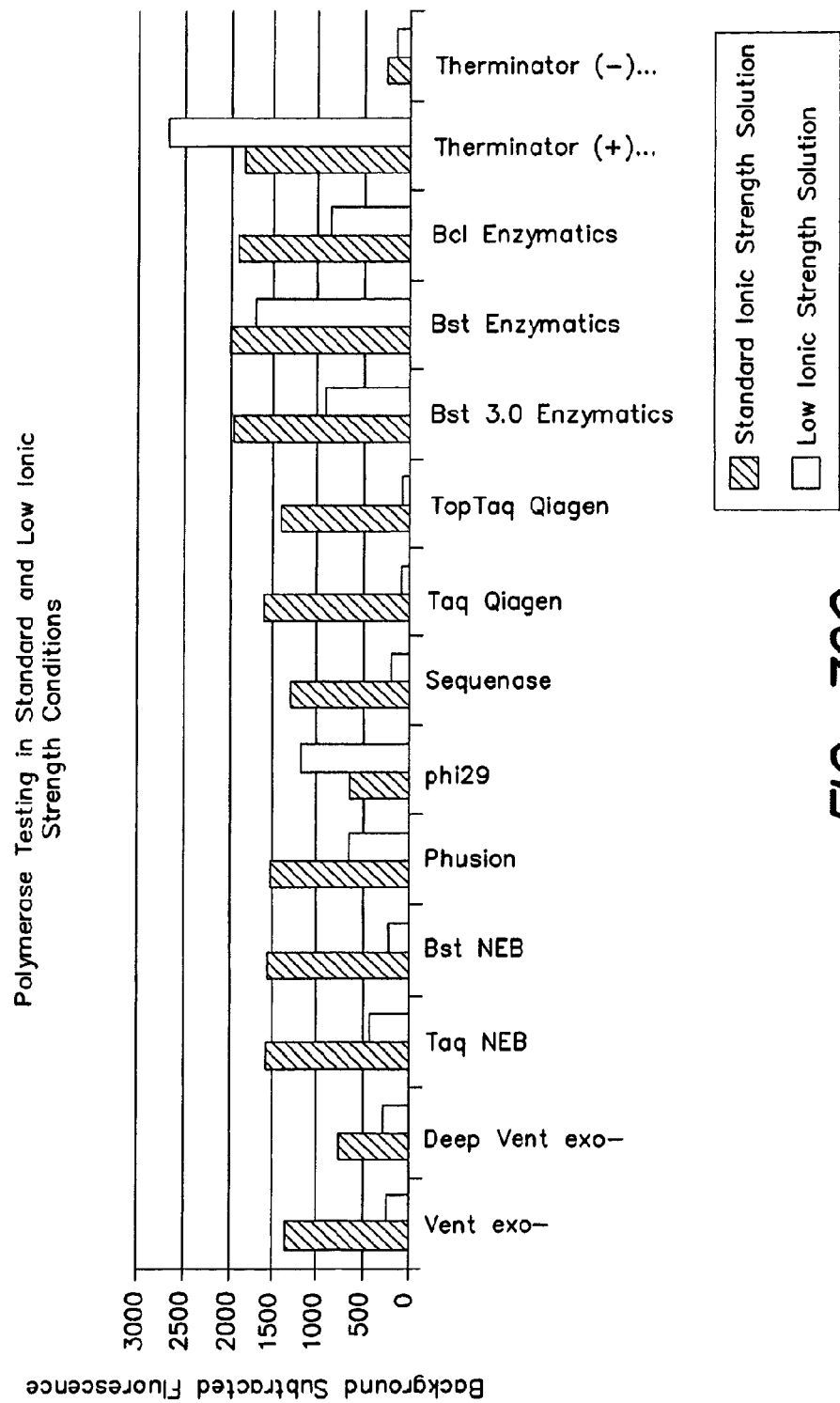

In particular, the data shown in FIGS. 72B and 72C was generated by binding polymerases to bead-immobilized, primer/template hybrids in the absence of dNTPs. After washing away unbound polymerase and binding solution components, the indicated extension mix (e.g., standard or low ionic strength) supplemented with dNTPs was added to the beads and incubated for 10 minutes at 40° C. The activity assay was subsequently completed as described above to measure the activity of the indicated polymerases and the background subtracted fluorescence is plotted. In FIG. 72C "Therminator(+)" indicates the addition of dNTPs in the extension solution, and "Therminator(−)" indicates the absence of dNTPs in the extension solution i.e. a positive and negative control, respectively.

Using this assay polymerase activity has been measured in both standard and low ionic strength reaction conditions. A number of polymerases are relatively active in low ionic strength conditions when compared to standard conditions (FIGS. 72B and 72C).

Figure 73:
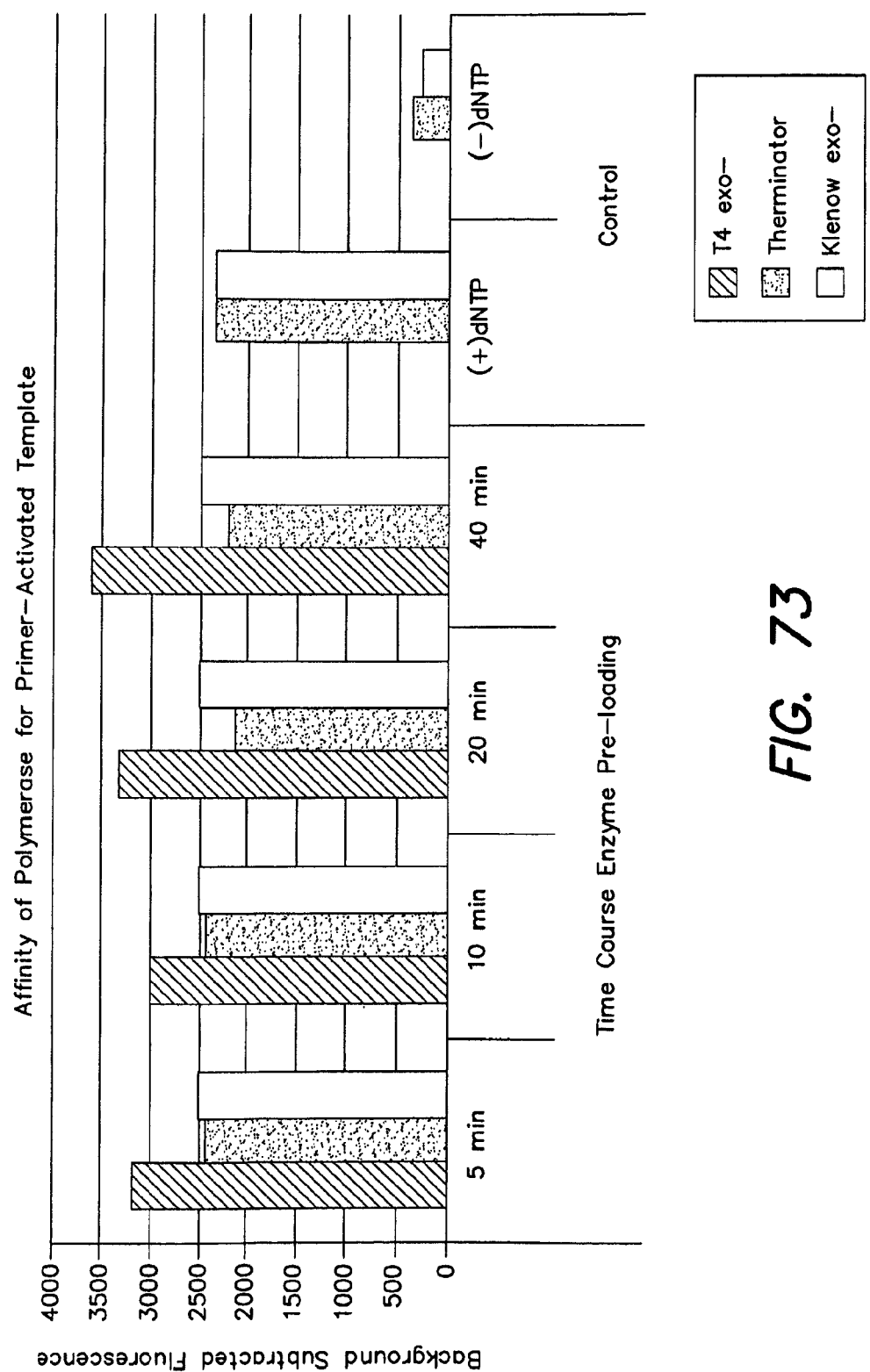
FIG. 73 provides data relating to polymerase affinity in low ionic strength.

Polymerase Affinity in Low Ionic Strength. The affinity of a polymerase for a template/primer hybrid can be measured indirectly with our standard assay (FIG. 72A). Three different DNA polymerases (T4exo−, Therminator, Klenow exo−) were bound to a primer-activated, bead-immobilized template (FIG. 72A, step 1) in a standard extension solution without dNTP for 15 minutes at room temperature. Beads are then washed to remove unbound polymerase and other components, and then resuspended and incubated in a low ionic strength solution (e.g., 0.5 mM Tris, 100 µM $MgCl_2$, pH 9.0 at 25° C.) at 40° C. After the times indicated in FIG. 73, the beads were washed and resuspended in low ionic strength solution (e.g., 0.5 mM Tris, 100 µM $MgCl_2$, pH 9.0 at 25° C. for Therminator and Klenow exo− or 0.5 mM Tris, 80 µM MgCl2, pH 9.0 at 25° C. for T4 exo−) supplemented with 20 µM each dNTP. If the polymerase has a low affinity for the template/primer hybrid it would be expected to fall off and be washed away, and as a result there would be no primer extension. However, if the polymerase has a high affinity for the template/primer hybrid it would remain bound and could extend the template when incubated with dNTP. The amount of extended primer is measured using our standard assay (FIG. 72A) and is plotted in FIG. 73. Primer extension was equivalent at all time points suggesting that all three polymerases bind tightly to the primer-activated template for 40 minutes when incubated at 40° C. As a positive control (indicated as "(+)dNTP") primer extension without prebinding of the polymerase to primer-activated template was measured, and as a negative control (indicated as "(–) dNTP") fluorescence was measured if dNTPs were not added to extension solution. T4 exo– polymerase (3' to 5' exonuclease deficient), Therminator, and Klenow exo– extend primer after incubation for 40 minutes in low ionic strength solution suggesting that all three polymerases have a high affinity for template/primer hybrid in low ionic strength (FIG. 73).

Figure 74A:
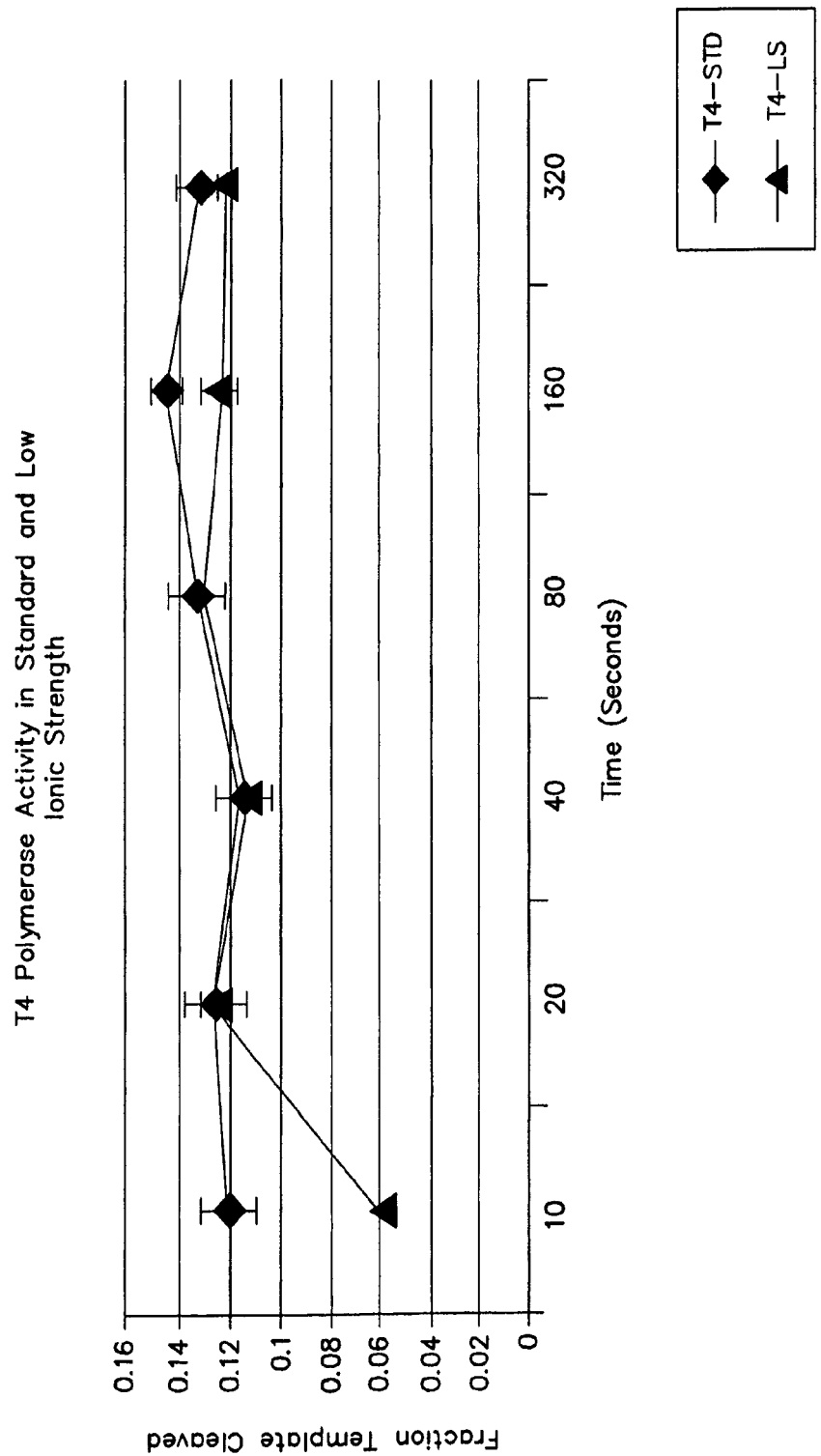
Figure 74C:
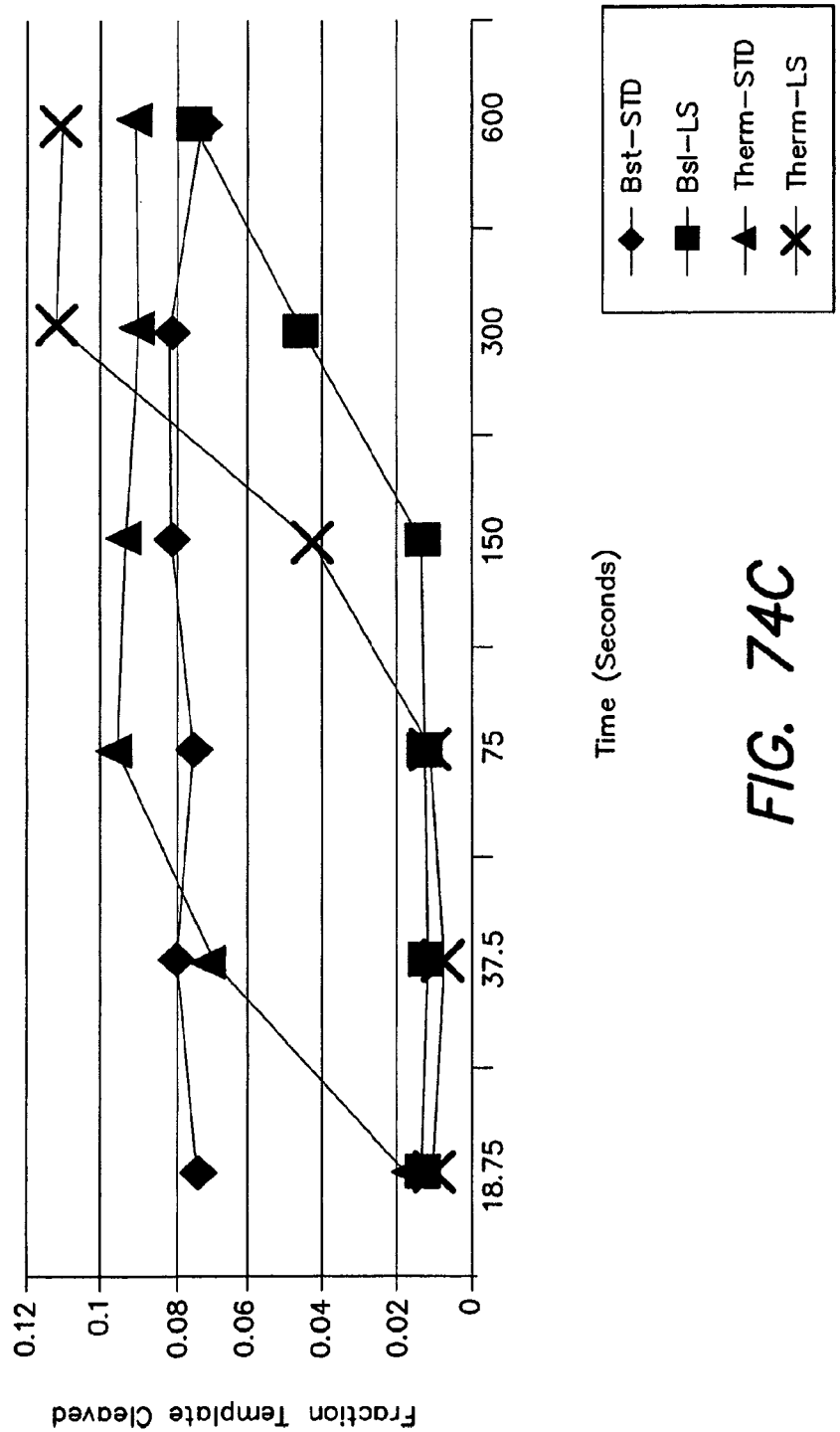

Rates of Polymerases. The rate at which a polymerase can extend a primer along a template can be measured with a standard assay by measuring the fraction of template extended per unit time. T4 exo– polymerase (3' to 5' exonuclease deficient) extends primer in both standard reaction conditions (STD; 10 mM Tris-HCl, 50 mM NaCl, 10 mM $MgCl_2$, 1 mM dithiothreitol, 20 µM each dNTP, pH 7.9 at 25° C.) and in low ionic strength conditions (LS; 0.5 mM Tris, 80 µM $MgCl_2$, 20 µM each dNTP, pH 9.0 at 25° C.), but at different rates. Previous studies of T4 demonstrate that T4 can extend a primer along a template at a maximal steady state rate of 4 nucleotides per second in a standard reaction solution (i.e., at standard ionic strength). At this rate, extension in the standard reaction solution is expected to be complete in 8.75 seconds, and indeed extension is complete at about 10 seconds experimentally (FIG. 74A, T4-STD). In low ionic strength reaction solution T4 completes extension in 20 seconds suggesting a two fold decrease. Furthermore, when the reaction solution is 0.5 mM Tris, 20 µM $MgCl_2$ and 5 µM of each dNTP the rate of T4 decreases by about twofold relative to 80 µM $MgCl_2$ and 20 µM for each dNTP (i.e., the low ionic strength solution of FIG. 74A, see FIG. 74B) and fourfold relative to 10 mM $MgCl_2$ and 20 µM for each dNTP (i.e., the standard solution of FIG. 74A, data not shown). T4 has been reported to polymerize with biphasic kinetics including an initial burst of polymerization (or incorporation) followed by a slower polymerization rate. This initial burst of polymerization can compensate for the slightly reduced rate observed at low ionic strength. (Capson et al. Biochemistry 1992 31:10984-10994.)

Therminator and Bst polymerases can extend primer in both standard reaction conditions (STD; 20 mM Tris-HCl, 10 mM $(NH2)_2SO_4$, 10 mM KCl, 2 mM $MgSO_4$, 0.1% Triton X-100, pH 8.8 at 25° C.) and in low ionic strength conditions (LS; 0.5 mM Tris, 100 µM $MgCl_2$, 20 µM each dNTP, pH 9.0 at 25° C.). The steady state rate in low ionic strength conditions is slower than extension by these polymerases in standard ionic strength conditions, and it is slower than the steady state rate of T4 primer extension in low ionic strength extension solutions.

Figure 75A:
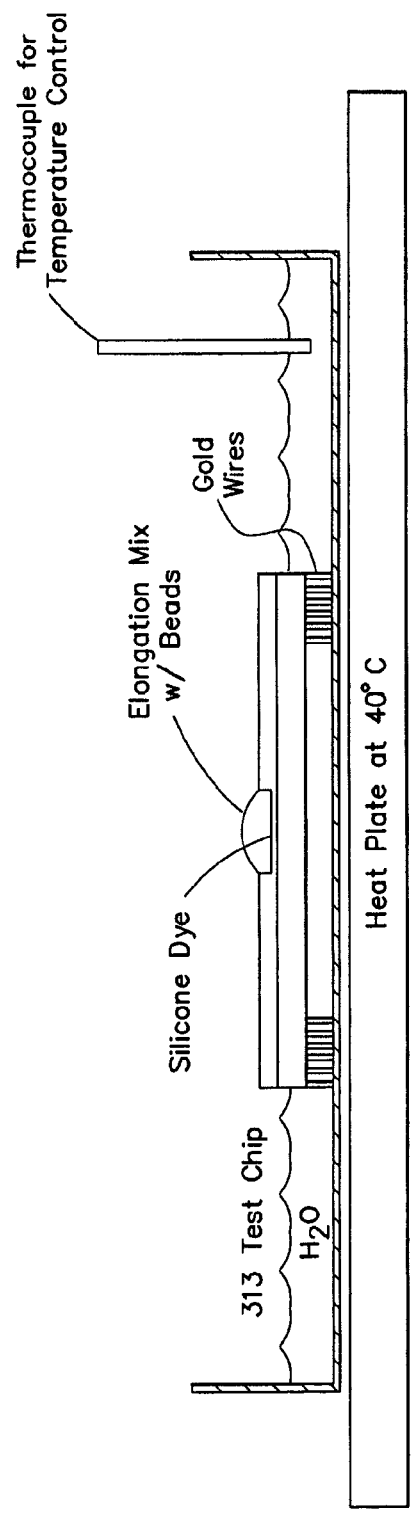
FIG. 75A-B illustrate the well and sensor system used to assay primer extension (A) and the results of such extension assays (B).
Figure 75B:
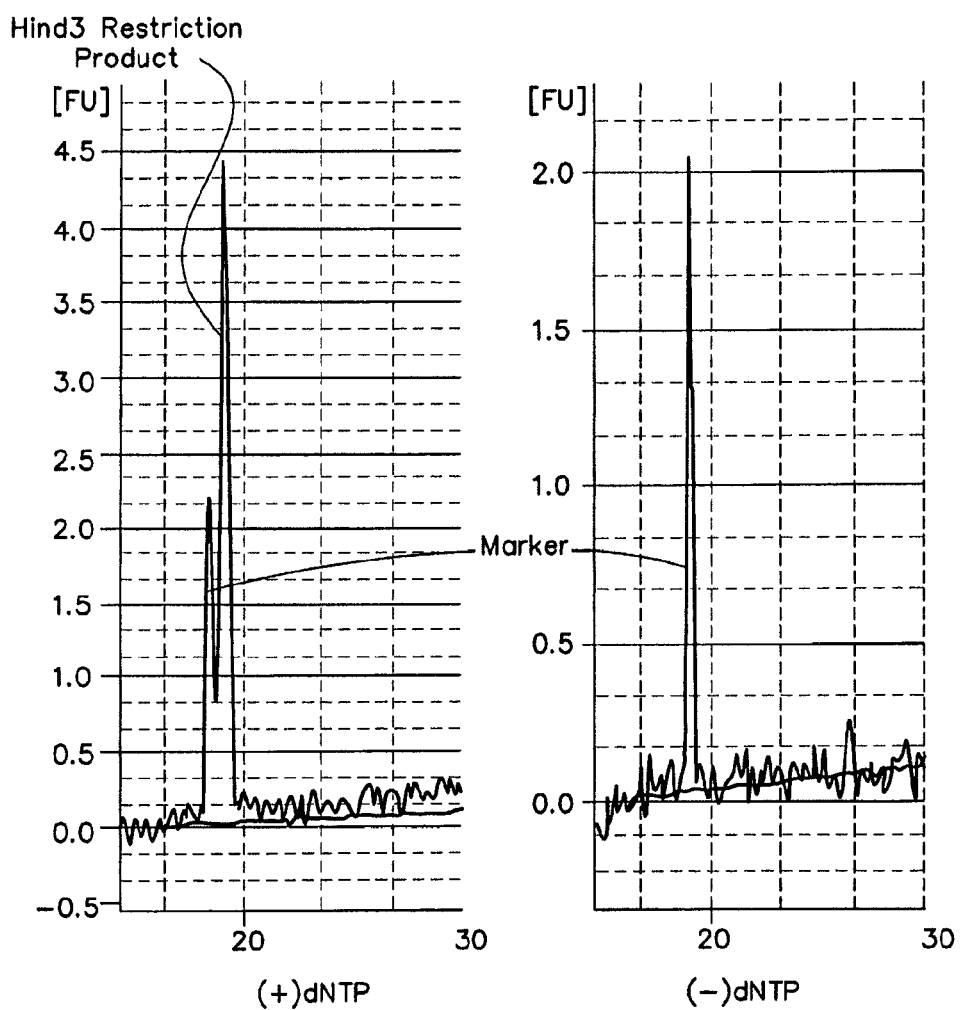

Primer Extension in Wells of Sensor. Using an assay similar to the standard activity assay (FIG. 72A) primer extension was tested in the silicon wells of a chemFET sensor to determine whether or not the sensor well wall material inhibits the polymerase. This assay differs from those described above only in that the template is not labeled with 6-FAM. Beads with polymerase-bound primer-activated template were pipetted onto the silicon dye (as shown in FIG. 75A), incubated for 1 minute at 40° C. followed by the addition of dNTPs in a low salt buffer. After the incubation the beads are recovered from the chip and subjected to a standard restriction digest. Primer extension was measured by DNA fragment separation using a BioAnalyzer. The addition of dNTPs resulted in a fragment whereas the reaction without dNTPs did not, suggesting that the sensor well wall material does not inhibit polymerase extension of the primer (FIG. 75B).

Example 3

Increasing Speed and Throughput

One advantage of the array architecture used on the ISFET/chemFET chips is that all microwells receive and process chemical materials in parallel and the outputs of the FETs are analyzed in parallel. While a single chip is limited to N wells and the number N will increase over time as semiconductor processes shrink devices ever smaller, no matter how many FETs and wells (also known as reaction chambers) are on a single chip, a system may readily be build with two or more chips in the same machine, operated in parallel; or multiple machines may be operated in parallel and as their FETs provide output, those outputs can be processed in parallel to reduce the time required to sequence a genome or perform another analysis. Parallel computing is well known and there are multiple known ways for computer scientists to configure the processing of the outputs of several chips to expedite the computation of the desired output. Hence, with multiple chips, each having 256 k or more microwells, it is readily achievable to extract from a sample a human genome in a span of one or just a few hours. As chip speeds increase and device sizes shrink, these times may be achievable with a single chip.

Having explained the theory and objective of the ion pulse detection approach, above, it may be helpful to some to provide basic examples of conditions that appear useful, based on simulation, in some circumstances, for achieving detection of DNA sequencing reactions.

The ions in solution. The ionic strength is a factor that is involved in determining the ion pulse response. It is helpful to limit the ions in the reaction buffer. Assuming 0.5 mM Tris and use of CF to balance the charge, the following may be determined:

| Species | Concentration (mM) |
| --- | --- |
| Tris | 0.452 |
| Tris-$H^+$ | 0.048 |
| $Cl^-$ | 0.048 |

Consider the case of 0.5 mM Tris, as other concentrations of Tris (e.g. 5-20 mM) are given by scaling the above concentrations. Assume the pH is constant at 8.8. The other species in the solution include the reactants and products:

| Species | Concentration dynamics (µM) |
| --- | --- |
| dNTP$^{---}$ | 0 → 6.5 |
| $H^+$ | $10^{-2.8}$ → transient → $10^{-2.8}$ |
| PPi$^{---}$ | 0 → transient → 0 |
| Pi$^{--}$ | 0 (if no PPi → Pi enzyme present) |

This is the situation for the reaction buffer, scaled to 0.5 mM Tris-HCl. It is assumed that all the $Mg^{++}$ is complexed to the enzyme by presoaking. From the solution of the reaction and diffusion equation for the sequencing reaction, the ionic strength is calculated, $I = \frac{1}{2}\Sigma_s q_s^2 C_s$, and the sensor dynamics is given by relationships set out above.

Since the concentration changes are small, it is possible to carry out an expansion of the ionic strength in concentration changes:

$$I=\{119.227+6.67[PPi]+2.78[Pi]+0.79[H+\text{ released}]-9.52(6.5\text{ μM}-[dNTP])\}\times 10^{-6} \quad (5)$$

The pH is 8.80.

For BST reaction buffer at 0.5 mM Tris, which contains ions and sulfuric acid:

$$I=\{1452.46+6.5[PPi]+2.87[Pi]+0.98[H+\text{ released}]-9.98(6.5\text{ μM}-[dNTP])\}\times 10^{-6} \quad (5')$$

For a 5 mM Tris buffer, the ionic strength is given by $$I=\{555.803+7.43[PPi]+2.92[Pi]+0.98[H+\text{ released}]-9.90(6.5\text{ μM}-[dNTP])\}\times 10^{-6} \quad (5'')$$

The pH is 9.03.

For a 0.5 mM Tris plus 1 mM MgCl$_2$, the ionic strength is given by $$I=\{3119.86+6.94[PPi]+2.78[Pi]+0.91[H+\text{ released}]-9.49(6.5\text{ μM}-[dNTP])\}\times 10^{-6} \quad (5''')$$

The pH is 8.81.

For a 5 mM Tris plus 1 mM MgCl$_2$, the ionic strength is given by $$I=\{3556.67+7.71[PPi]+2.93[Pi]+0.98[H+\text{ released}]-9.89(6.5\text{ μM}-[dNTP])\}\times 10^{-6} \quad (5'''')$$

The pH is 9.04.

For 0.5 mM Tris, the ionic strength is given by $$I=\{250.699+6.44[PPi]+2.83[Pi]+0.96[H+\text{ released}]-9.67(20\text{ μM}-[dNTP])\}\times 10^{-6} \quad (5''''')$$

The pH is 8.53 with the dNTP present and 8.97 without.

For 0.5 mM Tris plus 50 μM MgCl$_2$, the ionic strength is given by $$I=\{400.759+6.46[PPi]+2.84[Pi]+0.96[H+\text{ released}]-9.66(20\text{ μM}-[dNTP])\}\times 10^{-6} \quad (5'''''')$$

The pH is 8.53 with the dNTP present and 8.97 without.

Finally, consider a canonical buffer with pH=9 and ionic strength=300 mM in the absence of dNTP. The equation would be $$I=\{493.20+6.46[PPi]+2.84[Pi]+0.96[H+\text{ released}]-9.66(20\text{ μM}-[dNTP])\}\times 10^{-6} \quad (5''''''')$$

Note that the signal is proportional to $I^{-1/2}$, so it is desirable to keep the ionic strength of the reaction buffer solution as low as possible. Note that $(I_0+dI)^{-1/2}=I_0^{-1/2}-\frac{1}{2}(dI/I_0)I_0^{-1/2}$. Thus, the relative change to the signal is $-\frac{1}{2}(dI/I_0)$. By comparing Eqs. 5-5''''''', one sees that dI is roughly independent of the buffer ionic strength. Thus, if the initial ionic strength, $I_0$, is lower, the relative signal change is larger.

Reaction/Diffusion Calculation

The reactions that occur are $$d[DNA]/dt=-k_{bst}[dNTP][DNA]$$

$$d[PPi]/dt=k_{bst}[dNTP][DNA]$$

$$d[dNTP]/dt=k_{bst}[dNTP][DNA]$$

If the enzyme for the reaction PPi+H$_2$0→2Pi is present, then this reaction is assumed to occur instantaneously. All of these species diffuse with individual diffusion coefficients, except the DNA. The H$^+$ released by adding one more base of DNA, however, does diffuse.

A finite element method may be used to calculate the reaction and diffusion of these species. The method preferably is encoded in cylindrical coordinates. Reaction in each element follows the above scheme, with the note below about the effect of Mg$^{++}$ on the reaction rate. In addition, the diffusion of Mg$^{++}$ is also tracked. Recall that in the current calculations, however, Mg$^{++}$ is assumed to be constant.

The numerical code was a check against the analytical solution for diffusion into a cylinder of diameter D and depth H:

$$C(r,z,t)=c0-c0(2/\pi)\Sigma_{n=0}^{\infty}[e^{-D(n+1/2)^2\pi^2 2t/H^{2}/}(n+\tfrac{1}{2})]\sin[(n+\tfrac{1}{2})\pi z/H]$$

The results agreed to 0.1% accuracy if a grid of (D/2)/100 points in the r direction and H/100 points in the z direction are used.

To determine the parameter $k_{bst}$, the results from the Rothberg et al Nature paper were used. That paper presented a simplified, mass-transfer calculation of the relevant diffusion, from which the relevant reactions are $$d[DNA]/dt=-k_{bst}[dNTP][DNA]$$

$$d[PPi]/dt=k_{bst}[dNTP][DNA]-k_c([PPi])$$

$$d[dNTP]/dt=k_{bst}[dNTP][DNA]+k_c([dNTP]_0-[dNTP])$$

Summing the last two reactions, one finds $$d([PPi]+[dNTP])/dt=-k_{bst}[dNTP][DNA]-k_c([dNTP]_0-[PPi]-[dNTP])$$

These equations may be solved numerically to determine the values of $k_{bst}$ and $k_c$, yielding $k_{bst}$=2.38 (μM s)$^{-1}$ and $k_c$=0.2 s$^{-1}$ at 30° C.

The PPi→Pi Enzyme

The reaction PPi+H$_2$0→2Pi occurs at a finite rate. The rate constant in the presence of the enzyme and Mg$^{++}$ is about 10$^3$ s$^{-1}$ (Biochemistry 41 (2002) 12025). So, this reaction is over in 1 ms. Thus, one can say this conversion is instantaneous. However, in the absence of any enzyme or ionic catalyst, the rate constant is about 3$^{-1}$ years$^{-1}$ (J. Chem. Soc. Farady Trans, 93 (1007) 4295). In this case, the reaction does not proceed at all. Many ions, however, do catalyze this reaction to some extent. Thus, if this reaction is desired not to proceed, care must be taken that the solution is chosen so that no ions catalyzing the reaction are present.

Diffusion Coefficients

The signal due to the pH change from the sequencing reaction depends on the diffusion coefficients of the species involved. Reference (Biophys. J 78 (2000) 1657) gives values for Pi, PPi, and dNTP:

| Species | 10$^6$ D (cm$^2$/s) at 37° C. |
| --- | --- |
| Pi | 9.5 |
| PPi | 7.48 |
| ATP | 5.3 |

Reference (BBA 1291 (1996) 115) gives values for ATP over a temperature range. At 37° C., the value is 4.5×10$^{-6}$ cm$^2$/s, which is used herein. The values for Pi and PPi are calculated at temperature T by scaling the value above by the factor $D_{ATP}(T)/D_{ATP}(37° C.)$. The diffusion coefficients of the ions at 25° C. are (J. Chem. Phys. 119 (2003) 11342.)

| Species | 10$^5$ D (cm$^2$/s) at 25° C. |
| --- | --- |
| Mg++ | 1.25 (J. Amer. Chem. Soc. 77 (1955) 265) |
| Na+ | 1.33 (J. Chem. Phys. 119 (2003) 11342.) |

The diffusion coefficient of $H^+$ is assumed equal to that of $Na^+$, because by charge neutrality the $H^+$ must either diffusion with a negative ion as a pair, or the $H^+$ must exchange with another positive ion, of which the $N^+$ is the most rapidly diffusing.

One preferred implementation includes the use of small spheres (e.g. 0.1 µm) to decrease the diffusion coefficients of all the species. This shifts the pH curves to larger time by roughly the ratio that the diffusion coefficient is reduced. The textbook formula for the reduction of the diffusion coefficient is $$D_{eff}/D_0 = 2(1-\phi)/(2+\phi), \quad (6)$$

where $\phi$ is the volume fraction occupied by the spheres. The radius of the small spheres does not directly enter into this expression. For no spheres $\phi=0$. For randomly packed spheres, $\phi \approx 0.6$, and for close packed spheres, $\phi=0.74$.

Another approach is to use other methods to reduce the diffusion coefficient of the $H^+$, Pi, PPi, and dNTP. For example, the viscosity of the solution may be increased.

The Sequencing Reaction

Now consider the effect of the $Mg^{++}$ diffusing in. It is not known exactly how the enzyme reaction rate depends on $[Mg^{++}]$. However, a divalent metal ion is required for enzymatic activity. It is assumed that the rate is linearly proportional up to a maximum rate at 1 mM of $Mg^{++}$. Thus, it is assumed the reaction rate constant is equal to $$k_{bst} \min(1, [Mg^{++}]/1 \text{ mM}) \quad (7)$$

One may use a diffusion coefficient for $Mg^{++}$ of $1.25 \times 10^{-5}$ cm$^2$/2. For Model 2, at t=0, the $Mg^{++}$ is only at z=0, at concentration $[Mg^{++}]_0 = 1$ mM. For t>0 it diffuses in and affects the reaction rate by Eq. (8). For Model 1, the concentration of $Mg^{++}$ is 1 mM at all times in the well. Alternatively, we may assume that the enzyme is presoaked with $Mg^{++}$, so that the concentration of free $Mg^{++}$ in solution is zero.

In the range of 7-9 pH, the reactions release $H^+$ roughly as follows

| | |
|---|---|
| $DNA_n$ | n |
| $DNA_{n+1}$ | n + 1 |
| dNTP | 4 |
| PPi | 3 |
| 2 Pi | 4 |

This is because all the $H^+$ with pKa values lower than the pH of the solution will come off, to a good approximation. All of these species lower the pH if the solution is pH 7 to 9. So the net effect of the reaction $$dNTP + DNA_n \rightarrow PPi + DNA_{n+1} \quad (8)$$

is to not change the pH.

The net effect of the reaction $$PPi + H_2O \rightarrow 2Pi \quad (9)$$

is to change the pH by release of one net $H^+$.

The $H^+$ released by the DNA on the bead surface will diffuse out to beyond the DNA, and since the pH is much higher than the pKa of the DNA, these $H^+$ ions will diffuse out of the well during the equilibration time t<0. (All these $H^+$ diffuse away.) That is, if the DNA on the bead is allowed to equilibrate before the dNTP is added, the solution should just be the usual buffer solution (with a bit of extra $Na^+$ near the bead to balance the negative charge on the DNA, within the Debye length). When the extra base of DNA is added, a pulse of $H^+$ will come off—with a diffusion coefficient of something like $Na^+$.

Well Sizes

Simulation runs were done for small wells:

| D(µm) | H(µm) | 2 $R_{bead}$ (µm) | $V_{well}$ (pl) | [DNA]$_{well}$ (µM) |
|---|---|---|---|---|
| 1.5 | 2.25 | 1.05 | 0.005063 | 4.62 |
| 4 | 6 | 2.8 | 0.096 | 1.73 |
| 6 | 8 | 5.91 | 0.29 | 2.55 |

For D=1.5 µm, h=0.2 µm (1 layer of beads). For D=4 µm, h=1.1 µm. Otherwise h=1.5 µm. In addition, one run was done for the 4 µm×6 µm wells with a larger bead of radius 3.6 µm.

dNTP Front Thickness in Device Flow

The dNTP is assumed in the calculations to instantaneously change from 0 to 6.5 µM above the wells at t=0. This condition is approximately true if the dNTP flows quickly enough past the wells. Define V=velocity of flow of the fluid above the well
L=length of device
D=diffusivity of dNTP=$3.91 \times 10^{-6}$ cm$^2$/s
d=size of well
t=time to sweep flow across device
$t_0$=cutoff time for "instantaneous change"
$W_d$=width of front due to diffusion at end of device=$(2Dt)^{1/2}$
$W_m$=width of front due to mixing≈length of flush volume region
U=flush volume=15 µl (currently 52 µl)
u=flow rate=50 µl/s Flow cell geometries are as follows for two models, designated 313 and 314:

| Flow Cell | axis (mm) | Width (mm) | Height (mm) | Volume (µl) | Cell Volumes/s |
|---|---|---|---|---|---|
| 314 | 7.249 | 7.249 | 0.336 | 17.657 | 2.775 |
| 313 | 4.999 | 4.999 | 0.293 | 7.321 | 6.693 |

Take L=5 mm, d=4 µm and assume t=1/6.69 s. Q=50 µl/s. Then $W_d$=10.8 µm. Also, V=L/t=3.3 cm/s. $D_{eff} = D_0 2(1-\phi)/(2+\phi) = 1.20 \times 10^{-6}$ cm$^2$/s for $\phi=0.6$. The value of $t_0$ depends on the well size. It should be much shorter than the time at which dNTP diffuses to the bottom of the well for $N_{poly}$=0 (i.e. much shorter than the time at which this ion pulse response occurs), say 10% of that value. For the 4×6 µm well the time for the dNTP to diffuse to the bottom of the well, assuming no obstruction to the diffusion is $H^2/(2D)$, so that $t_0=10\% \times H^2/(2D)=0.015$ s. Simulation reveals the sphere with the DNA on it slows down the diffusion, so that perhaps $t_0=10\%*0.2$ s=0.02 s. Define W=max($W_d$, $W_m$). The time the leading edge of the front takes to cross the device is d/V. The time it takes the whole front (leading plus trailing edge) to cross a well is (W+d)/V. The condition of "instantaneous" rise of the dNTP concentration is (W+d)/V<<$t_0$. (W+d)/V≈U/u. Since U/u=0.3 s, and $t_0$=0.02 s, this condition is not satisfied by the above assumptions. Either U must be made smaller or u must be made larger, or both, by a factor of 10. The condition that $W_m$ is given by the length of the flush region may be a bit too strict: the width of the mixing region may be substantially smaller than the length of the entire flush region. This is a conservative condition. However, $W_d/V \ll t_0$, so diffusive spreading of the front can be ignored.

Now, a different calculation. It is desirable for the concentration of dNTP at the wall of the channel to rise from 0 to 6.5

μM in less than $t_0$. The concentration $C(x,y,z)$ at $t=0$ may be assumed to be $c_0=6.5$ μM at $t=0$. Take $0<x<L$, $-B<y<B$, $0<z<W$. It is desired to know the concentration at $y=B$ for any value of $0<x<L$. Strictly speaking, the concentration at the wall stays 0, since the velocity there is zero, unless diffusion is considered. So, it is necessary to consider convection in the x direction and diffusion in the z direction. Calculating the convection [6]

$$v=[(p_0-p_L)B^2/(2\mu L)][1-(y/B)^2] \quad (10)$$

The flow rate is $Q=(2/3)(p_0-p_L)B^3W/(\mu L)$. Calculate the time it takes for the average flow at the end of the device to be $0.95c_0$. First, note that without diffusion, the concentration is given by $$c(x,y,z)=0, t<t^*$$

$$c_0, t>t^*$$

$$t^*=x/v(y) \quad (11)$$

The flow becomes 95% of the maximum concentration at $t'=L/v(0.95B)$. The time to clear one volume is $t''=\text{volume}/Q$, where volume=2BWL. It can be found that $t'=2/3/0.0975t''=6.87t''$. Thus it takes 7 device volumes to bring the average concentration up to 95% of the final value (not 3). Of concern is the value of the concentration at the device wall. The concentration obeys the equation $$\partial c/\partial t+v(y)\partial c/\partial x=D\partial^2 c/\partial y^2 \quad (12)$$

$$c(x,y,0)=0$$

$$c(0,y,t)=c_0$$

$$\partial c(x,\pm B,t)/\partial y=0$$

ignoring diffusion in the y direction as dominated by convection. Now the concentration reaches the wall by diffusion in a time δt, but diffusion from the concentration profile that existed at a smaller $x-\delta x$ and $y=y-\delta y$, since convection occurs during this time δt. Note $(\delta y)^2=2D\delta t$. From the above, it is known that the concentration can diffuse on the order of $\delta y=10$ μm by diffusion during a time $t''=1/6.69$ s. It is desired that it diffuse during a time $t_0=0.02$ s, which implies a diffusion distance of 3.95 μM. So, as a conservative calculation, one could calculate from Eq. (11) $t^*=L/v(B-3.95 \mu m)$. By the time $t^*+t_0$, the concentration at the wall will be approximately $c_0$ through a combination of diffusion and convection. Thus $$v=(3/4)(1/BW)Q[1-(y/B)^2]$$

Using this, $t^*=L/v(B-3.95 \mu m)=1.84$ s. At a value $t_0$ later, the concentration at the wall will rise approximately to the maximum. Unfortunately, this calculation ignores that during 1.84 s, material from velocity profiles from smaller values of y will also have had the chance to diffuse to the wall. It is also ignoring that the diffusion which starts for smaller values of x proceeds to the right with lower velocities as y gets larger.

Thus, one can ask when diffusion over the boundary layer is faster than convection. By diffusion $\delta/t=2D/\delta$. By convection $\delta/t=v(B-\delta)$. These two are equal for $\delta=0.001$ mm=1.0 μm. So, when the front has reached this value of $\delta=L/v(B-\delta)=6.78$ s, the progression of the material to the wall is entirely dominated by diffusion. And the concentration will rise to approximately $c_0$ during the time $\delta^2/(2D)=0.01$ s. So, for $\delta<1.0$ μm, convection is more important than diffusion in the x direction.

A numerical solution of Eq. (12) is necessary to check the above approximate calculations. A finite element method can be used to numerically solve Eq. (12). We find that for the above device, the concentration at the wall rises in about 0.15 s at $x=0.5$ mm and about 0.5 s at $x=5.0$ mm. This is too slow. The Reynolds number is Re=1 g/cm$^3$*0.5 cm/(1/6.69 s)*0.0293 cm/0.01 cp=9.8. If one sets the height to be 0.1 mm, one finds that the concentration at the wall rises in about 0.04 s at $x=0.5$ mm and about 0.15 s at $x=5.0$ mm. This is probably too slow. Re=9.8. If set alternatively set Q=240 μl/s, the concentration at the wall rises in about 0.05 s at $x=0.5$ mm and about 0.2 s at $x=5.0$ mm. This is probably too slow. Re=47. If one sets both the height to be 0.1 mm and Q=240 μl/s, the concentration at the wall rises in about 0.013 s at $x=0.5$ mm and about 0.07 s at $x=5.0$ mm. This is probably fast enough. Re=47. The flow in all cases should be laminar.

The above may be a bit too strict, in that the biggest signal is coming from the breakthrough of the dNTP, and this breakthrough is quite sharp. It is possible that the dNTP rise at the top of the well need not be complete in 0.02 s. Perhaps the rise just has to be complete significantly before the dNTP breakthrough at the bottom of the well occurs. And this is on the order of seconds. So, one needs to solve the reaction/diffusion equations with a dNTP concentration that is rising at the top of the well. Let it rise from 0 to 6.5 μM linearly between 0 and t, where t is the value specified in the previous paragraph for the rise time at the end of the device.

From these numerical simulations, it may be found that a finite rise time of the dNTP at the surface of the well reduces the performance of the ion pulse device only slightly. For a 6 μm×8 μm device, a finite rise time of 0.2 s affects the observed sensor response curves only slightly. A finite rise time of 0.5 s affects the observed sensor response curves by shifting to longer times the first peak as well as reducing the height of the peaks for all values of $N_{poly}$. A surface with a slower response time would be less affected by this finite dNTP rise time. The effects are similar, if a bit more dramatic, for the 4 μm×6 μm, since the characteristic diffusion times for this device are smaller and therefore the finite rise time is a larger relative perturbation to the idealized case of instantaneous dNTP rise at the surface of the well.

Parametric Sensitivity of Results

To determine the sensitivity of the ion pulse response to experimental variables, the 4 μm×6 μm system was taken as a reference. Since this detection method relies on diffusion, the well geometry has a significant impact on the resolution of any $N_{poly}$ curves that are plotted.

The dNTP concentration was halved to 3.25 μM and doubled to 13 μM. The DNA on the bead surface was increased by a factor of 3. A run was done with a larger 3.6 μm bead. Both the DNA on the bead surface and the dNTP were increased by a factor of 3. The reaction rate, k, of the enzyme was halved and doubled. Sensor response curves for the 5 μM Tris, no free $Mg^{++}$, were produced for all of the above.

Double the enzyme reaction rate constant makes the peaks very slightly higher.

One possibility is that the DNA concentration on the beads is so high that the reaction is effectively diffusion limited, and so the enzyme rate constant is not a major factor affecting the concentration curves. Similarly, reducing the enzyme reaction rate by ½ has little effect on the sensor curves. It spreads them out in time only very slightly.

The large bead works very well. Since there is more mass of DNA on the bead, consuming it takes longer. In addition, the bead is taking up more space in the volume, so that diffusion to the well bottom takes a bit longer. The peaks are spread out to larger times.

A larger concentration of DNA on the bead spreads out the peaks in time. This is because the larger concentration of DNA means a greater mass of DNA on the beads. This greater mass of DNA takes a longer time to reaction. Thus the final breakthrough of the dNTP takes longer.

Lowering the solution dNTP concentration to 3.25 µM spreads out the peaks in time, but also reduces the peak height. The two effects probably approximately cancel in terms of distinguishing the different $N_{poly}$ curves. Conversely, increasing the dNTP concentration to 13 µM shifts the peaks to smaller time. While the peaks are higher, they are also substantially closer in time. The curves are at such a shorter time that they are running into the response time of the sensor. It appears the 13 µM curves may be less distinguishable than the 6.5 µM case.

Increasing the concentration of DNA on the beads three times and increasing the dNTP concentration in the solution to 13 µM makes the peaks about 3 times higher but does not spread them out in time. The time scale is relatively unchanged because while the amount of DNA on the beads is greater, the reaction rate is also greater due to the higher dNTP concentration. The peaks are higher because there is more mass released in the same time.

Packing Beads—Φ (Phi)

The desirability for packing beads (to slow down diffusion of all species) is seen by comparing the Ion Pulse Response between similar well dimensions and between the 4×6 micron (width×height) and 6×8 micron wells. The $N_{poly}$ curves resolve with increased depth of the well and with packing beads (Φ=0.6).

The formula to see the effect of Φ is the effective diffusion coefficient $$D_{eff} = D_0 * 2(1-\Phi)/(2+\Phi)$$

For Φ=0.6, $D_0/D_{eff}$=3.25 e.g. 3.25× slowdown due to beads
For Φ=0.9, $D_0/D_{eff}$=14.5 e.g. 14.5× slowdown due to this
The other formula needed is the characteristic time in the well $$H^2 = 2D_{eff} t$$

So, for a 6 um well at Φ=0.6

$$t = 6^2/(2/3.25 * D_0) = 58.5/D_0$$

A 2.25 well at Φ=0.9 yields $$t = 2.25^2/(2/14.5 * D_0) = 36.7/D_0$$

So, the 2.25 um well at Φ=0.9 would have all times about 36.7/58.5=0.63 smaller than the 6 um well at Φ=0.6. The smaller well will still be a little bit faster. If one had Φ=0.936, the smaller well would operate just about exactly as the larger well (assuming the well diameter and the DNA bead are scaled the same way as the well height).

Signal to Noise

The signal-to-noise ratio is proportional to the difference in mV between a $N_{poly}$ and $N_{poly+1}$ signal and also to the square root of the length of time over which the mV curves are different. Define σ as the sensor noise and f as the number of frames per second. Define the average difference of the absolute value between signal 1 and signal 2 during $0<t<t_{max}$ as Δ, i.e.

$$\Delta = \int_0^{t_{max}} |v_1 - v_2|/t_{max}.$$

Take the absolute value because the difference between the curves can have both signs. Thus the condition is $$\Delta > \sigma [2/(ft_{max})]^{1/2}$$

Consider, as an example, for the D=4 µm, H=6 µm wells, φ=0, dNTP=20 µM, 10×DNA case. Take f=20 Hz, and $t_{max}$=2 s. The value of Δ is 0.6861. Thus $$0.6861 > 0.22\sigma$$

So, using the value of σ=0.25 mV, this device will work (1−P=$10^{-35}$). Consider as another example the D=4 µm, H=6 µm wells, φ=0, dNTP=6.5 µM, 10×DNA case. Take f=20 Hz, and $t_{max}$=4 s. The value of Δ is 0.1862. Thus $$0.1862 > 0.1581\sigma$$

So, using the value of σ=0.25 mV, this device will probably work (1−P=2.4×$10^{-6}$).

Note there is an optimal value of $t_{max}$: too small a value, and one does not have enough signal; too large a value, and one is seeing mostly noise. The value of $t_{max}$ is only roughly here.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for nucleic acid sequencing, the method comprising:
    disposing at least one template nucleic acid in a reaction chamber communicating with a chemical sensor;
    introducing known nucleotides into the reaction chamber;
    detecting an output pulse from the chemical sensor indicating an end of an incorporation interval of the known nucleotides into the template nucleic acid; and
    determining a number of known nucleotides incorporated during the incorporation interval based on a time interval between the introduction of the known nucleotides and the detection of the output pulse.

2. The method of claim 1, wherein the end of the incorporation interval defines an end of incorporation events of the known nucleotides into the at least one template nucleic acid.

3. The method of claim 1, wherein the output pulse is due to a change in ion concentration within the reaction chamber at the end of the incorporation interval.

4. The method of claim 3, wherein the change in ion concentration is due to a change in concentration of unincorporated known nucleotides within the reaction chamber.

5. The method of claim 4, wherein the change in ion concentration is further due to a diffusion of ions out of the reaction chamber.

6. The method of claim 1, wherein the incorporated known nucleotides are of a single type.

7. The method of claim 1, wherein the chemical sensor is coupled to the reaction chamber via a passivation layer.

8. The method of claim 7, wherein a rate of ion generation within the reaction chamber due to incorporation of the known nucleotides is greater than a rate of change in surface charge density of the passivation layer.

9. The method of claim 1, wherein the chemical sensor is a chemically-sensitive field effect transistor (chemFET), and the output pulse is based on a threshold voltage of the chemFET.

10. The method of claim 9, wherein the chemFET includes a floating gate coupled to the reaction chamber via a passivation layer.

11. A method for nucleic acid sequencing, the method comprising:
    disposing at least one template nucleic acid in a reaction chamber communicating with a chemical sensor;
    introducing known nucleotides into the reaction chamber;
    detecting a first output pulse from the chemical sensor indicating a beginning of incorporation events of the known nucleotides into the template nucleic acid;
    detecting a second output pulse from the chemical sensor indicating an end of incorporation events of the known nucleotides into the template nucleic acid; and
    determining a number of known nucleotides incorporated into the at least one template nucleic acid based on a time interval between the detection of the first output pulse and the detection of the second output pulse.

12. The method of claim 11, wherein the first pulse is due at least in part to generation of PPi within the reaction chamber resulting from the incorporation events.

13. The method of claim 12, wherein the second pulse is due at least in part to a change in concentration of unincorporated known nucleotides within the reaction chamber.

14. The method of claim 11, wherein the first pulse and the second pulse are each due to changes in ion concentration within the reaction chamber.

15. The method of claim 11, wherein the chemical sensor is coupled to the reaction chamber via a passivation layer.

16. The method of claim 15, wherein a rate of ion generation within the reaction chamber due to incorporation of the known nucleotides is greater than a rate of change in surface charge density of the passivation layer.

17. The method of claim 11, wherein the chemical sensor is a chemically-sensitive field effect transistor (chemFET), and the output pulse is based on a threshold voltage of the chemFET.

18. The method of claim 17, wherein the chemFET includes a floating gate coupled to the reaction chamber via a passivation layer.

19. A method for nucleic acid sequencing, the method comprising:
- disposing at least one template nucleic acid in a reaction chamber communicating with a chemical sensor;
- introducing known nucleotides into the reaction chamber; and
- detecting incorporation of at least one of the known nucleotides into the at least one template nucleic acid by receiving a pair of output pulses from the chemical sensor in response to introducing the known nucleotides.

20. The method of claim 19, further comprising:
- introducing second known nucleotides into the reaction chamber; and
- detecting a lack of incorporation of the second known nucleotides by receiving a single output pulse from the chemical sensor in response to introducing the second known nucleotides.

\* \* \* \* \*

UNITED STATES PATENT AND TRADEMARK OFFICE
CERTIFICATE OF CORRECTION

PATENT NO. : 8,470,164 B2
APPLICATION NO. : 13/001182
DATED : June 25, 2013
INVENTOR(S) : Rothberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 340 days.

Signed and Sealed this
Eighth Day of September, 2015

Michelle K. Lee
*Director of the United States Patent and Trademark Office*